United States Patent
Jones et al.

(10) Patent No.: US 11,787,786 B2
(45) Date of Patent: *Oct. 17, 2023

(54) FUSED 1,4-DIHYDRODIOXIN DERIVATIVES AS INHIBITORS OF HEAT SHOCK TRANSCRIPTION FACTOR 1

(71) Applicant: Cancer Research Technology Limited, London (GB)

(72) Inventors: Keith Jones, Sutton Coldfield (GB); Carl Rye, Sutton Coldfield (GB); Nicola Chessum, Sutton Coldfield (GB); Matthew D. Cheeseman, Sutton Coldfield (GB); Adele E. Pasqua, Sutton Coldfield (GB); Kurt G. Pike, Cambridge (GB); Paul F. Faulder, Stockport (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/406,640

(22) Filed: Aug. 19, 2021

(65) Prior Publication Data

US 2022/0220097 A1 Jul. 14, 2022

Related U.S. Application Data

(60) Continuation of application No. 16/212,455, filed on Dec. 6, 2018, now Pat. No. 11,124,501, which is a division of application No. 15/332,472, filed on Oct. 24, 2016, now Pat. No. 10,189,821, which is a continuation of application No. 15/026,911, filed as application No. PCT/GB2014/052992 on Oct. 3, 2014, now Pat. No. 9,701,664.

(30) Foreign Application Priority Data

Oct. 4, 2013 (GB) .................................... 1317609

(51) Int. Cl.

| | | |
|---|---|---|
| *C07D 405/14* | (2006.01) | |
| *A61K 31/496* | (2006.01) | |
| *A61P 35/00* | (2006.01) | |
| *C07D 405/12* | (2006.01) | |
| *C07D 319/18* | (2006.01) | |
| *C07D 407/12* | (2006.01) | |
| *C07D 409/12* | (2006.01) | |
| *C07D 417/12* | (2006.01) | |
| *C07D 417/14* | (2006.01) | |
| *C07D 471/04* | (2006.01) | |
| *C07D 487/08* | (2006.01) | |
| *C07D 491/056* | (2006.01) | |

(52) U.S. Cl.
CPC ......... *C07D 405/12* (2013.01); *C07D 319/18* (2013.01); *C07D 405/14* (2013.01); *C07D 407/12* (2013.01); *C07D 409/12* (2013.01); *C07D 417/12* (2013.01); *C07D 417/14* (2013.01); *C07D 471/04* (2013.01); *C07D 487/08* (2013.01); *C07D 491/056* (2013.01)

(58) Field of Classification Search
CPC .. C07D 405/12; C07D 405/14; C07D 319/18; C07D 407/12; C07D 409/12; C07D 417/12; C07D 417/14; C07D 471/04; C07D 487/08; C07D 491/056; A61K 31/357; A61K 31/404; A61K 31/428; A61K 31/436; A61K 31/496; A61P 35/00
See application file for complete search history.

(56) References Cited

U.S. PATENT DOCUMENTS

| | | |
|---|---|---|
| 5,137,805 A | 8/1992 | Kingston et al. |
| 5,714,502 A | 2/1998 | Prucher et al. |
| (Continued) | | |

FOREIGN PATENT DOCUMENTS

| | | |
|---|---|---|
| DE | 19531321 A1 | 2/1997 |
| EP | 0995745 A1 | 4/2000 |
| (Continued) | | |

OTHER PUBLICATIONS

Whitesell et al. Expert Opinion Ther. Targets 2009, 13(4), 469-478.*
Velayutham et al. Frontiers in Oncology 2018, vol. 8, article 97, p. 1-5.*
Carpenter et al. Curr Cancer Drug Targets 2019, 19(7), 515-524.*
Dong et al. Trends in Pharmacological Sciences 2019, 40 (12), 986-1005.*
Foster Trends in Pharmacological Sciences 1984, 524-527.*
U.S. Pat. No. 9,701,664, issued on Jul. 11, 2017; U.S. Appl. No. 15/026,911; published as US 2016-0289216 A1 on Oct. 6, 2016, Fused 1,4-Dihydrodioxin Derivatives as Inhibitors of Heat Shock Transcription Factor 1, filed Jul. 11, 2017.

(Continued)

*Primary Examiner* — Irina Neagu
(74) *Attorney, Agent, or Firm* — Goodwin Procter LLP

(57) ABSTRACT

The present invention relates to compounds of formula I wherein $A_1$, $A_2$ $R_4$ and Q are as defined herein. The compounds of the present invention are inhibitors of heat shock factor 1 (HSF1). In particular, the present invention relates to the use of these compounds as therapeutic agents for the treatment and/or prevention of proliferative diseases, such as cancer. The present invention also relates to processes for the preparation of these compounds, and to pharmaceutical compositions comprising them.

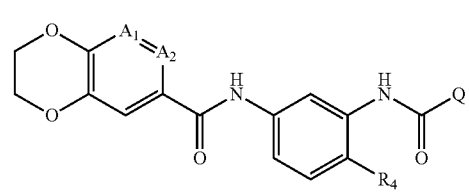

1 Claim, No Drawings

(56) References Cited

U.S. PATENT DOCUMENTS

| | | | |
|---|---|---|---|
| 5,756,343 | A | 5/1998 | Wu et al. |
| 6,455,520 | B1 | 9/2002 | Brown et al. |
| 6,867,036 | B1 | 3/2005 | Vile et al. |
| 9,701,664 | B2 | 7/2017 | Jones et al. |
| 10,189,821 | B2 | 1/2019 | Jones et al. |
| 10,647,678 | B2 | 5/2020 | Jones et al. |
| 11,124,501 | B2 | 9/2021 | Jones et al. |
| 2002/0001629 | A1 | 1/2002 | Voellmy |
| 2002/0058679 | A1 | 5/2002 | Yokota et al. |
| 2005/0192219 | A1 | 9/2005 | Voellmy |
| 2005/0207972 | A1 | 9/2005 | Friebe et al. |
| 2006/0154278 | A1 | 7/2006 | Brody et al. |
| 2007/0105794 | A1 | 5/2007 | Lipinski et al. |
| 2007/0238682 | A1 | 10/2007 | Nudler et al. |
| 2009/0062222 | A1 | 3/2009 | Sherman et al. |
| 2009/0092600 | A1 | 4/2009 | Kufe |
| 2009/0117589 | A1 | 5/2009 | Southern |
| 2009/0163545 | A1 | 6/2009 | Goldfarb |
| 2010/0015605 | A1 | 1/2010 | Zucman-Rossi et al. |
| 2010/0216660 | A1 | 8/2010 | Nikolsky et al. |
| 2011/0112073 | A1 | 5/2011 | Thiele et al. |
| 2011/0123512 | A1 | 5/2011 | Prahlad et al. |
| 2011/0166038 | A1 | 7/2011 | Zhang et al. |
| 2011/0166058 | A1 | 7/2011 | Hinkle et al. |
| 2011/0182881 | A1 | 7/2011 | Chin et al. |
| 2011/0251096 | A1 | 10/2011 | Southern |
| 2011/0311508 | A1 | 12/2011 | Morimoto et al. |
| 2013/0133108 | A1 | 5/2013 | Warpeha et al. |
| 2014/0234858 | A1 | 8/2014 | Santagata et al. |
| 2014/0302042 | A1 | 10/2014 | Chin et al. |
| 2014/0315214 | A1 | 10/2014 | Taipale et al. |
| 2016/0289216 | A1 | 10/2016 | Jones et al. |
| 2017/0037036 | A1 | 2/2017 | Jones et al. |
| 2018/0093955 | A1 | 4/2018 | Jones et al. |
| 2019/0106413 | A1 | 4/2019 | Jones et al. |
| 2020/0039965 | A1 | 2/2020 | Jones et al. |

FOREIGN PATENT DOCUMENTS

| | | |
|---|---|---|
| WO | WO-9601825 A1 | 1/1996 |
| WO | WO-1998017648 A1 | 4/1998 |
| WO | WO-9932433 A1 | 7/1999 |
| WO | WO-1999/59959 A1 | 11/1999 |
| WO | WO-2000007991 A1 | 2/2000 |
| WO | WO-2000/18738 A1 | 4/2000 |
| WO | WO-0056341 A1 | 9/2000 |
| WO | WO-2000055153 A1 | 9/2000 |
| WO | WO-02/36576 A1 | 5/2002 |
| WO | WO-2003020227 A1 | 3/2003 |
| WO | WO-2004004703 A1 | 1/2004 |
| WO | WO-2004006858 A2 | 1/2004 |
| WO | WO-2004013117 A1 | 2/2004 |
| WO | WO-2004/019873 A2 | 3/2004 |
| WO | WO-2004/021988 A2 | 3/2004 |
| WO | WO-2004018414 A2 | 3/2004 |
| WO | WO-2004024083 A2 | 3/2004 |
| WO | WO-2004056774 A2 | 7/2004 |
| WO | WO-2005007151 A1 | 1/2005 |
| WO | WO-2005026334 A2 | 3/2005 |
| WO | WO-2005042496 A1 | 5/2005 |
| WO | WO-2006003378 A1 | 1/2006 |
| WO | WO-2006040568 A1 | 4/2006 |
| WO | WO-2006124874 A2 | 11/2006 |
| WO | WO-2007059157 A1 | 5/2007 |
| WO | WO-2008031534 A1 | 3/2008 |
| WO | WO-2008077165 A1 | 7/2008 |
| WO | WO-2008152013 A1 | 12/2008 |
| WO | WO-2009075874 A1 | 6/2009 |
| WO | WO-2010043631 A1 | 4/2010 |
| WO | WO-10053655 A2 | 5/2010 |
| WO | WO-2010093419 A1 | 8/2010 |
| WO | WO-11025167 A2 | 3/2011 |
| WO | WO-13030778 A2 | 3/2013 |
| WO | WO-13166427 A1 | 11/2013 |
| WO | WO-13172640 A1 | 11/2013 |
| WO | WO-14187959 A2 | 11/2014 |
| WO | WO-2015049535 A1 | 4/2015 |
| WO | WO-2016156872 A1 | 10/2016 |

OTHER PUBLICATIONS

U.S. 10,189,821, issued on Jan. 29, 2019; U.S. Appl. No. 15/332,472; published as US 2017-0037036 A1 on Feb. 9, 2017, Fused 1,4-Dihydrodioxin Derivatives as Inhibitors of Heat Shock Transcription Factor 1, filed Jan. 29, 2019.

U.S. Pat. No. 11,124,501, issued on Sep. 21, 2021; U.S. Appl. No. 16/212,455; published as US 2019-0106413 A1 on Apr. 11, 2019, Fused 1,4-Dihydrodioxin Derivatives as Inhibitors of Heat Shock Transcription Factor 1, filed Sep. 21, 2021.

U.S. pt. No. 10,647,678, issued on May 12, 2020; U.S. Appl. No. 15/563,501; published as US 2018-0093955 A1 on Apr. 5, 2018, Quinoline Derivatives as Inhibitors of Heat Shock Factor 1 Pathway Activity, filed May 12, 2020.

U.S. Appl. No. 16/339,056: published as US-2020-0039965-A1 on Feb. 6, 2020, Deuterated N-(5-(2,3-Dihydrobenzo[B][1,4]Dioxine-6-Carboxamido)-2-Fluorophenyl)-2-((4-Ethylpiperazin-1-yl)Methyl)Quinoune-6-Carboxamide.

AKos Screening Library (Aug. 20, 2013) Order No. AKOS006882384 and CHEMCATS accession No. 0097075038 (CAS Registry No. 1298093-46-5).

Ambinter Stock Screening Collection, published Sep. 15, 2014, Order No. Cat. Amb10715307.

Ambinter Stock Screening Collection, published Sep. 15, 2014, Order No. Cat. Amb8261001.

Ashton et al., "New Low-Density Lipoprotein Receptor Upregulators Acting via a Novel Mechanism," J Med Chem, 39(17): 3343-3356 (1996).

Buteau, K., "Deurated Drugs: Unexpectedly Unobvious?" J. High Tech L., pp. 22-74 (2009).

Carpenter et al., "HSF1 as a Cancer Biomarker and Therapeutic Target," Curr. Cancer Drug Targets, 19(7):515-524 (2019).

Cheeseman et al., "Discovery of a Chemical Probe Bisamide (CCT251236): An Orally Bioavailable Efficacious Pirin Ligand from a Heat Shock Transcription Factor 1 (HSF1) Phenotypic Screen," J. Med. Chem., 60(1):180-201 (2017).

Chen et al., "Nucleoside analog inhibits microRNA-214 through targeting heat-shock factor 1 in human epithelial ovarian cancer," Cancer Sci, 104(12):1683-1689 (2013).

Dai et al., "Heat shock factor 1 is a powerful multifaceted modifier of carciogenesis," Cell, 130:1005-1018 (2007).

Database PubChem Compound [Online] NCBI; Feb. 20, 2008 (Feb. 20, 2008). XP002731865. Database accession No. CID 23854223 abstract.

Dong et al., "Inhibiting Heat Shock Factor 1 in Cancer: A Unique Therapeutic Opportunity," Trends in Pharmacological Sciences 2019, 40 (12), 986-1005.

Dorwald., "Side Reaction in Organic Synthesis," A Guide to Successful Synthesis Design, Wiley-VCH, 1-15 (2005).

Jin et al., "Heat shock transcription factor 1 is a key determinant of HCC development by regulating hepatic steatosis and metabolic syndrome," Cell, 14:91-103 (2011).

Kim et al., "New Diarylureas and Diarylamides Possessing Acet(benz)amidophenyl Scaffold: Design, Synthesis, and Biorg. Med. and Antiproliferative Activty Against Melanoma Cell Line," Chem. Lett. 22:3269-3273 (2012).

Lee et al., "Synthesis of aminoquinazoline derivatives and their antiproliferative activities against melanoma cell line," Bioorgan Med Chem Lee, 20(19): 5722-5725 (2010).

Mendillo et al., "HSF1 drives a transcriptional program distinct from heat shock to support highly malignant human cancers," Cell, 150:549-562 (2012).

Mustafi et al., "Modulation of Akt and ERK1/2 pathways by resveratrol in chronic myelogenous leukemia (CML) cells results in the downregulation of Hsp70," PLoS ONE, 5(1):e8719 (2010).

Neustadt et al., "Combinatorial Libraries Based on a Novel and Readily Accessible "Centroid" Scaffold," Tetrahedron Lett, 39(30): 5317-5320 (1998).

(56) References Cited

OTHER PUBLICATIONS

Niume et al., "Heat-Resistant Polymers with Thianthrene Analog Units. II. Aromatic Polyamides," J Polym Sci, 18(7): 2163-2174 (1980).
TimTec Stock Building Blocks and Screening Compounds, published May 16, 2014, Order No. Cat. ST50925835.
Venkatesh et al., "Role of the Development Scientist in Compound Lead Selection and Optimization," Journal of Pharmaceutical Sciences, 89(2):145-154 (2000).
Whitesell et al., "Inhibiting the Transcript Factor HSF1 as an Anticancer Strategy," Expert Opinion Ther. Targets 13(4):469-478 (2009).
Zhou et al., "Synthesis and SAR of novel, non-MPEP chemotype mGluR5 NAMs identified by functional HTS," Bioorgan Med Chem Lett, 19(23): 6502-6506 (2009).
International Search Report and Written Opinion in PCT/GB2014/052992, dated Nov. 18, 2014 9 pages.
International Search Report and Written Opinion in PCT/GB2016/050938, dated May 18, 2016 12 pages.
International Search Report and Written Opinion in PCT/GB2017/053033, dated Nov. 22, 2017 10 pages.

\* cited by examiner

FUSED 1,4-DIHYDRODIOXIN DERIVATIVES AS INHIBITORS OF HEAT SHOCK TRANSCRIPTION FACTOR 1

CROSS REFERENCE TO RELATED APPLICATIONS

This application is a continuation of U.S. patent application Ser. No. 16/212,455 filed Dec. 6, 2018, which is a division of U.S. patent application Ser. No. 15/332,472 filed Oct. 24, 2016, which is a continuation on U.S. patent application Ser. No. 15/026,911 filed Apr. 1, 2016, which is a national stage filing under 35 U.S.C. § 371 of PCT/GB2014/052992 filed Oct. 3, 2014, which claims the benefit of, and priority to, United Kingdom (GB) Patent Application No. 1317609.4 filed Oct. 4, 2013, all of which are hereby incorporated by reference in their entirety.

INTRODUCTION

The present invention relates to novel compounds that act as inhibitors of heat shock factor 1 (HSF1) activity. The present invention further relates to processes for preparing the compounds defined herein, to pharmaceutical compositions comprising them, and to their use in the treatment of HSF1-mediated conditions or diseases (such as cancer, autoimmune diseases and viral diseases).

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the identification of a number of molecular targets associated with key metabolic pathways that are known to be associated with malignancy.

Heat shock factor 1 (HSF1) is one such target molecule. HSF1 is the master regulator of the heat shock response, in which multiple genes are induced in response to temperature increase and other stresses. At non-shock temperatures in humans and other vertebrates, HSF1 is produced constitutively, but is inactive and bound by protein HSP90. At an elevated temperature, HSF1 is released by HSP90, moves from the cytoplasm to the nucleus, and trimerizes. This active HSF1 form binds to sequences called heat shock elements (HSE) in DNA and activates transcription of heat shock genes by RNA polymerase II. The HSE has a consensus sequence of three repeats of NGAAN and is present in the promoter regions of the HSP90, HSP70 and HSP27 genes. During cessation of the heat shock response, HSF1 is phosphorylated by mitogen-activated protein kinases (MAPKs) and glycogen synthase kinase 3 (GSK3) and returns to an inactive state. The biochemistry of HSFl is described in more detail in, inter alia, Chu et al. 1996 J. Biol. Chem. 271:30847-30857 and Huang et al. 1997 J. Biol. Chem. 272:26009-26016.

HSF1 also interacts with additional factors. For example, HSF1 binds to DNA-dependent protein kinase (DNA-PK), which is involved in DNA repair. HSF1 is also target of mitogen-activated protein kinases, and its activity is downregulated when the RAS signaling cascade is active.

Additional heat shock factor proteins in humans include HSF2, HSF3, and HSF4. HSF 1, HSF2, and HSF3 are all positive regulators of heat shock gene expression, while HSF4 is a negative regulator. HSF1, HSF2 and HSF4 play a role in transcriptional control of other heat shock proteins. The various HSF proteins share about 40% sequence identity.

HSF1 activity has been implicated in several diseases, including cancer, and autoimmune, and viral diseases. HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g., promyelocytic leukemia), and Hodgkin's disease.

Accordingly, there is need for pharmacologically active agents that are capable of inhibiting HSF1. Such agents are potentially useful chemotherapeutic agents for the treatment of diseases or conditions in which HSF1 activity is mediated.

SUMMARY OF THE INVENTION

In one aspect, the present invention provides a compound, or a pharmaceutically acceptable salt or solvate thereof, as defined herein.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of HSF1-mediated conditions or diseases (for example, cancer, autoimmune diseases or viral diseases).

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a HSF1 inhibitory effect.

In another aspect, the present invention provides the use of a compound as defined herein, or a pharmaceutically acceptable salt or solvate thereof, in the manufacture of a medicament for use in treatment of HSF1-mediated conditions or diseases (for example, cancer, autoimmune diseases or viral diseases).

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of a HSF1 inhibitory effect.

In another aspect, the present invention provides a method of inhibiting HSF1 in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a HSF1-mediated condition or disease (for example, cancer, autoimmune diseases or viral diseases), in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound as defined herein, or a pharmaceutically acceptable salt or solvate thereof.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicycle [2.2.2]octane, bicycle[2.1.1]hexane, bicycle[1.1.1]pentane and bicyclo[2.2.1]heptyl.

The term "(1-8C)heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "haloalkyl" or "haloalkoxy" is used herein to refer to an alkyl or alkoxy group respectively in which one or more hydrogen atoms have been replaced by halogen (e.g. fluorine) atoms. Examples of haloalkyl and haloalkoxy groups include fluoroalkyl and fluoroalkoxy groups such as —CHF$_2$, —CH$_2$CF$_3$, or perfluoroalkyl/alkoxy groups such as —CF$_3$, —CF$_2$CF$_3$ or —OCF$_3$.

The term "carbocyclyl", "carbocyclic" or "carbocycle" means a non-aromatic saturated or partially saturated monocyclic, or a fused, bridged, or spiro bicyclic carbocyclic ring system(s). Monocyclic carbocyclic rings contain from about 3 to 12 (suitably from 3 to 7) ring atoms. Bicyclic carbocycles contain from 7 to 17 carbon atoms in the rings, suitably 7 to 12 carbon atoms, in the rings. Bicyclic carbocyclic rings may be fused, spiro, or bridged ring systems.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen. Suitably, the term "heterocyclyl", "heterocyclic" or "heterocycle" will refer to 4, 5, 6 or 7 membered monocyclic rings as defined above.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4] octane, 2-oxa-6-azaspiro[3.4]octane, 2-azaspiro[3.3]heptanes and 2-oxa-6-azaspiro[3.3]heptanes.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Suitably, the term "heteroaryl" or "heteroaromatic" will refer to 5 or 6 membered monocyclic heteroaryl rings as defined above.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;

l) a thiophene ring fused to a 5- or 6-membered ring containing 1, 2 or 3 ring heteroatoms;

m) a furan ring fused to a 5- or 6-membered ring containing 1, 2 or 3 ring heteroatoms;

n) a cyclohexyl ring fused to a 5- or 6-membered heteroaromatic ring containing 1, 2 or 3 ring heteroatoms; and o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl or naphthyl, especially phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention provides a compound of formula I shown below:

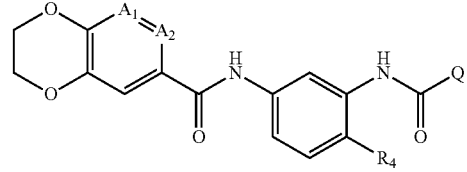

I wherein:
$A_1$ is selected from N or $CR_1$, $A_2$ is selected from N or $CR_2$, with the proviso that only one of $A_1$ or $A_2$ can be N;
$R_1$ and $R_2$ are each independently selected from hydrogen, fluoro, chloro, cyano, (1-2C)alkyl, (1-2C)alkoxy, (1-2C)haloalkyl or (1-2C)haloalkoxy;
$R_4$ is selected from hydrogen, fluoro, chloro, bromo, iodo, $CF_3$, $OCF_3$, cyano, $NO_2$, (1-4C)alkyl, (1-4C)alkoxy, or a group of the formula:

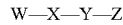

W—X—Y—Z wherein
W is absent or (1-3C)alkylene;
X is —O— or —N($R^a$)—, wherein $R^a$ is selected from hydrogen or (1-2C)alkyl;
Y is absent or a (1-3C)alkylene;
Z is hydrogen, (1-6C)alkyl or (3-6C)cycloalkyl;

and wherein any alkylene, alkyl or cycloalkyl group present in a $R_4$ substituent group is optionally further substituted by one or more substituent groups independently selected from halo, hydroxy, $NR^bR^c$, (1-2C)alkoxy, (1-2C)haloalkyl or (1-2C)haloalkoxy, and wherein $R^b$ and $R^c$ are each independently selected from hydrogen or (1-3C)alkyl;
Q is selected from a group of formula II:

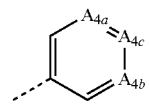

II wherein
$A_{4a}$ and $A_{4b}$ are each independently selected from N or $CR_9$, wherein each $R_9$ present is independently selected from hydrogen, halo, cyano, nitro, hydroxy, $NR^dR^e$, (1-3C)alkyl, (1-3C)alkoxy, 5 or 6-membered heteroaryl, or 5 or 6 membered heterocyclyl; wherein $R^d$ and $R^e$ are each independently selected from hydrogen or (1-3C)alkyl; and wherein any (1-3C)alkyl, (1-3C)alkoxy, 5 or 6-membered heteroaryl, or 5 or 6 membered heterocyclyl group present in a $R_9$ substituent group is optionally substituted by one or more substituents selected from halo, cyano, nitro, hydroxy, $NR^fR^g$ or (1-3C)alkoxy, wherein $R^f$ and $R^g$ are each independently selected from hydrogen or (1-3C)alkyl;
$A_{4c}$ is N or $CR_{10}$;
$R_{10}$ is selected from hydrogen, halo, amino, cyano, nitro, hydroxy or a group

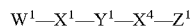

$W^1$—$X^1$—$Y^1$—$X^4$—$Z^1$ wherein
$W^1$ is absent or a linker group of the formula —$[CR^hR^i]_p$— in which p is an integer selected from 1, 2, 3 or 4, and $R^h$ and $R^i$ are each independently selected from hydrogen or (1-2C)alkyl;

$X^1$ is absent or —O—, —C(O)—, —C(O)O—, —OC(O)—, —CH(OR$^j$)—, —N(R$^j$)—, —N(R$^j$)—C(O)—, —N(R$^j$)—C(O)O—, —C(O)—N(R$^j$)—, —N(R$^j$)C(O)N(R$^j$)—, —S—, —SO—, —SO$_2$—, —S(O)$_2$N(R$^j$)—, or —N(R$^j$)SO$_2$— wherein R$^j$ is selected from hydrogen or methyl;

$Y^1$ is absent or a linker group of the formula —[CR$^k$R$^l$]$_q$— in which q is an integer selected from 1, 2, 3 or 4, and R$^k$ and R$^l$ are each independently selected from hydrogen or (1-2C)alkyl;

$X^4$ is absent or —O—, —C(O)—, —C(O)O—, —OC(O)—, —CH(OR$^j$)—, —N(R$^j$)—, —N(R$^j$)—C(O)—, —N(R$^j$)—C(O)O—, —C(O)—N(R$^i$)—, —N(R$^j$)C(O)N(R$^j$)—, —S—, —SO—, —SO$_2$—, —S(O)$_2$N(R$^j$)—, or —N(R$^j$)SO$_2$— wherein R$^i$ is selected from hydrogen or methyl; and $Z^1$ is (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^1$ is optionally further substituted by one or more substituent groups independently selected from oxo, halo, cyano, nitro, hydroxy, caboxy, NR$^m$R$^n$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^m$R$^n$, NR$^m$C(O)R$^n$, NR$^m$S(O)$_2$R$^n$ and S(O)$_2$NR$^m$R$^n$;

wherein R$^m$ and R$^n$ are each independently selected from hydrogen, (1-4C)alkyl or (3-6C)cycloalkyl or (3-6C)cycloalkyl(1-2C)alkyl; or R$^m$ and R$^n$ can be linked such that, together with the nitrogen atom to which they are attached, they form a 4-6 membered heterocyclic ring;

and wherein any alkyl, aryl, heterocyclyl or heteroaryl group present in a substituent group on $Z^1$ is optionally further substituted by halo, cyano, nitro, hydroxy, caboxy, NR$^o$R$^p$, (1-2C) alkoxy, or (1-2C)alkyl;

wherein R$^o$ and R$^p$ are selected from hydrogen or (1-2C)alkyl;

with the proviso that $R_{10}$ is only hydrogen or t-butyl when at least one of $A_{4a}$ and $A_{4b}$ is N or CR$_9$ in which R$_9$ is a substituent as defined above other than hydrogen;

or Q is a group of formula III:

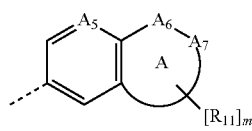

III wherein $A_5$ is selected from N or CR$_5$, where R$_5$ is selected from hydrogen, halo, cyano, nitro, hydroxy, NR$^q$R$^u$, (1-3C)alkyl, (1-3C)alkoxy, 5 or 6-membered heteroaryl, or 5 or 6 membered heterocyclyl; wherein R$^q$ and R$^u$ are each independently selected from hydrogen or (1-3C)alkyl, and wherein any (1-3C)alkyl, (1-3C)alkoxy, 5 or 6-membered heteroaryl, or 5 or 6 membered heterocyclyl group present in a R$_5$ substituent group is optionally substituted by one or more substitutents selected from halo, cyano, nitro, hydroxy, NR$^v$R$^w$, or (1-3C) alkoxy, wherein R$^v$ and R$^w$ are each independently selected from hydrogen or (1-3C)alkyl;

Ring A is:
a fused phenyl ring;
a fused 5 or 6 membered carbocyclic ring;
a fused 5 or 6 membered heteroaryl ring comprising one or two heteroatoms independently from N, S or O; or
a fused 5, 6 or 7-membered heterocyclic ring comprising one or two heteroatoms independently from N, S or O;

$A_6$ is selected from N, O, S, S(O), S(O)$_2$, CR$_6$, C(R$_6$)$_2$, NR$_{60}$, where R$_6$ is selected from hydrogen, oxo, fluoro, chloro, (1-2C)alkyl, (1-2C)alkoxy, (1-2C)haloalkoxy or (1-2C)haloalkyl and R$_{60}$ is hydrogen, O$^-$, (1-6C) alkyl, —C(O)—R$_{61}$, —C(O)O—R$_{61}$, or —C(O)N(R$_{62}$)R$_{61}$, wherein R$_{61}$ is selected from hydrogen, (1-6C) alkyl, (3-6C)cycloalkyl, aryl, heteroaryl or heterocyclyl and R$_{62}$ is selected from hydrogen or (1-3C)alkyl;

$A_7$ is selected from N, O, CR$_7$, S, S(O), S(O)$_2$, C(R$_7$)$_2$, NR$_{70}$, where R$_{70}$ is hydrogen, O$^-$, (1-6C)alkyl, —C(O)—R$_{71}$, —C(O)O—R$_{71}$, or —C(O)N(R$_{72}$)R$_{71}$, wherein R$_{71}$ is selected from hydrogen, (1-6C)alkyl, (3-6C)cycloalkyl, aryl, heteroaryl or heterocyclyl and R$_{72}$ is selected from hydrogen or (1-3C)alkyl; m is 0, 1 or 2;

R$_7$ and R$_{11}$ are each independently halo, cyano, oxo, or a group

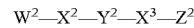

wherein $W^2$ is absent or a linker group of the formula —[CR$^x$R$^y$]$_r$— in which r is an integer selected from 1, 2, 3 or 4, and R$^x$ and R$^y$ are each independently selected from hydrogen or (1-2C)alkyl;

$X^2$ is absent, —O—, —C(O)—, —C(O)O—, —OC(O)—, —CH(OR$^z$)—, —N(R$^z$)—, —N(R$^z$)—C(O)—, —N(R$^z$)—C(O)O—, —C(O)—N(R$^z$)—, —N(R$^z$)C(O)N(R$^z$)—, —S—, —SO—, —SO$_2$—, —S(O)$_2$N(R$^z$)—, or —N(R$^z$)SO$_2$, wherein R$^z$ is selected from hydrogen or methyl;

$Y^2$ is absent or a linker group of the formula —[CR$^{aa}$R$^{bb}$]$_s$— in which s is an integer selected from 1, 2, 3 or 4, and R$^{aa}$ and R$^{bb}$ are each independently selected from hydrogen or (1-2C) alkyl;

$X^3$ is absent, —O—, —C(O)—, —C(O)O—, —OC(O)—, —CH(OR$^{cc}$)—, —N(R$^{cc}$), —N(R$^{cc}$)—C(O)—, —N(R$^{cc}$)—C(O)O—, —C(O)—N(R$^{cc}$)—, —N(R$^{cc}$)C(O)N(R$^{cc}$)—, —S—, —SO—, —SO$_2$—, —S(O)$_2$N(R$^{cc}$)—, or —N(R$^{cc}$)SO$_2$, wherein R is selected from hydrogen or methyl; and $Z^2$ is hydrogen, (1-6C)alkyl, (2-6C)alkenyl, (2-6C) alkynyl, aryl, (3-6C)cycloalkyl, (3-6C)cycloalkenyl, heteroaryl, or heterocyclyl, and wherein $Z^2$ is optionally further substituted by one or more substituent groups independently selected from oxo, halo, cyano, nitro, hydroxy, caboxy, NR$^{dd}$R$^{ee}$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-

2C)alkyl, heteroaryl, heteroaryloxy, heteroaryl-(1-2C)alkyl, C(O)NR$^{dd}$R$^{ee}$, NR$^{dd}$C(O)R$^{ee}$, NR$^{dd}$SO$_2$R$^{ee}$ and SO$_2$NR$^{dd}$R$^{ee}$; wherein R$^{dd}$ and R$^{ee}$ are each independently selected from hydrogen, (1-4C)alkyl, (3-6C)cycloalkyl or (3-6C)cycloalkyl(1-2C)alkyl; or R$^{dd}$ and R$^{ee}$ can be linked such that, together with the nitrogen atom to which they are attached, they form a 4-6 membered heterocyclic ring;

and wherein any alkyl, aryl, heterocyclyl or heteroaryl group present in a substituent group on Z$^2$ is optionally further substituted by halo, cyano, nitro, hydroxy, caboxy, NR$^{ff}$R$^{gg}$, (1-2C)alkoxy, or (1-2C)alkyl; wherein R$^{ff}$ and R$^{gg}$ are selected from hydrogen or (1-2C)alkyl;

with the proviso that when R$_7$ is hydrogen (i.e. when W$^2$, X$^2$, Y$^2$, and X$^3$ are absent and Z$^2$ is hydrogen) then ring A is not a fused dioxane ring;

or a pharmaceutically acceptable salt or solvate thereof. In an embodiment, when A$_1$ and A$_2$ are both CH and R$_4$ is H, Q is not pyrid-4-yl, i.e.

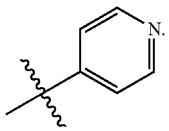 [SMILES: *c1ccncc1]

As indicated above, R$_{10}$ is only hydrogen or t-butyl when at least one of A$_{4a}$ and A$_{4b}$ is N or CR$_9$ in which R$_9$ is a substituent as defined herein other than hydrogen (i.e. R$_9$ is selected from halo, cyano, nitro, hydroxy, NR$^d$R$^e$, (1-3C)alkyl, (1-3C)alkoxy, 5 or 6-membered heteroaryl, or 5 or 6 membered heterocyclyl; wherein R$^d$ and R$^e$ are each independently selected from hydrogen or (1-3C)alkyl; and wherein any (1-3C)alkyl, (1-3C)alkoxy, 5 or 6-membered heteroaryl, or 5 or 6 membered heterocyclyl group present in a R$_9$ substituent group is optionally substituted by halo, cyano, nitro, hydroxy, NR$^f$R$^g$ or (1-3C)alkoxy, wherein R$^f$ and R$^g$ are each independently selected from hydrogen or (1-3C)alkyl).

The ring A fused ring systems shown in Formula III are made up of two carbon atoms from adjacent fused ring, the atoms A$_6$ and A$_7$ and either one, two or three additional ring atoms that link A$_7$ to the fused ring (depending on whether ring A is a fused 5, 6 or 7 membered ring respectively). For the avoidance of doubt, when m is 1 or 2 then each R$_{11}$ group present resides on the one, two or three additional ring atoms that are present in Ring A (i.e. they are not present on atoms A$_6$ and A$_7$).

Particular compounds of the invention include, for example, compounds of the formula I, or pharmaceutically acceptable salts or solvates thereof, wherein, unless otherwise stated, each of A$_1$, A$_2$, R$_1$, R$_2$, R$_4$, Q, A$_{4a}$, A$_{4b}$, A$_{4c}$, R$_{10}$, A$_5$, ring A, A$_6$, A$_7$, R$_7$, m and R$_{11}$ has any of the meanings defined hereinbefore or in any one of paragraphs (1) to (42) hereinafter:—

(1) A$_1$ is N;
(2) A$_1$ is CR$_1$;
(3) R$_1$ is selected from hydrogen, fluoro, chloro, cyano, methoxy, —CF$_3$ or —OCF$_3$;
(4) R$_1$ is selected from hydrogen or fluoro;
(5) R$_1$ is hydrogen;
(6) A$_2$ is N;
(7) A$_2$ is CR$_2$;

(8) R$_2$ is selected from hydrogen, fluoro, chloro, cyano, methyl, methoxy, —CF$_3$ or —OCF$_3$;
(9) R$_2$ is selected from hydrogen or fluoro;
(10) R$_2$ is hydrogen;
(11) R$_4$ is selected from fluoro, chloro, bromo, iodo, CF$_3$, OCF$_3$, cyano, NO$_2$, (1-4C)alkyl, (1-4C)alkoxy, or a group of the formula:

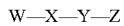

wherein
W is absent or (1-3C)alkylene;
X is —O— or —N(R$^a$)—, wherein R$^a$ is selected from hydrogen or (1-2C)alkyl;
Y is absent or a (1-3C)alkylene;
Z is hydrogen, (1-6C)alkyl or (3-6C)cycloalkyl;
and wherein any alkylene, alkyl or cycloalkyl group present in a R$_4$ substituent group is optionally further substituted by one or more substituent groups independently selected from halo, hydroxy, NR$^b$R$^c$, (1-2C)alkoxy, (1-2C)haloalkyl or (1-2C)haloalkoxy, and wherein R$^b$ and R$^c$ are each independently selected from hydrogen or methyl;

(12) R$_4$ is selected from fluoro, chloro, bromo, iodo, CF$_3$, OCF$_3$, cyano, NO$_2$, (1-4C)alkyl, (1-4C)alkoxy, or a group of the formula:

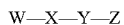

wherein
W is absent or (1-3C)alkylene;
X is —O— or —N(R$^a$)—, wherein R$^a$ is selected from hydrogen or (1-2C)alkyl;
Y is absent or a (1-2C)alkylene;
Z is hydrogen, (1-6C)alkyl or (3-6C)cycloalkyl;
and wherein any alkylene, alkyl or cycloalkyl group present in a R$_4$ substituent group is optionally further substituted by one or more substituent groups independently selected from halo, hydroxy, NR$^b$R$^c$, (1-2C)alkoxy, (1-2C)haloalkyl or (1-2C)haloalkoxy, and wherein R$^b$ and R$^c$ are each independently selected from hydrogen or methyl;

(13) R$_4$ is selected from fluoro, chloro, bromo, iodo, CF$_3$, OCF$_3$, cyano, (1-2C)alkyl, (1-2C)alkoxy, or a group of the formula:

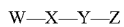

wherein
W is absent or (1-2C)alkylene;
X is —O— or —N(R$^a$)—, wherein R$^a$ is selected from hydrogen or (1-2C)alkyl;
Y is absent or a (1-2C)alkylene;
Z is hydrogen, (1-6C)alkyl or (3-6C)cycloalkyl;
and wherein any alkylene, alkyl or cycloalkyl group present in a R$_4$ substituent group is optionally further substituted by one or more substituent groups independently selected from halo, hydroxy, NR$^b$R$^c$, (1-2C) alkoxy, or (1-2C)haloalkyl; and wherein R$^b$ and R$^c$ are each independently selected from hydrogen or methyl;

(14) R$_4$ is selected from fluoro, chloro, bromo, CF$_3$, OCF$_3$, cyano, (1-2C)alkyl, (1-2C)alkoxy, or a group of the formula:

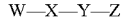

wherein
W is absent or methylene;
X is —O— or —N(R$^a$)—, wherein R$^a$ is selected from hydrogen or (1-2C)alkyl;

Y is absent or methylene;
Z is hydrogen or (1-6C)alkyl;
and wherein any alkylene or alkyl group present in a $R_4$ substituent group is optionally further substituted by one or more substituent groups independently selected from halo, hydroxy, $NR^bR^c$ or (1-2C)alkoxy, and wherein $R^b$ and $R^c$ are each independently selected from hydrogen or methyl;

(15) $R_4$ is selected from fluoro, chloro, bromo, $CF_3$, cyano, (1-2C)alkyl, or a group of the formula:

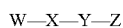

wherein
W is absent or methylene;
X is —O— or —N($R^a$)—, wherein $R^a$ is selected from hydrogen or (1-2C)alkyl;
Y is absent;
Z is hydrogen or (1-6C)alkyl;
and wherein any alkylene or alkyl group present in a $R_4$ substituent group is optionally further substituted by one or more substituent groups independently selected from halo, hydroxy, $NR^bR^c$ or (1-2C)alkoxy, and wherein $R^b$ and $R^c$ are each independently selected from hydrogen or methyl;

(16) $R_4$ is selected from fluoro, chloro or (1-2C)alkyl;
(17) $R_4$ is selected from fluoro, chloro or methyl;
(18) $R_4$ is selected from hydrogen, fluoro, chloro, bromo, iodo, $CF_3$, $OCF_3$, cyano, $NO_2$, (1-4C)alkyl, (1-4C)alkoxy, or a group of the formula:

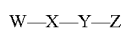

wherein
W is absent or (1-3C)alkylene;
X is —O— or —N($R^a$)—, wherein $R^a$ is selected from hydrogen or (1-2C)alkyl;
Y is absent or a (1-3C)alkylene;
Z is hydrogen, (1-6C)alkyl or (3-6C)cycloalkyl;
and wherein any alkylene, alkyl or cycloalkyl group present in a $R_4$ substituent group is optionally further substituted by one or more substituent groups independently selected from halo, hydroxy, $NR^bR^c$, (1-2C)alkoxy, (1-2C)haloalkyl or (1-2C)haloalkoxy, and wherein $R^b$ and $R^c$ are each independently selected from hydrogen or methyl;

(19) $R_4$ is selected from hydrogen, fluoro, chloro, bromo, iodo, $CF_3$, $OCF_3$, cyano, $NO_2$, (1-4C)alkyl, (1-4C)alkoxy, or a group of the formula:

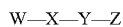

wherein
W is absent or (1-2C)alkylene;
X is —O— or —N($R^a$)—, wherein $R^a$ is selected from hydrogen or (1-2C)alkyl;
Y is absent or a (1-2C)alkylene;
Z is hydrogen, (1-6C)alkyl or (3-6C)cycloalkyl;
and wherein any alkylene, alkyl or cycloalkyl group present in a $R_4$ substituent group is optionally further substituted by one or more substituent groups independently selected from halo, hydroxy, $NR^bR^c$, (1-2C)alkoxy, (1-2C)haloalkyl or (1-2C)haloalkoxy, and wherein $R^b$ and $R^c$ are each independently selected from hydrogen or methyl;

(20) $R_4$ is selected from hydrogen, fluoro, chloro, bromo, iodo, $CF_3$, $OCF_3$, cyano, (1-2C)alkyl, (1-2C)alkoxy, or a group of the formula:

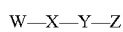

wherein
W is absent or (1-2C)alkylene;
X is —O— or —N($R^a$)—, wherein $R^a$ is selected from hydrogen or (1-2C)alkyl;
Y is absent or a (1-2C)alkylene;
Z is hydrogen, (1-6C)alkyl or (3-6C)cycloalkyl;
and wherein any alkylene, alkyl or cycloalkyl group present in a $R_4$ substituent group is optionally further substituted by one or more substituent groups independently selected from halo, hydroxy, $NR^bR^c$, (1-2C)alkoxy, or (1-2C)haloalkyl; and wherein $R^b$ and $R^c$ are each independently selected from hydrogen or methyl;

(21) $R_4$ is selected from hydrogen, fluoro, chloro, bromo, $CF_3$, $OCF_3$, cyano, (1-2C)alkyl, (1-2C)alkoxy, or a group of the formula:

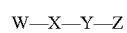

wherein
W is absent or methylene;
X is —O— or —N($R^a$)—, wherein $R^a$ is selected from hydrogen or (1-2C)alkyl;
Y is absent or methylene;
Z is hydrogen or (1-6C)alkyl;
and wherein any alkylene or alkyl group present in a $R_4$ substituent group is optionally further substituted by one or more substituent groups independently selected from halo, hydroxy, $NR^bR^c$ or (1-2C)alkoxy, and wherein $R^b$ and $R^c$ are each independently selected from hydrogen or methyl;

(22) $R_4$ is selected from hydrogen, fluoro, chloro, bromo, $CF_3$, cyano, (1-2C)alkyl, or a group of the formula:

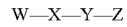

wherein
W is absent or methylene;
X is —O— or —N($R^a$)—, wherein $R^a$ is selected from hydrogen or (1-2C)alkyl;
Y is absent;
Z is hydrogen or (1-6C)alkyl;
and wherein any alkylene or alkyl group present in a $R_4$ substituent group is optionally further substituted by one or more substituent groups independently selected from halo, hydroxy, $NR^bR^c$ or (1-2C)alkoxy, and wherein $R^b$ and $R^c$ are each independently selected from hydrogen or methyl;

(23) Q is selected from a group of formula II:

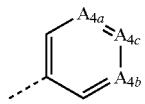

wherein
$A_{4a}$ and $A_{4b}$ are each independently selected from N or $CR_9$, wherein $R_9$ is selected from hydrogen, halo, cyano, nitro, hydroxy, $NR^dR^e$, (1-3C)alkyl, (1-3C)alkoxy, 5 or 6-membered heteroaryl, or 5 or 6 membered heterocyclyl; wherein $R^d$ and $R^e$ are each independently selected from hydrogen or (1-3C)alkyl;
and wherein any (1-3C)alkyl, (1-3C)alkoxy, 5 or 6-membered heteroaryl, or 5 or 6 membered heterocyclyl group present in a $R_9$ substituent group is optionally substituted by one or more substituents selected from halo, cyano, hydroxy, $NR^fR^g$ or (1-3C)alkoxy, wherein $R^f$ and $R^g$ are each independently selected from hydrogen or (1-2C)alkyl;

$A_4$, is N or $CR_{10}$;

$R_{10}$ is selected from hydrogen, halo, amino, cyano, nitro, hydroxy or a group $$W^1\text{—}X^1\text{—}Y^1\text{—}X^4\text{—}Z^1$$

wherein $W^1$ is absent or a linker group of the formula —$[CR^hR^i]_p$— in which p is an integer selected from 1 or 2, and $R^h$ and $R^i$ are each independently selected from hydrogen or methyl;

$X^1$ is absent or —O—, —C(O)—, —C(O)O—, —OC(O)—, —CH($OR^j$)—, —N($R^j$)—, —N($R^j$)—C(O)—, —N($R^j$)—C(O)O—, —C(O)—N($R^j$)—, —S—, —SO—, —SO$_2$—, —S(O)$_2$N($R^j$)—, or —N($R^j$)SO$_2$— wherein $R^j$ is selected from hydrogen or methyl;

$Y^1$ is absent or a linker group of the formula —$[CR^kR^l]_q$— in which q is an integer selected from 1, 2, 3 or 4, and $R^k$ and $R^l$ are each independently selected from hydrogen or (1-2C)alkyl;

$X^4$ is absent or —O—, —C(O)—, —C(O)O—, —OC(O)—, —CH($OR^j$)—, —N($R^j$)—, —N($R^j$)—C(O)—, —N($R^j$)—C(O)O—, —C(O)—N($R^j$)—, —S—, —SO—, —SO$_2$—, —S(O)$_2$N($R^j$)—, or —N($R^j$)SO$_2$— wherein $R^j$ is selected from hydrogen or methyl; and $Z^1$ is (1-6C)alkyl, aryl, heteroaryl or heterocyclyl;

and wherein $Z^1$ is optionally further substituted by one or more substituent groups independently selected from oxo, halo, cyano, hydroxy, caboxy, $NR^mR^n$, (1-2C)alkoxy, (1-2C)alkyl, (3-6C)cycloalkyl, (3-6C)cycloalkyl-(1-2C)alkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)$NR^mR^n$, $NR^mC(O)R^n$, $NR^mS(O)_2R^n$ and $S(O)_2NR^mR^n$; wherein $R^m$ and $R^n$ are each independently selected from hydrogen or (1-4C)alkyl; or $R^m$ and $R^n$ can be linked such that, together with the nitrogen atom to which they are attached, they form a 4-6 membered heterocyclic ring;

and wherein any alkyl, aryl, heterocyclyl or heteroaryl group present in a substituent group on $Z^1$ is optionally further substituted by halo, cyano, hydroxy, $NR^oR^p$, (1-2C)alkoxy, or (1-2C)alkyl; wherein $R^o$ and $R^p$ are selected from hydrogen or (1-2C)alkyl;

or Q is a group of formula III:

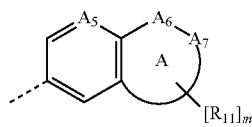

III wherein $A_5$ is selected from N or $CR_5$, where $R_5$ is selected from hydrogen, halo, cyano, hydroxy, $NR^qR^u$, (1-3C)alkyl, (1-3C)alkoxy, 5 or 6-membered heteroaryl, or 5 or 6 membered heterocyclyl; wherein $R^q$ and $R^u$ are each independently selected from hydrogen or (1-3C)alkyl;

and wherein any (1-3C)alkyl, (1-3C)alkoxy, 5 or 6-membered heteroaryl, or 5 or 6 membered heterocyclyl group present in a $R_5$ substituent group is optionally substituted by one or more substituents selected from halo, cyano, nitro, hydroxy, $NR^vR^w$, or (1-3C)alkoxy, wherein $R^v$ and $R^w$ are each independently selected from hydrogen or (1-3C)alkyl;

Ring A is:
 a fused phenyl ring;
 a fused 5 or 6 membered carbocyclic ring;
 a fused 5 or 6 membered heteroaryl ring comprising one or two
 heteroatoms independently from N, S or O; or
 a fused 5, 6 or 7-membered heterocyclic ring comprising one or two heteroatoms independently from N, S or O;

$A_6$ is selected from N, O, S, S(O)$_2$, $CR_6$, $C(R_6)_2$, $NR_{60}$, where $R_6$ is selected from hydrogen, oxo, fluoro, chloro, (1-2C)alkyl, (1-2C)alkoxy, (1-2C)haloalkoxy or (1-2C)haloalkyl and $R_{60}$ is hydrogen, O$^-$, (1-6C)alkyl, —C(O)—$R_{61}$, —C(O)O—$R_{61}$, or —C(O)N($R_{62}$) $R_{61}$, wherein $R_{61}$ is selected from hydrogen, (1-6C)alkyl, aryl, heteroaryl or heterocyclyl and $R_{62}$ is selected from hydrogen or (1-2C)alkyl;

$A_7$ is selected from N, O, $CR_7$, S, S(O)$_2$, $C(R_7)_2$, $NR_{70}$, where $R_{70}$ is hydrogen, O$^-$, (1-6C)alkyl, —C(O)—$R_{71}$, —C(O)O—$R_{71}$, or —C(O)N($R_2$)$R_7$, wherein $R_{71}$ is selected from hydrogen, (1-6C)alkyl, aryl, heteroaryl or heterocyclyl and $R_{72}$ is selected from hydrogen or (1-2C)alkyl;

m is 0, 1 or 2;

$R_7$ and $R_{11}$ are each independently halo, cyano, oxo, or a group $$W^2\text{—}X^2\text{—}Y^2\text{—}X^3\text{—}Z^2$$

wherein $W^2$ is absent or a linker group of the formula —$[CR^xR^y]_r$— in which r is an integer selected from 1, 2, 3 or 4, and $R^x$ and $R^y$ are each independently selected from hydrogen or (1-2C)alkyl;

$X^2$ is absent, —O—, —C(O)—, —C(O)O—, —OC(O)—, —CH($OR^z$)—, —N($R^z$)—, —N($R^z$)—C(O)—, —N($R^z$)—C(O)O—, —C(O)—N($R^z$)—, —S—, —SO—, —SO$_2$—, —S(O)$_2$N($R^z$)—, or —N($R^z$)SO$_2$, wherein $R^z$ is selected from hydrogen or methyl;

$Y^2$ is absent or a linker group of the formula —$[CR^{aa}R^{bb}]_s$— in which s is an integer selected from 1, 2, 3 or 4, and $R^{aa}$ and $R^{bb}$ are each independently selected from hydrogen or (1-2C)alkyl;

$X^3$ is absent, —O—, —C(O)—, —C(O)O—, —OC(O)—, —CH($OR^{cc}$)—, —N($R^{cc}$), —N($R^{cc}$)—C(O)—, —N($R^{cc}$)—C(O)O—, —C(O)—N($R^{cc}$)—, —S—, —SO—, —SO$_2$—, —S(O)$_2$N($R^{cc}$)—, or —N($R^{cc}$)SO$_2$, wherein $R^{cc}$ is selected from hydrogen or methyl; and $Z^2$ is hydrogen, (1-6C)alkyl, (2-6C)alkenyl, aryl, (3-6C)cycloalkyl, heteroaryl, or heterocyclyl, and wherein $Z^2$ is optionally further substituted by one or more substituent groups independently selected from oxo, halo, cyano, nitro, hydroxy, caboxy, $NR^{dd}R^{ee}$, (1-4C)alkoxy, (1-4C)alkyl, (3-8C)cycloalkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)$NR^{dd}R^{ee}$, $NR^{dd}C(O)R^{ee}$, $NR^{dd}SO_2R^{ee}$ and SO$_2$NR$^{dd}$R$^{ee}$; wherein R$^{dd}$ and R$^{ee}$ are each independently selected from hydrogen, (1-4C)alkyl, (3-6C)cycloalkyl; or R$^{dd}$ and R$^{ee}$ can be linked such that, together with the nitrogen atom to which they are attached, they form a 4-6 membered heterocyclic ring;

and wherein any alkyl, aryl, heterocyclyl or heteroaryl group present in a substituent group on Z$^2$ is optionally further substituted by halo, cyano, nitro, hydroxy, caboxy, NR$^{ff}$R$^{gg}$, (1-2C)alkoxy, or (1-2C)alkyl; wherein R$^{ff}$ and R$^{gg}$ are selected from hydrogen or (1-2C)alkyl;

(24) Q is a group of formula II as defined herein;

(25) A$_{4a}$ and A$_{4b}$ are each independently selected from N or CR$_9$, wherein R$_9$ is selected from hydrogen, halo, cyano, hydroxy, NR$^d$R$^e$, (1-3C)alkyl, (1-3C)alkoxy, 5 or 6-membered heteroaryl, or 5 or 6 membered heterocyclyl; wherein R$^d$ and R$^e$ are each independently selected from hydrogen or (1-2C)alkyl;

and wherein any (1-3C)alkyl, (1-3C)alkoxy, 5 or 6-membered heteroaryl, or 5 or 6 membered heterocyclyl group present in a R$_9$ substituent group is optionally substituted by one or more substituents selected from halo, cyano, hydroxy, NR$^f$R$^g$ or (1-3C)alkoxy, wherein R$^f$ and R$^g$ are each independently selected from hydrogen or (1-2C)alkyl;

(26) A$_{4a}$ and A$_{4b}$ are each independently selected from N or CR$_9$, wherein R$_9$ is selected from hydrogen, halo, cyano, hydroxy, NR$^d$R$^e$, (1-3C)alkyl, (1-3C)alkoxy, 5 or 6-membered heteroaryl, or 5 or 6 membered heterocyclyl; wherein R$^d$ and R$^e$ are each independently selected from hydrogen or (1-2C)alkyl;

(27) A$_{4c}$ is N;

(28) A$_{4c}$ is CR$_{10}$;

(29) R$_{10}$ is selected from hydrogen, halo, amino, cyano, hydroxy or a group

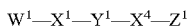

wherein

W$^1$ is absent or a linker group of the formula —[CR$^h$R$^i$]$_p$— in which p is an integer selected from 1 or 2, and R$^h$ and R$^i$ are hydrogen;

X$^1$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^i$ is selected from hydrogen or methyl;

Y$^1$ is absent or a linker group of the formula —[CR$^k$R$^l$]$_q$— in which q is an integer selected from 1, 2, 3 or 4, and R$^k$ and R$^l$ are each independently selected from hydrogen or methyl;

X$^4$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^i$ is selected from hydrogen or methyl; and Z$^1$ is (1-6C)alkyl, aryl, heteroaryl or heterocyclyl;

and wherein Z$^1$ is optionally further substituted by one or more substituent groups independently selected from oxo, halo, cyano, hydroxy, caboxy, NR$^m$R$^n$, (1-2C)alkoxy, (1-2C)alkyl, (3-6C)cycloalkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^m$R$^n$, NR$^m$C(O)R$^n$, NR$^m$S(O)$_2$R$^n$ and S(O)$_2$NR$^m$R$^n$; wherein R$^m$ and R$^n$ are each independently selected from hydrogen or (1-4C)alkyl; or R$^m$ and R$^n$ can be linked such that, together with the nitrogen atom to which they are attached, they form a 4-6 membered heterocyclic ring;

and wherein any alkyl, aryl, heterocyclyl or heteroaryl group present in a substituent group on Z$^1$ is optionally further substituted by halo, cyano, hydroxy, NR$^o$R$^p$, (1-2C)alkoxy, or (1-2C)alkyl; wherein R$^o$ and R$^p$ are selected from hydrogen or (1-2C)alkyl;

(30) R$_{10}$ is selected from hydrogen, halo, amino, cyano, hydroxy or a group

wherein

W$^1$ is absent;

X$^1$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^i$ is selected from hydrogen or methyl;

Y$^1$ is absent or a linker group of the formula —[CR$^k$R$^l$]$_q$— in which q is an integer selected from 1, 2, 3 or 4, and R$^k$ and R$^l$ are hydrogen;

X$^4$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^j$ is selected from hydrogen or methyl; and Z$^1$ is (1-6C)alkyl, aryl, heteroaryl or heterocyclyl;

and wherein Z$^1$ is optionally further substituted by one or more substituent groups independently selected from oxo, halo, cyano, hydroxy, NR$^m$R$^n$, (1-2C)alkoxy, (1-2C)alkyl, (3-6C)cycloalkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^m$R$^n$, NR$^m$C(O)R$^n$, NR$^m$S(O)$_2$R$^n$ and S(O)$_2$NR$^m$R$^n$; wherein R$^m$ and R$^n$ are each independently selected from hydrogen or (1-4C)alkyl; or R$^m$ and R$^n$ can be linked such that, together with the nitrogen atom to which they are attached, they form a 4-6 membered heterocyclic ring;

and wherein any alkyl, aryl, heterocyclyl or heteroaryl group present in a substituent group on Z$^1$ is optionally further substituted by halo, cyano, hydroxy, NR$^o$R$^p$, (1-2C)alkoxy, or (1-2C)alkyl; wherein R$^o$ and R$^p$ are selected from hydrogen or (1-2C)alkyl;

(31) A$_{4a}$ and A$_{4b}$ are CR$_9$ and A$_{4c}$ is CR$_{10}$, or one or two of A$_{4a}$, A$_{4b}$ and A$_{4c}$ are N and the others are CR$_9$ (in the case of A$_{4a}$ and A$_{4b}$) or CR$_{10}$ (in the case of A$_{4c}$);

(32) A$_{4a}$ and A$_{4b}$ are CR$_9$ and A$_{4c}$ is CR$_{10}$, or one of A$_{4a}$, A$_{4b}$ and A$_{4c}$ is N and the others are CR$_9$ (in the case of A$_{4a}$ and A$_{4b}$) or CR$_{10}$ (in the case of A$_{4c}$);

(33) A$_5$ is selected from N or CR$_5$, where R$_5$ is selected from hydrogen, halo, cyano, hydroxy, NR$^q$R$^u$, (1-3C)alkyl, (1-3C)alkoxy, 5 or 6-membered heteroaryl, or 5 or 6 membered heterocyclyl; wherein R$^q$ and R$^u$ are each independently selected from hydrogen or (1-3C)alkyl;

and wherein any (1-3C)alkyl, (1-3C)alkoxy, 5 or 6-membered heteroaryl, or 5 or 6 membered heterocyclyl group present in a R$_5$ substituent group is optionally substituted by one or more substituents selected from halo, cyano, hydroxy, NR$^v$R$^w$, or (1-3C)alkoxy, wherein R$^v$ and R$^w$ are each independently selected from hydrogen or (1-3C)alkyl;

(34) $A_5$ is selected from N or $CR_5$, where $R_5$ is selected from hydrogen, halo, cyano, hydroxy, $NR^qR^u$, (1-3C)alkyl, or (1-3C)alkoxy; wherein $R^q$ and $R^u$ are each independently selected from hydrogen or (1-3C)alkyl; and wherein any (1-3C)alkyl, (1-3C)alkoxy group present in a $R_5$ substituent group is optionally substituted by one or more substitutents selected from halo, cyano, hydroxy, $NR^vR^w$, or (1-2C)alkoxy, wherein $R^v$ and $R^w$ are each independently selected from hydrogen or (1-2C)alkyl;

(35) Ring A is:
a fused 5 or 6 membered heteroaryl ring comprising one or two heteroatoms independently from N, S or O; or
a fused 5, 6 or 7-membered heterocyclic ring comprising one or two heteroatoms independently from N, S or O;

(36) $A_6$ is selected from N, O, S, $S(O)_2$, $CR_6$, $C(R_6)_2$, $NR_{60}$, where $R_6$ is selected from hydrogen, oxo, fluoro, chloro, (1-2C)alkyl, (1-2C)alkoxy, (1-2C)haloalkoxy or (1-2C)haloalkyl; and
$R_{60}$ is hydrogen, $O^-$, (1-6C)alkyl, —C(O)—$R_{61}$, —C(O)O—$R_{61}$, or —C(O)N($R_{62}$)$R_{61}$, wherein $R_{61}$ is selected from hydrogen, (1-6C)alkyl, aryl, 5 or 6 membered heteroaryl or 5 or 6 membered heterocyclyl and $R_{62}$ is selected from hydrogen or (1-2C)alkyl;

(37) $A_6$ is selected from N, O, S, $S(O)_2$, $CR_6$, $C(R_6)_2$, $NR_{60}$, where $R_6$ is selected from hydrogen, oxo, (1-2C)alkyl, (1-2C)alkoxy, (1-2C)haloalkoxy or (1-2C)haloalkyl; and
$R_{60}$ is hydrogen, $O^-$, (1-6C)alkyl, —C(O)—$R_{61}$, —C(O)O—$R_{61}$, or —C(O)N($R_{62}$)$R_{61}$, wherein $R_{61}$ is selected from hydrogen or (1-6C)alkyl, and $R_{62}$ is selected from hydrogen or (1-2C)alkyl;

(38) $A_7$ is selected from N, O, $CR_7$, S, $S(O)_2$, $C(R_7)_2$, $NR_{70}$, where $R_{70}$ is hydrogen, $O^-$, (1-6C)alkyl, —C(O)—$R_{71}$, —C(O)O—$R_{71}$, or —C(O)N($R_{72}$)$R_{71}$, wherein $R_{71}$ is selected from hydrogen, (1-6C)alkyl, aryl, 5 or 6 membered heteroaryl or 5 or 6 membered heterocyclyl and $R_{72}$ is selected from hydrogen or (1-2C)alkyl;

(39) $A_7$ is selected from N, O, $CR_7$, S, $S(O)_2$, $C(R_7)_2$, $NR_{70}$, where $R_{70}$ is hydrogen, $O^-$, (1-6C)alkyl, —C(O)—$R_{71}$, —C(O)O—$R_{71}$, or —C(O)N($R_{72}$)$R_{71}$, wherein $R_{71}$ is selected from hydrogen, (1-6C)alkyl, aryl, 5 or 6 membered heteroaryl or 5 or 6 membered heterocyclyl and $R_{72}$ is selected from hydrogen or (1-2C)alkyl;

(40) $R_7$ is selected from halo, cyano, oxo, or a group $$W^2—X^2—Y^2—X^3—Z^2$$

wherein
$W^2$ is absent or a linker group of the formula —$[CR^xR^y]_r$— in which r is an integer selected from 1, 2, or 3, and $R^x$ and $R^y$ are each independently selected from hydrogen or (1-2C)alkyl;
$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —$SO_2$—, —$S(O)_2$N($R^z$)—, or —N($R^z$)$SO_2$, wherein $R^z$ is selected from hydrogen or methyl;
$Y^2$ is absent or a linker group of the formula —$[CR^{aa}R^{bb}]_s$— in which s is an integer selected from 1, 2, 3 or 4, and $R^{aa}$ and $R^{bb}$ are each independently selected from hydrogen or (1-2C)alkyl;
$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —$SO_2$—, —$S(O)_2$N($R^{cc}$)—, or —N($R^{cc}$)$SO_2$, wherein $R^{cc}$ is selected from hydrogen or methyl; and $Z^2$ is hydrogen, (1-6C)alkyl, (2-6C)alkenyl, aryl, (3-6C)cycloalkyl, heteroaryl, or heterocyclyl,
and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, C(O)$NR^{dd}R^{ee}$, $NR^{dd}$C(O)$R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;
and wherein any alkyl, aryl, heterocyclyl or heteroaryl group present in a substituent group on $Z^2$ is optionally further substituted by halo, cyano, nitro, hydroxy, caboxy, $NR^{ff}R^{gg}$, (1-2C)alkoxy, or (1-2C)alkyl; wherein $R^{ff}$ and $R^{gg}$ are selected from hydrogen or (1-2C)alkyl;

(41) $R_7$ is selected from halo, cyano, oxo, or a group $$W^2—X^2—Y^2—X^3—Z^2$$

wherein
$W^2$ is absent or a linker group of the formula —$[CR^xR^y]_r$— in which r is an integer selected from 1, 2, or 3, and $R^x$ and $R^y$ are each independently selected from hydrogen or (1-2C)alkyl;
$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —$SO_2$—, —$S(O)_2$N($R^z$)—, or —N($R^z$)$SO_2$, wherein $R^z$ is selected from hydrogen or methyl;
$Y^2$ is absent or a linker group of the formula —$[CR^{aa}R^{bb}]_s$— in which s is an integer selected from 1, 2, 3 or 4, and $R^{aa}$ and $R^{bb}$ are each independently selected from hydrogen or (1-2C)alkyl;
$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —$SO_2$—, —$S(O)_2$N($R^{cc}$)—, or —N($R^{cc}$)$SO_2$, wherein $R^{cc}$ is selected from hydrogen or methyl; and
$Z^2$ is hydrogen, (1-6C)alkyl, (2-6C)alkenyl, phenyl, (3-6C)cycloalkyl, 5 or 6 membered heteroaryl, or 5 or 6 membered heterocyclyl,
and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, C(O)$NR^{dd}R^{ee}$, $NR^{dd}$C(O)$R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;

(42) m is 0 or 1;
(43) m is 0;
(44) m is 1;
(45) m is 2;
(46) $R_{11}$ is selected from halo, cyano, oxo, or a group $$W^2—X^2—Y^2—X^3—Z^2$$

wherein
$W^2$ is absent or a linker group of the formula —$[CR^xR^y]_r$— in which r is an integer selected from 1, 2, or 3, and $R^x$ and $R^y$ are each independently selected from hydrogen or (1-2C)alkyl;

$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —SO$_2$—, —S(O)$_2$N($R^z$)—, or —N($R^z$)SO$_2$, wherein $R^z$ is selected from hydrogen or methyl;

$Y^2$ is absent or a linker group of the formula —[$CR^{aa}R^{bb}$]$_s$— in which s is an integer selected from 1, 2, 3 or 4, and $R^{aa}$ and $R^{bb}$ are each independently selected from hydrogen or (1-2C)alkyl;

$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —SO$_2$—, —S(O)$_2$N($R^{cc}$)—, or —N($R^{cc}$)SO$_2$, wherein $R^{cc}$ is selected from hydrogen or methyl; and $Z^2$ is hydrogen, (1-6C)alkyl, (2-6C)alkenyl, aryl, (3-6C)cycloalkyl, heteroaryl, or heterocyclyl, and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, $C(O)NR^{dd}R^{ee}$, $NR^{dd}C(O)R^{ee}$, $NR^{Id}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;

and wherein any alkyl, aryl, heterocyclyl or heteroaryl group present in a substituent group on $Z^2$ is optionally further substituted by halo, cyano, nitro, hydroxy, caboxy, $NR^{ff}R^{gg}$, (1-2C)alkoxy, or (1-2C)alkyl; wherein $R^{ff}$ and $R^{gg}$ are selected from hydrogen or (1-2C)alkyl;

(47) $R_{11}$ is selected from halo, cyano, oxo, or a group $$W^2—X^2—Y^2—X^3—Z^2$$

wherein $W^2$ is absent or a linker group of the formula —[$CR^xR^y$]$_r$— in which r is an integer selected from 1, 2, or 3, and $R^x$ and Ry are each independently selected from hydrogen or (1-2C)alkyl;

$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —SO$_2$—, —S(O)$_2$N($R^z$)—, or —N($R^z$)SO$_2$, wherein $R^z$ is selected from hydrogen or methyl;

$Y^2$ is absent or a linker group of the formula —[$CR^{aa}R^{bb}$]$_s$— in which s is an integer selected from 1, 2, 3 or 4, and $R^{aa}$ and $R^{bb}$ are each independently selected from hydrogen or (1-2C)alkyl;

$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —SO$_2$—, —S(O)$_2$N($R^{cc}$)—, or —N($R^{cc}$)SO$_2$, wherein $R^{cc}$ is selected from hydrogen or methyl; and $Z^2$ is hydrogen, (1-6C)alkyl, (2-6C)alkenyl, phenyl, (3-6C)cycloalkyl, 5 or 6 membered heteroaryl, or 5 or 6 membered heterocyclyl, and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, $C(O)NR^{dd}R^{ee}$, $NR^{dd}C(O)R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;

(48) Q is a group of formula III as defined herein;

(49) Q is a group of formula III as defined herein in which Ring A is a fused 5 or 6-membered heterocyclic or ring comprising one N atom;

(50) Q is a group of formula:

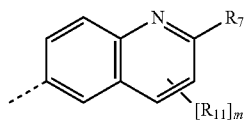

wherein $R_7$, $R_{11}$ and m each have any one of the definitions set out herein.

(51) Q is a group of formula:

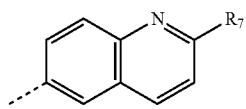

wherein $R_7$ has any one of the definitions set out herein.

(52) Q is a group of formula:

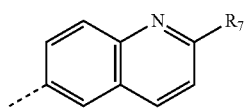

wherein $R_7$ is a group $$W^2—X^2—Y^2—X^3—Z^2$$

wherein $W^2$ is a linker group of the formula —[$CR^xR^y$]$_r$— in which r is 1, $R^x$ is hydrogen and $R^y$ is selected from hydrogen or methyl;

$X^2$ is absent;

$Y^2$ is absent;

$X^3$ is absent; and $Z^2$ is a 4, 5, 6 or 7-membered nitrogen-linked heterocyclyl optionally comprising one further nitrogen atom, and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (3-6C)cycloalkyl, (3-6C)cycloalkyl(1-2C)alkyl, (2C)alkanoyl, (1-2C)alkylsulphonyl, $C(O)NR^{dd}R^{ee}$, $NR^{dd}C(O)R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl;

(53) Q is a group of formula:

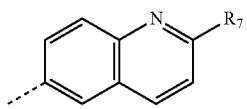

wherein R$_7$ is a group

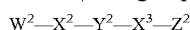

wherein
W$^2$ is a linker group of the formula —[CR$^x$R$^y$]$_r$— in which r is 1, R$^x$ is hydrogen and R$^y$ is selected from hydrogen or methyl;
X$^2$ is absent;
Y$^2$ is absent;
X$^3$ is absent; and
Z$^2$ is a 4, 5, 6 or 7-membered nitrogen-linked heterocyclyl optionally comprising one further nitrogen atom,
and wherein Z$^2$ is optionally further substituted on the further nitrogen atom by methyl, ethyl, propyl or cyclopropylmethyl and/or on a carbon atom by methyl, fluoro or chloro.

Suitably, both A$_1$ and A$_2$ are CR$_1$ and CR$_2$ respectively, or A$_1$ is N and A$_2$ is CR$_2$.

Suitably, R$_1$ and R$_2$ are selected from hydrogen or halo (e.g. fluoro). More suitably, R$_1$ and R$_2$ are selected from hydrogen or fluoro. Most suitably, R$_1$ and R$_2$ are hydrogen.

In an embodiment, A$_1$ and A$_2$ are CR$_1$ and CR$_2$ respectively. Such compounds have the structural formula IA shown below:

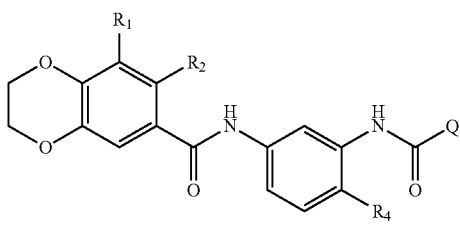

IA wherein
R$_1$, R$_2$, R$_4$ and Q each have any one the definitions set out herein.

Suitably, in the compounds of formula I or IA, R$_1$ and R$_2$ are both selected from hydrogen or one of R$_1$ and R$_2$ is halo (especially fluoro) and the other is hydrogen. Most suitably, both of R$_1$ and R$_2$ are hydrogen.

In an embodiment, A$_1$ and A$_2$ are both CH. Such compounds have the structural formula IB shown below:

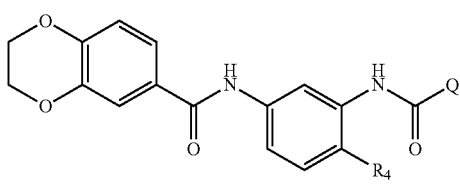

IB wherein
R$_4$ and Q each have any one the definitions set out herein.

Suitably, in compounds of formula I, IA or IB, R$_4$ has any one of the definitions set out in paragraphs (11) to (22) above. Most suitably, R$_4$ is as defined in any one of paragraphs (14), (15), (16) or (17) above. In a particular embodiment, R$_4$ is methyl, fluoro or chloro.

Suitably, in compounds of formula I, IA or IB, Q is as defined in any one of paragraphs (23) to (53) above. In a particular embodiment, Q is as defined in any one of paragraphs (50), (51), (52) or (53) above.

In an embodiment of the compounds of formula I, IA or IB, Q has one of the structural formulae IIa, IIb, IIc, IId, IIe, IIIa and IIIb shown below:

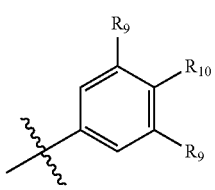

IIa

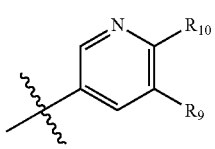

IIb

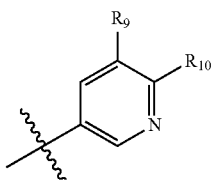

IIc

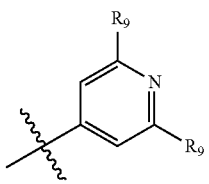

IId

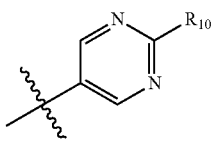

IIe

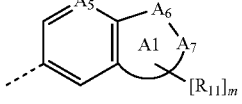

IIIa

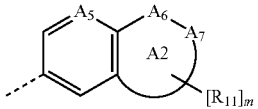

IIIb wherein R$_9$, R$_{10}$, A$_5$, A$_6$, A$_7$, R$_{11}$ and m each have any one of the definitions hereinbefore;
ring A1 is a fused 5-membered carbocyclic ring, 5-membered heterocyclic ring or 5-membered heteroaryl ring;
ring A2 is a fused 6 or 7-membered carbocyclic ring, 6 or 7-membered heterocyclic ring or 6-membered heteroaryl ring.

Suitably, in compounds of formula I, IA or IB, ring A1 is a fused 5-membered heterocyclic ring or 5-membered heteroaryl ring comprising one or two heteroatoms selected from N, O or S.

Suitably, in compounds of formula I, IA or IB ring A2 is a fused 6-membered heterocyclic or 6-membered heteroaryl comprising one or two heteroatoms selected from N, O or S.

In an embodiment of the compounds of formula I, IA or IB, Q is a group of structural formula IIIa or IIIb as shown above.

In a particular embodiment of the compounds of formula I, IA or IB, Q is a group of structural formula IIIb as defined above.

In an embodiment of the compounds of formula I, IA or IB Q is selected from one of the following:

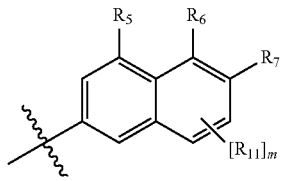

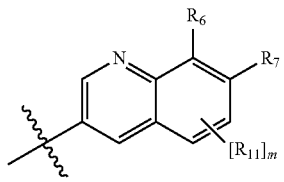

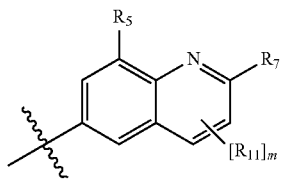

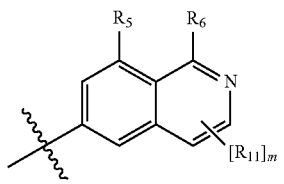

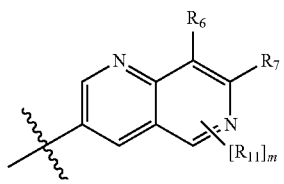

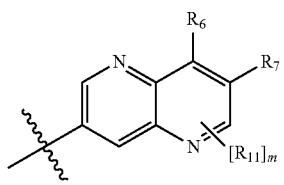

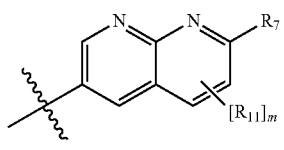

-continued

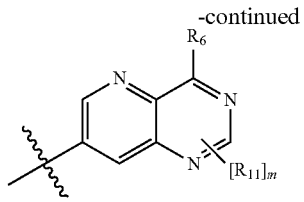

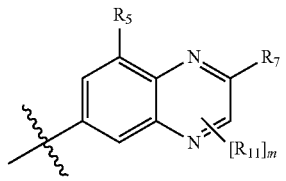

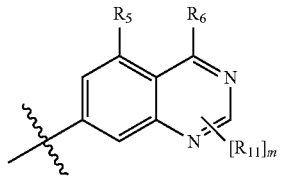

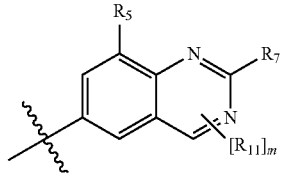

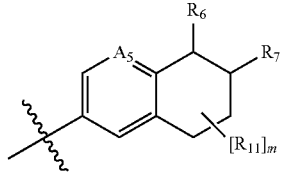

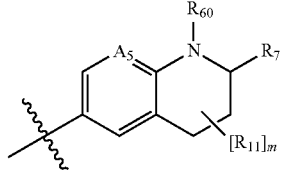

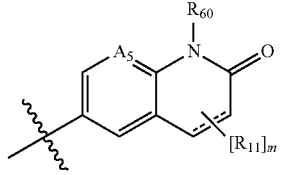

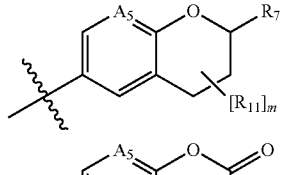

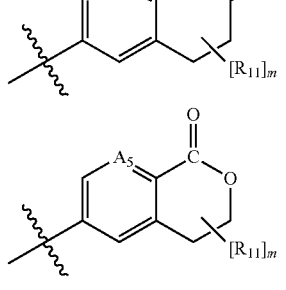

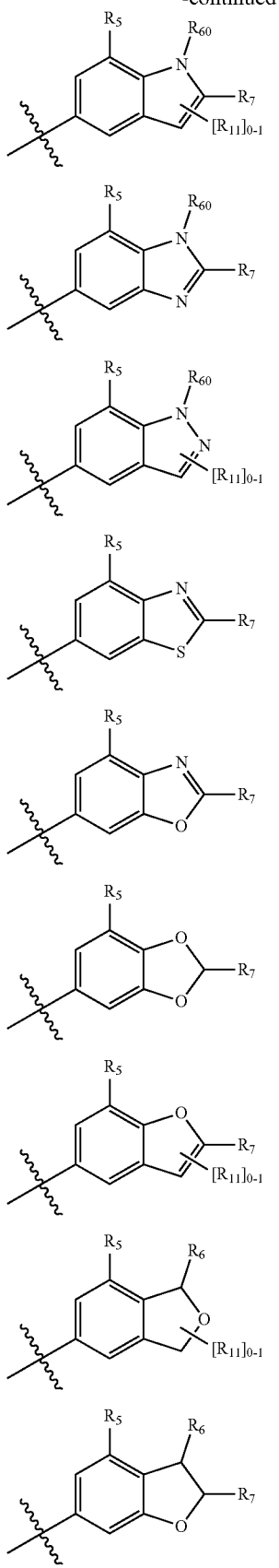
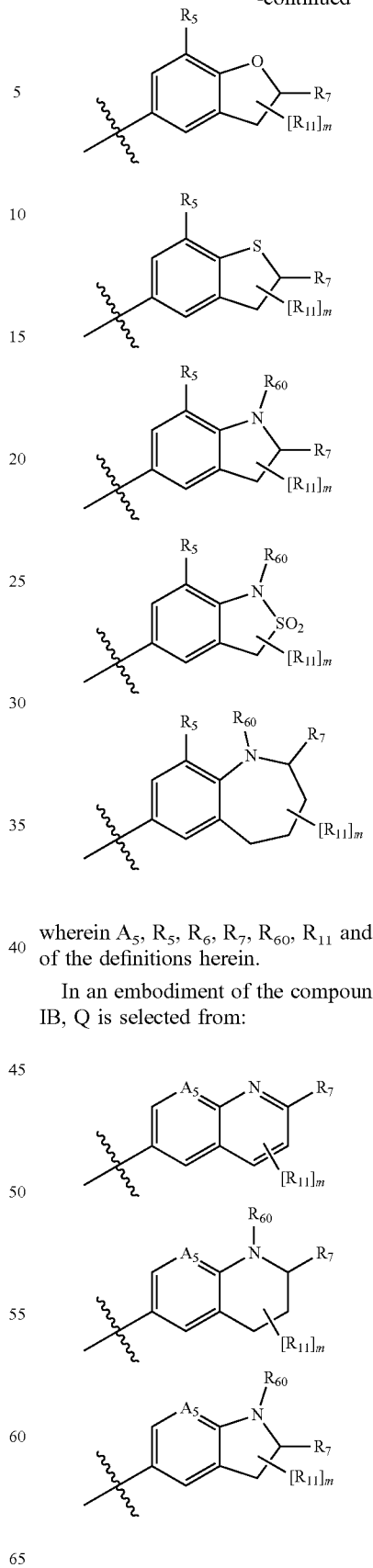
wherein $A_5$, $R_5$, $R_6$, $R_7$, $R_{60}$, $R_{11}$ and m each have any one of the definitions herein.
In an embodiment of the compounds of formula I, IA or IB, Q is selected from:
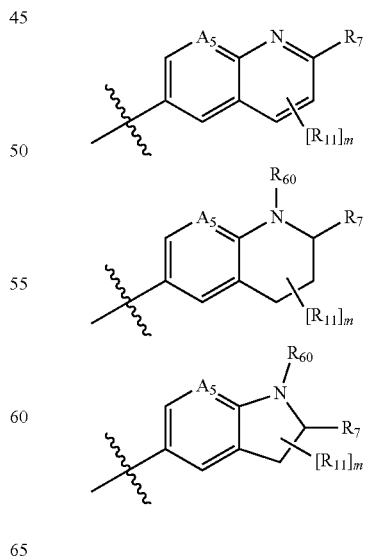
wherein $A_5$, $R_{60}$, $R_7$, $R_{11}$ and m each have any one of the definitions herein.

In an embodiment of the compounds of formula I, IA or IB, Q is selected from:

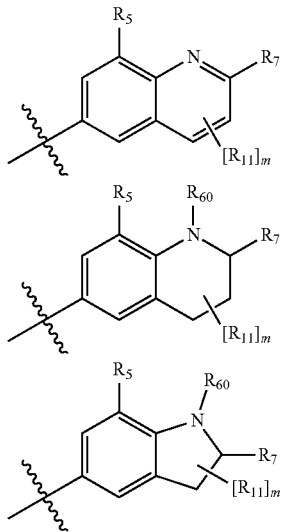

wherein $R_5$, $R_{60}$, $R_7$, $R_{11}$ and m each have any one of the definitions herein.

In a particular embodiment of the compounds of formula I, IA or IB, Q is selected from:

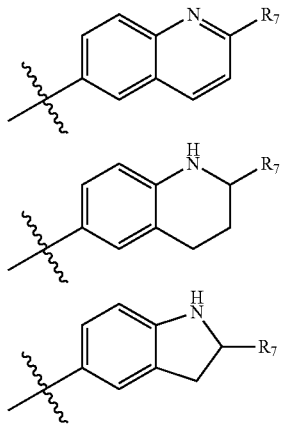

wherein $R_7$ has any one of the definitions set out hereinbefore.

In a particular embodiment of the compounds of formula I, IA or IB, Q is:

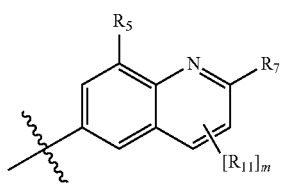

wherein $R_5$, $R_7$, $R_{11}$ and m each have any one of the definitions herein.

In a particular embodiment of the compounds of formula I or IA, Q is:

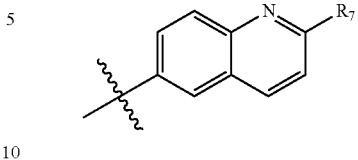

wherein $R_7$ has any one of the definitions set out hereinbefore.

Suitably, $R_7$ is as defined in any one of paragraphs (50), (51), (52) or (53) above.

Particular compounds of the present invention include any one of the compounds exemplified in the present application, or a pharmaceutically acceptable salt or solvate thereof, and, in particular, any one of the following:

N-(5-(2,3-dihydrobenzo[b][1,4]dioxine-6-carboxamido)-2-methylphenyl)quinoline-6-carboxamide;
N-(5-(2,3-dihydrobenzo[b][1,4]dioxine-6-carboxamido)-2-methylphenyl)isoquinoline-7-carboxamide;
N-(5-(2,3-dihydrobenzo[b][1,4]dioxine-6-carboxamido)-2-methylphenyl)-2-(2-methoxyethoxy)quinoline-6-carboxamide;
N-(4-methyl-3-(2-oxo-2H-chromene-6-carboxamido)phenyl)-2,3-dihydrobenzo[b][1,4]dioxine-6-carboxamide;
N-(3-(3,4-dimethoxybenzamido)-4-methylphenyl)-2,3-dihydrobenzo[b][1,4]dioxine-6-carboxamide;
N-(3-(2,3-dihydrobenzofuran-5-carboxamido)-4-methylphenyl)-2,3-dihydrobenzo[b][1,4]dioxine-6-carboxamide;
N-(5-(2,3-dihydrobenzo[b][1,4]dioxine-6-carboxamido)-2-methylphenyl)-1-methylindoline-5-carboxamide;
N-(4-methyl-3-(1-oxo-1,3-dihydroisobenzofuran-5-carboxamido)phenyl)-2,3-dihydrobenzo[b][1,4]dioxine-6-carboxamide;
N-(3-(chroman-6-carboxamido)-4-methylphenyl)-2,3-dihydrobenzo[b][1,4]dioxine-6-carboxamide;
N-(5-(2,3-dihydrobenzo[b][1,4]dioxine-6-carboxamido)-2-methylphenyl)quinazoline-6-carboxamide;
N-(5-(2,3-dihydrobenzo[b][1,4]dioxine-6-carboxamido)-2-methylphenyl)-4-methoxyquinoline-6-carboxamide;
2-chloro-N-(5-(2,3-dihydrobenzo[b][1,4]dioxine-6-carboxamido)-2-methylphenyl)quinoline-6-carboxamide;
N-(5-(2,3-dihydrobenzo[b][1,4]dioxine-6-carboxamido)-2-methylphenyl)-6-(thiazol-4-ylmethoxy)nicotinamide;
N-(4-methyl-3-(2-methyl-2,3-dihydrobenzofuran-5-carboxamido)phenyl)-2,3-dihydrobenzo[b][1,4]dioxine-6-carboxamide;
N-(3-(1,3-dihydroisobenzofuran-5-carboxamido)-4-methylphenyl)-2,3-dihydrobenzo[b][1,4]dioxine-6-carboxamide;
N-(5-(2,3-dihydrobenzo[b][1,4]dioxine-6-carboxamido)-2-methylphenyl)-1-methyl-1H-indole-5-carboxamide;
N-(3-(benzofuran-5-carboxamido)-4-methylphenyl)-2,3-dihydrobenzo[b][1,4]dioxine-6-carboxamide;
N-(3-(benzo[b]thiophene-5-carboxamido)-4-methylphenyl)-2,3-dihydrobenzo[b][1,4]dioxine-6-carboxamide;
N-(4-methyl-3-(4-(pyridin-2-ylmethoxy)benzamido)phenyl)-2,3-dihydrobenzo[b][1,4]dioxine-6-carboxamide;
N-(4-methyl-3-(4-(thiazol-5-ylmethoxy)benzamido)phenyl)-2,3-dihydrobenzo[b][1,4]dioxine-6-carboxamide;
tert-butyl (2-((6-((5-(2,3-dihydrobenzo[b][1,4]dioxine-6-carboxamido)-2-methylphenyl)carbamoyl)quinolin-2-yl)oxy)ethyl)carbamate;
N-(5-(2,3-dihydrobenzo[b][1,4]dioxine-6-carboxamido)-2-methylphenyl)-4-methoxy-2-(2-methoxyethoxy)quinoline-6-carboxamide;

6-((5-(2,3-dihydrobenzo[b][1,4]dioxine-6-carboxamido)-2-methylphenyl)carbamoyl)quinoline 1-oxide;

4-cyano-N-(5-(2,3-dihydrobenzo[b][1,4]dioxine-6-carboxamido)-2-methylphenyl)quinoline-6-carboxamide;

N-(5-(2,3-dihydrobenzo[b][1,4]dioxine-6-carboxamido)-2-methylphenyl)-6-(pyridin-2-ylmethoxy)nicotinamide;

N-(3-(4-methoxy-3-methylbenzamido)-4-methylphenyl)-2,3-dihydrobenzo[b][1,4]dioxine-6-carboxamide;

N-(3-(4-methoxybenzamido)-4-methylphenyl)-2,3-dihydrobenzo[b][1,4]dioxine-6-carboxamide;

N-(3-(3-chloro-4-methoxybenzamido)-4-methylphenyl)-2,3-dihydrobenzo[b][1,4]dioxine-6-carboxamide;

N-(5-(2,3-dihydrobenzo[b][1,4]dioxine-6-carboxamido)-2-methylphenyl)-2-methoxyquinoline-6-carboxamide;

tert-butyl 5-((5-(2,3-dihydrobenzo[b][1,4]dioxine-6-carboxamido)-2-methylphenyl)carbamoyl)indoline-1-carboxylate;

tert-butyl 6-((5-(2,3-dihydrobenzo[b][1,4]dioxine-6-carboxamido)-2-methylphenyl)carbamoyl)-3,4-dihydroisoquinoline-2(1H)-carboxylate;

N-(5-(2,3-dihydrobenzo[b][1,4]dioxine-6-carboxamido)-2-methylphenyl)-2-morpholinoquinoline-6-carboxamide;

N5-(5-(2,3-dihydrobenzo[b][1,4]dioxine-6-carboxamido)-2-methylphenyl)-N2-methylpyridine-2,5-dicarboxamide;

N-(4-methyl-3-(5,6,7,8-tetrahydronaphthalene-2-carboxamido)phenyl)-2,3-dihydrobenzo[b][1,4]dioxine-6-carboxamide;

tert-butyl (3-((6-((5-(2,3-dihydrobenzo[b][1,4]dioxine-6-carboxamido)-2-methylphenyl)carbamoyl)quinolin-2-yl)oxy)propyl)carbamate;

N-(5-(2,3-dihydrobenzo[b][1,4]dioxine-6-carboxamido)-2-methylphenyl)quinoxaline-6-carboxamide;

N-(5-(2,3-dihydrobenzo[b][1,4]dioxine-6-carboxamido)-2-methylphenyl)-6-phenylnicotinamide;

N-(5-(2,3-dihydrobenzo[b][1,4]dioxine-6-carboxamido)-2-methylphenyl)-6-((3-iodophenyl)amino)nicotinamide;

N-(5-(2,3-dihydrobenzo[b][1,4]dioxine-6-carboxamido)-2-methylphenyl)-2-methylquinoline-6-carboxamide;

N-(3-(3-methoxybenzamido)-4-methylphenyl)-2,3-dihydrobenzo[b][1,4]dioxine-6-carboxamide;

N-(3-(4-bromo-3-methoxybenzamido)-4-methylphenyl)-2,3-dihydrobenzo[b][1,4]dioxine-6-carboxamide;

N-(3-(4-methoxy-3,5-dimethylbenzamido)-4-methylphenyl)-2,3-dihydrobenzo[b][1,4]dioxine-6-carboxamide;

N-(5-(2,3-dihydrobenzo[b][1,4]dioxine-6-carboxamido)-2-methylphenyl)-1,6-naphthyridine-3-carboxamide;

N-(5-(2,3-dihydrobenzo[b][1,4]dioxine-6-carboxamido)-2-methylphenyl)-1,7-naphthyridine-3-carboxamide;

N-(5-(2,3-dihydrobenzo[b][1,4]dioxine-6-carboxamido)-2-methylphenyl)-1,8-naphthyridine-3-carboxamide;

N-(5-(2,3-dihydrobenzo[b][1,4]dioxine-6-carboxamido)-2-methylphenyl)isoquinoline-6-carboxamide;

N-(5-(2,3-dihydrobenzo[b][1,4]dioxine-6-carboxamido)-2-methylphenyl)quinoline-3-carboxamide;

N-(5-(2,3-dihydrobenzo[b][1,4]dioxine-6-carboxamido)-2-methylphenyl)-2-oxo-1,2-dihydroquinoline-6-carboxamide;

(R)—N-(5-(2,3-dihydrobenzo[b][1,4]dioxine-6-carboxamido)-2-methylphenyl)-2-((1-methylpyrrolidin-3-yl)oxy)quinoline-6-carboxamide;

N-(5-(2,3-dihydrobenzo[b][1,4]dioxine-6-carboxamido)-2-methylphenyl)-2-((1-methylpiperidin-4-yl)oxy)quinoline-6-carboxamide;

N-(5-(2,3-dihydrobenzo[b][1,4]dioxine-6-carboxamido)-2-methylphenyl)-2-(3-(dimethylamino)propoxy)quinoline-6-carboxamide;

N-(5-(2,3-dihydrobenzo[b][1,4]dioxine-6-carboxamido)-2-methylphenyl)-2-(3-(piperidin-1-yl)propoxy)quinoline-6-carboxamide;

(S)—N-(5-(2,3-dihydrobenzo[b][1,4]dioxine-6-carboxamido)-2-methylphenyl)-2-((1-methylpyrrolidin-2-yl)methoxy)quinoline-6-carboxamide;

N-(5-(2,3-dihydrobenzo[b][1,4]dioxine-6-carboxamido)-2-methylphenyl)-2-(2-(piperidin-1-yl)ethoxy)quinoline-6-carboxamide;

N-(5-(2,3-dihydrobenzo[b][1,4]dioxine-6-carboxamido)-2-methylphenyl)-2-(3-morpholinopropoxy)quinoline-6-carboxamide;

N-(5-(2,3-dihydrobenzo[b][1,4]dioxine-6-carboxamido)-2-methylphenyl)-2-(3-(pyrrolidin-1-yl)propoxy)quinoline-6-carboxamide;

N-(5-(2,3-dihydrobenzo[b][1,4]dioxine-6-carboxamido)-2-methylphenyl)-2-(2-(3-fluoropiperidin-1-yl)ethoxy)quinoline-6-carboxamide;

N-(5-(2,3-dihydrobenzo[b][1,4]dioxine-6-carboxamido)-2-methylphenyl)-2-((2-(dimethylamino)ethyl)(methyl)amino)quinoline-6-carboxamide;

N-(5-(2,3-dihydrobenzo[b][1,4]dioxine-6-carboxamido)-2-methylphenyl)-2-(2-(pyrrolidin-1-yl)ethyl)quinoline-6-carboxamide;

2-(2-(azetidin-1-yl)ethoxy)-N-(5-(2,3-dihydrobenzo[b][1,4]dioxine-6-carboxamido)-2-methylphenyl)quinoline-6-carboxamide;

N-(5-(2,3-dihydrobenzo[b][1,4]dioxine-6-carboxamido)-2-methylphenyl)-2-(2-(2-methylpyrrolidin-1-yl)ethoxy)quinoline-6-carboxamide;

N-(5-(2,3-dihydrobenzo[b][1,4]dioxine-6-carboxamido)-2-methylphenyl)-2-(2-(dimethylamino)ethoxy)quinoline-6-carboxamide;

N-(5-(2,3-dihydrobenzo[b][1,4]dioxine-6-carboxamido)-2-methylphenyl)-2-(2-(pyrrolidin-1-yl)ethoxy)quinoline-6-carboxamide;

N-(5-(2,3-dihydrobenzo[b][1,4]dioxine-6-carboxamido)-2-methylphenyl)-2-(methyl(2-(pyrrolidin-1-yl)ethyl)amino)quinoline-6-carboxamide;

(S)—N-(5-(2,3-dihydrobenzo[b][1,4]dioxine-6-carboxamido)-2-methylphenyl)-2-(2-(3-fluoropyrrolidin-1-yl)ethoxy)quinoline-6-carboxamide;

N-(5-(2,3-dihydrobenzo[b][1,4]dioxine-6-carboxamido)-2-methylphenyl)-2-(2-morpholinoethoxy)quinoline-6-carboxamide;

N-(5-(2,3-dihydrobenzo[b][1,4]dioxine-6-carboxamido)-2-methylphenyl)-2-(pyrrolidin-1-ylmethyl)quinoline-6-carboxamide formate;

N-(5-(2,3-dihydrobenzo[b][1,4]dioxine-6-carboxamido)-2-methylphenyl)-2-(2-(pyrrolidin-1-yi)propoxy)quinoline-6-carboxamide;

N-(5-(2,3-dihydrobenzo[b][1,4]dioxine-6-carboxamido)-2-methylphenyl)-2-(2-(dimethylamino)ethyl)quinoline-6-carboxamide;

N-(5-(2,3-dihydrobenzo[b][1,4]dioxine-6-carboxamido)-2-methylphenyl)-2-((4-methylpiperazin-1-yl)methyl)quinoline-6-carboxamide;

N-(5-(2,3-dihydrobenzo[b][1,4]dioxine-6-carboxamido)-2-methylphenyl)-2-((dimethylamino)methyl)quinoline-6-carboxamide;

2-(2-(4,4-difluoropiperidin-1-yl)ethoxy)-N-(5-(2,3-dihydrobenzo[b][1,4]dioxine-6-carboxamido)-2-methylphenyl)quinoline-6-carboxamide;

N-(5-(2,3-dihydrobenzo[b][1,4]dioxine-6-carboxamido)-2-methylphenyl)-2-((1-(pyrrolidin-1-yl)propan-2-yl)oxy)quinoline-6-carboxamide;

N-(5-(2,3-dihydrobenzo[b][1,4]dioxine-6-carboxamido)-2-methylphenyl)-2-(4-methylpiperazin-1-yl)quinoline-6-carboxamide;
N-(5-(2,3-dihydrobenzo[b][1,4]dioxine-6-carboxamido)-2-methylphenyl)-2-(2-hydroxyethyl)quinoline-6-carboxamide;
N-(5-(2,3-dihydrobenzo[b][1,4]dioxine-6-carboxamido)-2-methylphenyl)-2-(3-(methylamino)propoxy)quinoline-6-carboxamide;
N-(5-(2,3-dihydrobenzo[b][1,4]dioxine-6-carboxamido)-2-methylphenyl)-2-ethylquinoline-6-carboxamide;
N-(5-(2,3-dihydrobenzo[b][1,4]dioxine-6-carboxamido)-2-methylphenyl)-2-((N-methylpropionamido)methyl)quinoline-6-carboxamide;
N-(5-(2,3-dihydrobenzo[b][1,4]dioxine-6-carboxamido)-2-methylphenyl)-2-(methylamino)quinoline-6-carboxamide;
N-(5-(2,3-dihydrobenzo[b][1,4]dioxine-6-carboxamido)-2-methylphenyl)-1,2,3,4-tetrahydroquinoline-6-carboxamide;
N-(5-(2,3-dihydrobenzo[b][1,4]dioxine-6-carboxamido)-2-methylphenyl)-2-(2-propionamidoethoxy)quinoline-6-carboxamide;
N-(5-(2,3-dihydrobenzo[b][1,4]dioxine-6-carboxamido)-2-methylphenyl)-2,3,4,5-tetrahydro-1H-benzo[b]azepine-7-carboxamide;
N-(5-(2,3-dihydrobenzo[b][1,4]dioxine-6-carboxamido)-2-methylphenyl)-2-((2-propionamidoethyl)amino)quinoline-6-carboxamide;
N-(5-(2,3-dihydrobenzo[b][1,4]dioxine-6-carboxamido)-2-methylphenyl)indoline-5-carboxamide;
tert-butyl ((6-((5-(2,3-dihydrobenzo[b][1,4]dioxine-6-carboxamido)-2-methylphenyl)carbamoyl)-1,2,3,4-tetrahydroquinolin-2-yl)methyl)(methyl)carbamate;
N-(5-(2,3-dihydrobenzo[b][1,4]dioxine-6-carboxamido)-2-methylphenyl)-2-((methylamino)methyl)-1,2,3,4-tetrahydroquinoline-6-carboxamide;
N-(5-(2,3-dihydrobenzo[b][1,4]dioxine-6-carboxamido)-2-methylphenyl)-2-((dimethylamino)methyl)-1,2,3,4-tetrahydroquinoline-6-carboxamide;
N-(5-(2,3-dihydrobenzo[b][1,4]dioxine-6-carboxamido)-2-methylphenyl)-1,2,3,4-tetrahydroisoquinoline-6-carboxamide;
2-(2-aminoethoxy)-N-(5-(2,3-dihydrobenzo[b][1,4]dioxine-6-carboxamido)-2-methylphenyl)quinoline-6-carboxamide;
N-(5-(2,3-dihydrobenzo[b][1,4]dioxine-6-carboxamido)-2-methylphenyl)-2-(trifluoromethyl)-1H-benzo[d]imidazole-6-carboxamide;
2-amino-N-(5-(2,3-dihydrobenzo[b][1,4]dioxine-6-carboxamido)-2-methylphenyl)benzo[d]thiazole-6-carboxamide;
N-(5-(2,3-dihydrobenzo[b][1,4]dioxine-6-carboxamido)-2-methylphenyl)-3H-imidazo[4,5-b]pyridine-6-carboxamide;
N-(3-(4-hydroxybenzamido)-4-methylphenyl)-2,3-dihydrobenzo[b][1,4]dioxine-6-carboxamide;
N-(5-(2,3-dihydrobenzo[b][1,4]dioxine-6-carboxamido)-2-methylphenyl)-6-(phenylamino)nicotinamide;
2-amino-N-(5-(2,3-dihydrobenzo[b][1,4]dioxine-6-carboxamido)-2-methylphenyl)-4-methoxybenzo[d]thiazole-6-carboxamide;
N-(5-(2,3-dihydrobenzo[b][1,4]dioxine-6-carboxamido)-2-methylphenyl)-2-(1H-1,2,4-triazol-1-yl)isonicotinamide;
N-(5-(2,3-dihydrobenzo[b][1,4]dioxine-6-carboxamido)-2-methylphenyl)-1H-indazole-5-carboxamide;
N-(5-(2,3-dihydrobenzo[b][1,4]dioxine-6-carboxamido)-2-methylphenyl)-2-morpholinoisonicotinamide;
N-(5-(2,3-dihydrobenzo[b][1,4]dioxine-6-carboxamido)-2-methylphenyl)-2-methyl-1H-pyrrolo[2,3-b]pyridine-5-carboxamide;
N-(5-(2,3-dihydrobenzo[b][1,4]dioxine-6-carboxamido)-2-methylphenyl)-1H-pyrrolo[2,3-b]pyridine-5-carboxamide;
N-(4-methyl-3-(4-(thiazol-4-ylmethoxy)benzamido)phenyl)-2,3-dihydrobenzo[b][1,4]dioxine-6-carboxamide;
N-(5-(2,3-dihydrobenzo[b][1,4]dioxine-6-carboxamido)-2-methylphenyl)-6-(ethylamino)nicotinamide;
N-(5-(2,3-dihydrobenzo[b][1,4]dioxine-6-carboxamido)-2-methylphenyl)-2-oxo-1,2,3,4-tetrahydroquinoline-6-carboxamide;
6-amino-N-(5-(2,3-dihydrobenzo[b][1,4]dioxine-6-carboxamido)-2-methylphenyl)nicotinamide;
2-amino-N-(5-(2,3-dihydrobenzo[b][1,4]dioxine-6-carboxamido)-2-methylphenyl)isonicotinamide;
N-(5-(2,3-dihydrobenzo[b][1,4]dioxine-6-carboxamido)-2-methylphenyl)-6-(1H-pyrazol-1-yl)nicotinamide;
N-(3-(4-(1H-pyrazol-1-yl)benzamido)-4-methylphenyl)-2,3-dihydrobenzo[b][1,4]dioxine-6-carboxamide;
N-(4-methyl-3-(6-methyl-2-naphthamido)phenyl)-2,3-dihydrobenzo[b][1,4]dioxine-6-carboxamide;
N-(5-(2,3-dihydrobenzo[b][1,4]dioxine-6-carboxamido)-2-methylphenyl)-3-methyl-4-oxo-3,4-dihydroquinazoline-6-carboxamide;
N-(5-(2,3-dihydrobenzo[b][1,4]dioxine-6-carboxamido)-2-methylphenyl)-4-(2-(dimethylamino)ethylamino)-2-methylquinoline-6-carboxamide;
N-(5-(2,3-dihydrobenzo[b][1,4]dioxine-6-carboxamido)-2-methylphenyl)-4-(3-(dimethylamino)propylamino)-2-methylquinoline-6-carboxamide;
N-(5-(2,3-dihydrobenzo[b][1,4]dioxine-6-carboxamido)-2-methylphenyl)-2-methyl-4-(methyl(1-methylpyrrolidin-3-yl)amino)quinoline-6-carboxamide;
N-(3-(2,3-dihydrobenzo[b][1,4]dioxine-6-carboxamido)phenyl)-2-methylquinoline-6-carboxamide;
N-(5-(2,3-dihydrobenzo[b][1,4]dioxine-6-carboxamido)-2-methylphenyl)benzo[d]thiazole-6-carboxamide;
N-(5-(2,3-dihydrobenzo[b][1,4]dioxine-6-carboxamido)-2-methylphenyl)-2-(methylamino)benzo[d]thiazole-6-carboxamide;
2-amino-N-(5-(2,3-dihydrobenzo[b][1,4]dioxine-6-carboxamido)-2-methylphenyl)benzo[d]thiazole-7-carboxamide;
N-(5-(2,3-dihydrobenzo[b][1,4]dioxine-6-carboxamido)-2-methylphenyl)-2-methyl-4-(2-(pyrrolidin-1-yl)ethylamino)quinoline-6-carboxamide;
N-(5-(2,3-dihydrobenzo[b][1,4]dioxine-6-carboxamido)-2-methylphenyl)-2-methyl-4-(2-morpholinoethylamino)quinoline-6-carboxamide;
N-(5-(2,3-dihydrobenzo[b][1,4]dioxine-6-carboxamido)-2-methylphenyl)-4-((2-(dimethylamino)ethyl)(methyl)amino)-2-methylquinoline-6-carboxamide;
N-(5-(2,3-dihydrobenzo[b][1,4]dioxine-6-carboxamido)-2-methylphenyl)-2-methyl-4-(2-(pyrrolidin-1-yl)ethoxy)quinoline-6-carboxamide;
N-(5-(2,3-dihydrobenzo[b][1,4]dioxine-6-carboxamido)-2-methylphenyl)-6-(3-(1-methylpiperidin-4-yloxy)phenylamino)nicotinamide;
N-(5-(2,3-dihydrobenzo[b][1,4]dioxine-6-carboxamido)-2-methylphenyl)-6-(3-(4-methylpiperazin-1-yl)propylamino)nicotinamide;

N-(5-(2,3-dihydrobenzo[b][1,4]dioxine-6-carboxamido)-2-methylphenyl)-6-(3-((4-methylpiperazin-1-yl)methyl)phenylamino)nicotinamide;

N-(5-(2,3-dihydrobenzo[b][1,4]dioxine-6-carboxamido)-2-methylphenyl)-6-(3-((dimethylamino)methyl)phenylamino)nicotinamide;

N-(5-(2,3-dihydrobenzo[b][1,4]dioxine-6-carboxamido)-2-methylphenyl)-6-(3-(3-(dimethylamino)pyrrolidin-1-yl)phenylamino)nicotinamide;

N-(3-(2,3-dihydrobenzo[b][1,4]dioxine-6-carboxamido)phenyl)-1H-pyrrolo[2,3-b]pyridine-5-carboxamide;

N-(5-(2,3-dihydrobenzo[b][1,4]dioxine-6-carboxamido)-2-fluorophenyl)-1H-pyrrolo[2,3-b]pyridine-5-carboxamide;

N-(5-(2,3-dihydrobenzo[b][1,4]dioxine-6-carboxamido)-2-fluorophenyl)-2-methylquinoline-6-carboxamide;

N-(5-(2,3-dihydrobenzo[b][1,4]dioxine-6-carboxamido)-2-(trifluoromethyl)phenyl)-2-methylquinoline-6-carboxamide;

N-(5-(7-fluoro-2,3-dihydrobenzo[b][1,4]dioxine-6-carboxamido)-2-methylphenyl)-2-methylquinoline-6-carboxamide;

N-(5-(benzo[d][1,3]dioxole-5-carboxamido)-2-methylphenyl)quinoline-6-carboxamide;

N-(5-(3,4-dihydro-2H-benzo[b][1,4]dioxepine-7-carboxamido)-2-methylphenyl)-2-methylquinoline-6-carboxamide;

N-(5-(2,3-dihydrobenzo[b][1,4]dioxine-6-carboxamido)-2-ethylphenyl)quinoline-6-carboxamide;

N-(4-methyl-3-(2-(2-(pyrrolidin-1-yl)ethoxy)quinoline-6-carboxamido)phenyl)-2,3-dihydro-[1,4]dioxino[2,3-b]pyridine-7-carboxamide;

N-(4-methyl-3-(2-methylquinoline-6-carboxamido)phenyl)-2,3-dihydro-[1,4]dioxino[2,3-b]pyridine-7-carboxamide;

N-(5-(2,3-dihydrobenzo[b][1,4]dioxine-6-carboxamido)-2-methylphenyl)-8-fluoroquinoline-6-carboxamide;

N-(5-(2,3-dihydrobenzo[b][1,4]dioxine-6-carboxamido)-2-methylphenyl)-2-(methoxymethyl)quinoline-6-carboxamide;

N-(2-bromo-5-(2,3-dihydrobenzo[b][1,4]dioxine-6-carboxamido)phenyl)quinoline-6-carboxamide;

N-(2-bromo-5-(2,3-dihydrobenzo[b][1,4]dioxine-6-carboxamido)phenyl)-2-(2-(pyrrolidin-1-yl)ethoxy)quinoline-6-carboxamide;

N-(2-cyano-5-(2,3-dihydrobenzo[b][1,4]dioxine-6-carboxamido)phenyl)quinoline-6-carboxamide;

N-(5-(2,3-dihydrobenzo[b][1,4]dioxine-6-carboxamido)-2-methylphenyl)-5,6,7,8-tetrahydroquinoline-3-carboxamide;

N-(5-(2,3-dihydrobenzo[b][1,4]dioxine-6-carboxamido)-2-methylphenyl)-2-(1-hydroxyethyl)quinoline-6-carboxamide;

N-(5-(2,3-dihydrobenzo[b][1,4]dioxine-6-carboxamido)-2-methylphenyl)-1-methyl-1,2,3,4-tetrahydroquinoline-6-carboxamide;

N-(5-(2,3-dihydrobenzo[b][1,4]dioxine-6-carboxamido)-2-methylphenyl)-2-(2-morpholinoethyl)quinoline-6-carboxamide;

N-(5-(2,3-dihydrobenzo[b][1,4]dioxine-6-carboxamido)-2-methylphenyl)-2-(isopropoxymethyl)quinoline-6-carboxamide;

N-(5-(2,3-dihydrobenzo[b][1,4]dioxine-6-carboxamido)-2-methylphenyl)-2-(((tetrahydrofuran-2-yl)methoxy)methyl)quinoline-6-carboxamide;

N-(5-(2,3-dihydrobenzo[b][1,4]dioxine-6-carboxamido)-2-methylphenyl)-2-((2-(pyrrolidin-1-yl)ethoxy)methyl)quinoline-6-carboxamide;

N-(5-(2,3-dihydrobenzo[b][1,4]dioxine-6-carboxamido)-2-methylphenyl)-5-((2-(pyrrolidin-1-yl)ethyl)amino)quinoline-3-carboxamide;

N-(2-chloro-5-(2,3-dihydrobenzo[b][1,4]dioxine-6-carboxamido)phenyl)quinoline-6-carboxamide;

N-(5-(2,3-dihydrobenzo[b][1,4]dioxine-6-carboxamido)-2-methylphenyl)-3-((2-methoxyethyl)amino)-2-(2-(pyrrolidin-1-yl)ethoxy)quinoline-6-carboxamide;

N-(5-(2,3-dihydrobenzo[b][1,4]dioxine-6-carboxamido)-2-methylphenyl)-2-(isobutoxymethyl)quinoline-6-carboxamide;

N-(5-(2,3-dihydrobenzo[b][1,4]dioxine-6-carboxamido)-2-methylphenyl)-2-methyl-1,2,3,4-tetrahydroquinoline-6-carboxamide;

N-(5-(2,3-dihydrobenzo[b][1,4]dioxine-6-carboxamido)-2-methylphenyl)-2-(1-methoxyethyl)quinoline-6-carboxamide;

(S)—N-(5-(2,3-dihydrobenzo[b][1,4]dioxine-6-carboxamido)-2-methylphenyl)-2-methyl-1,2,3,4-tetrahydroquinoline-6-carboxamide;

(R)—N-(5-(2,3-dihydrobenzo[b][1,4]dioxine-6-carboxamido)-2-methylphenyl)-2-methyl-1,2,3,4-tetrahydroquinoline-6-carboxamide;

N-(5-(2,3-dihydrobenzo[b][1,4]dioxine-6-carboxamido)-2-methylphenyl)-3-(2-(pyrrolidin-1-yl)ethoxy)isoquinoline-6-carboxamide;

N-(5-(2,3-dihydrobenzo[b][1,4]dioxine-6-carboxamido)-2-methylphenyl)-5-(2-hydroxyethyl)quinoline-3-carboxamide;

N-(5-(2,3-dihydrobenzo[b][1,4]dioxine-6-carboxamido)-2-methylphenyl)-5-(2-(pyrrolidin-1-yl)ethyl)quinoline-3-carboxamide;

N-(5-(2,3-dihydrobenzo[b][1,4]dioxine-6-carboxamido)-2-methylphenyl)-1,2-dimethyl-1,2,3,4-tetrahydroquinoline-6-carboxamide;

N-(5-(2,3-dihydrobenzo[b][1,4]dioxine-6-carboxamido)-2-methylphenyl)-8-(2-methoxyethoxy)quinoline-6-carboxamide;

5-allyl-N-(5-(2,3-dihydrobenzo[b][1,4]dioxine-6-carboxamido)-2-methylphenyl)quinoline-3-carboxamide;

N-(5-(2,3-dihydrobenzo[b][1,4]dioxine-6-carboxamido)-2-methylphenyl)-8-((2-(dimethylamino)ethyl)(methyl)amino)quinoline-6-carboxamide;

3-((6-((5-(2,3-dihydrobenzo[b][1,4]dioxine-6-carboxamido)-2-methylphenyl)carbamoyl)quinolin-2-yl)(methyl)amino)propanoic acid;

tert-butyl (4-((6-((5-(2,3-dihydrobenzo[b][1,4]dioxine-6-carboxamido)-2-methylphenyl)carbamoyl)quinolin-2-yl)oxy)butyl)carbamate;

N-(5-amino-2-((dimethylamino)methyl)phenyl)-2-methylquinoline-6-carboxamide;

N-(5-amino-2-((dimethylamino)methyl)phenyl)-2-methylquinoline-6-carboxamide;

N-(5-(2,3-dihydrobenzo[b][1,4]dioxine-6-carboxamido)-2-(methoxymethyl)phenyl)-2-methylquinoline-6-carboxamide;

N-(5-(2,3-dihydrobenzo[b][1,4]dioxine-6-carboxamido)-2-(hydroxymethyl)phenyl)-2-methylquinoline-6-carboxamide;

N-(5-(2,3-dihydrobenzo[b][1,4]dioxine-6-carboxamido)-2-methylphenyl)-1-methyl-1,3-dihydrobenzo[c]isothiazole-5-carboxamide 2,2-dioxide;

N-(5-(2,3-dihydrobenzo[b][1,4]dioxine-6-carboxamido)-2-fluorophenyl)-2-((4-ethylpiperazin-1-yl)methyl)quinoline-6-carboxamide;

N-(5-(2,3-dihydrobenzo[b][1,4]dioxine-6-carboxamido)-2-fluorophenyl)-2-(pyrrolidin-1-ylmethyl)quinoline-6-carboxamide;

2-(azetidin-1-ylmethyl)-N-(5-(2,3-dihydrobenzo[b][1,4]dioxine-6-carboxamido)-2-fluorophenyl)quinoline-6-carboxamide;

N-(5-(2,3-dihydrobenzo[b][1,4]dioxine-6-carboxamido)-2-fluorophenyl)-2-(piperidin-1-ylmethyl)quinoline-6-carboxamide N-(5-(2,3-dihydrobenzo[b][1,4]dioxine-6-carboxamido)-2-fluorophenyl)-2-((4-methylpiperazin-1-yl)methyl)quinoline-6-carboxamide;

N-(5-(2,3-dihydrobenzo[b][1,4]dioxine-6-carboxamido)-2-fluorophenyl)-2-(piperazin-1-ylmethyl)quinoline-6-carboxamide;

(S)—N-(5-(2,3-dihydrobenzo[b][1,4]dioxine-6-carboxamido)-2-fluorophenyl)-2-((2-methylpyrrolidin-1-yl)methyl)quinoline-6-carboxamide;

(R)—N-(5-(2,3-dihydrobenzo[b][1,4]dioxine-6-carboxamido)-2-fluorophenyl)-2-((2-methylpyrrolidin-1-yl)methyl)quinoline-6-carboxamide;

2-((4-(tert-butyl)piperazin-1-yl)methyl)-N-(5-(2,3-dihydrobenzo[b][1,4]dioxine-6-carboxamido)-2-fluorophenyl)quinoline-6-carboxamide;

2-((4-cyclopropylpiperazin-1-yl)methyl)-N-(5-(2,3-dihydrobenzo[b][1,4]dioxine-6-carboxamido)-2-fluorophenyl)quinoline-6-carboxamide;

2-((4-(sec-butyl)piperazin-1-yl)methyl)-N-(5-(2,3-dihydrobenzo[b][1,4]dioxine-6-carboxamido)-2-fluorophenyl)quinoline-6-carboxamide;

N-(5-(2,3-dihydrobenzo[b][1,4]dioxine-6-carboxamido)-2-fluorophenyl)-2-(((1S,4S)-5-ethyl-2,5-diazabicyclo[2.2.1]heptan-2-yl)methyl)quinoline-6-carboxamide;

2-(2-azaspiro[3.3]heptan-2-ylmethyl)-N-(5-(2,3-dihydrobenzo[b][1,4]dioxine-6-carboxamido)-2-fluorophenyl)quinoline-6-carboxamide;

N-(5-(2,3-dihydrobenzo[b][1,4]dioxine-6-carboxamido)-2-fluorophenyl)-2-((3-methylazetidin-1-yl)methyl)quinoline-6-carboxamide;

N-(5-(2,3-dihydrobenzo[b][1,4]dioxine-6-carboxamido)-2-fluorophenyl)-2-((3,3-dimethylazetidin-1-yl)methyl)quinoline-6-carboxamide;

N-(5-(2,3-dihydrobenzo[b][1,4]dioxine-6-carboxamido)-2-fluorophenyl)-2-((4-ethyl-1,4-diazepan-1-yl)methyl)quinoline-6-carboxamide;

N-(5-(2,3-dihydrobenzo[b][1,4]dioxine-6-carboxamido)-2-fluorophenyl)-2-((4-isopropylpiperazin-1-yl)methyl)quinoline-6-carboxamide;

N-(5-(2,3-dihydrobenzo[b][1,4]dioxine-6-carboxamido)-2-fluorophenyl)-2-(3-(piperidin-1-yl)propoxy)quinoline-6-carboxamide N-(5-(2,3-dihydrobenzo[b][1,4]dioxine-6-carboxamido)-2-fluorophenyl)-2-(3-(pyrrolidin-1-yl)propoxy)quinoline-6-carboxamide;

N-(5-(2,3-dihydrobenzo[b][1,4]dioxine-6-carboxamido)-2-fluorophenyl)-2-(2-(pyrrolidin-1-yl)ethoxy)quinoline-6-carboxamide;

N-(2-chloro-5-(2,3-dihydrobenzo[b][1,4]dioxine-6-carboxamido)phenyl)-2-(3-(piperidin-1-yl)propoxy)quinoline-6-carboxamide;

(rac)-N-(5-(2,3-dihydrobenzo[b][1,4]dioxine-6-carboxamido)-2-fluorophenyl)-2-((2-methylpyrrolidin-1-yl)methyl)quinoline-6-carboxamide;

2-((4-(tert-butyl)piperazin-1-yl)methyl)-N-(2-chloro-5-(2,3-dihydrobenzo[b][1,4]dioxine-6-carboxamido)phenyl)quinoline-6-carboxamide;

N-(2-chloro-5-(2,3-dihydrobenzo[b][1,4]dioxine-6-carboxamido)phenyl)-2-(piperazin-1-ylmethyl)quinoline-6-carboxamide;

2-((4-(sec-butyl)piperazin-1-yl)methyl)-N-(2-chloro-5-(2,3-dihydrobenzo[b][1,4]dioxine-6-carboxamido)phenyl)quinoline-6-carboxamide;

N-(2-chloro-5-(2,3-dihydrobenzo[b][1,4]dioxine-6-carboxamido)phenyl)-2-((4-cyclopropylpiperazin-1-yl)methyl)quinoline-6-carboxamide;

N-(2-chloro-5-(2,3-dihydrobenzo[b][1,4]dioxine-6-carboxamido)phenyl)-2-((4-methylpiperazin-1-yl)methyl)quinoline-6-carboxamide;

N-(2-chloro-5-(2,3-dihydrobenzo[b][1,4]dioxine-6-carboxamido)phenyl)-2-((4-ethylpiperazin-1-yl)methyl)quinoline-6-carboxamide;

N-(2-chloro-5-(2,3-dihydrobenzo[b][1,4]dioxine-6-carboxamido)phenyl)-2-((4-isopropylpiperazin-1-yl)methyl)quinoline-6-carboxamide;

N-(2-chloro-5-(2,3-dihydrobenzo[b][1,4]dioxine-6-carboxamido)phenyl)-2-(pyrrolidin-1-ylmethyl)quinoline-6-carboxamide 2-(azetidin-1-ylmethyl)-N-(2-chloro-5-(2,3-dihydrobenzo[b][1,4]dioxine-6-carboxamido)phenyl)quinoline-6-carboxamide;

N-(2-chloro-5-(2,3-dihydrobenzo[b][1,4]dioxine-6-carboxamido)phenyl)-2-((3-methylazetidin-1-yl)methyl)quinoline-6-carboxamide;

N-(2-chloro-5-(2,3-dihydrobenzo[b][1,4]dioxine-6-carboxamido)phenyl)-2-((3,3-dimethylazetidin-1-yl)methyl)quinoline-6-carboxamide;

N-(5-(2,3-dihydrobenzo[b][1,4]dioxine-6-carboxamido)-2-methylphenyl)-2-((4-isopropylpiperazin-1-yl)methyl)quinoline-6-carboxamide;

2-(azetidin-1-ylmethyl)-N-(5-(2,3-dihydrobenzo[b][1,4]dioxine-6-carboxamido)-2-methylphenyl)quinoline-6-carboxamide;

N-(5-(2,3-dihydrobenzo[b][1,4]dioxine-6-carboxamido)-2-methylphenyl)-2-((4-ethylpiperazin-1-yl)methyl)quinoline-6-carboxamide;

N-(5-(2,3-dihydrobenzo[b][1,4]dioxine-6-carboxamido)-2-methylphenyl)-2-((2-methylpyrrolidin-1-yl)methyl)quinoline-6-carboxamide;

N-(5-(2,3-dihydrobenzo[b][1,4]dioxine-6-carboxamido)-2-methylphenyl)-2-((2-methylpyrrolidin-1-yl)methyl)quinoline-6-carboxamide;

(R)—N-(5-(2,3-dihydrobenzo[b][1,4]dioxine-6-carboxamido)-2-methylphenyl)-2-((3-fluoropyrrolidin-1-yl)methyl)quinoline-6-carboxamide;

(S)—N-(5-(2,3-dihydrobenzo[b][1,4]dioxine-6-carboxamido)-2-methylphenyl)-2-((3-fluoropyrrolidin-1-yl)methyl)quinoline-6-carboxamide;

N-(5-(2,3-dihydrobenzo[b][1,4]dioxine-6-carboxamido)-2-methylphenyl)-2-((3-methoxypyrrolidin-1-yl)methyl)quinoline-6-carboxamide;

N-(5-(2,3-dihydrobenzo[b][1,4]dioxine-6-carboxamido)-2-methylphenyl)-2-(piperidin-1-ylmethyl)quinoline-6-carboxamide;

N-(5-(2,3-dihydrobenzo[b][1,4]dioxine-6-carboxamido)-2-vinylphenyl)-2-methylquinoline-6-carboxamide;

N-(2-chloro-5-(2,3-dihydrobenzo[b][1,4]dioxine-6-carboxamido)phenyl)-2-(2-(pyrrolidin-1-yl)ethoxy)quinoline-6-carboxamide;

(R)—N-(5-(2,3-dihydrobenzo[b][1,4]dioxine-6-carboxamido)-2-fluorophenyl)-2-((4-ethyl-2-methylpiperazin-1-yl)methyl)quinoline-6-carboxamide;

(S)—N-(5-(2,3-dihydrobenzo[b][1,4]dioxine-6-carboxamido)-2-fluorophenyl)-2-((4-ethyl-2-methylpiperazin-1-yl)methyl)quinoline-6-carboxamide
N-(5-(2,3-dihydrobenzo[b][1,4]dioxine-6-carboxamido)-2-fluorophenyl)-2-(1-(4-ethylpiperazin-1-yl)ethyl)quinoline-6-carboxamide;
N-(2-bromo-5-(2,3-dihydrobenzo[b][1,4]dioxine-6-carboxamido)phenyl)-2-((4-ethylpiperazin-1-yl)methyl)quinoline-6-carboxamide;
2-(azetidin-1-ylmethyl)-N-(2-bromo-5-(2,3-dihydrobenzo[b][1,4]dioxine-6-carboxamido)phenyl)quinoline-6-carboxamide;
(S)—N-(5-(2,3-dihydrobenzo[b][1,4]dioxine-6-carboxamido)-2-fluorophenyl)-2-((4-isopropyl-2-methylpiperazin-1-yl)methyl)quinoline-6-carboxamide
(R)—N-(5-(2,3-dihydrobenzo[b][1,4]dioxine-6-carboxamido)-2-fluorophenyl)-2-((4-isopropyl-2-methylpiperazin-1-yl)methyl)quinoline-6-carboxamide;
or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess HSF1 inhibitory activity.

The present invention also encompasses compounds of the invention as defined herein which comprise one or more isotopic substitutions. For example, H may be in any isotopic form, including $^1H$, $^2H$ (D) and $^3H$ (T); C may be in any isotopic form including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess HSF1 inhibitory activity.

It is also to be understood that certain compounds of the invention may exhibit polymorphism, and that the invention encompasses all such forms that possess HSF1 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

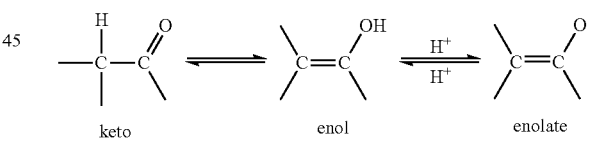

keto   enol   enolate

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I or IA as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I or IA is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_3$-cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described herein, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The compounds of the invention may be prepared using synthetic techniques that are known in the art (as illustrated in the accompanying examples).

In a particular aspect, the present invention provides a method of synthesising a compound of the formula I as defined herein, or a pharmaceutically acceptable salt or solvate thereof, the method comprising:

a) reacting a compound of formula A:

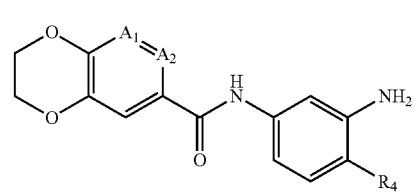

Formula A wherein $A_1$, $A_2$, and $R_4$ each have any one of the meanings as defined hereinbefore;
with a compound of formula B:

Q-COOH      Formula B wherein Q is as defined herein; and
b) optionally thereafter, and if necessary:
   i) removing any protecting groups present;
   ii) converting the compound formula I into another compound of formula I; and/or
   iii) forming a pharmaceutically acceptable salt or solvate thereof.

Suitably the coupling reaction between formula A and formula B takes place in the presence of a suitable solvent. Any suitable solvent or solvent mixture may be used for this reaction. A person skilled in the art will know how to select suitable solvents or solvent mixtures for use in these reactions. Examples of suitable solvents include DMA, 1,4-dioxane, DMF and toluene.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out at room temperature or at an elevated temperature for a suitable time period of, for example, 2 hours to 7 days, or more suitably 2 to 10 hours. If desired, the reaction mixture may be heated either conventionally or by using microwave irradiation.

Suitably the coupling reaction between formula A and formula B takes place in the presence of a coupling agent. Suitable coupling agents are known in the art and described in, for example, Chem. Soc. Rev., 2009, 38, 606-631. An example of a suitable coupling agent is HATU.

The compound of formula A can be prepared by processes known in the art, and suitably by the processes described herein with reference to the examples.

The compound of formula B can be prepared by processes known in the art, and suitably by the processes described herein with reference to the examples.

In step (b) of the above processes, if a suitable protecting group is present then additional deprotection conditions may be employed. Suitable protecting groups include tert-butoxycarbonate and dimethylacetal. Typical conditions comprise a suitable acid in a suitable solvent such as trifluoroacetic acid in either DCM or THF.

A racemic compound of formula 1 may be separated using suitable chiral separation chromatography to furnish the desired enantiomers.

In another aspect, the present invention provides a method of synthesising a compound of the formula II, or a pharmaceutically acceptable salt or solvate thereof, the method comprising:

a) reacting a compound of formula C:

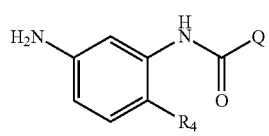

Formula C wherein Q and $R_4$ each have any one of the meanings as defined hereinbefore;
with a compound of formula D:

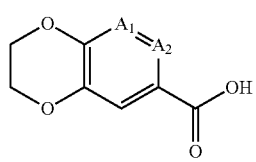

Formula D wherein $A_1$ and $A_2$ are as defined hereinbefore; and
b) optionally thereafter, and if necessary:
   i) removing any protecting groups present;
   ii) converting the compound formula II into another compound of formula II; and/or
   iii) forming a pharmaceutically acceptable salt or solvate thereof.

Suitably the reaction conditions for the coupling between compound C and compound D are as defined above for the coupling between compounds A and B.

In a further aspect of the invention, there is provided a compound of formula II obtainable by/obtained by/or directly obtained by any one of the processes defined or exemplified herein.

Biological Activity

The following biological assays may be used to measure the pharmacological effects of the compounds of the present invention.

Arrayscan Assay

U2OS cells (1500 per well) were plated in 40 μL of DMEM media (containing 10% fetal calf serum and 2 mM Glutamax T-1) in costar 384-well plates and left overnight at 37° C. and 5% $CO_2$ to adhere.

Cells were then dosed with compound diluted in DMSO (120 nL added to each well to give 0.0313-30 μM concentrations of compound) and incubated at 37° C. and 5% $CO_2$. After 1 h of treatment with compound, all wells except min wells were dosed with 17-AAG diluted in DMSO (10 nL added to each well to give 250 nM final concentration) and plates were incubated overnight at 37° C. and 5% $CO_2$. The following day the cells were fixed by addition of 20 μL/well of 12% formaldehyde with 1:1700 Hoechst in PBS for 10 min at room temperature. The fixative was decanted and the wells washed once with 50 μL of phosphate buffer saline (PBS). The PBS was subsequently aspirated, and the cells were permeabilized by addition of 20 μL/well of PBS 0.3% Triton X-100 for 20 min at room temperature. The wells were then washed with 80 μL of PBS prior to the addition of 20 μL of combined primary and secondary antibodies diluted in PBS (1:10 000 mouse anti-Hsp72 #SPA-810 purchased from Stressgen and 1:3000 Alexa Fluor 488 goat anti-mouse IgG (H+L) #A-11001 molecular probes), for 2 h at room temperature. The wells were then washed with 50 μL of PBS. Finally, 50 μL of PBS was added to each well, and the plates were sealed ready to analyze. Analysis was carried out using a Cellomics Arrayscan VTI instrument and the Cellomics Arrayscan Compartmental Analysis algorithm to measure cellular levels of HSP72. Results are reported as $IC_{50}$ values for inhibition of HSP72 levels and are averages of at least 2 independent measurements.

Cell-Based ELISA (Cellisa) Assay

U2OS cells (5-8×10$^4$ cells/mL) or SK-OV-3 cells (5-8×10$^4$ cells/mL) were seeded into 96-well plates and incubated at 37° C. for 48 h. Compounds were then added at a range of concentrations and incubated for 1 h before addition of 17-AAG (250 nM). Cells were then incubated for 18 h. The medium was removed washed 2× with PBS and cells were then fixed with fixing solution (4% paraformaldehyde, 0.3% TritonX-100 in PBS) for 30 min at 4° C. The plates were then washed 2× with PBS before blocking with 5% milk for 30 min at 37° C. After washing the plates 4× with 0.1% Tween-20/deionised water, HSP72 antibody (SPA-810, Enzo Life) was added for 1.5 h at 37° C. Following 4× washes, the plates were incubated with europium-labelled anti-mouse antibody (0.6 ug/ml) in Delfia assay buffer (Perkin Elmer) for 1 h at 37° C. After washing the plates, Delfia enhancement solution was added, shaken for 10 min before reading in the Envision plate reader (Perkin-Elmer) with excitation at 340 nm and emission at 615 nm. The plates were washed again before protein determination using the bicinchoninic acid assay (BCA assay, Pierce Biotechnology). The europium counts were normalised for the amount of protein in each well. The 50% inhibitory concentration value of the compound was then calculated.

Titre Blue Assay

The cell titre blue viability (Promega, USA) assay provides a homogenous, fluorometric method for estimating the number of viable cells. It uses the dark blue indicator dye resazurin to measure the metabolic capacity of cells which is an indicator of cell viability. Viable cells are able to reduce resazurin into resorufin (pink) which is highly fluorescent. Briefly, U2OS or SK-OV-3 (6×10$^3$ cells/mL) were seeded into 384-well plates and were incubated for 24 h. Compounds (at a range of concentrations) were added using the ECHO 550 liquid handler (Labcyte, USA) and then left at 37° C. for 96 h. Titre blue reagent was added to each well and left at 37° C. for 3-4 h. Fluorescence was measured using the Envision machine (Perkin Elmer, UK).

In general, activity possessed by compounds of the formula I, may be demonstrated in the Arrayscan and Cellisa assays by an $IC_{50}$ value of less than 15 μM. Suitably compounds have an $IC_{50}$ value of less than 10 μM in these assays, more suitably less than 5 μM, even more suitably less than 2 μM and most suitably less than 1 μM. Preferred compounds of the invention have an $IC_{50}$ value of less than 500 nM in the Arrayscan and Cellulisa assays.

The activities of compounds of the invention in the above assay are shown in the accompanying example section.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the present invention function as inhibitors of HSF1 activity. Accordingly, the compounds of the invention are potentially useful agents for the treatment of diseases or conditions in which HSF1 activity is implicated.

In one aspect, the present invention provides a compound of formula I, or a pharmaceutically acceptable salt or solvate thereof, or a pharmaceutical composition as defined herein for use in therapy.

In another aspect, the present invention provides a method of inhibiting HSF1 activity in a cell, the method comprising administering to said cell compound of formula I as defined herein, or a pharmaceutically acceptable salt or solvate thereof.

In a further aspect, the present invention provides a method of inhibiting HSF1 in vitro or in vivo, said method comprising contacting a cell with an effective amount of a compound, or a pharmaceutically acceptable salt or solvate thereof, as defined herein.

In another aspect, the present invention provides a method of inhibiting HSF1 activity in a human or animal subject in need of such inhibition, the method comprising administering to said subject an effective amount of a compound of formula I as defined herein, or a pharmaceutically acceptable salt or solvate thereof.

In another aspect, the present invention provides a compound of formula I as defined herein, or a pharmaceutically acceptable salt or solvate thereof for use in the treatment of disease or condition associated with HSF1 activity.

In another aspect, the present invention provides the use of a compound of formula I as defined herein, or a pharmaceutically acceptable salt or solvate thereof, in the manufacture of a medicament for use in the treatment of disease or condition associated with HSF1 activity.

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

HSF1 activity has been implicated in several diseases, including cancer, and autoimmune, and viral diseases.

The broad activity of HSF1 and the role it plays in many disease states is discussed in the scientific literature, see for example:

Evans, C. G.; Chang, L.; Gestwicki, J. E., Heat Shock Protein 70 (Hsp70) as an Emerging Drug Target. *J Med Chem* 2010, 53 (12), 4585-4602;

Calderwood, S. K.; Khaleque, M. A.; Sawyer, D. B.; Ciocca, D. R., Heat shock proteins in cancer: chaperones of tumorigenesis. *Trends Biochem Sci* 2006, 31 (3), 164-172;

Dai, C.; Whitesell, L.; Rogers, A. B.; Lindquist, S., Heat shock factor 1 is a powerful multifaceted modifier of carcinogenesis. *Cell* 2007, 130 (6), 1005-1018;

Whitesell, L.; Lindquist, S., Inhibiting the transcription factor HSF1 as an anticancer strategy. *Expert Opin Ther Tar* 2009, 13 (4), 469-478; and Powers, M. V.; Workman, P., Inhibitors of the heat shock response: Biology and pharmacology. *Febs Lett* 2007, 581 (19), 3758-3769;

the entire contents of which are incorporated herein by reference.

HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g. promyelocytic leukemia), head and neck cancer, and Hodgkin's disease.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their HSF1 inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery, radiotherapy or therapy with a chemotherapeutic agent or a molecularly targeted agent. Such additional therapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the plateletderived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) HSP90 inhibitors (for example, geldanamycin, radicicol or 17-N-Allylamino-17-demethoxygeldanamycin (17AAG));

(ix) antisense therapies, for example those which are directed to the targets listed above, such as ISIS 2503, an anti-ras antisense;

(x) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (xi) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

It is anticipated that the HSF1 inhibitors of the present invention are particularly suited to combination therapy with anti-tumour agents that inhibit HSP90 (for example, geldanamycin, radicicol or 17-N-Allylamino-17-demethoxygeldanamycin (17AAG)).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(xi) above.

In a further aspect of the invention there is provided a compound of the invention or a pharmaceutically acceptable salt or solvate thereof, in combination with an anti-tumour agent selected from one listed under (i)-(xi) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(xi) herein above, in association with a pharmaceutically acceptable diluent or carrier.

In another aspect, the compounds of the present invention may be used for the treatment of other HSF1-mediated diseases or conditions, such as autoimmune and viral diseases. In the case of autoimmune diseases, the compounds of the invention may be combined with other agents for the treatment of autoimmune conditions, for example, steroids and other immunosuppressant agents. In the case of viral diseases, the compounds of the invention may be administered with one or more additional antiviral agents.

EXAMPLES

Preparation of Compound 1, N-(4-methyl-3-nitrophenyl)-2,3-dihydrobenzo[b][1,4]dioxine-6-carboxamide Oxalyl chloride (1.40 mL, 16.6 mmol) was added dropwise to a solution of 1,4-benzodioxane-6-carboxylic acid (2.486 g, 13.80 mmol) and DMF (0.027 mL, 0.34 mmol) in dry DCM (34 mL). The reaction mixture was stirred at rt for 3.5 h, and then concentrated. The residue was dissolved in DCM and concentrated again. This residue was dissolved in dry DCM (12 mL) and added dropwise to a solution of 4-methyl-3-nitroaniline (2.100 g, 13.80 mmol) and pyridine (2.23 mL, 27.6 mmol) in dry DCM (25 mL). The reaction mixture was stirred at rt for 2 h, and then concentrated. The resulting solid was suspended in MeOH, diluted with water and then isolated by filtration and washed with water to afford the title compound (4.24 g, 98%) as a pale tan coloured solid. $^1$H NMR (500 MHz, DMSO) δ 10.39 (s, 1H), 8.54 (d, J=2.2 Hz, 1H), 7.99 (dd, J=8.4, 2.3 Hz, 1H), 7.55 (d, J=2.1 Hz, 1H), 7.52 (dd, J=8.4, 2.2 Hz, 1H), 7.47 (dd, J=8.4, 0.8 Hz, 1H), 7.01 (d, J=8.4 Hz, 1H), 4.34-4.29 (m, 4H), 2.49 (s, 3H). HRMS (ESI⁺): calcd for $C_{16}H_{15}N_2O_5$ (M+H)⁺, 315.0976; found 315.0982.

Preparation of Compound 2, N-(3-amino-4-methylphenyl)-2,3-dihydrobenzo[b][1,4]dioxine-6-carboxamide Palladium (10% on activated carbon, 0.567 g) was added to a suspension of Compound 1 (4.237 g, 13.48 mmol) in ethanol (90 mL) and ethyl acetate (90 mL). The reaction mixture was stirred under hydrogen (1 atm) at 28° C. overnight, filtered through celite with EtOAc, and concentrated, to afford the title compound (3.803 g, 99%) as a pale yellow amorphous solid. ¹H NMR (500 MHz, DMSO) δ 9.70 (s, 1H), 7.49 (d, J=2.2 Hz, 1H), 7.46 (dd, J=8.3, 2.2 Hz, 1H), 7.10 (d, J=2.0 Hz, 1H), 6.95 (d, J=8.4 Hz, 1H), 6.83 (d, J=8.1 Hz, 1H), 6.79 (dd, J=8.1, 2.0 Hz, 1H), 4.81 (s, 2H), 4.32-4.26 (m, 4H), 2.01 (s, 3H). HRMS (ESI⁺): calcd for $C_{16}H_{17}N_2O_3$ (M+H)⁺, 285.1234; found 285.1233.

Example 1, N-(5-(2,3-dihydrobenzo[b][1,4]dioxine-6-carboxamido)-2-methylphenyl)quinoline-6-carboxamide 2-(7-Aza-1H-benzotriazole-1-yl)-1,1,3,3-tetramethyluronium hexafluorophosphate (HATU, 3.34 g, 8.79 mmol) was added to a solution of 6-quinolinecarboxylic acid (1.34 g, 7.74 mmol) and N,N-diisopropylethylamine (DIEA, 2.76 mL, 15.8 mmol) in dry DMF (40 mL). The reaction mixture was stirred for 6 min, before Compound 2 was added (2.00 g, 7.03 mmol). The reaction mixture was stirred at rt overnight, diluted with water and the resulting precipitate isolated by filtration, washed with water and dried to afford the title compound (3.09 g, 100%) as an off-white solid. ¹H NMR (500 MHz, DMSO) δ 10.18 (s, 1H), 10.08 (s, 1H), 9.02 (dd, J=4.2, 1.7 Hz, 1H), 8.67 (d, J=2.0 Hz, 1H), 8.54 (dd, J=8.4, 1.9 Hz, 1H), 8.29 (dd, J=8.8, 2.1 Hz, 1H), 8.15 (d, J=8.8 Hz, 1H), 7.88 (d, J=2.2 Hz, 1H), 7.65 (dd, J=8.3, 4.2 Hz, 1H), 7.59 (dd, J=8.2, 2.2 Hz, 1H), 7.54 (d, J=2.2 Hz, 1H), 7.51 (dd, J=8.4, 2.2 Hz, 1H), 7.25 (d, J=8.4 Hz, 1H), 6.98 (d, J=8.4 Hz, 1H), 4.34-4.28 (m, 4H), 2.25 (s, 3H). HRMS (ESI⁺): calcd for $C_{26}H_{22}N_3O_4$ (M+H)⁺, 440.1605; found 440.1598.

Examples 2 to 48

The following compounds were synthesised according to the procedure for Example 1, by substituting the appropriate carboxylic acid for 6-quinolinecarboxylic acid:

Example 2, N-(5-(2,3-dihydrobenzo[b][1,4]dioxine-6-carboxamido)-2-methylphenyl)isoquinoline-7-carboxamide Example 3, N-(5-(2,3-dihydrobenzo[b][1,4]dioxine-6-carboxamido)-2-methylphenyl)-2-(2-methoxyethoxy)quinoline-6-carboxamide Example 4, N-(4-methyl-3-(2-oxo-2H-chromene-6-carboxamido)phenyl)-2,3-dihydrobenzo[b][1,4]dioxine-6-carboxamide Example 5, N-(3-(3,4-dimethoxybenzamido)-4-methylphenyl)-2,3-dihydrobenzo[b][1,4]dioxine-6-carboxamide Example 6, N-(3-(2,3-dihydrobenzofuran-5-carboxamido)-4-methylphenyl)-2,3-dihydrobenzo[b][1,4]dioxine-6-carboxamide Example 7, N-(5-(2,3-dihydrobenzo[b][1,4]dioxine-6-carboxamido)-2-methylphenyl)-1-methylindoline-5-carboxamide Example 8, N-(4-methyl-3-(1-oxo-1,3-dihydroisobenzofuran-5-carboxamido)phenyl)-2,3-dihydrobenzo[b][1,4]dioxine-6-carboxamide Example 9, N-(3-(chroman-6-carboxamido)-4-methylphenyl)-2,3-dihydrobenzo[b][1,4]dioxine-6-carboxamide Example 10, N-(5-(2,3-dihydrobenzo[b][1,4]dioxine-6-carboxamido)-2-methylphenyl)quinazoline-6-carboxamide Example 11, N-(5-(2,3-dihydrobenzo[b][1,4]dioxine-6-carboxamido)-2-methylphenyl)-4-methoxyquinoline-6-carboxamide Example 12, 2-chloro-N-(5-(2,3-dihydrobenzo[b][1,4]dioxine-6-carboxamido)-2-methylphenyl)quinoline-6-carboxamide Example 13, N-(5-(2,3-dihydrobenzo[b][1,4]dioxine-6-carboxamido)-2-methylphenyl)-6-(thiazol-4-ylmethoxy)nicotinamide Example 14, N-(4-methyl-3-(2-methyl-2,3-dihydrobenzofuran-5-carboxamido)phenyl)-2,3-dihydrobenzo[b][1,4]dioxine-6-carboxamide Example 15, N-(3-(1,3-dihydroisobenzofuran-5-carboxamido)-4-methylphenyl)-2,3-dihydrobenzo[b][1,4]dioxine-6-carboxamide Example 16, N-(5-(2,3-dihydrobenzo[b][1,4]dioxine-6-carboxamido)-2-methylphenyl)-1-methyl-1H-indole-5-carboxamide Example 17, N-(3-(benzofuran-5-carboxamido)-4-methylphenyl)-2,3-dihydrobenzo[b][1,4]dioxine-6-carboxamide Example 18, N-(3-(benzo[b]thiophene-5-carboxamido)-4-methylphenyl)-2,3-dihydrobenzo[b][1,4]dioxine-6-carboxamide Example 19, N-(4-methyl-3-(4-(pyridin-2-ylmethoxy)benzamido)phenyl)-2,3-dihydrobenzo[b][1,4]dioxine-6-carboxamide Example 20, N-(4-methyl-3-(4-(thiazol-5-ylmethoxy)benzamido)phenyl)-2,3-dihydrobenzo[b][1,4]dioxine-6-carboxamide Example 21, tert-butyl (2-((6-((5-(2,3-dihydrobenzo[b][1,4]dioxine-6-carboxamido)-2-methylphenyl)carbamoyl)quinolin-2-yl)oxy)ethyl)carbamate Example 22, N-(5-(2,3-dihydrobenzo[b][1,4]dioxine-6-carboxamido)-2-methylphenyl)-4-methoxy-2-(2-methoxyethoxy)quinoline-6-carboxamide Example 23, 6-((5-(2,3-dihydrobenzo[b][1,4]dioxine-6-carboxamido)-2-methylphenyl)carbamoyl)quinoline 1-oxide Example 24, 4-cyano-N-(5-(2,3-dihydrobenzo[b][1,4]dioxine-6-carboxamido)-2-methylphenyl)quinoline-6-carboxamide Example 25, N-(5-(2,3-dihydrobenzo[b][1,4]dioxine-6-carboxamido)-2-methylphenyl)-6-(pyridin-2-ylmethoxy)nicotinamide Example 26, N-(3-(4-methoxy-3-methylbenzamido)-4-methylphenyl)-2,3-dihydrobenzo[b][1,4]dioxine-6-carboxamide Example 27, N-(3-(4-methoxybenzamido)-4-methylphenyl)-2,3-dihydrobenzo[b][1,4]dioxine-6-carboxamide Example 28, N-(3-(3-chloro-4-methoxybenzamido)-4-methylphenyl)-2,3-dihydrobenzo[b][1,4]dioxine-6-carboxamide Example 29, N-(5-(2,3-dihydrobenzo[b][1,4]dioxine-6-carboxamido)-2-methylphenyl)-2-methoxyquinoline-6-carboxamide Example 30, tert-butyl 5-((5-(2,3-dihydrobenzo[b][1,4]dioxine-6-carboxamido)-2-methylphenyl)carbamoyl)indoline-1-carboxylate Example 31, tert-butyl 6-((5-(2,3-dihydrobenzo[b][1,4]dioxine-6-carboxamido)-2-methylphenyl)carbamoyl)-3,4-dihydroisoquinoline-2(1H)-carboxylate Example 32, N-(5-(2,3-dihydrobenzo[b][1,4]dioxine-6-carboxamido)-2-methylphenyl)-2-morpholinoquinoline-6-carboxamide Example 33, N5-(5-(2,3-dihydrobenzo[b][1,4]dioxine-6-carboxamido)-2-methylphenyl)-N2-methylpyridine-2,5-dicarboxamide Example 34, N-(4-methyl-3-(5,6,7,8-tetrahydronaphthalene-2-carboxamido)phenyl)-2,3-dihydrobenzo[b][1,4]dioxine-6-carboxamide Example 35, tert-butyl (3-((6-((5-(2,3-dihydrobenzo[b][1,4]dioxine-6-carboxamido)-2-methylphenyl)carbamoyl)quinolin-2-yl)oxy)propyl)carbamate Example 36, N-(5-(2,3-dihydrobenzo[b][1,4]dioxine-6-carboxamido)-2-methylphenyl)quinoxaline-6-carboxamide Example 37, N-(5-(2,3-dihydrobenzo[b][1,4]dioxine-6-carboxamido)-2-methylphenyl)-6-phenylnicotinamide Example 38, N-(5-(2,3-dihydrobenzo[b][1,4]dioxine-6-carboxamido)-2-methylphenyl)-6-((3-iodophenyl)amino)nicotinamide Example 39, N-(5-(2,3-dihydrobenzo[b][1,4]dioxine-6-carboxamido)-2-methylphenyl)-2-methylquinoline-6-carboxamide Example 40, N-(3-(3-methoxybenzamido)-4-methylphenyl)-2,3-dihydrobenzo[b][1,4]dioxine-6-carboxamide Example 41, N-(3-(4-bromo-3-methoxybenzamido)-4-methylphenyl)-2,3-dihydrobenzo[b][1,4]dioxine-6-carboxamide Example 42, N-(3-(4-methoxy-3,5-dimethylbenzamido)-4-methylphenyl)-2,3-dihydrobenzo[b][1,4]dioxine-6-carboxamide Example 43, N-(5-(2,3-dihydrobenzo[b][1,4]dioxine-6-carboxamido)-2-methylphenyl)-1,6-naphthyridine-3-carboxamide Example 44, N-(5-(2,3-dihydrobenzo[b][1,4]dioxine-6-carboxamido)-2-methylphenyl)-1,7-naphthyridine-3-carboxamide Example 45, N-(5-(2,3-dihydrobenzo[b][1,4]dioxine-6-carboxamido)-2-methylphenyl)-1,8-naphthyridine-3-carboxamide Example 46, N-(5-(2,3-dihydrobenzo[b][1,4]dioxine-6-carboxamido)-2-methylphenyl)isoquinoline-6-carboxamide Example 47, N-(5-(2,3-dihydrobenzo[b][1,4]dioxine-6-carboxamido)-2-methylphenyl)quinoline-3-carboxamide Example 48, N-(5-(2,3-dihydrobenzo[b][1,4]dioxine-6-carboxamido)-2-methylphenyl)-2-oxo-1,2-dihydroquinoline-6-carboxamide

TABLE A

|  | 1H NMR | Mass Spec |
|---|---|---|
| Example 2 | $^1$H NMR (500 MHz, DMSO) δ 10.25 (s, 1H), 10.08 (s, 1H), 9.57 (s, 1H), 8.86 (s, 1H), 8.65 (d, J = 5.8 Hz, 1H), 8.36 (dd, J = 8.6, 1.5 Hz, 1H), 8.18 (d, J = 8.6 Hz, 1H), 8.04 (d, J = 5.8 Hz, 1H), 7.90 (d, J = 1.9 Hz, 1H), 7.59 (dd, J = 8.3, 2.1 Hz, 1H), 7.54 (d, J = 2.1 Hz, 1H), 7.51 (dd, J = 8.4, 2.1 Hz, 1H), 7.26 (d, J = 8.4 Hz, 1H), 6.98 (d, J = 8.4 Hz, 1H), 4.31 (m, 4H), 2.25 (s, 3H). | Found [M + H]$^+$ = 440.1604 C26H22N3O4 requires 440.1605 |
| Example 3 | $^1$H NMR (500 MHz, DMSO) δ 10.07 (s, 1H), 10.07 (s, 1H), 8.57 (d, J = 1.9 Hz, 1H), 8.39 (d, J = 8.8 Hz, 1H), 8.22 (dd, J = 8.7, 2.0 Hz, 1H), 7.86 (m, 2H), 7.58 (dd, J = 8.3, 2.1 Hz, 1H), 7.54 (d, J = 2.1 Hz, 1H), 7.51 (dd, J = 8.4, 2.2 Hz, 1H), 7.23 (d, J = 8.4 Hz, 1H), 7.13 (d, J = 8.8 Hz, 1H), 6.98 (d, J = 8.4 Hz, 1H), 4.60-4.56 (m, 2H), 4.33-4.28 (m, 4H), 3.78-3.70 (m, 2H), 3.33 (s, 3H), 2.23 (s, 3H). | Found [M + H]$^+$ = 514.1969 C29H28N3O6 requires 514.1973 |
| Example 4 | $^1$H NMR (500 MHz, DMSO) δ 10.08 (s, 1H), 10.07 (s, 1H), 8.37 (d, J = 2.2 Hz, 1H), 8.22 (d, J = 2.1 Hz, 1H), 8.19 (d, J = 9.4 Hz, 1H), 7.84 (d, J = 2.2 Hz, 1H), 7.60-7.52 (m, 3H), 7.51 (dd, J = 8.5, 2.2 Hz, 1H), 7.23 (d, J = 8.5 Hz, 1H), 6.98 (d, J = 8.4 Hz, 1H), 6.60 (d, J = 9.6 Hz, 1H), 4.31 (m, 4H), 2.21 (s, 3H). | Found [M + H]$^+$ = 457.1395 C26H21N2O6 requires 457.1394 |
| Example 5 | $^1$H NMR (500 MHz, DMSO) δ 10.05 (s, 1H), 9.79 (s, 1H), 7.80 (d, J = 2.2 Hz, 1H), 7.64 (dd, J = 8.4, 2.1 Hz, 1H), 7.58-7.55 (m, 2H), 7.53 (d, J = 2.1 Hz, 1H), 7.50 (dd, J = 8.4, 2.2 Hz, 1H), 7.22 (d, J = 8.5 Hz, 1H), 7.08 (d, J = 8.5 Hz, 1H), 6.98 (d, J = 8.4 Hz, 1H), 4.35-4.26 (m, 4H), 3.84 (s, 3H), 3.84 (s, 3H), 2.19 (s, 3H). | Found [M + H]$^+$ = 449.1707 C25H25N2O6 requires 449.1707 |
| Example 6 | $^1$H NMR (500 MHz, DMSO) δ 10.04 (s, 1H), 9.68 (s, 1H), 7.89 (d, J = 1.9 Hz, 1H), 7.82-7.78 (m, 2H), 7.56 (dd, J = 8.2, 2.2 Hz, 1H), 7.53 (d, J = 2.1 Hz, 1H), 7.50 (dd, J = 8.5, 2.2 Hz, 1H), 7.20 (d, J = 8.4 Hz, 1H), 6.98 (d, J = 8.4 Hz, 1H), 6.87 (d, J = 8.2 Hz, 1H), 4.63 (t, J = 8.7 Hz, 2H), 4.30 (m, 4H), 3.25 (t, J = 8.7 Hz, 2H), 2.18 (s, 3H). | Found [M + H]$^+$ = 431.1586 C25H23N2O5 requires 431.1602 |
| Example 7 | $^1$H NMR (500 MHz, DMSO) δ 10.02 (s, 1H), 9.46 (s, 1H), 7.78 (d, J = 2.2 Hz, 1H), 7.75 (dd, J = 8.2, 1.9 Hz, 1H), 7.68 (d, J = 1.9 Hz, 1H), 7.58-7.52 (m, 2H), 7.50 (dd, J = 8.5, 2.3 Hz, 1H), 7.18 (d, J = 8.3 Hz, 1H), 6.97 (d, J = 8.4 Hz, 1H), 6.53 (d, J = 8.2 Hz, 1H), 4.33-4.28 (m, 4H), 3.40 (t, J = 8.3 Hz, 2H), 2.96 (t, J = 8.3 Hz, 2H), 2.79 (s, 3H), 2.17 (s, 3H). | Found [M + H]$^+$ = 444.1920 C26H26N3O4 requires 444.1918 |
| Example 8 | $^1$H NMR (500 MHz, DMSO) δ 10.21 (s, 1H), 10.08 (s, 1H), 8.23 (s, 1H), 8.15 (d, J = 8.0 Hz, 1H), 8.01 (d, J = 8.0 Hz, 1H), 7.85 (d, J = 2.2 Hz, 1H), 7.59 (dd, J = 8.2, 2.2 Hz, 1H), 7.53 (d, J = 2.1 Hz, 1H), 7.51 (dd, J = 8.3, 2.2 Hz, 1H), 7.24 (d, J = 8.4 Hz, 1H), 6.98 (d, J = 8.4 Hz, 1H), 5.51 (s, 2H), 4.33-4.28 (m, 4H), 2.21 (s, 3H). | Found [M + H]$^+$ = 445.1396 C25H21N2O6 requires 445.1394 |
| Example 9 | $^1$H NMR (500 MHz, DMSO) δ 10.03 (s, 1H), 9.68 (s, 1H), 7.79-7.75 (m, 2H), 7.73 (dd, J = 8.5, 2.2 Hz, 1H), 7.56 (dd, J = 8.3, 2.2 Hz, 1H), 7.53 (d, J = 2.1 Hz, 1H), 7.50 (dd, J = 8.4, 2.2 Hz, 1H), 7.20 (d, J = 8.5 Hz, 1H), 6.98 (d, J = 8.4 Hz, 1H), 6.84 (d, J = 8.5 Hz, 1H), 4.34- | Found [M + H]$^+$ = 445.1753 C26H25N2O5 |

TABLE A-continued

|  | 1H NMR | Mass Spec |
|---|---|---|
|  | 4.27 (m, 4H), 4.23-4.17 (m, 2H), 2.82 (t, J = 6.3 Hz, 2H), 2.17 (s, 3H), 2.00-1.92 (m, 2H). | requires 445.1758 |
| Example 10 | $^1$H NMR (500 MHz, DMSO) δ 10.31 (s, 1H), 10.09 (s, 1H), 9.79 (s, 1H), 9.41 (s, 1H), 8.84 (d, J = 1.9 Hz, 1H), 8.54 (dd, J = 8.8, 2.0 Hz, 1H), 8.16 (d, J = 8.8 Hz, 1H), 7.89 (d, J = 2.2 Hz, 1H), 7.59 (dd, J = 8.2, 2.2 Hz, 1H), 7.54 (d, J = 2.2 Hz, 1H), 7.51 (dd, J = 8.5, 2.2 Hz, 1H), 7.26 (d, J = 8.6 Hz, 1H), 6.98 (d, J = 8.5 Hz, 1H), 4.33-4.28 (m, 4H), 2.25 (s, 3H). | Found [M + H]$^+$ = 441.1553 C25H21N4O4 requires 441.1557 |
| Example 11 | $^1$H NMR (500 MHz, DMSO) δ 10.25 (s, 1H), 10.07 (s, 1H), 8.87-8.82 (m, 2H), 8.28 (dd, J = 8.8, 2.1 Hz, 1H), 8.07 (d, J = 8.8 Hz, 1H), 7.84 (d, J = 2.2 Hz, 1H), 7.59 (dd, J = 8.3, 2.2 Hz, 1H), 7.54 (d, J = 2.2 Hz, 1H), 7.51 (dd, J = 8.5, 2.2 Hz, 1H), 7.24 (d, J = 8.2 Hz, 1H), 7.15 (d, J = 5.3 Hz, 1H), 6.98 (d, J = 8.4 Hz, 1H), 4.33-4.28 (m, 4H), 4.12 (s, 3H), 2.23 (s, 3H). | Found [M + H]$^+$ = 470.1699 C27H24N3O5 requires 470.1710 |
| Example 12 | $^1$H NMR (500 MHz, DMSO) δ 10.22 (s, 1H), 10.08 (s, 1H), 8.72 (d, J = 1.9 Hz, 1H), 8.63 (d, J = 8.4 Hz, 1H), 8.34 (dd, J = 8.8, 2.0 Hz, 1H), 8.09 (d, J = 8.8 Hz, 1H), 7.88 (d, J = 2.1 Hz, 1H), 7.71 (d, J = 8.6 Hz, 1H), 7.59 (dd, J = 8.3, 2.2 Hz, 1H), 7.54 (d, J = 2.1 Hz, 1H), 7.51 (dd, J = 8.5, 2.2 Hz, 1H), 7.25 (d, J = 8.5 Hz, 1H), 6.98 (d, J = 8.4 Hz, 1H), 4.33-4.28 (m, 4H), 2.24 (s, 3H). | Found [M + H]$^+$ = 474.1181 C26H21$^{35}$ClN3O4 requires 474.1215 |
| Example 13 | $^1$H NMR (500 MHz, DMSO) δ 10.06 (s, 1H), 9.95 (s, 1H), 9.13 (d, J = 1.9 Hz, 1H), 8.83 (dd, J = 2.4, 0.8 Hz, 1H), 8.28 (dd, J = 8.7, 2.5 Hz, 1H), 7.83 (d, J = 2.2 Hz, 1H), 7.80-7.79 (m,, 1H), 7.57 (d, J = 8.3, 2.2 Hz, 1H), 7.53 (d, J = 2.2 Hz, 1H), 7.51 (dd, J = 8.4, 2.2 Hz, 1H), 7.22 (d, J = 8.6 Hz, 1H), 7.02 (dd, J = 8.7, 0.8 Hz, 1H), 6.98 (d, J = 8.4 Hz, 1H), 5.56 (s, 2H), 4.33-4.28 (m,, 4H), 2.20 (s, 3H). | Found [M + H]$^+$ = 503.1380 C26H23N4O5S requires 503.1384 |
| Example 14 | $^1$H NMR (500 MHz, DMSO) δ 10.04 (s, 1H), 9.67 (s, 1H), 7.87-7.85 (m, 1H), 7.82-7.77 (m, 2H), 7.56 (dd, J = 8.3, 2.2 Hz, 1H), 7.53 (d, J = 2.0 Hz, 1H), 7.50 (dd, J = 8.4, 2.2 Hz, 1H), 7.20 (d, J = 8.4 Hz, 1H), 6.98 (d, J = 8.4 Hz, 1H), 6.84 (d, J = 8.4 Hz, 1H), 5.06-4.98 (m, 1H), 4.33-4.28(m, 4H), 3.39 (dd, J = 15.8, 8.9 Hz, 1H), 2.85 (d, J = 15.8, 7.4 Hz,1H), 2.18 (s, 3H), 1.41 (d, J = 6.2 Hz, 3H). | Found [M + H]$^+$ = 445.1757 C26H25N2O5 requires 445.1758 |
| Example 15 | $^1$H NMR (500 MHz, DMSO) δ 10.06 (s, 1H), 9.91 (s, 1H), 7.94-7.89 (m, 2H), 7.82 (d, J = 2.1 Hz, 1H), 7.58 (dd, J = 8.3, 2.2 Hz, 1H), 7.53 (d, J = 2.2 Hz, 1H), 7.51 (dd, J = 8.4, 2.2 Hz, 1H), 7.46 (d, J = 8.2 Hz, 1H), 7.22 (d, J = 8.5 Hz, 1H), 6.98 (d, J = 8.4 Hz, 1H), 5.08 (s, 4H), 4.33-4.28 (m, 4H), 2.20 (s, 3H). | Found [M + H]$^+$ = 431.1600 C22H23N2O5 requires 431.1602 |
| Example 16 | $^1$H NMR (500 MHz, DMSO) δ 10.04 (s, 1H), 9.76 (s, 1H), 8.29 (d, J = 1.7 Hz, 1H), 7.86-7.80 (m, 2H), 7.58 (d, J = 8.2, 2.2 Hz, 1H), 7.56-7.53 (m, 2H), 7.51 (dd, J = 8.3, 2.2 Hz, 1H), 7.45 (d, J = 3.1 Hz, 1H), 7.21 (d, J = 8.3 Hz, 1H), 6.98 (d, J = 8.4 Hz, 1H), 6.58 (d, J = 3.0 Hz, 1H), 4.33-4.28 (m, 4H), 3.85 (s, 3H), 2.22 (s, 3H). | Found [M + H]$^+$ = 442.17556 C26H24N3O4 requires 442.1761 |
| Example 17 | $^1$H NMR (500 MHz, DMSO) δ 10.06 (s, 1H), 9.94 (s, 1H), 8.34 (d, J = 1.6 Hz, 1H), 8.12 (d, J = 2.2 Hz, 1H), 7.97 (dd, J = 8.6, 1.8 Hz, 1H), 7.84 (d, J = 2.1 Hz, 1H), 7.74 (d, J = 8.6 Hz, 1H), 7.58 (dd, J = 8.3, 2.2 Hz, 1H), 7.54 (d, J = 2.1 Hz, 1H), 7.51 (dd, J = 8.4, 2.1 Hz, 1H), 7.22 (d, J = 8.4 Hz, 1H), 7.11 (dd, J = 2.2, 0.9 Hz, 1H), 6.98 (d, J = 8.4 Hz, 1H), 4.33-4.28 (m, 4H), 2.22 (s, 3H). | Found [M + H]$^+$ = 429.1435 C25H21N2O5 requires 429.1445 |
| Example 18 | $^1$H NMR (500 MHz, DMSO) δ 10.07 (s, 1H), 10.01 (s, 1H), 8.54 (d, J = 1.4 Hz, 1H), 8.16 (d, J = 8.4 Hz, 1H), 7.96 (d, J = 8.5, 1.7 Hz, 1H), 7.90 (d, J = 5.4 Hz, 1H), 7.85 (d, J = 2.2 Hz, 1H), 7.61 (d, J = 5.5, 0.8 Hz, 1H), 7.59 (dd, J = 8.2, 2.2 Hz, 1H), 7.54 (d, J = 2.1 Hz, 1H), 7.51 (dd, J = 8.5, 2.2 Hz, 1H), 7.23 (d, J = 8.4 Hz, 1H), 6.98 (d, J = 8.4 Hz, 1H), 4.34-4.27 (m, 4H), 2.23 (s, 3H). | Found [M + H]$^+$ = 445.1214 C25H21N2O4S requires 445.1216 |
| Example 19 | $^1$H NMR (500 MHz, DMSO) δ 10.04 (s, 1H), 9.76 (s, 1H), 8.60 (ddd, J = 4.9, 1.8, 0.9 Hz, 1H), 7.97 (d, J = 8.8 Hz, 2H), 7.85 (td, J = 7.7, 1.8 Hz, 1H), 7.80 (d, J = 2.2 Hz, 1H), 7.59-7.52 (m, 3H), 7.50 (dd, J = 8.5, 2.2 Hz, 1H), 7.37 (ddd, J = 7.6, 4.8, 1.2 Hz, 1H), 7.20 (d, J = 8.4 Hz, 1H), 7.16 (d, J = 8.8 Hz, 2H), 6.98 (d, J = 8.4 Hz, 1H), 5.28 (s, 2H), 4.33-4.28 (m, 4H), 2.18 (s, 3H). | Found [M + H]$^+$ = 496.1867 C29H26N4O5 requires 496.1867 |
| Example 20 | $^1$H NMR (500 MHz, DMSO) δ 10.05 (s, 1H), 9.78 (s, 1H), 9.14 (d, J = 0.8 Hz, 1H), 8.06 (d, J = 0.9 Hz, 1H), 7.98 (d, J = 8.8 Hz, 2H), 7.81 (d, J = 2.2 Hz, 1H), 7.56 (d, J = 8.2, 2.2 Hz, 1H), 7.53 (d, J = 2.1 Hz, 1H), 7.50 (dd, J = 8.5, 2.2 Hz, 1H), 7.21 (d, J = 8.8 Hz, 1H), 7.17 (d, J = 8.8 Hz, 2H), 6.98 (d, J = 8.4 Hz, 1H), 5.50 (s, 2H), 4.33-4.28 (m, 4H), 2.19 (s, 3H). | Found [M + H]$^+$ = 502.1429 C27H24N3O5S requires 502.1431 |
| Example 21 | $^1$H NMR (500 MHz, DMSO) δ 10.07 (s, 1H), 10.07 (s, 1H), 8.57 (d, J = 2.1 Hz, 1H), 8.39 (d, J = 8.8 Hz, 1H), 8.22 (dd, J = 8.8, 2.1 Hz, 1H), 7.86 (d, J = 8.8 Hz, 1H), 7.86 (d, J = 2.2 Hz, 1H), 7.58 (dd, J = 8.5, 2.2 Hz, 1H), 7.54 (d, J = 2.0 Hz, 1H), 7.51 (dd, J = 8.4, 2.2 Hz, 1H), 7.24 (d, J = 8.5 Hz, 1H), 7.09 (d, J = 8.9 Hz, 1H), 7.06 (t, J = 5.6 Hz, 1H), 6.98 (d, J = 8.4 Hz, 1H), 4.45 (t, J = 5.7 Hz, 2H), 4.33-4.28 (m, 2H), 3.39 (ap q, J = 5.7 Hz, 2H), 2.24 (s, 3H), 1.38 (s, 9H). | Found [M + H]$^+$ = 599.2495 C33H35N4O7 requires 599.2500 |
| Example 22 | $^1$H NMR (500 MHz, DMSO) δ 10.13 (s, 1H), 10.06 (s, 1H), 8.69 (d, J = 2.1 Hz, 1H), 8.21 (dd, J = 8.7, 2.1 Hz, 1H), 7.82 (d, J = 2.2 Hz, 1H), 7.79 (d, J = 8.7 Hz, 1H), 7.58 (dd, J = 8.3, 2.3 Hz, 1H), 7.54 (d, J = | Found [M + H]$^+$ = 554.2064 |

TABLE A-continued

|  | 1H NMR | Mass Spec |
|---|---|---|
|  | 2.1 Hz, 1H), 7.51 (dd, J = 8.4, 2.2 Hz, 1H), 7.23 (d, J = 8.3 Hz, 1H), 6.98 (d, J = 8.4 Hz, 1H), 6.60 (s, 1H), 4.59-4.53 (m, 2H), 4.33-4.28 (m, 4H), 3.75-3.68 (m, 2H), 3.33 (s, 3H), 2.21 (s, 3H). | $C_{30}H_{30}N_3O_7$ requires 554.2078 |
| Example 23 | $^1$H NMR (500 MHz, DMSO) δ 10.28 (s, 1H), 10.09 (s, 1H), 8.73 (d, J = 1.9 Hz, 1H), 8.69 (dd, J = 6.1, 1.0 Hz, 1H), 8.64 (d, J = 9.0 Hz, 1H), 8.31 (dd, J = 9.1, 1.9 Hz, 1H), 8.10 (d, J = 8.6 Hz, 1H), 7.88 (d, J = 2.2 Hz, 1H), 7.61-7.55 (m, 2H), 7.54 (d, J = 2.1 Hz, 1H), 7.51 (dd, J = 8.4, 2.2 Hz, 1H), 7.25 (d, J = 8.4 Hz, 1H), 6.98 (d, J = 8.4 Hz, 1H), 4.33-4.28 (m, 4H), 2.24 (s, 3H). | Found $[M + H]^+$ = 456.1553 $C_{26}H_{25}N_3O_5$ requires 456.1554 |
| Example 24 | $^1$H NMR (500 MHz, DMSO) δ 10.49 (s, 1H), 10.10 (s, 1H), 9.24 (d, J = 4.3 Hz, 1H), 8.77 (d, J = 2.0 Hz, 1H), 8.47 (dd, J = 8.8, 2.0 Hz, 1H), 8.34 (d, J = 8.8 Hz, 1H), 8.27 (d, J = 4.3 Hz, 1H), 7.89 (d, J = 2.3 Hz, 1H), 7.61 (dd, J = 8.3, 2.2 Hz, 1H), 7.54 (d, J = 2.2 Hz, 1H), 7.51 (dd, J = 8.5, 2.2 Hz, 1H), 7.27 (d, J = 8.5 Hz, 1H), 6.99 (d, J = 8.4 Hz, 1H), 4.33-4.28 (m, 4H), 2.25 (s, 3H). | Found $[M + H]^+$ = 465.1557 $C_{27}H_{21}N_4O_4$ requires 465.1557 |
| Example 25 | $^1$H NMR (500 MHz, DMSO) δ 10.06 (s, 1H), 9.94 (s, 1H), 8.79 (dd, J = 2.5, 0.8 Hz, 1H), 8.57 (ddd, J = 4.8, 1.8, 0.9 Hz, 1H), 8.29 (dd, J = 8.7, 2.5 Hz, 1H), 7.85-7.79 (m, 2H), 7.57 (dd, J = 8.3, 2.2 Hz, 1H), 7.53 (d, J = 2.2 Hz, 1H), 7.50 (dd, J = 8.4, 2.2 Hz, 1H), 7.48 (dt, J = 7.8, 1.0 Hz, 1H), 7.34 (ddd, J = 7.6, 4.8, 1.1 Hz, 1H), 7.22 (d, J = 8.5 Hz, 1H), 7.09 (dd, J = 8.7, 0.8 Hz, 1H), 6.98 (d, J = 8.4 Hz, 1H), 5.52 (s, 2H), 4.33-4.28 (m, 4H), 2.19 (s, 3H). | Found $[M + H]^+$ = 497.1816 $C_{28}H_{25}N_4O_5$ requires 497.1820 |
| Example 26 | $^1$H NMR (500 MHz, DMSO) δ 10.04 (s, 1H), 9.71 (s, 1H), 7.87 (dd, J = 8.5, 2.3 Hz, 1H), 7.82 (d, J = 2.2 Hz, 1H), 7.79 (d, J = 2.2 Hz, 1H), 7.56 (dd, J = 8.4, 2.2 Hz, 1H), 7.53 (d, J = 2.1 Hz, 1H), 7.50 (dd, J = 8.5, 2.1 Hz, 1H), 7.20 (d, J = 8.3 Hz, 1H), 7.06 (d, J = 8.6 Hz, 1H), 6.98 (d, J = 8.4 Hz, 1H), 4.33-4.28 (m, 4H), 3.87 (s, 3H), 2.22 (s, 3H), 2.18 (s, 3H). | Found $[M + H]^+$ = 433.1745 $C_{25}H_{25}N_2O_5$ requires 433.1758 |
| Example 27 | $^1$H NMR (500 MHz, DMSO) δ 10.04 (s, 1H), 9.75 (s, 1H), 7.98 (d, J = 8.8 Hz, 2H), 7.80 (d, J = 2.1 Hz, 1H), 7.57 (dd, J = 8.3, 2.2 Hz, 1H), 7.53 (d, J = 2.1 Hz, 1H), 7.50 (dd, J = 8.4, 2.2 Hz, 1H), 7.21 (d, J = 8.4 Hz, 1H), 7.06 (d, J = 8.8 Hz, 2H), 6.98 (d, J = 8.4 Hz, 1H), 4.34-4.27 (m, 4H), 3.84 (s, 3H), 2.19 (s, 3H). | Found $[M + H]^+$ = 419.1560 $C_{24}H_{23}N_2O_5$ requires 419.1602 |
| Example 28 | $^1$H NMR (500 MHz, DMSO) δ 10.05 (s, 1H), 9.90 (s, 1H), 8.08 (d, J = 2.2 Hz, 1H), 7.99 (dd, J = 8.6, 2.2 Hz, 1H), 7.79 (d, J = 2.2 Hz, 1H), 7.57 (dd, J = 8.2, 2.3 Hz, 1H), 7.53 (d, J = 2.1 Hz, 1H), 7.50 (dd, J = 8.5, 2.2 Hz, 1H), 7.30 (d, J = 8.7 Hz, 1H), 7.21 (d, J = 8.3 Hz, 1H), 6.98 (d, J = 8.4 Hz, 1H), 4.33-4.28 m, 4H), 3.95 (s, 3H), 2.18 (s, 3H). | Found $[M + H]^+$ = 453.1210 $C_{24}H_{22}{}^{35}ClN_2O_5$ requires 453.1212 |
| Example 29 | $^1$H NMR (500 MHz, DMSO) δ 10.07 (s, 1H), 10.07 (s, 1H), 8.57 (d, J = 1.9 Hz, 1H), 8.39 (d, J = 8.9 Hz, 1H), 8.23 (dd, J = 8.7, 2.0 Hz, 1H), 7.89 (d, J = 8.7 Hz, 1H), 7.86 (d, J = 2.1 Hz, 1H), 7.58 (dd, J = 8.3, 2.1 Hz, 1H), 7.54 (d, J = 2.1 Hz, 1H), 7.51 (dd, J = 8.4, 2.2 Hz, 1H), 7.24 (d, J = 8.4 Hz, 1H), 7.12 (d, J = 8.8 Hz, 1H), 6.98 (d, J = 8.4 Hz, 1H), 4.33-4.28 (m, 4H), 4.03 (s, 3H), 2.24 (s, 3H). | Found $[M + H]^+$ = 470.1670 $C_{27}H_{24}N_3O_5$ requires 470.1710 |
| Example 30 | $^1$H NMR (500 MHz, CDCl$_3$) δ 8.08 (d, J = 2.2 Hz, 1H), 7.77 (s, 1H), 7.75-7.70 (m, 2H), 7.67 (dd, J = 8.4, 1.9 Hz, 1H), 7.65 (s, 1H), 7.43 (d, J = 2.2 Hz, 1H), 7.36 (dd, J = 8.4, 2.2 Hz, 1H), 7.21 (d, J = 8.1 Hz, 1H), 6.94 (d, J = 8.4 Hz, 1H), 4.33-4.28 (m, 4H), 4.05 (t, J = 8.5 Hz, 2H), 3.17 (t, J = 8.7 Hz, 2H), 2.32 (s, 3H), 1.59 (s, 9H). | Found $[M + H]^+$ = 530.2270 $C_{30}H_{32}N_3O_6$ requires 530.2286 |
| Example 31 | $^1$H NMR (500 MHz, DMSO) δ 10.05 (s, 1H), 9.86 (s, 1H), 7.82-7.78 (m, 3H), 7.57 (dd, J = 8.3, 2.2 Hz, 1H), 7.53 (d, J = 2.1 Hz, 1H), 7.50 (dd, J = 8.4, 2.2 Hz, 1H), 7.33 (d, J = 8.5 Hz, 1H), 7.21 (d, J = 8.5 Hz, 1H), 6.98 (d, J = 8.4 Hz, 1H), 4.58 (br s, 2H), 4.33-4.28 (m, 4H), 3.59 (t, J = 5.8 Hz, 2H), 2.87 (t, J = 5.9 Hz, 2H), 2.18 (s, 3H), 1.44 (s, 9H). | Found $[M + H]^+$ = 544.2376 $C_{31}H_{34}N_3O_6$ requires 544.2442 |
| Example 32 | $^1$H NMR (500 MHz, DMSO) δ 10.06 (s, 1H), 9.94 (s, 1H), 8.41 (d, J = 2.0 Hz, 1H), 8.19 (d, J = 9.1 Hz, 1H), 8.11 (dd, J = 8.8, 2.1 Hz, 1H), 7.85 (d, J = 2.1 Hz, 1H), 7.64 (d, J = 8.8 Hz, 1H), 7.57 (dd, J = 8.3, 2.2 Hz, 1H), 7.54 (d, J = 2.1 Hz, 1H), 7.51 (dd, J = 8.4, 2.2 Hz, 1H), 7.32 (d, J = 9.3 Hz, 1H), 7.23 (d, J = 8.5 Hz, 1H), 6.98 (d, J = 8.4 Hz, 1H), 4.33-4.27 (m, 4H), 3.77-3.69 (m, 8H), 2.23 (s, 3H). | Found $[M + H]^+$ = 525.2126 $C_{30}H_{29}N_4O_5$ requires 525.2132 |
| Example 33 | $^1$H NMR (500 MHz, DMSO) δ 10.26 (s, 1H), 10.08 (s, 1H), 9.15 (s, 1H), 8.96-8.90 (m, 1H), 8.50 (dd, J = 8.1, 2.0 Hz, 1H), 8.17 (d, J = 8.1 Hz, 1H), 7.88 (d, J = 1.7 Hz, 1H), 7.58 (dd, J = 8.3, 2.1 Hz, 1H), 7.53 (d, J = 2.1 Hz, 1H), 7.51 (dd, J = 8.4, 2.2 Hz, 1H), 7.24 (d, J = 8.5 Hz, 1H), 6.98 (d, J = 8.4 Hz, 1H), 4.33-4.28 (m, 4H), 2.85 (d, J = 4.8 Hz, 3H), 2.22 (s, 3H). | Found $[M + H]^+$ = 447.1662 $C_{24}H_{23}N_4O_5$ requires 447.1663 |
| Example 34 | $^1$H NMR (500 MHz, DMSO) δ 10.04 (s, 1H), 9.78 (s, 1H), 7.79 (d, J = 2.2 Hz, 1H), 7.72-7.68 (m, 2H), 7.57 (dd, J = 8.2, 2.2 Hz, 1H), 7.53 (d, J = 2.1 Hz, 1H), 7.50 (dd, J = 8.5, 2.2 Hz, 1H), 7.20 (ap t, J = 7.7 Hz, 2H), 6.98 (d, J = 8.4 Hz, 1H), 4.33-4.28 (m, 4H), 2.84-2.73 (m, 4H), 2.18 (s, 3H), 1.82-1.73 (m, 4H). | Found $[M + H]^+$ = 443.1954 $C_{27}H_{27}N_2O_4$ requires 443.1965 |
| Example 35 | $^1$H NMR (500 MHz, DMSO) δ 10.07 (s, 2H), 8.56 (d, J = 2.1 Hz, 1H), 8.38 (d, J = 9.0 Hz, 1H), 8.22 (dd, J = 8.7, 2.1 Hz, 1H), 7.88-7.83 | Found $[M + H]^+$ = |

TABLE A-continued

| | 1H NMR | Mass Spec |
|---|---|---|
| | (m, 2H), 7.58 (dd, J = 8.4, 2.2 Hz, 1H), 7.54 (d, J = 2.2 Hz, 1H), 7.51 (dd, J = 8.5, 2.2 Hz, 1H), 7.24 (d, J = 8.3 Hz, 1H), 7.10 (d, J = 8.9 Hz, 1H), 6.98 (d, J = 8.4 Hz, 1H), 6.94 (t, J = 5.8 Hz, 1H), 4.45 (t, J = 6.4 Hz, 1H), 4.33-4.28 (m, 4H), 3.16-3.09 (m, 2H), 2.23 (s, 1H), 1.95-1.88 (m, 2H), 1.37 (s, 9H). | 613.2650 C34H37N4O7 requires 613.2657 |
| Example 36 | $^{1}$H NMR (500 MHz, DMSO) δ 10.34 (s, 1H), 10.09 (s, 1H), 9.10-9.05 (m, 2H), 8.78 (d, J = 2.0 Hz, 1H), 8.38 (dd, J = 8.7, 2.0 Hz, 1H), 8.25 (d, J = 8.7 Hz, 1H), 7.89 (d, J = 2.2 Hz, 1H), 7.61 (dd, J = 8.2, 2.2 Hz, 1H), 7.54 (d, J = 2.2 Hz, 1H), 7.51 (dd, J = 8.4, 2.2 Hz, 1H), 7.26 (d, J = 8.2 Hz, 1H), 6.98 (d, J = 8.4 Hz, 1H), 4.33-4.28 (m, 4H), 2.26 (s, 3H). | Found [M + H]$^+$ = 441.1552 C25H21N4O4 requires 441.1557 |
| Example 37 | $^{1}$H NMR (500 MHz, DMSO) δ 10.14 (s, 1H), 10.08 (s, 1H), 9.23 (d, J = 1.7 Hz, 1H), 8.42 (dd, J = 8.3, 2.2 Hz, 1H), 8.23-8.14 (m, 3H), 7.88 (d, J = 1.9 Hz, 1H), 7.59 (dd, J = 8.3, 2.1 Hz, 1H), 7.58-7.47 (m, 5H), 7.25 (d, J = 8.4 Hz, 1H), 6.98 (d, J = 8.4 Hz, 1H), 4.33-4.28 (m, 4H), 2.24 (s, 3H). | Found [M + H]$^+$ = 466.1762 C28H24N3O4 requires 466.1761 |
| Example 38 | $^{1}$H NMR (500 MHz, DMSO) δ 10.05 (s, 1H), 9.76 (s, 1H), 9.61 (s, 1H), 8.85 (d, J = 2.3 Hz, 1H), 8.32 (t, J = 1.8 Hz, 1H), 8.12 (dd, J = 8.7, 2.4 Hz, 1H), 7.83 (d, J = 2.0 Hz, 1H), 7.70-7.65 (m 1H), 7.57 (dd, J = 8.3, 2.1 Hz, 1H), 7.53 (d, J = 2.1 Hz, 1H), 7.51 (dd, J = 8.4, 2.1 Hz, 1H), 7.30 (d, J = 7.8 Hz, 1H), 7.21 (d, J = 8.5 Hz, 1H), 7.11 (t, J = 8.0 Hz, 1H), 6.98 (d, J = 8.4 Hz, 1H), 6.91 (d, J = 8.7 Hz, 1H), 4.34-4.28 (m, 4H), 2.21 (s, 3H). | Found [M + H]$^+$ = 607.0833 C28H24IN4O4 requires 607.0837 |
| Example 39 | $^{1}$H NMR (500 MHz, DMSO) δ 10.16 (s, 1H), 10.08 (s, 1H), 8.65 (s, 1H), 8.51 (br d, J = 7.3 Hz, 1H), 8.29 (d, J = 8.7 Hz, 1H), 8.06 (d, J = 8.8 Hz, 1H), 7.88 (d, J = 2.1 Hz, 1H), 7.64-7.56 (m, 2H), 7.54 (d, J = 2.1 Hz, 1H), 7.51 (dd, J = 8.4, 2.2 Hz, 1H), 7.25 (d, J = 8.5 Hz, 1H), 6.98 (d, J = 8.4 Hz, 1H), 4.35-4.26 (m, 4H), 2.74 (s, 3H), 2.24 (s, 3H). | Found [M + H]$^+$ = 454.1733 C27H24N3O4 requires 454.1761 |
| Example 40 | $^{1}$H NMR (500 MHz, DMSO) δ 10.06 (s, 1H), 9.91 (s, 1H), 7.81 (d, J = 2.1 Hz, 1H), 7.60-7.55 (m, 2H), 7.55-7.52 (m, 2H), 7.51 (dd, J = 8.4, 2.2 Hz, 1H), 7.45 (t, J = 7.9 Hz, 1H), 7.22 (d, J = 8.6 Hz, 1H), 7.16 (ddd, J = 8.2, 2.7, 1.0 Hz, 1H), 6.98 (d, J = 8.4 Hz, 1H), 4.33-4.28 (m, 4H), 3.84 (s, 3H), 2.19 (s, 3H). | Found [M + H]$^+$ = 419.1606 C24H23N2O5 requires 419.1602 |
| Example 41 | $^{1}$H NMR (500 MHz, DMSO) δ 10.06 (s, 1H), 10.02 (s, 1H), 7.83 (d, J = 2.2 Hz, 1H), 7.75 (d, J = 8.2 Hz, 1H), 7.66 (d, J = 1.9 Hz, 1H), 7.57 (dd, J = 8.2, 2.2 Hz, 1H), 7.55-7.48 (m, 3H), 7.23 (d, J = 8.5 Hz, 1H), 6.98 (d, J = 8.4 Hz, 1H), 4.33-4.28 (m, 4H), 3.95 (s, 3H), 2.19 (s, 3H). | Found [M + H]$^+$ = 497.0705 C24H22$^{79}$BrN2O5 requires 497.0707 |
| Example 42 | $^{1}$H NMR (500 MHz, DMSO) δ 10.05 (s, 1H), 9.76 (s, 1H), 7.78 (d, J = 2.2 Hz, 1H), 7.68 (s, 3H), 7.56 (dd, J = 8.2, 2.2 Hz, 1H), 7.53 (d, J = 2.1 Hz, 1H), 7.50 (dd, J = 8.4, 2.2 Hz, 1H), 7.20 (d, J = 8.4 Hz, 1H), 6.98 (d, J = 8.4 Hz, 1H), 4.33-4.28 (m, 4H), 3.71 (s, 3H), 2.30 (s, 6H), 2.17 (s, 3H). | Found [M + H]$^+$ = 447.1909 C26H27N2O5 requires 447.1914 |
| Example 43 | $^{1}$H NMR (500 MHz, DMSO) δ 10.40 (s, 1H), 10.10 (s, 1H), 9.61-9.57 (m, 2H), 9.19 (d, J = 1.7 Hz, 1H), 8.87 (d, J = 5.9 Hz, 1H), 8.03 (d, J = 5.9 Hz, 1H), 7.93 (d, J = 2.2 Hz, 1H), 7.59 (dd, J = 8.2, 2.2 Hz, 1H), 7.54 (d, J = 2.2 Hz, 1H), 7.51 (dd, J = 8.5, 2.2 Hz, 1H), 7.27 (d, J = 8.3 Hz, 1H), 6.99 (d, J = 8.4 Hz, 1H), 4.35-4.26 (m, 4H), 2.26 (s, 3H). | Found [M + H]$^+$ = 441.1540 C25H21N4O4 requires 441.1557 |
| Example 44 | $^{1}$H NMR (500 MHz, DMSO) δ 10.43 (s, 1H), 10.10 (s, 1H), 9.55-9.47 (m, 2H), 9.05-9.00 (m, 1H), 8.74 (d, J = 5.5 Hz, 1H), 8.10 (dd, J = 5.6, 1.0 Hz, 1H), 7.93 (d, J = 2.2 Hz, 1H), 7.59 (dd, J = 8.3, 2.2 Hz, 1H), 7.54 (d, J = 2.2 Hz, 1H), 7.51 (dd, J = 8.4, 2.2 Hz, 1H), 7.26 (d, J = 8.4 Hz, 1H), 6.99 (d, J = 8.4 Hz, 1H), 4.35-4.25 (m, 4H), 2.26 (s, 3H). | Found [M + H]$^+$ = 441.1559 C25H21N4O4 requires 441.1557 |
| Example 45 | $^{1}$H NMR (500 MHz, DMSO) δ 10.36 (s, 1H), 10.10 (s, 1H), 9.56 (d, J = 2.6 Hz, 1H), 9.21 (dd, J = 4.2, 2.0 Hz, 1H), 9.08 (d, J = 2.6 Hz, 1H), 8.66 (dd, J = 8.1, 2.0 Hz, 1H), 7.92 (d, J = 2.3 Hz, 1H), 7.76 (dd, J = 8.2, 4.2 Hz, 1H), 7.59 (dd, J = 8.3, 2.2 Hz, 1H), 7.54 (d, J = 2.2 Hz, 1H), 7.51 (dd, J = 8.4, 2.2 Hz, 1H), 7.26 (d, J = 8.3 Hz, 1H), 6.98 (d, J = 8.4 Hz, 1H), 4.35-4.26 (m, 4H), 2.26 (s, 3H). | Found [M + H]$^+$ = 441.1573 C25H21N4O4 requires 441.1557 |
| Example 46 | $^{1}$H NMR (500 MHz, DMSO-d6) δ 10.24 (s, 1H), 10.08 (s, 1H), 9.44 (s, 1H), 8.67-8.55 (m, 2H), 8.28 (d, J = 8.6 Hz, 1H), 8.18 (dd, J = 8.5, 1.5 Hz, 1H), 8.00 (d, J = 5.8 Hz, 1H), 7.89 (d, J = 2.0 Hz, 1H), 7.59 (dd, J = 8.3, 2.2 Hz, 1H), 7.56-7.45 (m, 2H), 7.25 (d, J = 8.5 Hz, 1H), 6.98 (d, J = 8.4 Hz, 1H), 4.39-4.21 (m, 4H), 2.25 (s, 3H). | Found [M + H]$^+$ = 440.1589 C26H22N3O4 Requires 440.1605 |
| Example 47 | $^{1}$H NMR (500 MHz, DMSO-d6) δ 10.31 (s, 1H), 10.10 (s, 1H), 9.40 (d, J = 2.2 Hz, 1H), 9.00 (d, J = 1.9 Hz, 1H), 8.18 (d, J = 8.5 Hz, 1H), 8.14 (d, J = 8.8 Hz, 1H), 7.95-7.87 (m, 3H), 7.74 (ddd, J = 8.1, 6.9, 1.1 Hz, 2H), 7.61 (dd, J = 8.3, 2.2 Hz, 1H), 7.57-7.50 (m, 2H), 7.27 (d, J = 8.6 Hz, 1H), 6.99 (d, J = 8.4 Hz, 1H), 4.32 (td, J = 5.1, 3.6 Hz, 4H), 2.27 (s, 3H). | Found [M + H]$^+$ = 440.1592 C26H22N3O4 Requires 440.1605 |

TABLE A-continued

| | 1H NMR | Mass Spec |
|---|---|---|
| Example 48 | $^1$H NMR (500 MHz, DMSO-d6) δ 12.00 (br s, 1H), 10.06 (s, 1H), 9.94 (s, 1H), 8.34 (d, J = 1.8 Hz, 1H), 8.10 (dd, J = 8.6, 2.0 Hz, 1H), 8.01 (d, J = 9.6 Hz, 1H), 7.83 (d, J = 2.1 Hz, 1H), 7.57 (dd, J = 8.3, 2.2 Hz, 1H), 7.53 (d, J = 2.1 Hz, 1H), 7.50 (dd, J = 8.4, 2.2 Hz, 1H), 7.39 (d, J = 8.6 Hz, 1H), 7.22 (d, J = 8.5 Hz, 1H), 6.98 (d, J = 8.4 Hz, 1H), 6.58 (dd, J = 9.5, 1.9 Hz, 1H), 4.33-4.27 (m, 4H), 2.20 (s, 3H). | Found [M + H]$^+$ = 456.1537 C26H22N3O5 Requires 456.1554 |

Preparation of Compound 3, (R)-6-bromo-2-((1-methylpyrrolidin-3-yl)oxy)quinoline NaH (60% in mineral oil, 0.049 g, 1.24 mmol) was added to a solution of (R)-(−)-1-methyl-3-hydroxypyrrolidine (0.125 g, 1.24 mmol) in dry THF (3.5 mL) at 0° C. The reaction mixture was stirred at 0° C. for 5 min, then allowed to warm to rt, and stirred for 35 min before 6-bromo-2-chloroquinoline (0.250 g, 1.03 mmol) was added. The reaction mixture was then heated at reflux for 5 h, cooled to rt, concentrated to remove most of the THF, diluted with water and saturated NaHCO$_3$(aq), extracted with DCM (3×). The combined organic phases were washed with water (1×), dried (MgSO4), and concentrated. The crude material was purified by silica gel column chromatography using a gradient of 2 to 5% MeOH in DCM to afford the title compound (206 mg, 65%) as a pale yellow oil. $^1$H NMR (500 MHz, CDCl$_3$) δ 7.86 (d, J=8.9 Hz, 1H), 7.85-7.83 (m, 1H), 7.68-7.64 (m, 2H), 6.92 (d, J=8.8 Hz, 1H), 5.68-5.63 (m, 1H), 2.94-2.88 (m, 2H), 2.83 (dd, J=10.8, 5.9 Hz, 1H), 2.49-2.36 (m, 5H), 2.08-2.01 (m, 1H). HRMS (ESI$^+$): calcd for C$_{14}$H$_{15}$$^{79}$BrN$_2$O (M+H)$^+$, 307.0440; found 307.0447.

Preparation of Compound 4, (R)-2-((1-methylpyrrolidin-3-yl)oxy)quinoline-6-carboxylic acid hydrochloride nBuLi (2.28 M in hexanes, 0.437 mL, 0.996 mmol) was added dropwise to a solution of Compound 3 (0.204 g, 0.664 mmol) in dry THF (2.2 mL) at −78° C. A precipitate formed which hampered efficient stirring, thus additional THF (1.0 mL) was added. The reaction mixture was stirred at −78° C. for 40-45 min before solid CO$_2$ was added. The reaction mixture was stirred for a few minutes, before being allowed to warm to rt. Water was added, and the reaction mixture concentrated to remove THF. The resulting aqueous solution was washed with EtOAc (1×) and then acidified with 2 M HCl to pH 2-3, and then conc to dryness to afford the title compound (266 mg, contains LiBr), as an off-white solid, and was used in subsequent reactions without further purification. Note: the $^1$H NMR shows 2 sets of peaks for each proton which show positive NOE correlations indicating that these are 2 inter-converting species. $^1$H NMR (500 MHz, DMSO) δ 13.11 (v br s, 1H), 11.46 (br s, 0.5H), 11.15 (br s, 0.5H), 8.61-8.58 (m, 1H), 8.50-8.46 (m, 1H), 8.19-8.14 (m, 1H), 7.7-7.814 (m, 1H), 7.17-7.10 (m, 1H), 5.81-5.76 (m, 0.5H), 5.73-5.69 (m, 0.5H), 4.15-4.06 (m, 0.5H), 3.80-3.74 (m, 0.5H), 3.73-3.61 (m, 1H), 3.59-3.53 (m, 0.5H), 3.32-3.10 (m, 1.5H), 2.89-2.83 (m, 3H), 2.74-2.62 (m, 0.5H), 2.50-2.40 (m, 0.5H), 2.38-2.28 (m, 0.5H), 2.26-2.15 (m, 0.5H). HRMS (ESI$^+$): calcd for C$_{15}$H$_{17}$N$_2$O$_3$ (M+H)$^+$, 273.1234; found 273.1234.

Example 49, (R)—N-(5-(2,3-dihydrobenzo[b][1,4]dioxine-6-carboxamido)-2-methylphenyl)-2-((1-methylpyrrolidin-3-yl)oxy)quinoline-6-carboxamide 2-(7-Aza-1H-benzotriazole-1-yl)-1,1,3,3-tetramethyluronium hexafluorophosphate (HATU, 0.111 g, 0.293 mmol) was added to a solution of Compound 4 (0.086 g, 0.23 mmol) and N,N-diisopropylethylamine (0.17 mL, 1.0 mmol) in dry DMF (1.7 mL). The reaction mixture was stirred for 4 min, before Compound 2 (0.050 g, 0.18 mmol) was added. The reaction mixture was stirred at rt overnight, diluted with water and the resulting precipitate isolated by filtration, washed with water, and dried. The crude material was purified by silica gel column chromatography using a gradient of 5 to 12% MeOH in DCM to afford the title compound (73 mg, 77%) as a white solid. $^1$H NMR (500 MHz, DMSO) δ 10.07 (s, 1H), 10.07 (s, 1H), 8.57 (d, J=2.1 Hz, 1H), 8.38 (d, J=8.9 Hz, 1H), 8.23 (dd, J=8.8, 2.1 Hz, 1H), 7.88-7.83 (m, 2H), 7.58 (dd, J=8.2, 2.2 Hz, 1H), 7.54 (d, J=2.1 Hz, 1H), 7.51 (dd, J=8.4, 2.2 Hz, 1H), 7.24 (d, J=8.4 Hz, 1H), 7.09 (d, J=8.8 Hz, 1H), 6.98 (d, J=8.4 Hz, 1H), 5.65-5.58 (m, 1H), 4.35-4.26 (m, 4H), 2.99-2.94 (m, 1H), 2.84-2.77 (m, 2H), 2.50-2.36 (m, 2H), 2.35 (s, 3H), 2.23 (s, 3H), 1.98-1.87 (m, 1H). HRMS (ESI$^+$): calcd for C$_{31}$H$_{31}$N$_4$O$_5$ (M+H)$^+$, 539.2289; found 539.2285.

Examples 50 to 74

The following compounds were prepared as for Example 49 by substituting the appropriate carboxylic acid compound for Compound 4.

Example 50, N-(5-(2,3-dihydrobenzo[b][1,4]dioxine-6-carboxamido)-2-methylphenyl)-2-((1-methylpiperidin-4-yl)oxy)quinoline-6-carboxamide Example 51, N-(5-(2,3-dihydrobenzo[b][1,4]dioxine-6-carboxamido)-2-methylphenyl)-2-(3-(dimethylamino)propoxy)quinoline-6-carboxamide Example 52, N-(5-(2,3-dihydrobenzo[b][1,4]dioxine-6-carboxamido)-2-methylphenyl)-2-(3-(piperidin-1-yl)propoxy)quinoline-6-carboxamide Example 53, (S)—N-(5-(2,3-dihydrobenzo[b][1,4]dioxine-6-carboxamido)-2-methylphenyl)-2-((1-methylpyrrolidin-2-yl)methoxy)quinoline-6-carboxamide Example 54, N-(5-(2,3-dihydrobenzo[b][1,4]dioxine-6-carboxamido)-2-methylphenyl)-2-(2-(piperidin-1-yl)ethoxy)quinoline-6-carboxamide Example 55, N-(5-(2,3-dihydrobenzo[b][1,4]dioxine-6-carboxamido)-2-methylphenyl)-2-(3-morpholinopropoxy)quinoline-6-carboxamide Example 56, N-(5-(2,3-dihydrobenzo[b][1,4]dioxine-6-carboxamido)-2-methylphenyl)-2-(3-(pyrrolidin-1-yl)propoxy)quinoline-6-carboxamide Example 57, N-(5-(2,3-dihydrobenzo[b][1,4]dioxine-6-carboxamido)-2-methylphenyl)-2-(2-(3-fluoropiperidin-1-yl)ethoxy)quinoline-6-carboxamide Example 58, N-(5-(2,3-dihydrobenzo[b][1,4]dioxine-6-carboxamido)-2-methylphenyl)-2-((2-(dimethylamino)ethyl)(methyl)amino)quinoline-6-carboxamide Example 59, N-(5-(2,3-dihydrobenzo[b][1,4]dioxine-6-carboxamido)-2-methylphenyl)-2-(2-(pyrrolidin-1-yl)ethyl)quinoline-6-carboxamide Example 60, 2-(2-(azetidin-1-yl)ethoxy)-N-(5-(2,3-dihydrobenzo[b][1,4]dioxine-6-carboxamido)-2-methylphenyl)quinoline-6-carboxamide Example 61, N-(5-(2,3-dihydrobenzo[b][1,4]dioxine-6-carboxamido)-2-methylphenyl)-2-(2-(2-methylpyrrolidin-1-yl)ethoxy)quinoline-6-carboxamide Example 62, N-(5-(2,3-dihydrobenzo[b][1,4]dioxine-6-carboxamido)-2-methylphenyl)-2-(2-(dimethylamino)ethoxy)quinoline-6-carboxamide Example 63, N-(5-(2,3-dihydrobenzo[b][1,4]dioxine-6-carboxamido)-2-methylphenyl)-2-(2-(pyrrolidin-1-yl)ethoxy)quinoline-6-carboxamide Example 64, N-(5-(2,3-dihydrobenzo[b][1,4]dioxine-6-carboxamido)-2-methylphenyl)-2-(methyl(2-(pyrrolidin-1-yl)ethyl)amino)quinoline-6-carboxamide Example 65, (S)—N-(5-(2,3-dihydrobenzo[b][1,4]dioxine-6-carboxamido)-2-methylphenyl)-2-(2-(3-fluoropyrrolidin-1-yl)ethoxy)quinoline-6-carboxamide Example 66, N-(5-(2,3-dihydrobenzo[b][1,4]dioxine-6-carboxamido)-2-methylphenyl)-2-(2-morpholinoethoxy)quinoline-6-carboxamide Example 67, N-(5-(2,3-dihydrobenzo[b][1,4]dioxine-6-carboxamido)-2-methylphenyl)-2-(pyrrolidin-1-ylmethyl)quinoline-6-carboxamide formate Example 68, N-(5-(2,3-dihydrobenzo[b][1,4]dioxine-6-carboxamido)-2-methylphenyl)-2-(2-(pyrrolidin-1-yl)propoxy)quinoline-6-carboxamide Example 69, N-(5-(2,3-dihydrobenzo[b][1,4]dioxine-6-carboxamido)-2-methylphenyl)-2-(2-(dimethylamino)ethyl)quinoline-6-carboxamide Example 70, N-(5-(2,3-dihydrobenzo[b][1,4]dioxine-6-carboxamido)-2-methylphenyl)-2-((4-methylpiperazin-1-yl)methyl)quinoline-6-carboxamide Example 71, N-(5-(2,3-dihydrobenzo[b][1,4]dioxine-6-carboxamido)-2-methylphenyl)-2-((dimethylamino)methyl)quinoline-6-carboxamide Example 72, 2-(2-(4,4-difluoropiperidin-1-yl)ethoxy)-N-(5-(2,3-dihydrobenzo[b][1,4]dioxine-6-carboxamido)-2-methylphenyl)quinoline-6-carboxamide Example 73, N-(5-(2,3-dihydrobenzo[b][1,4]dioxine-6-carboxamido)-2-methylphenyl)-2-((1-(pyrrolidin-1-yl)propan-2-yl)oxy)quinoline-6-carboxamide Example 74, N-(5-(2,3-dihydrobenzo[b][1,4]dioxine-6-carboxamido)-2-methylphenyl)-2-(4-methylpiperazin-1-yl)quinoline-6-carboxamide

TABLE B

| | 1H NMR | Mass Spec |
|---|---|---|
| Example 50 | $^1$H NMR (500 MHz, DMSO) δ 10.07 (s, 2H), 8.56 (d, J = 2.1 Hz, 1H), 8.37 (d, J = 8.8 Hz, 1H), 8.22 (dd, J = 8.7, 2.1 Hz, 1H), 7.86 (d, J = 2.1 Hz, 1H), 7.84 (d, J = 8.7 Hz, 1H), 7.58 (dd, J = 8.3, 2.2 Hz, 1H), 7.54 (d, J = 2.1 Hz, 1H), 7.51 (dd, J = 8.4, 2.2 Hz, 1H), 7.24 (d, J = 8.3 Hz, 1H), 7.08 (d, J = 8.9 Hz, 1H), 6.98 (d, J = 8.4 Hz, 1H), 5.35-5.27 (m, 1H), 4.34-4.26 (m, 4H), 2.78 (br s, 2H), 2.38 (br s, 2H), 2.30 (br s, 2H), 2.23 (s, 3H), 2.14-2.06 (m, 2H), 1.85-1.76 (m, 2H). | Found [M + H]$^+$ = 553.2443 C32H32N4O5 requires 553.2446 |
| Example 51 | $^1$H NMR (500 MHz, DMSO) δ 10.07 (s, 2H), 8.56 (d, J = 2.0 Hz, 1H), 8.37 (d, J = 8.8 Hz, 1H), 8.22 (dd, J = 8.7, 2.0 Hz, 1H), 7.88-7.84 (m, 2H), 7.58 (dd, J = 8.3, 2.2 Hz, 1H), 7.54 (d, J = 2.1 Hz, 1H), 7.51 (dd, J = 8.4, 2.2 Hz, 1H), 7.24 (d, J = 8.5 Hz, 1H), 7.10 (d, J = 8.8 Hz, 1H), 6.98 (d, J = 8.4 Hz, 1H), 4.47 (t, J = 6.7 Hz, 2H), 4.34-4.27 (m, 4H), 2.39 (t, J = 7.1 Hz, 2H), 2.24 (s, 3H), 2.17 (s, 6H), 1.93 (p, J = 6.8 Hz, 2H). | Found [M + H]$^+$ = 541.24423 C31H33N4O5 requires 541.2446 |
| Example 52 | $^1$H NMR (500 MHz, DMSO) δ 10.07 (s, 2H), 8.57 (d, J = 2.1 Hz, 1H), 8.38 (d, J = 8.9 Hz, 1H), 8.23 (dd, J = 8.8, 2.1 Hz, 1H), 7.89-7.83 (m, 2H), 7.58 (dd, J = 8.3, 2.1 Hz, 1H), 7.54 (d, J = 2.1 Hz, 1H), 7.51 (dd, J = 8.5, 2.2 Hz, 1H), 7.24 (d, J = 8.4 Hz, 1H), 7.10 (d, J = 8.8 Hz, 1H), 6.98 (d, J = 8.4 Hz, 1H), 4.49 (t, J = 6.5 Hz, 2H), 4.34-4.26 (m, 4H), 2.70-2.30 (m, 6H), 2.24 s, 3H), 2.02 (br s, 2H), 1.56 (br s, 4H), 1.42 (br s, 2H). | Found [M + H]$^+$ = 581.2759 C34H37N4O5 requires 581.2758 |
| Example 53 | $^1$H NMR (500 MHz, DMSO) δ 10.07 (s, 1H), 10.07 (s, 1H), 8.57 (d, J = 1.9 Hz, 1H), 8.39 (d, J = 8.9 Hz, 1H), 8.23 (dd, J = 8.7, 2.0 Hz, 1H), 7.89-7.85 (m, 2H), 7.58 (dd, J = 8.3, 2.1 Hz, 1H), 7.54 (d, J = 2.1 Hz, 1H), 7.51 (dd, J = 8.5, 2.2 Hz, 1H), 7.24 (d, J = 8.5 Hz, 1H), 7.12 (d, J = 8.8 Hz, 1H), 6.98 (d, J = 8.4 Hz, 1H), 4.49 (dd, J = 10.9, 5.3 Hz, 1H), 4.40 (br s, 1H), 4.34-4.26 (m, 4H), 3.05 (br s, 1H), 2.78 (br s, 1H), 2.47 (br s, 3H), 2.37-2.26 (m, 1H), 2.24 (s, 3H), 2.07-1.98 (m, 1H), 1.78-1.66 (m, 3H). | Found [M + H]$^+$ = 553.2448 C32H33N4O5 requires 553.2446 |
| Example 54 | $^1$H NMR (500 MHz, DMSO) δ 10.07 (s, 2H), 8.57 (d, J = 1.9 Hz, 1H), 8.38 (d, J = 8.9 Hz, 1H), 8.22 (dd, J = 8.7, 2.0 Hz, 1H), 7.88-7.84 (m, 2H), 7.58 (dd, J = 8.3, 2.2 Hz, 1H), 7.54 (d, J = 2.1 Hz, 1H), 7.51 (dd, J = 8.4, 2.2 Hz, 1H), 7.24 (d, J = 8.5 Hz, 1H), 7.11 (d, J = 8.8 Hz, 1H), 6.98 (d, J = 8.4 Hz, 1H), 4.60-4.54 (m, 1H), 4.34-4.27 (m, 4H), 2.75 (br s, 1H), 2.61-2.36 (br s, 4H), 2.24 (s, 3H), 1.51 (br s, 4H), 1.39 (brs, 2H). | Found [M + H]$^+$ = 567.2598 C33H35N4O5 requires 567.2602 |
| Example 55 | $^1$H NMR (500 MHz, DMSO) δ 10.07 (s, 2H), 8.56 (d, J = 2.1 Hz, 1H), 8.37 (d, J = 8.9 Hz, 1H), 8.22 (dd, J = 8.7, 2.0 Hz, 1H), 7.88-7.83 (m, 2H), 7.58 (dd, J = 8.4, 2.2 Hz, 1H), 7.54 (d, J = 2.2 Hz, 1H), 7.51 (dd, J = 8.5, 2.2 Hz, 1H), 7.24 (d, J = 8.3 Hz, 1H), 7.10 (d, J = 8.8 Hz, 1H), 6.98 (d, J = 8.4 Hz, 1H), 4.49 (t, J = 6.6 Hz, 2H), 4.34-4.27 (m, 4H), 3.59 (t, J = 4.7 Hz, 4H), 2.50-2.44 (m, 2H), 2.39 (br s, 4H), 2.24 (s, 3H), 1.97 (p, J = 6.7 Hz, 2H). | Found [M + H]$^+$ = 583.2586 C33H35N4O6 requires 583.2551 |
| Example 56 | $^1$H NMR (500 MHz, DMSO) δ 10.07 (s, 2H), 8.57 (d, J = 2.0 Hz, 1H), 8.38 (d, J = 8.8 Hz, 1H), 8.22 (dd, J = 8.8, 2.1 Hz, 1H), 7.88-7.84 (m, 2H), 7.58 (dd, J = 8.3, 2.2 Hz, 1H), 7.54 (d, J = 2.2 Hz, 1H), 7.51 | Found [M + H]$^+$ = 567.2594 |

TABLE B-continued

| | 1H NMR | Mass Spec |
|---|---|---|
| | (dd, J = 8.5, 2.2 Hz, 1H), 7.24 (d, J = 8.3 Hz, 1H), 7.10 (d, J = 8.8 Hz, 1H), 6.98 (d, J = 8.4 Hz, 1H), 4.49 (t, J = 6.6 Hz, 2H), 4.33-4.28 (m, 4H), 2.65 (br s, 2H), 2.54 (br s, 4H), 2.23 (s, 3H), 1.99 (p, J = 6.8 Hz, 2H), 1.72 (br s, 4H). | C33H35N4O5 requires 567.2602 |
| Example 57 | $^1$H NMR (500 MHz, DMSO) δ 10.07 (s, 2H), 8.57 (d, J = 2.0 Hz, 1H), 8.38 (d, J = 8.9 Hz, 1H), 8.22 (dd, J = 8.7, 2.0 Hz, 1H), 7.88-7.84 (m, 2H), 7.58 (dd, J = 8.2, 2.2 Hz, 1H), 7.54 (d, J = 2.1 Hz, 1H), 7.51 (dd, J = 8.4, 2.1 Hz, 1H), 7.24 (d, J = 8.3 Hz, 1H), 7.11 (d, J = 8.8 Hz, 1H), 6.98 (d, J = 8.4 Hz, 1H), 4.69-4.52 (m, 3H), 4.35-4.26 (m, 4H), 2.93-2.84 (m, 1H), 2.84-2.80 (m, 2H), 2.61-2.53 (m, 1H), 2.50-2.45 (m, 1H), 2.41-2.34 (m, 1H), 2.24 (s, 3H), 1.88-1.76 (m, 1H), 1.74-1.66 (m, 1H), 1.55-1.40 (m, 2H). | Found $[M + H]^+$ = 585.2505 C33H34FN4O5 requires 585.2509 |
| Example 58 | $^1$H NMR (500 MHz, DMSO) δ 10.06 (s, 1H), 9.91 (s, 1H), 8.38 (d, J = 2.1 Hz, 1H), 8.12 (d, J = 9.2 Hz, 1H), 8.08 (dd, J = 8.7, 2.1 Hz, 1H), 7.85 (d, J = 2.2 Hz, 1H), 7.60-7.56 (m, 2H), 7.54 (d, J = 2.1 Hz, 1H), 7.51 (dd, J = 8.4, 2.2 Hz, 1H), 7.22 (d, J = 8.3 Hz, 1H), 7.14 (d, J = 9.2 Hz, 1H), 6.98 (d, J = 8.4 Hz, 1H), 4.34-4.27 (m, 4H), 3.82 (t, J = 6.6 Hz, 2H), 3.18 (s, 3H), 2.59 (br s, 2H), 2.30 (br s, 6H), 2.23 (s, 3H). | Found $[M + H]^+$ = 540.2604 C31H34N5O4 requires 540.2605 |
| Example 59 | $^1$H NMR (500 MHz, DMSO) δ 10.14 (s, 1H), 10.07 (s, 1H), 8.62 (d, J = 2.0 Hz, 1H), 8.44 (d, J = 8.5 Hz, 1H), 8.25 (dd, J = 8.8, 2.0 Hz, 1H), 8.06 (d, J = 8.8 Hz, 1H), 7.88 (d, J = 2.2 Hz, 1H), 7.61-7.57 (m, 2H), 7.54 (d, J = 2.2 Hz, 1H), 7.51 (dd, J = 8.3, 2.2 Hz, 1H), 7.24 (d, J = 8.3 Hz, 1H), 6.98 (d, J = 8.4 Hz, 1H), 4.33-4.28 (m, 4H), 3.22-3.14 (m, 2H), 3.02 (bt s, 2H), 2.64 (bt s, 4H), 2.24 (s, 3H), 1.72 (bt s, 4H). | Found $[M + H]^+$ = 537.2498 C32H33N4O4 requires 537.2496 |
| Example 60 | $^1$H NMR (500 MHz, DMSO) δ 10.08 (s, 1H), 10.07 (s, 1H), 8.57 (d, J = 2.0 Hz, 1H), 8.39 (d, J = 8.9 Hz, 1H), 8.22 (dd, J = 8.7, 2.0 Hz, 1H), 7.89-7.83 (m, 2H), 7.58 (dd, J = 8.3, 2.2 Hz, 1H), 7.54 (d, J = 2.1 Hz, 1H), 7.51 (dd, J = 8.4, 2.1 Hz, 1H), 7.24 (d, J = 8.3 Hz, 1H), 7.10 (d, J = 8.8 Hz, 1H), 6.98 (d, J = 8.4 Hz, 1H), 4.43 (t, J = 5.6 Hz, 2H), 4.34-4.27 (m, 4H), 3.40-3.30 (m, 4H), 2.94-2.88 (m, 2H), 2.23 (s, 3H), 2.03 (p, J = 7.1 Hz, 2H). | Found $[M + H]^+$ = 539.2289 C31H31N4O5 requires 539.2289 |
| Example 61 | $^1$H NMR (500 MHz, DMSO) δ 10.08 (s, 2H), 8.57 (d, J = 2.1 Hz, 1H), 8.38 (d, J = 8.9 Hz, 1H), 8.23 (dd, J = 8.8, 2.1 Hz, 1H), 7.89-7.83 (m, 2H), 7.58 (dd, J = 8.3, 2.2 Hz, 1H), 7.54 (d, J = 2.1 Hz, 1H), 7.51 (dd, J = 8.4, 2.2 Hz, 1H), 7.24 (d, J = 8.3 Hz, 1H), 7.11 (d, J = 8.8 Hz, 1H), 6.98 (d, J = 8.4 Hz, 1H), 4.61-4.52 (m, 2H), 4.33-4.28 (m, 4H), 3.21 (br s, 2H), 2.54 (br s, 1H), 2.40 (br s, 1H), 2.25 (br s, 1H), 2.24 (s, 3H), 1.89 (br s, 1H), 1.68 (br s, 1H), 1.31 (br s, 1H), 1.07 (br s, 3H). | Found $[M + H]^+$ = 567.2597 C33H35N4O5 requires 567.2602 |
| Example 62 | $^1$H NMR (500 MHz, DMSO) δ 10.10 (s, 1H), 10.07 (s, 1H), 8.60 (d, J = 1.9 Hz, 1H), 8.44 (d, J = 8.9 Hz, 1H), 8.26 (dd, J = 8.7, 2.0 Hz, 1H), 7.92-7.86 (m, 2H), 7.56 (dd, J = 8.3, 2.2 Hz, 1H), 7.53 (d, J = 2.1 Hz, 1H), 7.51 (dd, J = 8.4, 2.2 Hz, 1H), 7.24 (d, J = 8.5 Hz, 1H), 7.15 (d, J = 8.8 Hz, 1H), 6.98 (d, J = 8.4 Hz, 1H), 4.77-4.72 (m, 2H), 4.34-4.27 (m, 4H), 3.39 (br s, 2H), 2.76 (br s, 6H), 2.24 (s, 3H). | Found $[M + H]^+$ = 527.2285 C30H31N4O5 requires 527.2289 |
| Example 63 | $^1$H NMR (500 MHz, DMSO) δ 10.07 (s, 2H), 8.57 (d, J = 2.0 Hz, 1H), 8.38 (d, J = 8.8 Hz, 1H), 8.22 (dd, J = 8.7, 2.0 Hz, 1H), 7.88-7.84 (m, 2H), 7.58 (dd, J = 8.3, 2.2 Hz, 1H), 7.54 (d, J = 2.1 Hz, 1H), 7.51 (dd, J = 8.5, 2.2 Hz, 1H), 7.24 (d, J = 8.5 Hz, 1H), 7.12 (d, J = 8.8 Hz, 1H), 6.98 (d, J = 8.4 Hz, 1H), 4.57 (t, J = 5.8 Hz, 2H), 4.34-4.27 (m, 4H), 2.89 (br s, 2H), 2.58 (br s, 4H), 2.24 (s, 3H), 1.70 (br s, 4H). | Found $[M + H]^+$ = 553.2467 C32H33N4O5 requires 553.2446 |
| Example 64 | $^1$H NMR (500 MHz, DMSO) δ 10.06 (s, 1H), 9.89 (s, 1H), 8.37 (d, J = 2.1 Hz, 1H), 8.11 (d, J = 9.2 Hz, 1H), 8.08 (dd, J = 8.7, 2.1 Hz, 1H), 7.85 (d, J = 2.1 Hz, 1H), 7.59-7.56 (m, 2H), 7.54 (d, J = 2.1 Hz, 1H), 7.51 (dd, J = 8.4, 2.2 Hz, 1H), 7.22 (d, J = 8.3 Hz, 1H), 7.14 (d, J = 9.2 Hz, 1H), 6.98 (d, J = 8.4 Hz, 1H), 4.34-4.28 (m, 4H), 3.80 (t, J = 7.0 Hz, 2H), 3.20 (s, 3H), 2.68 (t, J = 6.9 Hz, 2H), 2.54 (br s, 4H), 2.23 (s, 3H), 1.72-1.63 (m, 4H). | Found $[M + H]^+$ = 566.2759 C33H36N5O4 requires 566.2762 |
| Example 65 | $^1$H NMR (500 MHz, DMSO) δ 10.08 (s, 1H), 10.07 (s, 1H), 8.57 (d, J = 2.0 Hz, 1H), 8.38 (d, J = 8.7 Hz, 1H), 8.22 (dd, J = 8.7, 2.1 Hz, 1H), 7.89-7.84 (m, 2H), 7.58 (dd, J = 8.3, 2.2 Hz, 1H), 7.54 (d, J = 2.2 Hz, 1H), 7.51 (dd, J = 8.4, 2.2 Hz, 1H), 7.24 (d, J = 8.5 Hz, 1H), 7.12 (d, J = 8.8 Hz, 1H), 6.98 (d, J = 8.4 Hz, 1H), 5.28-5.11 (m, 1H), 4.60-4.53 (m, 2H), 4.34-4.27 (m, 4H), 2.99-2.84 (m, 4H), 2.72 (ddd, J = 31.6, 11.6, 5.0 Hz, 1H), 2.46-2.39 (m, 1H), 2.23 (s, 3H), 2.20-2.05 (m, 1H), 1.94-1.79 (m, 1H). | Found $[M + H]^+$ = 571.2349 C32H32FN4O5 requires 571.2351 |
| Example 66 | $^1$H NMR (500 MHz, DMSO) δ 10.07 (s, 2H), 8.57 (d, J = 2.0 Hz, 1H), 8.38 (d, J = 8.7 Hz, 1H), 8.22 (dd, J = 8.7, 2.0 Hz, 1H), 7.88-7.84 (m, 2H), 7.58 (dd, J = 8.3, 2.2 Hz, 1H), 7.54 (d, J = 2.1 Hz, 1H), 7.51 (dd, J = 8.4, 2.2 Hz, 1H), 7.24 (d, J = 8.5 Hz, 1H), 7.12 (d, J = 8.8 Hz, 1H), 6.98 (d, J = 8.4 Hz, 1H), 4.58 (t, J = 5.8 Hz, 2H), 4.34-4.27 (m, 4H), 3.61-3.54 (m, 4H), 2.77 (t, J = 5.8 Hz, 2H), 2.24 (s, 3H). | Found $[M + H]^+$ = 569.2392 C32H33N4O6 requires 569.2395 |

TABLE B-continued

| | 1H NMR | Mass Spec |
|---|---|---|
| Example 67 | $^1$H NMR (500 MHz, DMSO) δ 10.15 (s, 1H), 10.08 (s, 1H), 8.63 (d, J = 2.0 Hz, 1H), 8.48 (d, J = 8.5 Hz, 1H), 8.26 (dd, J = 8.8, 2.1 Hz, 1H), 8.16 (s, 1H), 8.08 (d, J = 8.8 Hz, 1H), 7.88 (d, J = 2.2 Hz, 1H), 7.72 (d, J = 8.5 Hz, 1H), 7.59 (dd, J = 8.2, 2.2 Hz, 1H), 7.54 (d, J = 2.1 Hz, 1H), 7.51 (dd, J = 8.5, 2.2 Hz, 1H), 7.25 (d, J = 8.4 Hz, 1H), 6.98 (d, J = 8.4 Hz, 1H), 4.34-4.27 (m, 4H), 3.94 (s, 2H), 2.61-2.52 (m, 4H), 2.25 (s, 3H), 1.77-1.73 (m,, 4H). | Found [M + H]$^+$ = 523.2363 C31H31N4O4 requires 523.2340 |
| Example 68 | $^1$H NMR (500 MHz, DMSO) δ 10.08 (s, 1H), 10.07 (s, 1H), 8.57 (d, J = 2.0 Hz, 1H), 8.39 (d, J = 8.9 Hz, 1H), 8.23 (dd, J = 8.8, 2.1 Hz, 1H), 7.88-7.84 (m, 2H), 7.58 (dd, J = 8.3, 2.2 Hz, 1H), 7.54 (d, J = 2.1 Hz, 1H), 7.51 (dd, J = 8.4, 2.2 Hz, 1H), 7.24 (d, J = 8.4 Hz, 1H), 7.13 (d, J = 8.8 Hz, 1H), 6.98 (d, J = 8.4 Hz, 1H), 4.58 (dd, J = 11.0, 4.8 Hz, 1H), 4.37 (br s, 1H), 4.35-4.25 (m, 4H), 2.67 (br s, 4H), 2.23 (s, 3H), 1.71 (br s, 4H), 1.25-1.17 (m, 3H). | Found [M + H]$^+$ = 567.2597 C33H35N4O5 requires 567.2602 |
| Example 69 | $^1$H NMR (500 MHz, DMSO) δ 10.18 (s, 1H), 10.08 (s, 1H), 8.66 (d, J = 1.8 Hz, 1H), 8.52 (d, J = 8.4 Hz, 1H), 8.30 (dd, J = 8.8, 1.9 Hz, 1H), 8.12 (d, J = 8.8 Hz, 1H), 7.90 (d, J = 2.0 Hz, 1H), 7.61 (d, J = 8.5 Hz, 1H), 7.56 (dd, J = 8.3, 2.1 Hz, 1H), 7.54 (d, J = 2.1 Hz, 1H), 7.51 (dd, J = 8.4, 2.2 Hz, 1H), 7.25 (d, J = 8.5 Hz, 1H), 6.98 (d, J = 8.4 Hz, 1H), 4.34-4.28 (m, 4H), 3.64-3.53 (m, 2H), 3.42 (t, J = 7.3 Hz, 2H), 2.86 (s, 6H), 2.24 (s, 3H). | Found [M + H]$^+$ = 511.2341 C30H31N4O4 requires 511.2340 |
| Example 70 | $^1$H NMR (500 MHz, DMSO) δ 10.15 (s, 1H), 10.07 (s, 1H), 8.63 (d, J = 2.0 Hz, 1H), 8.48 (d, J = 8.6 Hz, 1H), 8.26 (dd, J = 8.8, 2.0 Hz, 1H), 8.08 (d, J = 8.8 Hz, 1H), 7.88 (d, J = 2.2 Hz, 1H), 7.72 (d, J = 8.5 Hz, 1H), 7.59 (dd, J = 8.2, 2.2 Hz, 1H), 7.54 (d, J = 2.1 Hz, 1H), 7.51 (dd, J = 8.5, 2.2 Hz, 1H), 7.25 (d, J = 8.3 Hz, 1H), 6.98 (d, J = 8.4 Hz, 1H), 4.3-4.28 (m, 4H), 3.79 (s, 2H), 2.48 (br s, 4H), 2.36 (br s, 4H), 2.24 (s, 3H), 2.17 (s, 3H). | Found [M + H]$^+$ = 552.2591 C32H35N5O4 requires 552.2605 |
| Example 71 | $^1$H NMR (500 MHz, DMSO) δ 10.15 (s, 1H), 10.08 (s, 1H), 8.64 (d, J = 1.9 Hz, 1H), 8.49 (d, J = 8.5 Hz, 1H), 8.26 (dd, J = 8.8, 2.0 Hz, 1H), 8.08 (d, J = 8.8 Hz, 1H), 7.88 (d, J = 2.1 Hz, 1H), 7.72 (d, J = 8.5 Hz, 1H), 7.59 (dd, J = 8.3, 2.2 Hz, 1H), 7.54 (d, J = 2.1 Hz, 1H), 7.51 (dd, J = 8.4, 2.2 Hz, 1H), 7.25 (d, J = 8.5 Hz, 1H), 6.98 (d, J = 8.4 Hz, 1H), 4.34-4.27 (m, 4H), 3.74 (s, 2H), 2.26 (s, 6H), 2.25 (s, 3H). | Found [M + H]$^+$ = 497.2183 C29H29N4O4 requires 497.2183 |
| Example 72 | $^1$H NMR (500 MHz, DMSO) δ 10.07 (s, 2H), 8.57 (d, J = 2.1 Hz, 1H), 8.38 (d, J = 8.8 Hz, 1H), 8.22 (dd, J = 8.7, 2.0 Hz, 1H), 7.88-7.84 (m, 2H), 7.58 (dd, J = 8.3, 2.2 Hz, 1H), 7.54 (d, J = 2.2 Hz, 1H), 7.51 (dd, J = 8.5, 2.2 Hz, 1H), 7.24 (d, J = 8.3 Hz, 1H), 7.11 (d, J = 8.8 Hz, 1H), 6.98 (d, J = 8.4 Hz, 1H), 4.58 (t, J = 5.8 Hz, 1H), 4.34-4.27 (m, 4H), 2.86 (t, J = 5.8 Hz, 2H), 2.65 (t, J = 5.7 Hz, 4H), 2.24 (s, 3H), 1.95 (tt, J = 14.0, 5.6 Hz, 4H). | Found [M + H]$^+$ = 603.2416 C33H33F2N4O5 requires 603.2414 |
| Example 73 | $^1$H NMR (500 MHz, DMSO) δ 10.07 (s, 2H), 8.56 (d, J = 2.1 Hz, 1H), 8.37 (d, J = 8.9 Hz, 1H), 8.22 (dd, J = 8.8, 2.1 Hz, 1H), 7.87 (d, J = 2.2 Hz, 1H), 7.84 (d, J = 8.7 Hz, 1H), 7.58 (dd, J = 8.3, 2.2 Hz, 1H), 7.54 (d, J = 2.2 Hz, 1H), 7.51 (dd, J = 8.5, 2.2 Hz, 1H), 7.24 (d, J = 8.3 Hz, 1H), 7.06 (d, J = 8.8 Hz, 1H), 6.98 (d, J = 8.4 Hz, 1H), 5.68-5.57 (m, 1H), 4.33-4.28 m, 4H), 2.88 (br s, 1H), 2.74 (br s, 1H), 2.64 (br s, 4 H), 2.23 (s, 3H), 1.68 (br s, 4H), 1.37 (d, J = 6.3 Hz, 3H). | Found [M + H]$^+$ = 567.2589 C33H35N4O5 requires 567.2602 |
| Example 74 | $^1$H NMR (500 MHz, CDCl$_3$) δ 8.18 (d, J = 1.8 Hz, 1H), 8.00-7.92 (m, 2H), 7.78 (d, J = 2.1 Hz, 1H), 7.70 (d, J = 8.8 Hz, 1H), 7.56 (dd, J = 8.2, 2.1 Hz, 1H), 7.43 (d, J = 2.0 Hz, 1H), 7.39 (dd, J = 8.4, 2.1 Hz, 1H), 7.19 (d, J = 8.3 Hz, 1H), 7.01 (d, J = 9.2 Hz, 1H), 6.88 (d, J = 8.4 Hz, 1H), 4.30-4.22 (m, 4H), 3.80 (br s, 4H), 2.59-2.51 (m, 4H), 2.34 (s, 3H), 2.28 (s, 3H). | Found [M + H]$^+$ = 538.2430 C31H32N5O4 requires 538.2449 |

Preparation of Compound 5,[1] ethyl 2-(6-bromoquinolin-2-yl)acetate nBuLi (1.84 M in hexanes, 7.54 mL, 13.9 mmol) was added dropwise to a solution of diisopropylamine (2.02 mL, 14.3 mmol) in dry diethyl ether (15 mL) at −78° C. The reaction mixture was stirred for 35 min at −78° C., before a solution of 6-bromo-2-methylquinoline (1.00 g, 4.50 mmol) in dry ether (15 mL) was added dropwise. This solution was stirred at −78° C. for 35 min, before ethyl chloroformate (0.495 mL, 5.18 mmol) in dry ether (3.75 mL) was added dropwise. The reaction mixture was stirred at −78° C. for 15 min, before quenching with water (4 mL). The reaction mixture was then allowed to warm to rt, diluted with EtOAc, washed with saturated NaHCO$_3$(aq) (2×), brine (1×), dried (MgSO$_4$), filtered and concentrated to a volume of several mLs. This slurry was diluted with an equal volume of heptane and the mixture stood in the fridge for 2 days. The solids were then isolated by filtration, washed with cold heptane:EtOAc (2:1). An additional amount of solid was isolated from this filtrate. This afforded the title compound (1.014 g, 77%) as a light orange solid. $^1$H NMR (500 MHz, CDCl$_3$) δ 8.05 (d, J=8.5 Hz, 1H), 7.97 (d, J=2.2 Hz, 1H), 7.93 (d, J=8.9 Hz, 1H), 7.77 (dd, J=9.0, 2.2 Hz, 1H), 7.46 (d, J=8.5 Hz, 1H), 4.21 (q, J=7.1 Hz, 2H), 4.02 (s, 2H), 1.27 (t, J=7.1 Hz, 2H). HRMS (ESI$^+$): calcd for C$_{13}$H$_{13}$$^{79}$BrNO$_2$ (M+H)$^+$, 294.0124; found 294.0126.

Preparation of Compound 6,[1] 2-(6-bromoquinolin-2-yl)ethanol

Ethanol (1.97 mL, 33.8 mmol) was added dropwise to solution of Compound 5 (0.993 g, 3.38 mmol) and lithium borohydride (0.147 g, 6.75 mmol) in dry THF (37.5 mL) at rt. The reaction mixture was stirred at rt for 5 hrs, then quenched by the slow addition of MeOH (3.5 mL), concentrated, diluted with EtOAc, washed with saturade NaHCO$_3$ (aq) (1×), water (1×), brine (1×), dried (Na$_2$SO$_4$), filtered and concentrated. The crude material was purified by silica gel column chromatography using a gradient of 50 to 60% EtOAc in PE to afford the title compound (663 mg, 78%) as a light tan coloured solid. $^1$H NMR (500 MHz, CDCl$_3$) δ 8.01 (d, J=8.4 Hz, 1H), 7.96 (d, J=2.2 Hz, 1H), 7.88 (d, J=9.0 Hz, 1H), 7.76 (dd, J=8.9, 2.2 Hz, 1H), 7.30 (d, J=8.5 Hz, 1H), 4.46 (br s, 1H), 4.15 (t, J=5.4 Hz, 2H), 3.19 (t, J=5.4 Hz, 2H). HRMS (ESI$^+$): calcd for C$_{11}$H$_{11}$$^{79}$BrNO (M+H)$^+$, 252.0018; found 252.0019.

Preparation of Compound 7, 6-bromo-2-(2-((tert-butyldimethylsilyl)oxy)ethyl)quinoline To a solution of imidazole (0.122 g, 1.78 mmol) in dry DCM (7 mL) was added Compound 6 (0.300 g, 1.19 mmol) followed by tert-butyldimethylsilyl chloride (0.206 g, 1.37 mmol). The reaction mixture was stirred at rt for 70 min, washed with water (1×), 0.25 M HCl (1×), brine (1×), dried (MgSO$_4$), filtered and concentrated to afford the title compound (440 mg, 100%) as an off-white solid. $^1$H NMR (500 MHz, DMSO) δ 8.49 (br s, 1H), 8.36 (br s, 1H), 8.01 (br d, J=9.1 Hz 1H), 7.96 (br d, J=8.6 Hz, 1H), 7.69 (br d, J=7.5 Hz, 1H), 4.06 (t, J=6.3 Hz, 2H), 3.19 (t, J=6.1 Hz, 2H), 0.74 (s, 9H), −0.10 (s, 6H). HRMS (ESI$^+$): calcd for C$_{17}$H$_{25}$$^{79}$BrNOSi (M+H)$^+$, 366.0883; found 366.0883.

Preparation of Compound 8, 2-(2-((tert-butyldimethylsilyl)oxy)ethyl)quinoline-6-carboxylic acid To a suspension of Compound 7 (0.424 g, 1.16 mmol) in dry THF (8 mL) at −78° C. was added dropwise nBuLi (1.84 M in hexanes, 0.755 mL, 1.39 mmol). The reaction mixture was stirred at −78° C. for 40 min before solid CO$_2$ was added. The reaction mixture was stirred at −78° C. for 15 min, then allowed to warm to rt, concentrated, diluted with water, washed with DCM (2×). The aqueous phase was acidified to pH 3 with 2 M HCl, then extracted with DCM (2×). The initial DCM washes were then added to the aqueous phase, and after shaking, the pH of the aqueous phase was re-adjusted to 3. The layers were separated and the aqueous phase was extracted once more with DCM. The combined org phases were dried (MgSO$_4$), filtered, and concentrated, and the resulting crude material was purified by silica gel column chromatography using a gradient of 25 to 33% EtOAc in PE plus 0.5% acetic acid to afford the title compound (66 mg, 17%) as a pale yellow solid. $^1$H NMR (500 MHz, CDCl$_3$) δ 8.66 (d, J=1.7 Hz, 1H), 8.35 (dd, J=8.8, 1.9 Hz, 1H), 8.20 (d, J=8.4 Hz, 1H), 8.15 (d, J=8.8 Hz, 1H), 7.48 (d, J=8.4 Hz, 1H), 4.12 (t, J=6.3 Hz, 2H), 3.24 (t, J=6.3 Hz, 2H), 0.83 (s, 9H), −0.05 (s, 6H). HRMS (ESI$^+$): calcd for C$_{18}$H$_{26}$NO$_3$Si (M+H)$^+$, 322.1676; found 322.1676.

Example 75, N-(5-(2,3-dihydrobenzo[b][1,4]dioxine-6-carboxamido)-2-methylphenyl)-2-(2-hydroxyethyl)quinoline-6-carboxamide HATU (0.079 g, 0.21 mmol) was added to a solution of Compound 8 (0.060 mg, 0.18 mmol) and N,N-diisopropylethylamine (0.064 mL, 0.36 mmol) in dry DMF (1.2 mL). R$^x$n mix stirred for 4 min, before Compound 2 (0.047 g, 0.16 mmol) was added. The reaction mixture was stirred at rt overnight, diluted with water and the resulting precipitate was isolated by filtration, washed with water and dried. To 93 mg (0.16 mmol) of this intermediate in dry THF (4 mL), tetrabutylammonium fluoride (1 M in THF, 0.233 mL, 0.233 mmol) was added dropwise and the reaction mixture was stirred at rt for 5 hrs, diluted with water and the resulting precipitate was isolated by filtration, washed with water and dried to afford the title compound (58 mg, 74%) as a white solid. $^1$H NMR (500 MHz, DMSO) δ 10.14 (s, 1H), 10.07 (s, 1H), 8.62 (d, J=1.7 Hz, 1H), 8.42 (d, J=8.5 Hz, 1H), 8.25 (dd, J=8.8, 1.9 Hz, 1H), 8.06 (d, J=8.8 Hz, 1H), 7.88 (d, J=1.9 Hz, 1H), 7.61-7.55 (m, 2H), 7.54 (d, J=2.0 Hz, 1H), 7.51 (dd, J=8.4, 2.1 Hz, 1H), 7.24 (d, J=8.4 Hz, 1H), 6.98 (d, J=8.4 Hz, 1H), 4.75 (t, J=5.2 Hz, 1H), 4.35-4.27 (m, 4H), 3.89 (q, J=6.5 Hz, 2H), 3.12 (t, J=6.7 Hz, 2H), 2.25 (s, 3H). HRMS (ESI$^+$): calcd for C$_{28}$H$_{26}$N$_3$O$_5$ (M+H)$^+$, 484.1867; found 484.1868.

Preparation of Compound 9, tert-butyl (3-((6-bromoquinolin-2-yl)oxy)propyl) (methyl)carbamate Di-tert-butyl dicarbonate (0.749 g, 3.43 mmol) was added to a solution of 3-methylamino-1-propanol (0.327 mL, 3.37 mmol) in dry DCM (12 mL). The reaction mixture was stirred at rt for 2 hrs, and then washed with brine (1×). The aqueous phase was extracted with DCM (1×) and the combined organic phases were dried (MgSO4), filtered and concentrated to afford the intermediate compound (640 mg, 100%) as a colourless oil which was used without further purification. NaH (60% in mineral oil, 0.073 g, 1.82 mmol) was added to a solution of this intermediate (0.300 g, 1.58 mmol) in dry THF (5 mL) at 0° C. The reaction mixture was stirred for 5 min, then allowed to warm to rt, and stirred for 30 min before 6-bromo-2-chloroquinoline (0.384 g, 1.58 mmol) was added. The reaction mixture was heated at reflux for 4 hrs, cooled, concentrated, diluted with water and saturated NaHCO$_3$(aq), and extracted with DCM (2×). The organic phase was dried (MgSO$_4$), filtered and concentrated. Unreacted 6-bromo-2-chloroquinoline (~70 mg) was removed by crystallizing it from hot ethanol. The filtrate was concentrated and then purified by silica gel column chromatography using a gradient of 10 to 12.5% EtOAc in PE to afford the title compound (348 mg, 56%) as a colourless oil. $^1$H NMR (500 MHz, CDCl$_3$) δ 7.88 (d, J=8.9 Hz, 1H), 7.85 (br s, 1H), 7.68-7.65 (m, 2H), 6.90 (d, J=8.8 Hz, 1H), 4.47 (t, J=6.4 Hz, 2H), 3.42 (br s, 2H), 2.89 (s, 3H), 2.10-1.98 (m, 2H), 1.43 (s, 9H). HRMS (ESI$^+$): calcd for C$_{18}$H$_{24}$$^{79}$BrN$_2$O$_3$ (M+H)$^+$, 395.0965; found 395.0963.

Preparation of Compound 10, 2-(3-((tert-butoxycarbonyl)(methyl)amino)propoxy) quinoline-6-carboxylic acid nBuLi (2.2 M in hexanes, 0.13 mL, 0.29 mmol) was added dropwise to a solution of Compound 9 (0.105 g, 0.266 mmol) in dry THF (1 mL) at −78° C. The reaction mixture was stirred at this temp for 35 min before solid CO$_2$ was added. After stirring for 5 min, the reaction mixture was allowed to warm to rt, quenched with water, and then concentrated to remove THF, diluted with water, washed with EtOAc (1×). The aqueous phase was acidified with 2 M HCl to pH 2-3 then extracted with DCM (2×). The DCM phase was dried (MgSO$_4$), filtered and concentrated to afford the title compound (68 mg, 71%) as a colourless oil that solidified over time. $^1$H NMR (500 MHz, CDCl$_3$) δ 8.54 (br s, 1H), 8.26 (dd, J=8.8, 2.1 Hz, 1H), 8.07 (d, J=8.9 Hz, 1H), 7.85 (d, J=8.7 Hz, 1H), 6.96 (d, J=8.9 Hz, 1H), 4.53 (t, J=6.3 Hz, 2H), 3.44 (br s, 2H), 2.91 (s, 3H), 2.11-2.04 (m, 2H), 1.44 (s, 9H). HRMS (ESI$^+$): calcd for C$_{19}$H$_{25}$N$_2$O$_5$ (M+H)$^+$, 361.1758; found 361.1761.

Preparation of Compound 11, tert-butyl (3-((6-((5-(2,3-dihydrobenzo[b][1,4]dioxine-6-carboxamido)-2-methylphenyl)carbamoyl)quinolin-2-yl)oxy)propyl)(methyl)carbamate This was prepared as for Example 1, substituting Compound 10 for 6-quinolinecarboxylic acid. The crude material was purified by silica gel column chromatography using a gradient of 1 to 3% MeOH in DCM to afford the title compound in a yield of 71% as a white solid. $^1$H NMR (500 MHz, CDCl$_3$) δ 8.30 (d, J=2.2 Hz, 1H), 8.14 (d, J=2.3 Hz, 1H), 8.09 (d, J=9.0 Hz, 1H), 8.06 (dd, J=8.8, 2.1 Hz, 1H), 7.91 (d, J=8.6 Hz, 1H), 7.82 (s, 1H), 7.79 (s, 1H), 7.71 (dd, J=8.3, 1.9 Hz, 2H), 7.44 (d, J=2.2 Hz, 1H), 7.37 (dd, J=8.4, 2.2 Hz, 1H), 7.25 (d, coupling obscured by solvent peak, 1H), 6.98 (d, J=8.9 Hz, 1H), 6.95 (d, J=8.4 Hz, 1H), 4.53 (t, J=6.3 Hz, 2H), 4.34-4.27 (m, 4H), 3.49-3.42 (m, 2H), 2.91 (s, 3H), 2.37 (s, 3H), 2.12-2.04 (m, 2H), 1.44 (s, 9H). HRMS (ESI$^+$): calcd for C$_{35}$H$_{49}$N$_5$O$_7$ (M+H)$^+$, 627.2813; found 627.2815.

Example 76, N-(5-(2,3-dihydrobenzo[b][1,4]dioxine-6-carboxamido)-2-methylphenyl)-2-(3-(methylamino)propoxy)quinoline-6-carboxamide Trifluoroacetic acid (2.50 mL) was added to a solution of Compound 11 (0.080 g, 0.13 mmol) in dry DCM (3 mL). The reaction mixture was stirred at rt for 40 min, diluted with DCM, washed with saturated NaHCO$_3$(aq) (2×)—note a precipitate formed that stuck to the glassware—this was dissolved in MeOH, diluted with DCM, washed with water (1×), and this aqueous phase was extracted with DCM (2×). The combined organic phases were dried (MgSO$_4$), filtered and concentrated. The crude solid was triturated in ether and the solvent decanted (2×), to afford the title compound (46 mg, 68%) a white solid. $^1$H NMR (500 MHz, DMSO) δ 10.07 (s, 2H), 8.56 (d, J=2.1 Hz, 1H), 8.37 (d, J=8.8 Hz, 1H), 8.22 (dd, J=8.8, 2.1 Hz, 1H), 7.88-7.84 (m, 2H), 7.58 (dd, J=8.2, 2.2 Hz, 1H), 7.54 (d, J=2.1 Hz, 1H), 7.51 (dd, J=8.4, 2.2 Hz, 1H), 7.24 (d, J=8.4 Hz, 1H), 7.10 (d, J=8.8 Hz, 1H), 6.98 (d, J=8.5 Hz, 1H), 4.50 (t, J=6.5 Hz, 2H), 4.33-4.28 (m, 4H), 2.68 (t, J=6.9 Hz, 2H), 2.32 (s, 3H), 2.23 (s, 3H), 1.94 (p, J=6.7 Hz, 2H). HRMS (ESI$^+$): calcd for C$_{30}$H$_{31}$N$_4$O$_5$ (M+H)$^+$, 527.2289; found 527.2288.

Preparation of Compound 12, N-(5-(2,3-dihydrobenzo[b][1,4]dioxine-6-carboxamido)-2-methylphenyl)-2-vinylquinoline-6-carboxamide A mixture of Example 39 (0.034 g, 0.075 mmol), dibenzyl (chloromethyl) phosphate (0.037 g, 0.11 mmol), tetrabutylammonium bromide (2.4 mg, 7.6 µmol), and potassium carbonate (0.026 g, 0.19 mmol) in dry DMF (0.7 mL) was heated in a microwave at 100° C. for 30 min. The reaction mixture was then cooled to rt, diluted with water, and the resulting precipitate isolated by filtration, washed with water and dried. The crude material was purified by silica gel column chromatography using a gradient of 50 to 67% EtOAc in PE to afford the title compound (25 mg, 71%) as an off-white solid. $^1$H NMR (500 MHz, DMSO) δ 10.16 (s, 1H), 10.08 (s, 1H), 8.62 (d, J=1.9 Hz, 1H), 8.51 (d, J=8.6 Hz, 1H), 8.27 (dd, J=8.8, 2.0 Hz, 1H), 8.09 (d, J=8.8 Hz, 1H), 7.92 (d, J=8.6 Hz, 1H), 7.88 (d, J=2.1 Hz, 1H), 7.59 (dd, J=8.3, 2.2 Hz, 1H), 7.54 (d, J=2.1 Hz, 1H), 7.51 (dd, J=8.5, 2.2 Hz, 1H), 7.25 (d, J=8.5 Hz, 1H), 7.03 (dd, J=17.7, 10.9 Hz, 1H), 6.98 (d, J=8.4 Hz, 1H), 6.49 (dd, J=17.7, 0.9 Hz, 1H), 5.76 (dd, J=11.0, 0.8 Hz, 1H), 4.34-4.28 (m, 4H), 2.25 (s, 3H). HRMS (ESI$^+$): calcd for C$_{28}$H$_{24}$N$_3$O$_4$ (M+H)$^+$, 466.1761; found 466.1299.

Example 77, N-(5-(2,3-dihydrobenzo[b][1,4]dioxine-6-carboxamido)-2-methylphenyl)-2-ethylquinoline-6-carboxamide A suspension of Compound 12 (0.018 g, 0.039 mmol) in ethyl acetate (5 mL) and methanol (3 mL) was heated gently in order to dissolve the solid. The solution was degassed, to which 10% Pd/C (0.002 g, 0.04 mmol) was added and the reaction mixture was stirred under 1 atm hydrogen at rt for 3 hrs, filtered through celite with 1:1 MeOH:EtOAc, and concentrated. The residue was purified by silica gel column chromatography using a gradient of 25 to 33% EtOAc in DCM to afford the title compound (10 mg, 56%) as a white solid. $^1$H NMR (500 MHz, DMSO) δ 10.13 (s, 1H), 10.07 (s, 1H), 8.61 (d, J=1.9 Hz, 1H), 8.43 (d, J=8.4 Hz, 1H), 8.25 (dd, J=8.8, 2.0 Hz, 1H), 8.05 (d, J=8.8 Hz, 1H), 7.87 (d, J=2.1 Hz, 1H), 7.59 (dd, J=8.3, 2.2 Hz, 1H), 7.56 (d, J=8.5 Hz, 1H), 7.54 (d, J=2.1 Hz, 1H), 7.51 (dd, J=8.5, 2.2 Hz, 1H), 7.24 (d, J=8.5 Hz, 1H), 6.98 (d, J=8.4 Hz, 1H), 4.34-4.28 (m, 4H), 2.99 (q, J=7.6 Hz, 2H), 2.24 (s, 3H), 1.35 (t, J=7.6 Hz, 3H). HRMS (ESI$^+$): calcd for C$_{28}$H$_{26}$N$_3$O$_4$ (M+H)$^+$, 468.1918; found 468.1886.

Preparation of Compound 13, methyl 2-formylquinoline-6-carboxylate

Methyl 2-methylquinoline-6-carboxylate (1.00 g, 4.97 mmol) was added to a suspension of selenium dioxide (0.689 g, 6.21 mmol) in dry 1,4-dioxane (7.1 mL). The reaction mixture was heated to 80° C. overnight, cooled, diluted with DCM, filtered through celite with DCM, and the filtrate was concentrated. The residue was purified by silica gel column chromatography using gradient of 20 to 40% EtOAc in PE to afford the title compound (737 mg, 69%) as a yellow solid. $^1$H NMR (500 MHz, CDCl$_3$) δ 10.25 (d, J=0.9 Hz, 1H), 8.67 (d, J=1.8 Hz, 1H), 8.44 (d, J=8.5 Hz, 1H), 8.40 (dd, J=8.8, 1.9 Hz, 1H), 8.30 (d, J=8.8 Hz, 1H), 8.09 (d, J=8.5 Hz, 1H), 4.03 (s, 3H). HRMS (ESI$^+$): calcd for C$_{12}$H$_{10}$NO$_3$ (M+H)$^+$, 216.0655; found 216.0658.

Preparation of Compound 14, methyl 2-(((tert-butoxycarbonyl)(methyl)amino)methyl)quinoline-6-carboxylate Methylamine (2 M in THF, 2.79 mL, 5.58 mmol) was added to a solution of Compound 13 (0.400 g, 1.86 mmol) in dry DCM (15 mL). The reaction mixture was sealed and stirred at rt for 4 hrs. Na(OAc)$_3$BH (0.591 g, 2.79 mmol) was added and the reaction mixture was stirred for 4 hrs, after which time more methylamine solution (2 M in THF, 0.93 mL, 1.86 mmol) was added and the reaction mixture was stirred overnight at rt, diluted with DCM, washed with saturated NaHCO$_3$(aq). The aqueous phase was extracted with DCM (1×). The combined organic phases were dried (MgSO$_4$), filtered and concentrated to provide the secondary amine intermediate which as used without any further purification. This intermediate (0.483 g, 2.10 mmol) was dissolved in dry DCM (10 mL), to which was added di-tert-butyl dicarbonate (0.504 g, 2.31 mmol) and the reaction mixture was stirred at rt for 3 hrs, diluted with DCM, washed with brine (1×). The aqueous phase was extracted with DCM (1×). The combined organic phases were dried (MgSO$_4$), filtered and concentrated. The residue was purified by silica gel column chromatography using a gradient of 12.5 to 20% EtOAc in PE to afford the title compound (478 mg, 69%) as a pale yellow oil. $^1$H NMR (500 MHz, CDCl$_3$) δ 8.58 (br s, 1H), 8.29 (br d, J=8.7 Hz, 1H), 8.24 (br s, 1H), 8.07 (d, J=8.8 Hz, 1H), 7.43 (br dd, J=27.5, 8.2 Hz, 1H), 4.74 (ap d, 2H), 2.95 (ap d, 3H), 1.48 (ap d, 9H). Note that this NMR shows the presence of amide bond rotamers in ~1:1 ratio. HRMS (ESI$^+$): calcd for C$_{18}$H$_{23}$N$_2$O$_4$ (M+H)$^+$, 331.1652; found 331.1650.

Preparation of Compound 15, 2-(((tert-butoxycarbonyl)(methyl)amino)methyl)quinoline-6-carboxylic acid NaOH(aq) (1.988 M, 3.09 mL, 6.14 mmol) was added to a solution of Compound 14 (0.406 g, 1.23 mmol) in THF (6 mL). MeOH (2.5 mL) was added and the reaction mixture was stirred overnight at rt, concentrated to remove organic solvents, diluted with water, washed with EtOAc (1×). The aqueous phase was acidified with 2 M HCl to pH 3, and the resulting solid isolated by filtration, washed with water and dried to afford the title compound (344 mg, 88%) as a white solid. $^1$H NMR (500 MHz, CDCl$_3$) δ 8.66 (ap d, 1H), 8.38-8.32 (m, 1H), 8.32-8.23 (m, 1H), 8.13 (d, J=8.9 Hz, 1H), 7.52-7.40 (m, 1H), 4.77 (ap d, 2H), 2.97 (ap d, 3H), 1.48 (ap d, 9H). Note that this spectrum shows the presence of amide bond rotamers in ~1:1 ratio. HRMS (ESI$^+$): calcd for C$_{17}$H$_{21}$N$_2$O$_4$ (M+H)$^+$, 317.1496; found 317.1499.

Preparation of Compound 16, tert-butyl ((6-((5-(2, 3-dihydrobenzo[b][1,4]dioxine-6-carboxamido)-2-methylphenyl)carbamoyl)quinolin-2-yl)methyl)(methyl)carbamate The title compound was prepared as for Example 1 using Compound 15 in place of 6-quinolinecarboxylic acid. $^1$H NMR (500 MHz, CDCl$_3$) δ 8.40 (br s, 1H), 8.30-8.24 (m, 1H), 8.19-8.14 (m, 2H), 7.96 (br s, 1H), 7.92-7.86 (m, 2H), 7.72 (br d, J=8.1 Hz, 1H), 7.58-7.52 (m, 1H), 7.52-7.41 (m, 3H), 7.26 (d, J=8.0 Hz, 2H), 4.76 (ap d, 2H), 2.97 (ap d, 3H), 1.48 (ap d, 9H). Note that this spectrum shows a mixture of amide bond rotamers in ~1:1 ratio. Only the actual coupling constants are listed, not the apparent ones. HRMS (ESI$^+$): calcd for C$_{33}$H$_{35}$N$_4$O$_6$ (M+H)$^+$, 583.2554; found 583.2546.

Example 78, N-(5-(2,3-dihydrobenzo[b][1,4]dioxine-6-carboxamido)-2-methylphenyl)-2-((N-methylpropionamido)methyl)quinoline-6-carboxamide TFA (1.0 mL) was added to a solution of Compound 16 (0.056 g, 0.096 mmol) in dry DCM (1.5 mL). The reaction mixture was stirred at rt for 45 min, diluted with DCM, washed with saturated NaHCO$_3$(aq) (1×) which caused a sticky solid to form. This was dissolved using a mixture of DCM and MeOH, and this org phase was washed with saturated NaHCO$_3$(aq) (1×). This aqueous phase was extracted with DCM (1×), then diluted with water and brine, and then extracted with CHCl$_3$ (1×). The combined organic phases were washed with brine (1×), dried (MgSO$_4$), filtered and concentrated to afford the crude intermediate (44 mg) as an off-white solid, Propionyl chloride (3.0 µL, 0.034 mmol) was added to a solution of the intermediate (0.015 g, 0.031 mmol) and N,N-diisopropylethylamine (8.1 µL, 0.047 mmol) in dry DCM (0.5 mL). The reaction mixture was stirred at rt for 3.5 hrs, concentrated, and the resulting white solid triturated in water, and the solid isolated by filtration, washed with water and dried to afford the title compound (12.5 mg, 70% over 2 steps) as a white solid. $^1$H NMR (500 MHz, DMSO) δ 10.16 (s, 1H), 10.07 (s, 1H), 8.65 (ap dd, J=2.1 Hz, 1H), 8.52 (ap dd, J=8.5 Hz, 1H), 8.31-8.25 (m, 1H), 8.08 (ap dd, J=8.8 Hz, 2H), 7.88 (s, 1H), 7.59 (dd, J=8.3, 2.2 Hz, 1H), 7.54 (d, J=2.2 Hz, 1H), 7.51 (dd, J=8.5, 2.2 Hz, 1H), 7.44 (d, J=8.5 Hz, 1H), 7.25 (d, J=8.3 Hz, 1H), 6.98 (d, J=8.4 Hz, 1H), 4.85 (ap d, 2H), 4.36-4.25 (m, 4H), 3.02 (ap d, 3H), 2.43 (ap dq, J=7.3 Hz, 2H), 2.25 (s, 3H), 1.02 (ap dt, J=7.3 Hz, 5H). Note that this spectrum shows a mixture of amide bond rotamers in ~1.8:1 ratio. Only the actual coupling constants are listed, not the apparent ones. HRMS (ESI$^+$): calcd for C$_{31}$H$_{31}$N$_4$O$_5$ (M+H)$^+$, 539.2289; found 539.2283.

Preparation of Compound 17,[2] ethyl 2-chloroquinoline-6-carboxylate

3-Chloroperbenzoic acid (75%, 1.675 g, 7.280 mmol) was added to a solution of ethyl quinoline-6-carboxylate (1.127 g, 5.601 mmol) in dry DCM (16 mL) at 0° C. The reaction mixture was then allowed to warm to rt, and stirred overnight. The reaction mixture was washed with 10% aqueous sodium sulfite (1×), saturated NaHCO$_3$(aq) (1×), brine (1×), dried (MgSO$_4$), filtered and concentrated to give the N-oxide intermediate (1.22 g, 100%) as a pale brown solid. The N-oxide intermediate was dissolved in dry DCM (14 mL), and to this was added phosphorus oxychloride (6.94 mL, 74.5 mmol) and the reaction mixture was heated to 50° C. overnight, cooled to rt, concentrated, diluted with DCM, washed with saturated NaHCO$_3$(aq) (1×). Due to the presence of an emulsion, the organic phase (and majority of the mixed emulsion) was concentrated, diluted with EtOAc, washed with saturated NaHCO$_3$(aq) (2×). The aqueous phase was extracted with EtOAc (1×), and the combined organic phases washed with brine (1×), dried (MgSO$_4$), filtered and concentrated. The residue was purified by silica gel column chromatography first using a gradient of 6.7 to 25% EtOAc in PE, and this still impure material was re-purified by silica gel column chromatography using a gradient of 0 to 1.5% EtOAc in toluene to afford the title compound (270 mg, 20%) as a white solid. $^1$H NMR (500 MHz, CDCl$_3$) δ 8.58 (d, J=1.8 Hz, 1H), 8.34 (dd, J=8.8, 1.9 Hz, 1H), 8.21 (d, J=8.6 Hz, 1H), 8.06 (d, J=8.8 Hz, 1H), 7.46 (d, J=8.6 Hz, 1H), 4.46 (q, J=7.1 Hz, 2H), 1.45 (t, J=7.2 Hz, 3H). HRMS (ESI$^+$): calcd for C$_{12}$H$_{11}$$^{35}$ClNO$_2$ (M+H)$^+$, 236.0473; found 236.0473.

Preparation of Compound 18, 2-chloroquinoline-6-carboxylic acid

A suspension of Compound 17 (0.100 g, 0.424 mmol) in HCl (32%, 2 mL) was heated to 95° C. for 75 min, cooled to rt and concentrated to dryness. The residue was purified by silica gel column chromatography using 1:1 PE:EtOAc+ 0.5% acetic acid to afford the title compound (28 mg, 32%) as a white solid. $^1$H NMR (500 MHz, DMSO) δ 13.37 (br s, 1H), 8.73 (d, J=1.9 Hz, 1H), 8.66 (d, J=8.6 Hz, 1H), 8.26 (dd, J=8.8, 1.9 Hz, 1H), 8.03 (d, J=8.8 Hz, 1H), 7.71 (d, J=8.6 Hz, 1H). HRMS (ESI$^+$): calcd for C$_{10}$H$_7$$^{35}$ClNO$_2$ (M+H)$^+$, 208.0160; found 208.0162.

Preparation of Compound 19, 2-chloro-N-(5-(2,3-dihydrobenzo[b][1,4]dioxine-6-carboxamido)-2-methylphenyl)quinoline-6-carboxamide The title compound was prepared as for Example 1 using Compound 18 in place of 6-quinolinecarboxylic acid. $^1$H NMR (500 MHz, DMSO) δ 10.22 (s, 1H), 10.08 (s, 1H), 8.72 (d, J=1.9 Hz, 1H), 8.63 (d, J=8.4 Hz, 1H), 8.34 (dd, J=8.8, 2.0 Hz, 1H), 8.09 (d, J=8.8 Hz, 1H), 7.88 (d, J=2.1 Hz, 1H), 7.71 (d, J=8.6 Hz, 1H), 7.59 (dd, J=8.3, 2.2 Hz, 1H), 7.54 (d, J=2.1 Hz, 1H), 7.51 (dd, J=8.5, 2.2 Hz, 1H), 7.25 (d, J=8.5 Hz, 1H), 6.98 (d, J=8.4 Hz, 1H), 4.33-4.28 (m, 4H), 2.24 (s, 3H). HRMS (ESI+): calcd for $C_{26}H_{21}{}^{35}ClN_3O_4$ (M+H)+, 474.1215; found 474.1181.

Example 79, N-(5-(2,3-dihydrobenzo[b][1,4]dioxine-6-carboxamido)-2-methylphenyl)-2-(methylamino)quinoline-6-carboxamide A suspension of Compound 19 (0.025 g, 0.053 mmol) in methylamine (33% in EtOH, 0.75 mL) was heated in the microwave at 100° C. for 75 min, diluted with water producing a colloidal suspension that was not filterable. This mixture was concentrated nearly to dryness, then triturated in water. The resulting precipitate was isolated by filtration, washed with water and dried to afford the title compound (17 mg, 68%) as an off-white solid. $^1$H NMR (500 MHz, DMSO) δ 10.05 (s, 1H), 9.87 (s, 1H), 8.31 (s, 1H), 8.05 (d, J=8.6 Hz, 1H), 7.95 (d, J=8.8 Hz, 1H), 7.84 (s, 1H), 7.57 (d, J=8.6 Hz, 2H), 7.53 (s, 1H), 7.51 (d, J=8.5 Hz, 2H), 7.31 (d, J=4.5 Hz, 1H), 7.22 (d, J=8.3 Hz, 1H), 6.98 (d, J=8.4 Hz, 1H), 6.82 (d, J=8.9 Hz, 1H), 4.38-4.25 (m, 4H), 2.93 (d, J=4.6 Hz, 3H), 2.22 (s, 3H). HRMS (ESI+): calcd for $C_{27}H_{25}N_4O_4$ (M+H)+, 469.1870; found 469.1875.

Example 80—Preparation of N-(5-(2,3-dihydrobenzo[b][1,4]dioxine-6-carboxamido)-2-methylphenyl)-1,2,3,4-tetrahydroquinoline-6-carboxamide A suspension of Example 39 (0.097 g, 0.22 mmol) and Pd/C (10%, 0.025 g) in MeOH (8 mL), Ethyl acetate (6 mL), and 10 drops glacial acetic acid was stirred under 1 atm hydrogen at 40° C. overnight, filtered through celite with EtOAc, and concentrated. The residue was purified by silica gel column chromatography using a gradient of 10 to 22% EtOAC in DCM to afford the title compound (72 mg, 74%) as a white solid. $^1$H NMR (500 MHz, DMSO) δ 10.01 (s, 1H), 9.34 (s, 1H), 7.76 (d, J=2.2 Hz, 1H), 7.57-7.52 (m, 4H), 7.50 (dd, J=8.5, 2.2 Hz, 1H), 7.17 (d, J=8.4 Hz, 1H), 6.97 (d, J=8.4 Hz, 1H), 6.46 (d, J=9.0 Hz, 1H), 6.34 (br s, 1H), 4.34-4.27 (m, 4H), 3.27-3.20 (m, 2H), 2.71 (t, J=6.2 Hz, 2H), 2.16 (s, 3H), 1.85-1.76 (m, 2H).

HRMS (ESI+): calcd for $C_{26}H_{26}N_3O_4$ (M+H)+, 444.1718; found 444.1812.

Example 81—Preparation of N-(5-(2,3-dihydrobenzo[b][1,4]dioxine-6-carboxamido)-2-methylphenyl)-2-(2-propionamidoethoxy)quinoline-6-carboxamide Propionyl chloride (2.5 µL, 0.029 mmol) was added to a solution of Example 89 (0.013 g, 0.026 mmol) in dry DCM (0.75 mL) and DMF (0.15 mL). The reaction mixture was stirred at rt for 2.5 hrs, concentrated to remove DCM, then diluted with water, extracted with DCM (3×), dried over MgSO$_4$, filtered and concentrated. Added heptane and concentrated (2×) to remove residual DMF. The crude material was purified by silica gel column chromatography using a gradient of 2 to 3.5% MeOH in DCM to afford the title compound (10 mg, 71%) as a white solid. $^1$H NMR (500 MHz, DMSO) δ 10.07 (s, 1H), 10.07 (s, 1H), 8.57 (d, J=2.0 Hz, 1H), 8.39 (d, J=8.8 Hz, 1H), 8.23 (dd, J=8.7, 2.1 Hz, 1H), 8.04 (br t, J=5.5 Hz, 1H), 7.88-7.84 (m, 2H), 7.58 (dd, J=8.4, 2.2 Hz, 1H), 7.54 (d, J=2.1 Hz, 1H), 7.51 (dd, J=8.5, 2.2 Hz, 1H), 7.24 (d, J=8.4 Hz, 1H), 7.11 (d, J=8.8 Hz, 1H), 6.98 (d, J=8.4 Hz, 1H), 4.47 (t, J=5.7 Hz, 2H), 4.34-4.27 (m, 4H), 3.51 (q, J=5.7 Hz, 2H), 2.23 (s, 3H), 2.10 (q, J=7.6 Hz, 2H), 0.99 (t, J=7.6 Hz, 3H). HRMS (ESI+): calcd for $C_{31}H_{31}N_4O_6$ (M+H)+, 555.2238; found 555.2228.

Preparation of Compound 20,[3] 6-bromo-3,4-dihydronaphthalen-1(2H)-one

A solution of 6-amino-1,2,3,4-tetrahydronaphthalen-1-one (0.500 g, 3.10 mmol) in 8 mL 25% HBr(aq) and 1 mL 50% HBr(aq) was cooled to 0° C. before a solution of sodium nitrite (0.263 g, 3.82 mmol) in water (1.25 mL) was added dropwise. This reaction mixture was then added dropwise to a cooled solution of copper(I) bromide (0.458 g, 3.19 mmol) in 50% HBr(aq) (2.38 mL). The reaction mixture was stirred at 0° C. for 1 h, then warmed to rt, diluted with a bit of water, extracted with 4:1 Et$_2$O:EtOAc (3×). The combined organic phases were dried (Na$_2$SO$_4$), filtered and concentrated. The crude material was purified by silica gel column chromatography using 12:1 PE:EtOAc to afford the title compound (444 mg, 64%) as a pale orange oil. $^1$H NMR (500 MHz, CDCl$_3$) δ 7.89 (d, J=9.0 Hz, 1H), 7.46-7.42 (m, 2H), 2.94 (t, J=6.1 Hz, 2H), 2.68-2.61 (m, 2H), 2.14 (m, 2H). HRMS (ESI+): calcd for $C_{10}H_{10}{}^{79}BrO$ (M+H)+, 224.9910; found 224.9910.

Preparation of Compound 21, (E)-6-bromo-3,4-dihydronaphthalen-1(2H)-one oxime To a suspension of hydroxylamine hydrochloride (0.204 g, 2.93 mmol) in dry EtOH (2.5 mL) was added potassium acetate (0.288 g, 2.93 mmol), followed by a solution of Compound 20 (0.440 g, 1.96 mmol) in dry EtOH (2.5 mL). The reaction mixture was heated at reflux for 75 min, cooled, and concentrated. To the residue was added water and the resulting precipitate was isolated by filtration, washed with water and dried to afford the title compound (429 mg, 91%) as a pale yellow solid. $^1$H NMR (500 MHz, CDCl$_3$) δ 7.77 (d, J=8.9 Hz, 1H), 7.51 (br s, 1H), 7.34-7.30 (m, 2H), 2.79 (t, J=6.7 Hz, 2H), 2.76-2.71 (m, 2H), 1.92-1.82 (m, 2H). HRMS (ESI+): calcd for $C_{10}H_{11}{}^{79}BrNO$ (M+H)+, 240.0018; found 240-0018.

Preparation of Compound 22, tert-butyl 7-bromo-2,3,4,5-tetrahydro-1H-benzo[b]azepine-1-carboxylate Diisobutylaluminum hydride (1 M in hexanes) (9.86 mL, 9.86 mmol) was added dropwise over 10 min to a solution of Compound 21 (0.263 g, 1.10 mmol) in dry DCM (10 mL) at 0° C. After stirring for a few minutes, the reaction mixture was warmed to rt and stirred for 3 days, cooled to 0° C., then added sodium fluoride (1.84 g, 43.8 mmol) followed by water (0.75 mL) dropwise. Stirred at 0° C. for 1 hr, then filtered through celite with EtOAc, and the filtrate concentrated to afford the intermediate 7-bromo-2,3,4,5-tetrahydro-1H-benzo[b]azepine as a pale yellow oil. This material was combined with 45 mg of crude material from a separate reaction, dissolved in dry DCM (4 mL) to which di-tert-butyl dicarbonate (0.411 g, 1.88 mmol) was added and the reaction mixture was then stirred at rt overnight.

4-Dimethylaminopyridine (0.015 g, 0.13 mmol) was then added and reaction mixture was heated at reflux for 4 hrs, cooled, diluted with DCM, washed with 0.5 M HCl (1×), water (1×), dried (MgSO$_4$), filtered and concentrated. The crude residue was purified by silica gel column chromatography using a gradient of 5% to 8% EtOAc in PE to afford the title compound (258 mg, 63%) as a colourless oil. $^1$H NMR (500 MHz, CDCl$_3$) δ 7.36 (d, J=2.3 Hz, 1H), 7.33 (dd, J=8.3, 2.3 Hz, 1H), 7.08 (d, J=8.3 Hz, 1H), 2.95-2.86 (m, 2H), 2.86-2.75 (m, 2H), 2.05-1.95 (m, 2H), 1.93-1.73 (m, 2H), 1.41 (s, 9H). LRMS (ESI$^+$): 270.01, 272.01 (1:1, dp-$^t$Bu), and 226.02, 228.02 (1:1, dp-Boc)

Preparation of Compound 23, tert-butyl 7-((5-(2,3-dihydrobenzo[b][1,4]dioxine-6-carboxamido)-2-methylphenyl)carbamoyl)-2,3,4,5-tetrahydro-1H-benzo[b]azepine-1-carboxylate nBuLi (1.84 M in hexanes, 0.313 mL, 0.577 mmol) was added dropwise to a solution of Compound 22 (0.171 g, 0.524 mmol) in dry THF (2.5 mL) at −78° C. The reaction mixture was stirred at this temperature for 35 min, and then solid CO$_2$ was added. The reaction mixture was stirred at −78° C. for a few minutes, then allowed to warm to rt, stirred for 20 min, and then quenched with water and concentrated to dryness to afford the intermediate lithium 1-(tert-butoxycarbonyl)-2,3,4,5-tetrahydro-1H-benzo[b]azepine-7-carboxylate as a pale brown solid. A portion of this intermediate (0.060 g, 0.20 mmol) and N,N-diisopropylethylamine (0.088 mL, 0.50 mmol) was dissolved in dry DMF (1.5 mL). To this was added 2-(7-aza-1H-benzotriazole-1-yl)-1,1,3,3-tetramethyluronium hexafluorophosphate (HATU, 0.104 g, 0.272 mmol) followed by Compound 2 (0.043 g, 0.151 mmol) and the reaction mixture was stirred at rt overnight, diluted with water and the resulting precipitate isolated by filtration, washed with water and dried. The crude material was purified by silica gel column chromatography using a gradient of 10 to 14% EtOAc in DCM to afford the title compound (22 mg, 26%) as a pale brown amorphous solid. $^1$H NMR (500 MHz, CDCl$_3$) δ 8.09 (br s, 1H), 7.77 (br s, 1H), 7.73 (br s, 1H), 7.71-7.66 (m, 1H), 7.65 (dd, J=8.3, 2.2 Hz, 1H), 7.43 (d, J=2.2 Hz, 1H), 7.37 (dd, J=8.5, 2.2 Hz, 1H), 7.23 (d, J=8.5 Hz, 1H), 6.94 (d, J=8.3 Hz, 1H), 4.35-4.26 (m, 4H), 2.85-2.80 (m, 2H), 2.33 (br s, 3H), 1.89-1.75 (m, 4H), 1.52 (br s, 2H), 1.39 (br s, 9H). HRMS (ESI$^+$): calcd for C$_{32}$H$_{36}$N$_3$O$_6$ (M+H)$^+$, 558.2599; found 558.2582.

Example 82, N-(5-(2,3-dihydrobenzo[b][1,4]dioxine-6-carboxamido)-2-methylphenyl)-2,3,4,5-tetrahydro-1H-benzo[b]azepine-7-carboxamide Trifluoroacetic acid (0.50 mL, 6.5 mmol) was added to a solution of Compound 23 (0.016 g, 0.029 mmol) in dry DCM (0.75 mL). The reaction mixture was stirred at rt for 1 h, and then concentrated. A small amount of MeOH was added to dissolve the residue, followed by a small amount of water, and finally saturated NaHCO$_3$(aq). The resulting precipitate was isolated by filtration, washed with water and dried. The residue was purified by silica gel column chromatography using a gradient of 14 to 20% EtOAc in DCM to afford the title compound (7 mg, 53%) as an off-white solid. $^1$H NMR (500 MHz, DMSO) δ 10.03 (s, 1H), 9.53 (s, 1H), 7.78 (d, J=2.2 Hz, 1H), 7.69 (d, J=2.2 Hz, 1H), 7.62 (dd, J=8.3, 2.2 Hz, 1H), 7.54 (dd, J=8.3, 2.3 Hz, 1H), 7.53 (d, J=2.0 Hz, 1H), 7.50 (dd, J=8.4, 2.2 Hz, 1H), 7.18 (d, J=8.3 Hz, 1H), 6.97 (d, J=8.4 Hz, 1H), 6.84 (d, J=8.2 Hz, 1H), 4.33-4.27 (m, 4H), 3.07-3.02 (m, 2H), 2.79-2.72 (m, 2H), 2.17 (s, 3H), 1.76-1.70 (m, 2H), 1.69-1.63 (m, 2H). HRMS (ESI$^+$): calcd for C$_{27}$H$_{28}$N$_3$O$_4$ (M+H)$^+$, 458.2074; found 458.2081.

Preparation of Compound 24, ethyl 2-((2-((tert-butoxycarbonyl)amino)ethyl)amino)quinoline-6-carboxylate N-Boc-ethylenediamine (0.082 mL, 0.52 mmol) was added to a solution of Compound 17 (0.081 g, 0.34 mmol) and N,N-diisopropylethylamine (0.120 mL, 0.687 mmol) in dry THF (1.5 mL). The reaction mixture was heated at reflux for 24 hrs. The material was then transferred to a microwave vial and heated at 100° C. for 2 hrs, 110° C. for 8 hrs, and then at 120° C. for 3 hrs. An additional amount of N-Boc-ethylenediamine (0.054 mL, 0.34 mmol) was added and the reaction mixture was heated in the microwave at 120° C. for 2 hrs, and then stood at rt for 5 days, concentrated, diluted with EtOAc, washed with water. The aqueous phase was acidified with a few drops of 2 M HCl, then used to wash the organic phase. The resulting aqueous phase was again acidified and used to wash the organic phase. The resulting aqueous phase was adjusted to pH 3-4 with 1 M NaOH, then used to wash the organic phase. The organic phase was washed with brine (1×), dried (MgSO$_4$), filtered and concentrated. The crude residue was purified by silica gel column chromatography using a gradient of 28% to 50% EtOAc in PE to afford the title compound (39 mg, 32%) as an off-white amorphous solid. HRMS (ESI$^+$): calcd for C$_{19}$H$_{26}$N$_3$O$_4$ (M+H)$^+$, 360.1918; found 360.1924.

Preparation of Compound 25, 2-((2-((tert-butoxycarbonyl)amino)ethyl)amino)quinoline-6-carboxylic acid NaOH (0.95 M, 0.343 mL, 0.33 mmol) was added to a solution of Compound 24 (0.039 g, 0.11 mmol) in THF (1 mL), followed by MeOH (0.25 mL). The reaction mixture was stirred at rt overnight, and then more NaOH (0.95 M, 0.343 mL, 0.33 mmol) was added, and the reaction mixture was stirred at rt for 24 hrs. An additional aliquot of NaOH (0.95 M, 0.200 mL, 0.19 mmol) was added and the reaction mixture was stirred at rt for for 4 hrs, concentrated to remove organic solvents, diluted with water, and washed with EtOAc (1×). The aqueous phase was acidified with 2 M HCl to pH 4 (precipitate appeared), and the mixture was extracted with DCM (1×), CHCl$_3$(1×), and then EtOAC(2×). The combined organic phases were washed with brine (1×), dried (MgSO$_4$), filtered and concentrated to afford the title compound (23 mg, 64%) as a colourless glass. HRMS (ESI$^+$): calcd for C$_{17}$H$_{22}$N$_3$O$_4$ (M+H)$^+$, 332.1605; found 332.1602.

Preparation of Compound 26, tert-butyl (2-((6-((5-(2,3-dihydrobenzo[b][1,4]dioxine-6-carboxamido)-2-methylphenyl)carbamoyl)quinolin-2-yl)amino)ethyl)carbamate This was prepared as for Example 1, substituting Compound 8 for 6-quinolinecarboxylic acid. The crude material was purified by silica gel column chromatography using a gradient of 1 to 5% MeOH in DCM to afford the title compound in a yield of 26% as an off-white solid. HRMS (ESI$^+$): calcd for C$_{33}$H$_{36}$N$_5$O$_6$ (M+H)$^+$, 598.2660; found 598.2660.

Preparation of Compound 27, 2-((2-aminoethyl) amino)-N-(5-(2,3-dihydrobenzo[b][1,4]dioxine-6-carboxamido)-2-methylphenyl)quinoline-6-carboxamide TFA (0.5 mL) was added to a solution of Compound 26 (0.010 g, 0.018 mmol) in dry DCM (0.5 mL) and the reaction mixture was stirred at rt for 80 min, concentrated, diluted with DCM, washed with saturated NaHCO$_3$(aq) (1×). The aqueous phase was extracted with DCM (1×), EtOAc (1×). The combined organic phases were washed with brine (1×). A sticky residue on the walls of the separating funnel was dissolved in MeOH and added to the org phases before drying over MgSO$_4$, filtering and concentrating to afford the title compound (7.5 mg, 86%) as an off-white solid. HRMS (ESI$^+$): calcd for C$_{28}$H$_{28}$N$_5$O$_4$ (M+H)$^+$, 498.2136; found 498.2124.

Example 83, N-(5-(2,3-dihydrobenzo[b][1,4]dioxine-6-carboxamido)-2-methylphenyl)-2-((2-propionamidoethyl)amino)quinoline-6-carboxamide Propionyl chloride (1.4 μL, 0.017 mmol) was added to a solution of Compound 27 (0.0075 g, 0.015 mmol) and N,N-diisopropylethylamine (4.0 μL, 0.023 mmol) in dry DCM (0.5 mL). The reaction mixture was stirred at rt for 4.5 hrs, concentrated and the residue triturated in water. The resulting precipitate was isolated by filtration, washed with water and dried to afford the title compound (3.5 mg, 42%) as a white solid. $^1$H NMR (500 MHz, DMSO) δ 10.05 (s, 1H), 9.88 (s, 1H), 8.32 (s, 1H), 8.06 (d, J=7.5 Hz, 1H), 8.00-7.91 (m, 2H), 7.84 (d, J=2.2 Hz, 1H), 7.60-7.54 (m, 2H), 7.53 (d, J=2.2 Hz, 1H), 7.51 (dd, J=8.3, 2.2 Hz, 1H), 7.42-7.37 (m, 1H), 7.22 (d, J=8.4 Hz, 1H), 6.98 (d, J=8.4 Hz, 1H), 6.83 (br d, J=8.8 Hz, 1H), 4.34-4.28 (m, 4H), 3.52-3.46 (m, 2H), 3.34-3.28 (m, 2H), 2.22 (s, 3H), 2.09 (q, J=7.6 Hz, 2H), 0.99 (t, J=7.6 Hz, 3H). HRMS (ESI$^+$): calcd for C$_{31}$H$_{32}$N$_5$O$_5$ (M+H)$^+$, 554.2398; found 554.2386.

Preparation of Compound 28,[4] methyl indoline-5-carboxylate

A mixture of methyl indole-5-carboxylate (0.500 g, 2.85 mmol) in AcOH (5 mL) was warmed to dissolve all solid. The solution was then cooled in an ice bath, and sodium cyanoborohydride (0.538 g, 8.56 mmol) was added portionwise over 10 min. Note that upon addition, the solution froze, thus was warmed a bit in order to achieve stirring, and occasionally cooled during the addition. After the addition was complete, the reaction mixture was allowed to warm to rt, and stirred for 1 hr. Water (1.5 mL) was added, and the reaction mixture was concentrated to leave a viscous oil. EtOAc was added, washed with saturated NaHCO$_3$(aq) (2×). The aqueous phase was extracted with EtOAc (2×). The combined organic phases were washed with brine (1×), dried (MgSO$_4$), filtered and concentrated. The crude material was purified by silica gel column chromatography using 1:1 PE to afford the title compound (344 mg, 68%) as a white solid. $^1$H NMR (500 MHz, CDCl$_3$) δ 7.77-7.74 (m, 2H), 6.55 (d, J=8.6 Hz, 1H), 4.11 (br s, 1H), 3.84 (s, 3H), 3.65 (t, J=8.5 Hz, 2H), 3.06 (t, J=8.5 Hz, 2H). HRMS (ESI$^+$): calcd for C$_{10}$H$_{12}$NO$_2$ (M+H)$^+$, 178.0863; found 178.0865.

Preparation of Compound 29, 1-tert-butyl 5-methyl indoline-1,5-dicarboxylate Di-tert-butyl dicarbonate (0.489 g, 2.24 mmol), followed by triethylamine (0.315 mL, 2.24 mmol) was added to a solution of Compound 28 (0.328 g, 1.85 mmol) in dry DCM (5.8 mL) and the reaction mixture was stirred at rt for 26 hrs, concentrated. The residue was dissolved in EtOAc and washed with water (1×), brine (1×), dried (MgSO$_4$), filtered and concentrated. The crude material was recrystallized from hot EtOH to afford the title compound (373 mg, 73%) as a white solid. $^1$H NMR (500 MHz, CDCl$_3$) δ 7.88 (d, J=7.6 Hz, 1H), 7.82-7.79 (m, 1H), 4.02 (t, J=8.7 Hz, 2H), 3.88 (s, 3H), 3.14-3.09 (m, 2H), 1.57 (br s, 9H). Note that there also appears to be 2 extremely broad and weak singlets centred at 7.85 and 7.50 ppm which may be the missing aromatic CH. LRMS (ESI$^+$): 178.09 (loss of Boc) and very weak 278.15

Preparation of Compound 30, 1-(tert-butoxycarbonyl)indoline-5-carboxylic acid A solution of LiOH·H$_2$O (0.086 g, 2.05 mmol) in water (5 mL) was added to a solution of Compound 29 (0.284 g, 1.02 mmol) in THF (5 mL) and the reaction mixture was stirred at rt for 3 days after which point a small amount of MeOH was added to clear the cloudiness of the reaction mixture. NaOH (1.98 M, 1.03 mL, 2.05 mmol) was then added and the reaction mixture stirred at rt for 23.5 hrs, concentrated to remove organic solvents, then acidified with 2 M HCl to pH 3 and the resulting solid isolated by filtration, washed with water and dried to afford the title compound (257 mg, 95%) as a white solid. $^1$H NMR (500 MHz, DMSO) δ 12.56 (br s, 1H), 7.77 (dd, J=8.2, 1.8 Hz, 1H), 7.73 (d, J=1.3 Hz, 1H), 7.70 (v br s, 1H), 3.95 (t, J=8.8 Hz, 2H), 3.09 (t, J=8.7 Hz, 2H), 1.51 (s, 9H). LRMS (ESI$^+$): 164.07 (loss of Boc).

Example 84, N-(5-(2,3-dihydrobenzo[b][1,4]dioxine-6-carboxamido)-2-methylphenyl)indoline-5-carboxamide Trifluoroacetic acid (1.56 mL, 20.2 mmol) was added to a suspension of Example 30 (0.074 g, 0.14 mmol) in dry DCM (2 mL) and the reaction mixture was stirred at rt for 1.5 hrs, concentrated, added DCM and concentrated again. Water, followed by saturated NaHCO$_3$(aq) was added to the residue and mixture was then triturated and sonicated, and the resulting solid isolated by filtration, washed with water and dried. The crude material was purified by silica gel column chromatography using 2% MeOH in DCM to afford the title compound (47 mg, 78%) as a white solid. $^1$H NMR (500 MHz, DMSO) δ 10.02 (s, 1H), 9.40 (s, 1H), 7.78 (d, J=2.2 Hz, 1H), 7.68 (s, 1H), 7.64 (dd, J=8.2, 1.9 Hz, 1H), 7.56-7.52 (m, 2H), 7.50 (dd, J=8.4, 2.2 Hz, 1H), 7.17 (d, J=8.4 Hz, 1H), 6.97 (d, J=8.4 Hz, 1H), 6.50 (d, J=8.1 Hz, 1H), 6.12 (br s, 1H), 4.33-4.28 (m, 4H), 3.52 (td, J=8.7, 1.5 Hz, 2H), 2.98 (t, J=8.6 Hz, 2H), 2.17 (s, 3H). HRMS (ESI$^+$): calcd for C$_{25}$H$_{24}$N$_3$O$_4$ (M+H)$^+$, 430.1761; found 430.1747.

Example 85—Preparation of tert-butyl ((6-((5-(2,3-dihydrobenzo[b][1,4]dioxine-6-carboxamido)-2-methylphenyl)carbamoyl)-1,2,3,4-tetrahydroquinolin-2-yl)methyl)(methyl)carbamate All mixture of Compound 16 (0.177 g, 0.304 mmol) and Pd/C (10%, 0.035 g) in EtOAc (6 mL) and EtOH (6 mL) was stirred under 1 atm H$_2$ at 40° C. for 22 hrs after which time additional Pd/C (10%, 0.035 mg) was added and the reaction mixture stirred under 1 atm H2 at 45° C. for 18 hrs, then at 50° C. for 8 hrs, filtered through celite with EtOAc, concentrated and the residue was purified by silica gel column chromatography using 3:1 DCM:EtOAc to afford the title compound (151 mg, 85%) as a white amorphous solid. $^1$H NMR (500 MHz, CDCl$_3$) δ 8.07 (d, J=2.2 Hz, 1H), 7.79 (s, 1H), 7.75 (d, J=8.1 Hz, 1H), 7.57 (s, 1H), 7.54 (br s, 1H), 7.50 (br d, J=8.2 Hz, 1H), 7.43 (d, J=2.2 Hz, 1H), 7.36 (dd, J=8.4, 2.2 Hz, 1H), 7.20 (d, J=8.3 Hz, 1H), 6.93 (d, J=8.4 Hz, 1H), 6.48 (d, J=8.3 Hz, 1H), 4.33-4.28 (m, 4H), 3.67-3.60 (m, 1H), 3.39 (d, J=7.4 Hz, 1H), 3.30 (v br s, 1H), 2.95 (s, 3H), 2.86-2.83 (m, 2H), 2.31 (s, 3H), 1.98-1.90 (br s, 1H), 1.74-1.65 (m, 1H), 1.48 (s, 9H). HRMS (ESI$^+$): calcd for C$_{33}$H$_{39}$N$_4$O$_6$ (M+H)$^+$, 587.2864; found 587.2897.

Example 86—Preparation of N-(5-(2,3-dihydrobenzo[b][1,4]dioxine-6-carboxamido)-2-methylphenyl)-2-((methylamino)methyl)-1,2,3,4-tetrahydroquinoline-6-carboxamide TFA (1.5 mL) was added to a solution of Example 85 (0.144 g, 0.245 mmol) in dry DCM (2 mL) and the reaction mixture was stirred at rt for 1 hr, concentrated, added DCM and concentrated again. The residue was dissolved in DCM, and washed with saturated NaHCO$_3$(aq) causing a solid to form which stuck to the walls of the separating funnel. The aqueous phase was extracted with DCM (1×). The solid stuck to the flask was dissolved with a small amount of MeOH, then DCM was added and this mixture washed with water (1×). This aqueous phase was extracted with DCM (1×) and the combined organic phases were dried (Na$_2$SO$_4$), filtered and concentrated. The crude material was suspended in a few mLs of MeOH and then diluted with water. The resulting solid was isolated by filtration, washed with water and dried to afford the title compound (92 mg, 77%) as a white solid. $^1$H NMR (500 MHz, DMSO) δ 10.01 (s, 1H), 9.34 (s, 1H), 7.77 (d, J=2.2 Hz, 1H), 7.58-7.52 (m, 4H), 7.50 (dd, J=8.4, 2.2 Hz, 1H), 7.17 (d, J=8.3 Hz, 1H), 6.97 (d, J=8.3 Hz, 1H), 6.56 (d, J=8.4 Hz, 1H), 6.17 (s, 1H), 4.33-4.28 (m, 4H), 3.39-3.33 (m, 1H), 2.79-2.65 (m, 2H), 2.57 (dd, J=11.6, 5.2 Hz, 1H), 2.54-2.47 (m, 1H), 2.32 (s, 3H), 2.16 (s, 3H), 1.93-1.86 (m, 1H), 1.57-1.48 (m, 1H). HRMS (ESI$^+$): calcd for C$_{28}$H$_{31}$N$_4$O$_4$ (M+H)$^+$, 487.2340; found 487.2327.

Example 87—Preparation of N-(5-(2,3-dihydrobenzo[b][1,4]dioxine-6-carboxamido)-2-methylphenyl)-2-((dimethylamino)methyl)-1,2,3,4-tetrahydroquinoline-6-carboxamide A solution of MeI (50 uL in 2 mL CH$_3$CN) was made, and 113.2 uL of this solution was added slowly to a suspension of Example 86 (0.020 g, 0.041 mmol) and potassium carbonate (8.5 mg, 0.062 mmol) in dry acetonitrile (1.5 mL) at 0° C. The reaction mixture was stirred at 0° C. for 5 min, then allowed to warm to rt and stirred for 70 min, at which point solid adhering to the upper walls of the flask was rinsed into the reaction mixture with DMF (0.5 mL) and the reaction was stirred at rt for a further 2.5 hrs. An additional amount of MeI solution (0.020 mmol) was added and the reaction mixture stirred for a further 40 min, diluted with water, extracted with DCM (3×). The organic phase was dried (MgSO$_4$), filtered and concentrated. Heptane was added and the mixture concentrated (2×) to remove residual DMF. The crude material was purified by silica gel column chromatography using a gradient of 2% to 4% 2 M NH$_3$-MeOH in DCM, to afford the title compound (14 mg, 68%) as a white solid. $^1$H NMR (500 MHz, DMSO) δ 10.01 (s, 1H), 9.35 (s, 1H), 7.77 (d, J=2.2 Hz, 1H), 7.59-7.52 (m, 4H), 7.50 (dd, J=8.5, 2.2 Hz, 1H), 7.17 (d, J=8.4 Hz, 1H), 6.97 (d, J=8.4 Hz, 1H), 6.63 (d, J=8.3 Hz, 1H), 5.99 (s, 1H), 4.33-4.28 (m, 4H), 3.47-3.38 (m, 1H), 2.82-2.65 (m, 2H), 2.33 (dd, J=11.8, 8.5 Hz, 1H), 2.26-2.22 (m, 1H), 2.21 (s, 6H), 2.16 (s, 3H), 1.92-1.85 (m, 1H), 1.53-1.43 (m, 1H). HRMS (ESI$^+$): calcd for C$_{29}$H$_{33}$N$_4$O$_4$ (M+H)$^+$, 501.2496; found 501.2496.

Preparation of Compound 31, tert-butyl 6-((5-(2,3-dihydrobenzo[b][1,4]dioxine-6-carboxamido)-2-methylphenyl)carbamoyl)-3,4-dihydroisoquinoline-2 (1H)-carboxylate This was prepared as for Example 1, substituting N-Boc-1,2,3,4-tetrahydroisoquinoline-6-carboxylic acid for 6-quinolinecarboxylic acid. The crude material was purified by silica gel column chromatography using a gradient of 44 to 67% EtOAc in PE, then 3-5% MeOH in DCM to afford the title compound in a yield of 95% as a white solid. $^1$H NMR (500 MHz, DMSO) δ 10.05 (s, 1H), 9.86 (s, 1H), 7.82-7.78 (m, 3H), 7.57 (dd, J=8.3, 2.2 Hz, 1H), 7.53 (d, J=2.1 Hz, 1H), 7.50 (dd, J=8.4, 2.2 Hz, 1H), 7.33 (d, J=8.5 Hz, 1H), 7.21 (d, J=8.5 Hz, 1H), 6.98 (d, J=8.4 Hz, 1H), 4.58 (br s, 2H), 4.33-4.28 (m, 4H), 3.59 (t, J=5.8 Hz, 2H), 2.87 (t, J=5.9 Hz, 2H), 2.18 (s, 3H), 1.44 (s, 9H). LRMS (ESI$^+$): 544.24

Example 88, N-(5-(2,3-dihydrobenzo[b][1,4]dioxine-6-carboxamido)-2-methylphenyl)-1,2,3,4-tetrahydroisoquinoline-6-carboxamide TFA (2 mL) was added to a suspension of Compound 31 (0.104 g, 0.191 mmol) in dry DCM (3 mL) and the reaction mixture was stirred at rt for 1.5 hrs, diluted with saturated NaHCO$_3$(aq), and the resulting precipitate was isolated by filtration, washed with water and dried to afford the title compound (52 mg, 61%) as an off-white solid. Additional material (12 mg) was collected from the filtrate. $^1$H NMR (500 MHz, DMSO) δ 10.04 (s, 1H), 9.81 (s, 1H), 7.80 (d, J=2.0 Hz, 1H), 7.75-7.72 (m, 2H), 7.56 (dd, J=8.3, 2.1 Hz, 1H), 7.53 (d, J=2.1 Hz, 1H), 7.50 (dd, J=8.4, 2.1 Hz, 1H), 7.21 (d, J=8.4 Hz, 1H), 7.18 (d, J=8.5 Hz, 1H), 6.98 (d, J=8.4 Hz, 1H), 4.33-4.28 (m, 4H), 3.96 (s, 2H), 3.03 (t, J=5.9 Hz, 2H), 2.81 (t, J=5.6 Hz, 2H), 2.18 (s, 3H). HRMS (ESI$^+$): calcd for C$_{26}$H$_{26}$N$_3$O$_4$ (M+H)$^+$, 444.1918; found 444.1916.

Preparation of Compound 32, 4-((3-iodophenyl)amino)benzoic acid

Methanesulfonic acid (0.144 mL, 2.22 mmol) was added to a solution of 6-chloronicotinic acid (0.350 g, 2.22 mmol) and 3-iodoaniline (0.487 g, 2.22 mmol) in dry dioxane (5.5 mL). A thick ppt formed. The reaction mixture was heated at reflux overnight, cooled to rt, concentrated, diluted with 1 M NaOH and water, washed with DCM (2×). The aqueous phase was acidified to pH 3-4 with 2 M HCl, and the resulting precipitate was isolated by filtration, washed with water and dried to afford the title compound (647 mg, 86%) as a white solid. $^1$H NMR (500 MHz, DMSO) δ 12.75 (br s, 1H), 9.66 (s, 1H), 8.72 (d, J=2.2 Hz, 1H), 8.20 (t, J=1.8 Hz, 1H), 8.01 (dd, J=8.7, 2.4 Hz, 1H), 7.71 (ddd, J=8.2, 2.1, 0.8 Hz, 1H), 7.31 (ddd, J=7.7, 1.5, 0.9 Hz, 1H), 7.10 (t, J=8.0 Hz, 1H), 6.88-6.84 (m, 1H). LRMS (ESI$^+$): 340.97.

Preparation of Compound 33, 6-bromo-2-((1-methylpiperidin-4-yl)oxy)quinoline

This was prepared as for Compound 3, substituting 4-hydroxy-1-methylpiperidine for (R)-(−)-1-methyl-3-hydroxypyrrolidine. The crude material was purified by silica gel column chromatography using a gradient of 4-13% MeOH in DCM to afford the title compound as an off-white solid.

¹H NMR (500 MHz, CDCl₃) δ 7.87 (d, J=8.8 Hz, 1H), 7.84 (ap t, J=1.4 Hz, 1H), 7.67-7.65 (m, 2H), 6.89 (d, J=8.9 Hz, 1H), 5.35-5.28 (m, 1H), 2.79-2.71 (m, 2H), 2.40-4.32 (m, 2H), 2.34 (s, 3H), 2.16-2.09 (m, 2H), 1.94-1.86 (m, 2H). HRMS (ESI⁺): calcd for C₁₅H₁₈⁷⁹BrN₂O (M+H)⁺, 321.0597; found 321.0597.

Preparation of Compound 34, 2-((1-methylpiperidin-4-yl)oxy)quinoline-6-carboxylic acid hydrochloride This was prepared as for Compound 4, substituting Compound 33 for Compound 3 to afford the title compound as an off-white solid. ¹H NMR (500 MHz, DMSO) δ 13.10 (v br s, 1H), 11.07 (br s, 0.5H), 10.90 (br s, 0.5H), 8.58-8.56 (m, 1H), 8.48-8.43 (m, 1H), 8.17-8.12 (m, 1H), 7.83-7.78 (m, 1H), 7.13-7.08 (m, 1H), 5.57-5.53 (m, 0.5H), 5.46-5.38 (m, 0.5H), 3.36-3.13 (m, 4H), 2.78-2.73 (m, 3H), 2.38-2.32 (m, 1H), 2.30-2.17 (m, 2H), 2.10-2.00 (m, 1H). Note: this ¹H NMR spectrum shows a mixture of isomers in ~1:1 ratio; The peaks coalesce at 395 K. LRMS (ESI⁺): 287.14.

Preparation of Compound 35, 3-((6-bromoquinolin-2-yl)oxy)-N,N-dimethylpropan-1-amine This was prepared as for Compound 3, substituting 3-dimethylamino-1-propanol for (R)-(−)-1-methyl-3-hydroxypyrrolidine. The crude material was purified by silica gel column chromatography using a gradient of 3-6% MeOH in DCM to afford the title compound as a pale orange solid. ¹H NMR (500 MHz, CDCl₃) δ 7.87 (d, J=8.9 Hz, 1H), 7.85-7.84 (m, 1H), 7.70-7.64 (m, 2H), 6.90 (d, J=8.9 Hz, 1H), 4.50 (t, J=6.6 Hz, 2H), 2.47 (t, J=6.6 Hz, 2H), 2.27 (s, 6H), 2.00 (p, J=6.7 Hz, 2H). HRMS (ESI⁺): calcd for C₁₄H₁₈⁷⁹BrN₂O (M+H)⁺, 309.0597; found 309.0596.

Preparation of Compound 36, 2-(3-(dimethylamino)propoxy)quinoline-6-carboxylic acid hydrochloride This was prepared as for Compound 4, substituting Compound 35 for Compound 3 to afford the title compound as a white solid. ¹H NMR (500 MHz, DMSO) δ 13.07 (v br s, 1H), 10.84 (br s, 1H), 8.57 (d, J=1.9 Hz, 1H), 8.44 (d, J=8.8 Hz, 1H), 8.14 (dd, J=8.7, 2.0 Hz, 1H), 7.82 (d, J=8.7 Hz, 1H), 7.10 (d, J=8.9 Hz, 1H), 4.52 (t, J=6.2 Hz, 2H), 3.26-3.19 (m, 2H), 2.76 (d, J=4.9 Hz, 6H), 2.27-2.18 (m, 2H). HRMS (ESI⁺): calcd for C₁₅H₁₉N₂O₃ (M+H)⁺, 275.1390; found 275.1393.

Preparation of Compound 37, 6-bromo-2-(3-(piperidin-1-yl)propoxy)quinoline

This was prepared as for Compound 3, substituting 1-piperidinepropanol for (R)-(−)-1-methyl-3-hydroxypyrrolidine. The crude material was purified by silica gel column chromatography using a gradient of 2.5-6% MeOH in DCM to afford the title compound as a pale yellow solid. ¹H NMR (500 MHz, CDCl₃) δ 7.87 (d, J=8.8 Hz, 1H), 7.84 (d, J=1.9 Hz, 1H), 7.70-7.64 (m, 2H), 6.89 (d, J=8.8 Hz, 1H), 4.49 (t, J=6.5 Hz, 2H), 2.54-2.49 (m, 2H), 2.44 (br s, 4H), 2.04 (p, J=6.7 Hz, 2H), 1.64-1.58 (m, 4H), 1.45 (br s, 2H). HRMS (ESI⁺): calcd for C₁₇H₂₂⁷⁹BrN₂O (M+H)⁺, 349.0910; found 349.0911.

Preparation of Compound 38, 2-(3-(piperidin-1-yl)propoxy)quinoline-6-carboxylic acid hydrochloride This was prepared as for Compound 4, substituting Compound 37 for Compound 3 to afford the title compound as a pale yellow solid. ¹H NMR (500 MHz, DMSO) δ 13.05 (v br s, 1H), 10.72 (br s, 1H), 8.57 (d, J=1.9 Hz, 1H), 8.44 (d, J=8.9 Hz, 1H), 8.14 (dd, J=8.7, 2.0 Hz, 1H), 7.81 (d, J=8.7 Hz, 1H), 7.09 (d, J=8.9 Hz, 1H), 4.52 (t, J=6.2 Hz, 2H), 3.44 (br d, J=11.8 Hz, 2H), 3.21-3.15 (m, 2H), 2.91-2.82 (m, 2H), 2.32-2.25 (m, 2H), 1.90-1.65 (m, 6H). HRMS (ESI⁺): calcd for C₁₈H₂₃N₂O₃ (M+H)⁺, 315.1703; found 315.1699.

Preparation of Compound 39, 6-bromo-2-(2-methoxyethoxy)quinoline

This was prepared as for Compound 3, substituting 2-methoxyethanol for (R)-(−)-1-methyl-3-hydroxypyrrolidine. The reaction mixture was diluted with water causing the title compound to precipitate as an off-white solid and was used without further purification. ¹H NMR (500 MHz, CDCl₃) δ 7.89 (d, J=8.9 Hz, 1H), 7.86 (d, J=1.6 Hz, 1H), 7.71-7.65 (m, 2H), 6.98 (d, J=8.9 Hz, 1H), 4.66-4.61 (m, 2H), 3.83-3.77 (m, 2H), 3.46 (s, 3H). HRMS (ESI⁺): calcd for C₁₂H₁₃⁷⁹BrNO (M+H)⁺, 282.0124; found 282.0130.

Preparation of Compound 40, 2-(2-methoxyethoxy)quinoline-6-carboxylic acid

This was prepared as for Compound 4, substituting Compound 39 for Compound 3 to afford the title compound as a pale pink solid. ¹H NMR (500 MHz, CDCl₃) δ 8.55 (d, J=1.9 Hz, 1H), 8.27 (dd, J=8.7, 2.0 Hz, 1H), 8.09 (d, J=8.8 Hz, 1H), 7.87 (d, J=8.8 Hz, 1H), 7.04 (d, J=8.9 Hz, 1H), 4.72-4.67 (m, 2H), 3.85-3.81 (m, 2H), 3.48 (s, 2H). HRMS (ESI⁺): calcd for C₁₃H₁₄NO₄ (M+H)⁺, 248.0917; found 248.0918.

Preparation of Compound 41, (S)-6-bromo-2-((1-methylpyrrolidin-2-yl)methoxy)quinoline This was prepared as for Compound 3, substituting (S)-(−)-1-methyl-2-pyrrolidinemethanol for (R)-(−)-1-methyl-3-hydroxypyrrolidine. The crude material was purified by silica gel column chromatography using a gradient of 3-7% MeOH in DCM to afford the title compound as a pale orange oil. ¹H NMR (500 MHz, CDCl₃) δ 7.88 (d, J=8.9 Hz, 1H), 7.85 (d, J=1.9 Hz, 1H), 7.70-7.64 (m, 2H), 6.95 (d, J=8.9 Hz, 1H), 4.52 (dd, J=11.0, 5.1 Hz, 1H), 4.42 (dd, J=11.0, 5.1 Hz, 1H), 3.14 (t, J=8.0 Hz, 1H), 2.71-2.65 (m, 1 OH), 2.51 (s, 3H), 2.34-2.26 (m, 1H), 2.07-1.96 (m, 1H), 1.91-1.72 (m, 3H). HRMS (ESI⁺): calcd for C₁₅H₁₈⁷⁹BrN₂O (M+H)⁺, 321.0597; found 321.0585.

Preparation of Compound 42, (S)-2-((1-methylpyrrolidin-2-yl)methoxy)quinoline-6-carboxylic acid hydrochloride This was prepared as for Compound 4, substituting Compound 41 for Compound 3 to afford the title compound as a pale yellow solid. ¹H NMR (500 MHz, DMSO) δ 13.09 (v br s, 1H), 11.37 (br s, 1H), 8.59 (d, J=1.9 Hz, 19H), 8.48 (d, J=8.7 Hz, 1H), 8.16 (dd, J=8.7, 2.0 Hz, 1H), 7.85 (d, J=8.7 Hz, 1H), 7.20 (d, J=8.8 Hz, 1H), 4.85-4.78 (m, 2H), 3.91-3.84 (m, 1H), 3.63-3.54 (m, 1H), 3.15-3.06 (m, 1H), 2.94 (d, J=4.9 Hz, 3H), 2.35-2.25 (m, 1H), 2.08-1.83 (m, 3H). HRMS (ESI⁺): calcd for C₁₆H₁₉N₂O₃ (M+H)⁺, 287.1390; found 287.1390.

Preparation of Compound 43, 6-bromo-2-(2-(piperidin-1-yl)ethoxy)quinoline

This was prepared as for Compound 3, substituting 4-(2-hydroxyethyl)piperidine for (R)-(−)-1-methyl-3-hydroxypyrrolidine. The crude material was purified by silica gel column chromatography using a gradient of 4-5% MeOH in DCM to afford the title compound as a pale yellow oil. $^1$H NMR (500 MHz, CDCl$_3$) δ 7.87 (d, J=8.9 Hz, 1H), 7.85 (d, J=1.9 Hz, 1H), 7.70-7.64 (m, 2H), 6.93 (d, J=8.9 Hz, 1H), 4.60 (t, J=6.1 Hz, 2H), 2.81 (t, J=6.0 Hz, 2H), 2.53 (br s, 4H), 1.65-1.68 (m, 4H), 1.48-1.42 (m, 2H). HRMS (ESI$^+$): calcd for C$_{16}$H$_{20}$$^{79}$BrN$_2$O (M+H)$^+$, 335.0754; found 335.0755.

Preparation of Compound 44,
2-(2-(piperidin-1-yl)ethoxy)quinoline-6-carboxylic acid hydrochloride This was prepared as for Compound 4, substituting Compound 43 for Compound 3 to afford the title compound as an off-white solid. $^1$H NMR (500 MHz, DMSO) δ 13.10 (v br s, 1H), 10.99 (br s, 1H), 8.59 (d, J=1.9 Hz, 1H), 8.47 (d, J=8.9 Hz, 1H), 8.16 (dd, J=8.7, 2.0 Hz, 1H), 7.85 (d, J=8.7 Hz, 1H), 7.16 (d, J=8.9 Hz, 1H), 4.89-4.82 (m, 2H), 3.58-3.46 (m, 4H), 3.05-2.96 (m, 2H), 1.88-1.64 (m, 4H). HRMS (ESI$^+$): calcd for C$_{17}$H$_{21}$N$_2$O$_3$ (M+H)$^+$, 301.1547; found 301.1535.

Preparation of Compound 45,
2-oxo-2H-chromene-6-carboxylic acid

Water (0.65 mL) was added to 62.5% H$_2$SO$_4$ (3.05 mL), followed by 6-methylcoumarin (0.500 g, 3.12 mmol), and chlorobenzene (0.5 mL). The reaction mixture was heated to 85° C. and then manganese(IV) oxide (0.800 g, 9.20 mmol) was added portion-wise, followed by 62.5% H$_2$SO$_4$ (0.4 mL). The reaction mixture was stirred for 30 min at 85° C., cooled to rt, added water (2.9 mL), followed by NH$_3$(aq) (25%, 0.85 mL) dropwise. Next EtOAc (8 mL) was added and the aqueous layer was removed and extracted with a small amount of EtOAc, and the combined organic layers were washed with a small amount of water. To the organic phase was added DMSO (0.3 mL), followed by 25% NH$_3$ (aq) (0.2 mL) dropwise. The reaction mixture was heated to 30-40° C., and then sodium chlorite (80%, solution of 25% in water, 1.125 mL, 3.12 mmol) was added dropwise. The rxn mix was stirred at 40° C. for 1 hr, then 25% NH$_3$(aq) (0.27 mL) was added, and the phases were separated. To the aqueous layer was added MeOH (1.5 mL), HCl (0.1 mL), and then heated to 30° C. before sodium sulfite (0.039 g, 3.1 mmol) was added. The reaction mixture was stirred at 30° C. for 25 min, and then heated to 45° C. before HCl (0.5 mL) was added dropwise. The rxn mixture was then cooled in an ice bath, and the resulting solid collected by filtration, washed with water and dried to afford the title compound (25 mg, 4%) as a dull orange solid. $^1$H NMR (500 MHz, DMSO) δ 13.23 (br s, 1H), 8.36 (d, J=2.1 Hz, 1H), 8.20 (d, J=9.4 Hz, 1H), 8.12 (dd, J=8.6, 2.1 Hz, 1H), 7.49 (d, J=8.7 Hz, 1H), 6.59 (d, J=9.6 Hz, 1H). HRMS (ESI$^+$): calcd for C$_{10}$H$_7$O$_4$ (M+H)$^+$, 191.0339; found 191.0341.

Preparation of Compound 46, 4-(3-((6-bromoquinolin-2-yl)oxy)propyl)morpholine

This was prepared as for Compound 3, substituting 4-(3-hydroxypropyl)morpholine for (R)-(−)-1-methyl-3-hydroxypyrrolidine. The crude material was purified by silica gel column chromatography using a gradient of 1.5-3.5% MeOH in DCM to afford the title compound as a white solid. $^1$H NMR (500 MHz, CDCl$_3$) δ 7.88 (d, J=8.9 Hz, 1H), 7.86-7.84 (m, 1H), 7.69-7.65 (m, 2H), 6.90 (d, J=8.9 Hz, 1H), 4.51 (t, J=6.5 Hz, 2H), 3.73 (t, J=4.6 Hz, 4H), 2.57-2.53 (m, 2H), 2.49 (br s, 4H), 2.06-1.98 (m, 2H). HRMS (ESI$^+$): calcd for C$_{16}$H$_{20}$$^{79}$BrN$_2$O$_2$(M+H)$^+$, 351.0703; found 351.0712.

Preparation of Compound 47,
2-(3-morpholinopropoxy)quinoline-6-carboxylic acid hydrochloride This was prepared as for Compound 4, substituting Compound 46 for Compound 3 to afford the title compound as a pale yellow solid. $^1$H NMR (500 MHz, DMSO) δ 11.54 (br s, 1H), 8.57 (d, J=2.1 Hz, 1H), 8.44 (d, J=8.9 Hz, 1H), 8.14 (dd, J=8.7, 1.9 Hz, 1H), 7.82 (d, J=8.7 Hz, 1H), 7.10 (d, J=8.9 Hz, 1H), 4.53 (t, J=6.2 Hz, 2H), 3.97-3.92 (m, 2H), 3.91-3.81 (m, 2H), 3.45 (d, J=12.3 Hz, 2H), 3.31-3.23 (m, 2H), 3.12-3.02 (m, 2H), 2.34-2.25 (m, 2H). HRMS (ESI$^+$): calcd for C$_{17}$H$_{21}$N$_2$O$_4$ (M+H)$^+$, 317.1496; found 317.1501.

Preparation of Compound 48,[5]
3-(pyrrolidin-1-yl)propan-1-ol

Pyrrolidine (1.00 mL, 12.0 mmol) was added to a suspension of potassium carbonate (1.29 g, 9.35 mmol) and 3-bromopropanol (0.65 mL, 7.2 mmol) in dry THF (3 mL) at 0° C. The reaction mixture was then allowed to warm to rt, stirred overnight, diluted with EtOAc, filtered through a silica pad and the filtrate concentrated to afford the title compound (645 mg, 69%) as a colourless oil. $^1$H NMR (500 MHz, CDCl$_3$) δ 5.54 (br s, 1H), 3.84-3.77 (m, 2H), 2.77-2.68 (m, 2H), 2.60-2.53 (m, 4H), 1.80-1.68 (m, 6H). LRMS (ESI$^+$) (M+H)+: 130.12

Preparation of Compound 49,
6-bromo-2-(3-(pyrrolidin-1-yl)propoxy)quinoline

This was prepared as for Compound 3, substituting Compound 48 for (R)-(−)-1-methyl-3-hydroxypyrrolidine. The crude material was purified by silica gel column chromatography using a gradient of 3-3.6% MeOH in DCM to afford the title compound as an off-white solid. $^1$H NMR (500 MHz, CDCl$_3$) δ 7.87 (d, J=8.8 Hz, 1H), 7.84 (d, J=2.0 Hz, 1H), 7.70-7.64 (m, 2H), 6.90 (d, J=8.9 Hz, 1H), 4.51 (t, J=6.5 Hz, 2H), 2.70-2.62 (m, 2H), 2.56 (br s, 4H), 2.11-2.01 (m, 2H), 1.83-1.78 (m, 4H). HRMS (ESI$^+$): calcd for C$_{16}$H$_{20}$$^{79}$BrN$_2$O (M+H)$^+$, 335.0754; found 335.0749.

Preparation of Compound 50, 2-(3-(pyrrolidin-1-yl)propoxy)quinoline-6-carboxylic acid hydrochloride This was prepared as for Compound 4, substituting Compound 49 for Compound 3 to afford the title compound as a pale yellow solid. $^1$H NMR (500 MHz, DMSO) δ 10.84 (br s, 1H), 8.57 (d, J=1.9 Hz, 1H), 8.44 (d, J=8.8 Hz, 1H), 8.14 (dd, J=8.7, 2.0 Hz, 1H), 7.82 (d, J=8.7 Hz, 1H), 7.10 (d, J=8.9 Hz, 1H), 4.53 (t, J=6.2 Hz, 2H), 3.57-3.52 (m, 2H), 3.34-3.26 (m, 2H), 3.04-2.95 (m, 2H), 2.27-2.19 (m, 2H), 2.01-1.97 (m, 2H), 1.92-1.85 (m, 2H). HRMS (ESI$^+$): calcd for C$_{17}$H$_{21}$N$_2$O$_4$ (M+H)$^+$, 301.1547; found 301.1549.

Preparation of Compound 51, tert-butyl (2-((6-bromoquinolin-2-yl)oxy)ethyl)carbamate This was prepared as for Compound 3, substituting tert-butyl N-(2-hydroxyethyl)carbamate for (R)-(−)-1-methyl-3-hydroxypyrrolidine. The crude material was purified by silica gel column chromatography using a gradient of 20-25% diethyl ether in PE to afford the title compound as a white solid. $^1$H NMR (500 MHz, DMSO) b 8.22 (d, J=8.9 Hz, 1H), 8.17 (d, J=2.3 Hz, 1H), 7.77 (dd, J=8.9, 2.3 Hz, 1H), 7.69 (d, J=8.9 Hz, 1H), 7.05 (d, J=8.8 Hz, 1H), 7.03 (t, J=5.7 Hz, 1H), 4.39 (t, J=5.7 Hz, 2H), 3.36 (q, J=5.8 Hz, 2H), 1.37 (s, 9H). HRMS (ESI$^+$): calcd for $C_{16}H_{20}{}^{79}BrN_2O_3$ (M+H)$^+$, 367.0652; found 367.0649.

Preparation of Compound 52, 2-(2-((tert-butoxycarbonyl)amino)ethoxy)quinoline-6-carboxylic acid This was prepared as for Compound 4, substituting Compound 51 for Compound 3, and using 2.2 equivalents of nBuLi. In the work-up, when the aqueous solution was acidified, no precipitate formed, and thus the aqueous layer was extracted with DCM (3×), and this organic phase was dried over MgSO$_4$, filtered and concentrated to afford the title compound as a white solid. $^1$H NMR (500 MHz, DMSO) δ 13.06 (br s, 1H), 8.56 (d, J=1.9 Hz, 1H), 8.41 (d, J=8.9 Hz, 1H), 8.13 (dd, J=8.7, 2.0 Hz, 1H), 7.80 (d, J=8.8 Hz, 1H), 7.07 (d, J=8.9 Hz, 1H), 7.04 (t, J=5.7 Hz, 1H), 4.43 (t, J=5.8 Hz, 2H), 3.37 (q, J=5.6 Hz, 2H), 1.37 (s, 9H). HRMS (ESI$^+$): calcd for $C_{17}H_{21}N_2O_5$ (M+H)$^+$, 333.1445; found 333.1447.

Preparation of Compound 53, 2-(3-fluoropiperidin-1-yl)ethanol

2-Bromoethanol (0.184 mL, 2.60 mmol) was added to a suspension of 3-fluoropiperidine hydrochloride (0.352 g, 2.52 mmol) and potassium carbonate (0.767 g, 5.55 mmol) in dry acetonitrile (5.5 mL) and the reaction mixture was heated at reflux overnight, cooled to rt, filtered, concentrated, added diethyl ether, extracted with 1 M HCl (2×). The aqueous phase was made basic (pH>12) with solid NaOH, then extracted with DCM (3×). This organic phase was dried over K$_2$CO$_3$, filtered and concentrated to afford the title compound (201 mg, 54%), as a pale yellow oil. $^1$H NMR (500 MHz, CDCl$_3$) δ 4.83-4.69 (m, 1H), 3.75-3.68 (m, 2H), 3.02-2.94 (m, 1H), 2.76-2.63 (m, 4H), 2.57-2.50 (m, 1H), 1.98-1.85 (m, 2H), 1.76-1.61 (m, 2H). HRMS (ESI$^+$): calcd for $C_7H_{15}FNO$ (M+H)$^+$, 148.1132; found 148.1138.

Preparation of Compound 54, 6-bromo-2-(2-(3-fluoropiperidin-1-yl)ethoxy)quinoline This was prepared as for Compound 3, substituting Compound 53 for (R)-(−)-1-methyl-3-hydroxypyrrolidine. The crude material was purified by silica gel column chromatography using a gradient of 1 to 1.75% MeOH in DCM to afford the title compound as a very pale yellow oil. $^1$H NMR (500 MHz, CDCl$_3$) δ 7.90 (d, J=8.8 Hz, 1H), 7.87 (s, 1H), 7.70-7.67 (m, 2H), 6.94 (d, J=8.9 Hz, 1H), 4.71 (v br s, 3H), 3.01 (v br s, 3H), 2.68 (v br s, 3H), 1.92 (v br s, 2H), 1.67 (v br s, 2H). HRMS (ESI$^+$): calcd for $C_{16}H_{19}{}^{79}BrFN_2O$ (M+H)$^+$, 353.0659; found 353.0654.

Preparation of Compound 55, 2-(2-(3-fluoropiperidin-1-yl)ethoxy)quinoline-6-carboxylic acid hydrochloride This was prepared as for Compound 4, substituting Compound 54 for Compound 3 to afford the title compound as an off-white solid. $^1$H NMR (500 MHz, DMSO) δ 13.11 (v br s, 1H), 11.75 (br s, 0.3H), 10.47 (br s, 0.7H), 8.61-8.58 (m, 1H), 8.51-8.46 (m, 1H), 8.19-8.14 (m, 1H), 7.87-7.83 (m, 1H), 7.19-7.14 (m, 1H), 5.18-5.05 (m, 1H), 4.90-4.81 (m, 2H), 3.87-3.10 (m, 6H), 2.06-1.59 (m, 4H). Note: this is a mixture of isomers in ~7:3 ratio. HRMS (ESI$^+$): calcd for $C_{17}H_{20}FN_2O_3$(M+H)$^+$, 319.1452; found 319.1454.

Preparation of Compound 56, methyl 2-chloroquinoline-6-carboxylate and Compound 57, methyl 4-chloroquinoline-6-carboxylate 3-Chloroperbenzoic acid (3.20 g, 13.9 mmol) was added to a solution of methyl 6-quinolinecarboxylate (2.000 g, 10.68 mmol) in dry DCM (31 mL) at 0° C. The reaction mixture was then allowed to warm to rt, and stirred overnight. The reaction mixture was then diluted with DCM and washed with 10% sodium sulfite(aq) (1×). The aqueous phase was extracted with DCM (1×), and the combined organic phases were washed with saturated NaHCO$_3$(aq) (1×), brine (1×), dried (MgSO$_4$), filtered and concentrated to afford the 6-(methoxycarbonyl)quinoline 1-oxide intermediate as a tan coloured solid. The N-oxide intermediate (2.07 g) was dissolved in dry DCM (27 mL), and to this was added phosphorus oxychloride (13.25 mL, 142.0 mmol) slowly while cooling the flask in a water bath. After the addition the water bath was removed and the reaction mixture was heated to 50° C. overnight, cooled to rt, concentrated, diluted with EtOAc, washed with saturated NaHCO$_3$ (3×). The aqueous phase was made basic with 1 M NaOH, then extracted with EtOAc (1×). The combined organic phases were washed with brine (1×), dried (MgSO$_4$), filtered and concentrated. The crude material was purified by silica gel column chromatography using a gradient of 10 to 3% PE in toluene and then switching to a gradient of 5 to 10% EtOAc in toluene. The first to elute was Compound 56 (458 mg, 20%) as an off-white solid followed by Compound 57 (1.146, 51%) as a pale yellow solid.

Compound 56: $^1$H NMR (500 MHz, CDCl$_3$) δ 8.59 (d, J=1.9 Hz, 1H), 8.33 (dd, J=8.8, 1.9 Hz, 1H), 8.21 (d, J=8.5 Hz, 1H), 8.06 (ap dt, J=8.8, 0.7 Hz, 1H), 7.47 (d, J=8.6 Hz, 1H), 4.00 (s, 3H). HRMS (ESI$^+$): calcd for $C_{11}H_9ClNO_2$ (M+H)$^+$, 222.0316; found 222.0321.

Compound 57: $^1$H NMR (500 MHz, CDCl$_3$) δ 8.98 (dd, J=1.9, 0.6 Hz, 1H), 8.87 (d, J=4.7 Hz, 1H), 8.36 (dd, J=8.7, 1.9 Hz, 1H), 8.17 (dd, J=8.9, 0.7 Hz, 1H), 7.57 (d, J=4.7 Hz, 1H), 4.02 (s, 3H).

Preparation of Compound 58, methyl 2-((2-(dimethylamino)ethyl)(methyl)amino)quinoline-6-carboxylate A solution Compound 56 (0.084 g, 0.38 mmol), N,N,N'-trimethylethylenediamine (0.077 g, 0.76 mmol, and N,N-diisopropylethylamine (0.13 mL, 0.76 mmol) in dry dioxane (2.0 mL) was heated in the microwave at 150° C. for 3 hours, cooled, concentrated, diluted with EtOAc, washed with water (1×), brine (1×), dried (Na$_2$SO$_4$), filtered and concentrated. The residue was purified by silica gel column chromatography using a gradient of 5 to 16% MeOH in DCM to afford the title compound (90 mg, 83%) as an off-white solid. $^1$H NMR (500 MHz, CDCl$_3$) δ 8.33 (d, J=2.0 Hz, 1H), 8.10 (dd, J=8.8, 2.0 Hz, 1H), 7.90 (d, J=9.1 Hz, 1H), 7.64 (d, J=8.8 Hz, 1H), 6.90 (d, J=9.2 Hz, 1H), 3.94 (s, 3H), 3.83 (t, J=7.4 Hz, 2H), 3.24 (s, 3H), 2.58 (t, J=7.4 Hz, 2H), 2.35 (s, 6H). HRMS (ESI$^+$): calcd for $C_{16}H_{22}N_3O_2$ (M+H)$^+$, 288.1706; found 288.1710.

Preparation of Compound 59, 2-((2-(dimethylamino)ethyl)(methyl)amino)quinoline-6-carboxylic acid hydrochloride An aqueous solution of NaOH (0.95 M, 1.93 mL, 1.84 mmol) was added to a solution of Compound 58 (0.088 g, 0.31 mmol) in THF (2.0 mL), followed by MeOH (0.5 mL) and the reaction mixture was stirred at rt overnight, concentrated to remove organic solvents, diluted with water, and washed with EtOAc (1×). The aqueous phase was acidified with 2 M HCl to ~pH 3, then concentrated to dryness and used without further purification (contains NaCl). $^1$H NMR (500 MHz, DMSO) δ 10.73 (v br s, 1H), 8.49 (br s, 1H), 8.41 (br s, 1H), 8.18-8.08 (m, 2H), 7.43 (br s, 1H), 4.21 (br s, 2H), 2.86 (s, 6H). Note that the other signals are hidden underneath the large water peak. HRMS (ESI$^+$): calcd for $C_{15}H_{20}N_3O_2$ (M+H)$^+$, 274.1550; found 274.1549.

Preparation of Compound 60, methyl 2-(2-(pyrrolidin-1-yl)ethyl)quinoline-6-carboxylate A solution of pyrrolidine (0.082 mL, 0.99 mmol), hydrochloric acid (32%, 0.097 mL, 0.99 mmol) and formaldehyde solution, (37%, 0.074 mL, 0.99 mmol) was carefully made, and then added to a slurry of methyl 2-methylquinoline-6-carboxylate (0.400 g, 1.99 mmol) in MeOH (0.5 mL), The reaction mixture was then heated to 50° C. for 3 hrs and 20 min, cooled to rt diluted with water, the pH was adjusted to 3-4 with 2 M HCl, washed with EtOAc (2×). The aqueous phase was made basic with 2 M NaOH, then extracted with DCM (2×). This organic phase was dried (Na$_2$SO$_4$), filtered and concentrated. The crude material was purified by silica gel column chromatography using a gradient of 5 to 11% MeOH in DCM to afford the title compound (166 mg, 59%) as a pale purple solid. $^1$H NMR (500 MHz, CDCl$_3$) δ 8.56 (d, J=1.8 Hz, 1H), 8.28 (dd, J=8.8, 1.9 Hz, 1H), 8.19 (d, J=8.5 Hz, 1H), 8.03 (d, J=8.8 Hz, 1H), 7.45 (d, J=8.4 Hz, 1H), 3.99 (s, 3H), 3.60-3.35 (br m, 4H), 2.99 (br s, 4H), 2.03 (br s, 4H). HRMS (ESI$^+$): calcd for $C_{17}H_{21}N_2O_2$ (M+H)$^+$, 285.1598; found 285.1599.

Preparation of Compound 61, methyl 2-(2-(pyrrolidin-1-yl)ethyl)quinoline-6-carboxylate hydrochloride LiOH (0.99 M, 0.245 mL, 0.24 mmol) was added to a solution of Compound 60 (0.034 g, 0.12 mmol) in THF (1.5 mL), followed by MeOH (0.3 mL). A ppt appeared and so additional water (0.20 mL) was added and the reaction mixture was stirred at rt for 23.5 hrs, concentrated to remove organic solvents, diluted with water, washed with EtOAc (1×). The aqueous phase was acidified to pH 3 with 2 M HCl, and then concentrated to dryness to afford the title compound as a white solid (contains LiCl) which was used without further purification. HRMS (ESI$^+$): calcd for $C_{16}H_{19}N_2O_2$ (M+H)$^+$, 271.1441; found 271.1442.

Preparation of Compound 62,[6,7] 2-(azetidin-1-yl)ethanol

Triethylamine (0.271 mL, 1.93 mmol) was added to a solution of azetidine (0.118 mL, 1.75 mmol) in dry DCM (3.6 mL). The reaction mixture was stirred for 30 min at rt, before acetoxyacetyl chloride (0.188 mL, 1.75 mmol) was added slowly dropwise, while the flask was cooled in a water bath. A ppt formed during the addition. The reaction mixture was stirred at rt overnight, filtered, and the filtrate was washed with water (1×), dried (Na$_2$SO$_4$), filtered and concentrate, leaving the intermediate 3 2-(azetidin-1-yl)-2-oxoethyl acetate as a very pale yellow oil. A solution of this intermediate (0.275 g, 1.75 mmol) in dry THF (2.9 mL) was added dropwise to LiAlH$_4$ (1 M in THF, 1.925 mL, 1.925 mmol) at 0° C. over 5 min. The reaction mixture was then allowed to warm to rt and stirred for 1 hr 40 min, after which time water (73 uL) was added dropwise while the reaction flask was cooled in a water batch, followed by 10% NaOH (aq) (73 uL), and 4-5 mL Et$_2$O and the mixture was then stirred at rt for 1 hour. Water (219 uL) was then added and the mixture filtered through celite with Et$_2$O, and the filtrate was concentrated to afford the title compound (135 mg, 76%) as a colourless oil. $^1$H NMR (500 MHz, DMSO) δ 4.32 (t, J=5.5 Hz, 1H), 3.29 (q, J=6.0 Hz, 2H), 3.08 (t, J=6.9 Hz, 4H), 2.37 (t, J=6.3 Hz, 2H), 1.92 (p, J=6.9 Hz, 2H). HRMS (ESI$^+$): calcd for $C_5H_{12}NO$ (M+H)$^+$, 102.0913; found 102.0912.

Preparation of Compound 63, 2-(2-(azetidin-1-yl)ethoxy)-6-bromoquinoline

This was prepared as for Compound 3, substituting Compound 62 for (R)-(−)-1-methyl-3-hydroxypyrrolidine. The crude material was purified by silica gel column chromatography using a gradient of 2 to 6% MeOH in DCM to afford the title compound as a very pale yellow oil. $^1$H NMR (500 MHz, CDCl$_3$) δ 7.87 (d, J=8.9 Hz, 1H), 7.85 (d, J=1.8 Hz, 1H), 7.70-7.64 (m, 2H), 6.94 (d, J=8.9 Hz, 1H), 4.47-4.43 (m, 2H), 3.34 (t, J=7.0 Hz, 4H), 2.87 (t, J=5.5 Hz, 2H), 2.13 (p, J=7.1 Hz, 2H). HRMS (ESI$^+$): calcd for $C_{14}H_{16}^{79}BrN_2O$ (M+H)$^+$, 307.0440; found 307.0438.

Preparation of Compound 64, 2-(2-(azetidin-1-yl)ethoxy)quinoline-6-carboxylic acid hydrochloride This was prepared as for Compound 4, substituting Compound 63 for Compound 3 to afford the title compound as a pale yellow solid. $^1$H NMR (500 MHz, DMSO) δ 13.12 (v br s, 1H), 11.20 (br s, 1H), 8.59 (d, J=2.0 Hz, 1H), 8.47 (d, J=8.9 Hz, 1H), 8.16 (dd, J=8.7, 2.0 Hz, 1H), 7.84 (d, J=8.7 Hz, 1H), 7.14 (d, J=8.9 Hz, 1H), 4.69-4.62 (m, 2H), 4.16-4.10 (m, 4H), 3.68-3.57 (m, 2H), 2.45-2.35 (m, 1H), 2.30-2.22 (m, 1H). HRMS (ESI$^+$): calcd for $C_{15}H_{17}N_2O_3$(M+H)$^+$, 273.1234; found 273.1236.

Preparation of Compound 65,[8] 2-(2-methylpyrrolidin-1-yl)ethanol

2-Bromoethanol (0.255 mL, 3.59 mmol) was added to a suspension of 2-methylpyrrolidine (0.360 mL, 3.52 mmol) and potassium carbonate (0.536 g, 3.88 mmol) in dry cetonitrile (6.2 mL). The reaction mixture was then heated to reflux overnight, cooled to rt, filtered to remove solids and the filtrate was concentrated. To this was added Et$_2$O, extracted with 1 M HCl (2×). The aqueous phase was made basic (pH>12) with solid NaOH, then extracted with DCM (3×). This organic phase was dried over K$_2$CO$_3$, filtered and concentrated to afford the title compound (351 mg, 77%) as a pale yellow oil. $^1$H NMR (500 MHz, CDCl$_3$) δ 3.64 (td, J=10.2, 3.7 Hz, 1H), 3.60-3.54 (m, 1H), 3.15 (ddd, J=9.1, 8.0, 3.1 Hz, 1H), 2.97 (ddd, J=12.2, 9.9, 5.1 Hz, 1H), 2.81 (br s, 1H), 2.49-2.40 (m, 1H), 2.27 (dt, J=12.3, 3.4 Hz, 1H), 2.15 (q, J=8.8 Hz, 1H), 1.95-1.88 (m, 1H), 1.81-1.65 (m, 2H), 1.40 (dddd, J=12.4, 10.2, 8.3, 6.1 Hz, 1H), 1.08 (d, J=6.1 Hz, 3H). HRMS (ESI$^+$): calcd for $C_7H_{16}NO$ (M+H)$^+$, 130.1226; found 130.1229.

Preparation of Compound 66, 6-bromo-2-(2-(2-methylpyrrolidin-1-yl)ethoxy)quinoline This was prepared as for Compound 3, substituting Compound 65 for (R)-(−)-1-methyl-3-hydroxypyrrolidine. The crude material was purified by silica gel column chromatography using a gradient of 3 to 8% MeOH in DCM to afford the title compound as a very pale orange solid. $^1$H NMR (500 MHz, CDCl$_3$) δ 7.87 (d, J=8.9 Hz, 1H), 7.85 (d, J=1.9 Hz, 1H), 7.70-7.64 (m, 2H), 6.94 (d, J=8.9 Hz, 1H), 4.63-4.58 (m, 2H), 3.35-3.22 (m, 2H), 2.57 (dt, J=12.0, 5.4 Hz, 1H), 2.46-2.38 (m, 1H), 2.30 (q, J=8.9 Hz, 1H), 1.98-1.89 (m, 1H), 1.88-1.78 (m, 1H), 1.77-1.68 (m, 1H), 1.50-1.43 (m, 1H), 1.15 (d, J=6.0 Hz, 3H). HRMS (ESI$^+$): calcd for C$_{16}$H$_{20}$$^{79}$BrN$_2$O (M+H)$^+$, 335.0754; found 335.0753.

Preparation of Compound 67, 2-(2-(2-methylpyrrolidin-1-yl)ethoxy)quinoline-6-carboxylic acid hydrochloride This was prepared as for Compound 4, substituting Compound 66 for Compound 3 to afford the title compound as an off-white solid. $^1$H NMR (500 MHz, DMSO) δ 13.10 (br s, 1H), 10.99 (br s, 1H), 8.59 (d, J=1.9 Hz, 1H), 8.48 (d, J=8.9 Hz, 1H), 8.16 (dd, J=8.8, 1.9 Hz, 1H), 7.85 (d, J=8.7 Hz, 1H), 7.17 (d, J=8.8 Hz, 1H), 4.85-4.81 (m, 2H), 3.81-3.75 (m, 1H), 3.74-3.65 (m, 1H), 3.47 (br s, 2H), 3.25-3.18 (m, 1H), 2.22-2.12 (m, 1H), 2.00-1.92 (m, 2H), 1.71-1.60 (m, 1H), 1.44 (d, J=6.5 Hz, 3H). LRMS (ESI$^+$) (M+H)+: 301.29.

Preparation of Compound 68, 2-(2-(dimethylamino)ethoxy)quinoline-6-carboxylic acid hydrochloride N,N-Dimethylethanolamine (0.102 mL, 1.02 mmol) added to a suspension of NaH (60%, 0.041 g, 1.02 mmol) in dry dioxane (1.75 mL). The reaction mixture was stirred at rt for 35 min before Compound 17 (0.060 g, 0.26 mmol) was added and the reaction mixture was then heated to 60° C. for 1 hr 35 min at which time additional dioxane (2.0 mL) was added to help the thick mixture to stir. The reaction mixture was then heated to 80° C. for 4 hrs, and then at rt overnight, diluted with water, washed with EtOAc (1×). The aqueous phase was acidified to pH 3 with 2 M HCl, and then concentrated to afford the title compound as a white solid (contains NaCl). $^1$H NMR (500 MHz, DMSO) δ 8.59 (d, J=1.9 Hz, 1H), 8.47 (d, J=8.9 Hz, 1H), 8.16 (dd, J=8.7, 2.0 Hz, 1H), 7.85 (d, J=8.7 Hz, 1H), 7.16 (d, J=8.9 Hz, 1H), 4.85-4.77 (m, 2H), 3.56 (br s, 2H), 2.83 (br s, 6H). HRMS (ESI$^+$): calcd for C$_{14}$H$_{17}$N$_2$O$_3$ (M+H)$^+$, 261.1234; found 261.1235.

Preparation of Compound 69, 6-bromo-2-(2-(pyrrolidin-1-yl)ethoxy)quinoline

This was prepared as for Compound 3, substituting 4-(2-hydroxyethyl)pyrrolidine for (R)-(−)-1-methyl-3-hydroxypyrrolidine. The crude material was purified by silica gel column chromatography using a gradient of 3 to 6% MeOH in DCM to afford the title compound as a very pale yellow oil. $^1$H NMR (500 MHz, CDCl$_3$) δ 7.87 (d, J=8.9 Hz, 1H), 7.85 (d, J=1.9 Hz, 1H), 7.72-7.63 (m, 2H), 6.96 (d, J=8.9 Hz, 1H), 4.61 (t, J=5.9 Hz, 2H), 2.94 (t, J=5.9 Hz, 2H), 2.70-2.59 (m, 4H), 1.86-1.77 (m, 4H). HRMS (ESI$^+$): calcd for C$_{15}$H$_{18}$$^{79}$BrN$_2$O (M+H)$^+$, 321.0597; found 321.0587.

Preparation of Compound 70, 2-(2-(pyrrolidin-1-yl)ethoxy)quinoline-6-carboxylic acid hydrochloride This was prepared as for Compound 4, substituting Compound 69 for Compound 3 to afford the title compound as an off-white solid. $^1$H NMR (500 MHz, DMSO) δ 13.12 (v br s, 1H), 11.22 (br s, 1H), 8.59 (d, J=1.9 Hz, 1H), 8.48 (d, J=8.8 Hz, 1H), 8.16 (dd, J=8.7, 2.0 Hz, 1H), 7.85 (d, J=8.7 Hz, 1H), 7.18 (d, J=8.9 Hz, 1H), 4.83-4.76 (m, 2H), 3.68-3.56 (m, 4H), 3.15-3.07 (m, 2H), 2.06-1.95 (m, 2H), 1.96-1.84 (m, 2H). HRMS (ESI$^+$): calcd for C$_{16}$H$_{18}$N$_2$O$_3$(M+H)$^+$, 287.1390; found 287.1380.

Preparation of Compound 71, methyl 2-(methyl(2-(pyrrolidin-1-yl)ethyl)amino)quinoline-6-carboxylate A solution of Compound 56 (0.103 g, 0.464 mmol), methyl[2-(pyrrolidin-1-yl)ethyl]amine (0.119 g, 0.928 mmol), and N,N-diisopropylethylamine (0.16 mL, 0.93 mmol) in dry dioxane (2.0 mL) was heated in a microwave at 150° C. for 2.5 hrs, cooled, diluted with EtOAc, washed with water (1×), brine (1×), dried (Na$_2$SO$_4$), filtered and concentrated. The crude material was purified by silica gel column chromatography using a gradient of 5 to 13% MeOH in DCM to afford the title compound (130 mg, 89%) as a pale yellow-brown solid. $^1$H NMR (500 MHz, CDCl$_3$) δ 8.37 (d, J=2.0 Hz, 1H), 8.13 (dd, J=8.8, 2.0 Hz, 1H), 7.97 (d, J=9.2 Hz, 1H), 7.61 (d, J=8.8 Hz, 1H), 6.95 (d, J=9.2 Hz, 1H), 4.20 (br s, 2H), 3.95 (s, 3H), 2.08 (brs, 4H). The remaining protons appeared as an extremely broad hump from roughly 3.75-2.75 ppm which could not be integrated accurately. HRMS (ESI$^+$): calcd for C$_{18}$H$_{24}$N$_3$O$_2$ (M+H)$^+$, 314.1863; found 314.1864.

Preparation of Compound 72, 2-(methyl(2-(pyrrolidin-1-yl)ethyl)amino)quinoline-6-carboxylic acid hydrochloride NaOH (0.99 M, 2.40 mL, 2.37 mmol) was added to a suspension of Compound 71 (0.124 g, 0.396 mmol) in THF (4.0 mL), followed by MeOH (1.25 mL). The reaction mixture was stirred at rt overnight, concentrated to remove organic solvents, washed with EtOAc (1×). The aqueous phase was acidified to pH 3 with 2 M HCl, then concentrated to dryness to afford the title compound as an off-white solid (contains NaCl). $^1$H NMR (500 MHz, DMSO) δ 13.09, (v br s, 1H), 11.15 (v br s, 1H), 8.49 (br s, 1H), 4.40 (br s, 1H), 8.13 (br s, 1H), 7.44 (v br s, 2hH), 4.20 (br s, 2H), 3.88 (br s, 4H), 3.56 (br s, 2H), 3.47 (br s, 3H), 3.12 (br s, 2H), 2.11-1.76 (br m, 4H). HRMS (ESI$^+$): calcd for C$_{17}$H$_{22}$N$_3$O$_2$ (M+H)$^+$, 300.1706; found 300.1705.

Preparation of Compound 73, (R)-2-(3-hydroxypyrrolidin-1-yl)ethyl acetate

2-Bromoethyl acetate (1.535 mL, 13.54 mmol) was added dropwise to a mixture of (R)-3-hydroxypyrrolidine HCl (1.568 g, 12.31 mmol) and potassium carbonate (5.10 g, 36.9 mmol) in dry acetonitrile (35 mL) and the reaction mixture was heated at reflux for 6.5 hrs, cooled, filtered (washed through with EtOAc), and the filtrate was concentrated, diluted with DCM, and washed with water (1×). The aqueous phase was extracted with DCM (3×). The combined organic phases were dried (MgSO4), filtered and concentrated to afford the title compound (1.364 g, 64%) as a colourless oil. $^1$H NMR (500 MHz, CDCl$_3$) δ 4.36-4.32 (m, 1H), 4.19 (t, J=5.7 Hz, 2H), 2.93 (td, J=8.6, 5.2 Hz, 1H), 2.77-2.70 (m, 3H), 2.59 (dd, J=10.0, 5.1 Hz, 1H), 2.36 (td, J=8.9, 6.3 Hz, 1H), 2.18 (dddd, J=13.9, 8.7, 7.1, 5.2 Hz, 1H), 2.07 (s, 3H), 1.79-1.71 (m, 1H). HRMS (ESI$^+$): calcd for C$_8$H$_{16}$NO$_3$ (M+H)$^+$, 174.1125; found 174.1128.

Preparation of Compound 74, (S)-2-(3-fluoropyrrolidin-1-yl)ethyl acetate

N,N-Diethylaminosulfur trifluoride (2.58 ml, 19.5 mmol) was added dropwise to a solution of Compound 73 (1.35 g, 7.81 mmol) in dry DCM (35 ml) at −78° C. Upon completion of the addition, the reaction mixture was allowed to warm to rt and stirred for 3 hrs, then cooled to −5 to −10° C., and quenched with MeOH, washed with saturated NaHCO$_3$(aq) (2×). Added 1 M NaOH to the aqueous phase to insure pH>10, then extracted with DCM (3×). The combined organic phases were dried (MgSO$_4$), filtered and concentrated. The crude material was purified by silica gel column chromatography using a gradient of 1 to 4% MeOH in DCM to afford the title compound (418 mg, 31%) as a brown oil. $^1$H NMR (500 MHz, CDCl$_3$) δ 5.17 (dddt, J=55.6, 6.6, 5.0, 1.8 Hz, 1H), 4.20 (t, J=5.9 Hz, 2H), 2.95-2.72 (m, 5H), 2.56-2.50 (m, 1H), 2.20-1.98 (m, 2H), 2.07 (3H, s). HRMS (ESI$^+$): calcd for C$_8$H$_{15}$FNO$_2$ (M+H)$^+$, 176.1081; found 176.1084.

Preparation of Compound 75, (S)-2-(3-fluoropyrrolidin-1-yl)ethanol

A catalytic amount of NaOMe (enough to make the solution basic) was added to a solution of Compound 74 (0.416 g, 2.37 mmol) in dry MeOH (15 mL) The reaction mixture was stirred overnight at rt, concentrated, and the residue dissolved in DCM, washed with saturated NaHCO$_3$ (aq) (1×). The aqueous phase was extracted with DCM (3×). The organic phases were dried (MgSO$_4$), filtered and concentrated to afford the title compound (190 mg, 60%) as a dark brown oil. $^1$H NMR (500 MHz, CDCl$_3$) δ 5.25-5.10 (m, 1H), 3.64 (t, J=5.4 Hz, 2H), 2.97-2.86 (m, 2H), 2.80 (ddd, J=30.4, 11.6, 5.0 Hz, 1H), 2.70 (dd, J=6.1, 4.8 Hz, 2H), 2.55-2.48 (m, 1H), 2.22-1.99 (m, 2H). HRMS (ESI$^+$): calcd for C$_6$H$_{13}$FNO (M+H)$^+$, 134.0976; found 134.0974.

Preparation of Compound 76, (S)-6-bromo-2-(2-(3-fluoropyrrolidin-1-yl)ethoxy)quinoline This was prepared as for Compound 3, substituting Compound 75 for (R)-(−)-1-methyl-3-hydroxypyrrolidine. The crude material was purified by silica gel column chromatography using a gradient of 1 to 2% MeOH in DCM to afford the title compound as a pale yellow solid. $^1$H NMR (500 MHz, CDCl$_3$) δ 7.88 (d, J=8.8 Hz, 1H), 7.85 (d, J=1.9 Hz, 1H), 7.72-7.64 (m, 2H), 6.95 (d, J=8.9 Hz, 1H), 5.19 (dddt, J=55.6, 6.6, 5.0, 1.8 Hz, 1H), 4.66-4.57 (m, 2H), 3.04-2.87 (m, 5H), 2.67-2.60 (m, 1H), 2.25-2.01 (m, 2H). HRMS (ESI$^+$): calcd for C$_{15}$H$_{17}$$^{79}$BrFN$_2$O (M+H)$^+$, 339.0503; found 339.0500.

Preparation of Compound 77, (S)-2-(2-(3-fluoropyrrolidin-1-yl)ethoxy)quinoline-6-carboxylic acid hydrochloride This was prepared as for Compound 4, substituting Compound 76 for Compound 3 to afford the title compound as a pale yellow solid. $^1$H NMR (500 MHz, DMSO) δ 13.12 (br s, 1H), 11.79 (br s, 0.5H), 11.44 (br s, 0.5H), 8.59 (s, 1H), 8.49-8.46 (m, 1H), 8.18-8.14 (m, 1H), 7.85 (d, J=8.7 Hz, 1H), 7.21-7.16 (m, 1H), 5.56-5.36 (m, 1H), 4.88-4.74 (m, 2H), 4.04-3.85 (m, 1H), 3.83-3.65 (m, 3H), 3.62-3.35 (m, 2H), 2.40-2.06 (m, 2H). HRMS (ESI$^+$): calcd for C$_{16}$H$_{18}$FN$_2$O$_3$(M+H)$^+$, 305.1296; found 305.1296.

Preparation of Compound 78, 4-(2-((6-bromoquinolin-2-yl)oxy)ethyl)morpholine This was prepared as for Compound 3, substituting 4-(2-hydroxyethyl)morpholine for (R)-(−)-1-methyl-3-hydroxypyrrolidine. The product precipitated as a pale pink solid after the addition of water, and was isolated by filtration and used in the next step without further purification. $^1$H NMR (500 MHz, CDCl$_3$) δ 7.89 (d, J=8.9 Hz, 1H), 7.86 (s, 1H), 7.68 (s, 2H), 6.94 (d, J=8.9 Hz, 1H), 4.61 (t, J=5.8 Hz, 2H), 3.77-3.71 (m, 4H), 2.84 (t, J=5.8 Hz, 2H), 2.65-2.55 (m, 4H). HRMS (ESI$^+$): calcd for C$_{15}$H$_{18}$$^{79}$BrN$_2$O$_2$(M+H)$^+$, 337.0546; found 337.0544.

Preparation of Compound 79, 2-(2-morpholinoethoxy)quinoline-6-carboxylic acid hydrochloride This was prepared as for Compound 4, substituting Compound 78 for Compound 3 to afford the title compound as a pale yellow solid. $^1$H NMR (500 MHz, DMSO) δ 11.87 (br s, 1H), 8.59 (d, J=1.9 Hz, 1H), 8.47 (d, J=8.9 Hz, 1H), 8.16 (dd, J=8.7, 2.0 Hz, 1H), 7.85 (d, J=8.7 Hz, 1H), 7.16 (d, J=8.9 Hz, 1H), 4.91-4.85 (m, 2H), 3.99-3.85 (m, 4H), 3.66-3.59 (m, 4H), 3.56-3.48 (m, 2H), 3.25-3.17 (m, 2H). HRMS (ESI$^+$): calcd for C$_{16}$H$_{19}$N$_2$O$_4$ (M+H)$^+$, 303.1339; found 303.1340.

Preparation of Compound 80, methyl 2-(pyrrolidin-1-ylmethyl)quinoline-6-carboxylate Pyrrolidine (0.144 mL, 1.74 mmol) was added to a solution of Compound 13 (0.25 g, 1.16 mmol) in dry DCM (5.0 mL). The reaction mixture was stirred at rt for 6 hrs, before NaBH(OAc)$_3$ (0.369 g, 1.74 mmol) was added and the reaction mixture was stirred overnight at rt, diluted with DCM, washed with saturated NaHCO$_3$(aq) (1×). The aqueous phase was extracted with DCM (1×). The organic phase was dried (MgSO$_4$), filtered and concentrated. The crude material was purified by silica gel column chromatography using a gradient of 2 to 5% MeOH in DCM to afford the title compound (225 mg, 72% as a brown solid. $^1$H NMR (500 MHz, CDCl$_3$) δ 8.58 (d, J=1.9 Hz, 1H), 8.32-8.24 (m, 2H), 8.10 (d, J=8.8 Hz, 1H), 7.85 (v br s, 1H), 4.14 (br s, 2H), 4.00 (s, 3H), 2.83 (v br s, 4H), 1.94 (br s, 4H). HRMS (ESI$^+$): calcd for C$_{16}$H$_{19}$N$_2$O$_2$ (M+H)$^+$, 271.1441; found 271.1444.

Preparation of Compound 81, 2-(pyrrolidin-1-ylmethyl)quinoline-6-carboxylic acid hydrochloride NaOH (1.018 M, 2.29 mL, 2.33 mmol) was added to a solution of Compound 80 (0.210 g, 0.777 mmol) in THF (3.0 mL), followed by MeOH (1.0 mL) and the reaction mixture was stirred at rt overnight, and then heated to 35° C. for 23 hrs, cooled, concentrated to remove THF and MeOH. The remaining aqueous phase was washed with EtOAc (1×), acidified to pH 3 with 2 M HCl. A ppt formed, which was filtered off and discarded. The Filtrate was then concentrated to dryness to afford the title compound as a brown solid. HRMS (ESI$^+$): calcd for C$_{15}$H$_{17}$N$_2$O$_2$ (M+H)$^+$, 257.1284; found 257.1284.

Preparation of Compound 82, methyl 4-methoxyquinoline-6-carboxylate

Sodium methoxide (0.195 g, 3.61 mmol) was added to a suspension of Compound 57 (0.200 g, 0.902 mmol) in dry MeOH (5.0 mL). The reaction mixture was heated at reflux for 19 h, cooled to rt, and then 4 M HCl in dioxane (2.26 mL, 9.02 mmol) was added and the reaction mixture was heated to 70° C. for 6 h, cooled, concentrated, diluted with EtOAc, and washed with saturated NaHCO$_3$(aq) (1×). The aqueous phase was extracted with EtOAc (1×). The organic phases were washed with brine (1×), dried (MgSO$_4$), filtered and concentrated to afford the title compound (186 mg, 95%) as an off-white solid. $^1$H NMR (500 MHz, CDCl$_3$) δ 8.97 (d, J=1.9 Hz, 1H), 8.83 (br d, J=5.3 Hz, 1H), 8.28 (dd, J=8.8, 2.0 Hz, 1H), 8.07 (d, J=8.8 Hz, 1H), 6.80 (d, J=5.3 Hz, 1H), 4.09 (s, 3H), 3.99 (s, 3H). HRMS (ESI$^+$): calcd for C$_{12}$H$_{12}$NO$_3$ (M+H)$^+$, 218.0812; found 218.0818.

Preparation of Compound 83, 4-methoxyquinoline-6-carboxylic acid hydrochloride LiOH (0.97 M, 1.424 mL, 1.381 mmol) was added to a solution of Compound 82 (0.050 g, 0.23 mmol) in THF (2.0 mL) and MeOH (0.40 mL) and the reaction mixture was stirred at rt overnight, concentrated to remove organic solvents, diluted with water, and washed with EtOAc (1×). The aqueous phase was acidified to ~pH 2 with 2 M HCl, then concentrated to dryness to afford the title compound as a pale brown hygroscopic solid. $^1$H NMR (500 MHz, DMSO) δ 9.20 (d, J=6.4 Hz, 1H), 8.85 (d, J=1.9 Hz, 1H), 8.46 (dd, J=8.8, 1.9 Hz, 1H), 8.37 (d, J=8.9 Hz, 1H), 7.54 (d, J=6.3 Hz, 1H), 4.30 (s, 3H). HRMS (ESI$^+$): calcd for C$_{11}$H$_{10}$NO$_3$ (M+H)$^+$, 204.0655; found 204.0658.

Preparation of Compound 84, 2-(pyrrolidin-1-yl)propan-1-ol

A mixture of DL-alaninol (0.500 g, 6.66 mmol), 1,4-dibromobutane (1.51 g, 6.99 mmol), sodium bicarbonate (1.23 g, 14.6 mmol), and 3 Å molecular sieves (powdered) in dry toluene (5.4 mL) was heated to reflux for 22.5 h, cooled to rt, and filtered to remove solids. The filtrate was concentrated, re-dissolved in DCM, washed with 1 M NaOH (1×). The aqueous phase was extracted with DCM (2×). The combined organic phases were dried (MgSO$_4$), filtered and concentrated. This impure material was dissolved in 0.5 M HCl, and washed with DCM (1×). The aqueous phase was made basic (pH>12) with 1 M NaOH, then extracted w/DCM (6×). This latter organic phase was dried (MgSO$_4$), filtered and concentrated to afford the title compound (417 mg, 48%) as a pale yellow oil. $^1$H NMR (500 MHz, CDCl$_3$) δ 3.60 (dd, J=10.4, 4.5 Hz, 1H), 3.36 (dd, J=10.4, 6.3 Hz, 1H), 2.92 (br s, 1H), 2.73-2.65 (m, 1H), 2.61-2.56 (m, 4H), 1.81-1.72 (m, 4H), 1.04 (d, J=6.6 Hz, 3H). HRMS (ESI$^+$): calcd for C$_7$H$_{16}$NO (M+H)$^+$, 130.1226; found 130.1228.

Preparation of Compound 85, 6-bromo-2-(2-(pyrrolidin-1-yl)propoxy)quinoline

This was prepared as for Compound 3, substituting Compound 84 for (R)-(-)-1-methyl-3-hydroxypyrrolidine. The crude material was purified by silica gel column chromatography using a gradient of 3 to 15% MeOH in DCM to afford the title compound as a pale yellow solid. $^1$H NMR (500 MHz, CDCl$_3$) δ 7.88 (d, J=8.9 Hz, 1H), 7.85 (d, J=2.0 Hz, 1H), 7.70-7.65 (m, 2H), 6.97 (d, J=8.9 Hz, 1H), 4.61 (dd, J=11.0, 4.3 Hz, 1H), 4.41 (dd, J=11.0, 5.6 Hz, 1H), 2.81-2.66 (m, 5H), 1.84-1.79 (m, 4H), 1.30 (d, J=6.5 Hz, 3H). HRMS (ESI$^+$): calcd for C$_{16}$H$_{20}$$^{79}$BrN$_2$O (M+H)$^+$, 335.0754; found 335.0750.

Preparation of Compound 86, 2-(2-(pyrrolidin-1-yl)propoxy)quinoline-6-carboxylic acid hydrochloride This was prepared as for Compound 4, substituting Compound 85 for Compound 3 to afford the title compound as a pale yellow solid. $^1$H NMR (500 MHz, DMSO) δ 13.12 (v br s, 1H), 11.32 (br s, 1H), 8.59 (d, J=1.8 Hz, 1H), 8.48 (d, J=8.9 Hz, 1H), 8.16 (dd, J=8.8, 2.0 Hz, 1H), 7.85 (d, J=8.7 Hz, 1H), 7.20 (d, J=8.9 Hz, 1H), 4.79-4.67 (m, 2H), 3.85-3.77 (m, 1H), 3.61-3.48 (m, 2H), 3.25-3.15 (m, 2H), 2.04-1.83 (m, 4H), 1.46 (d, J=6.7 Hz, 3H). HRMS (ESI$^+$): calcd for C$_{17}$H$_{21}$N$_2$O$_3$ (M+H)$^+$, 301.1547; found 301.1546.

Preparation of Compound 87, ethyl 2-(2-(dimethylamino)ethyl)quinoline-6-carboxylate A solution of Me$_2$NH·HCl (0.190 g) and formaldehyde solution (37%, 0.175 mL) was made. 68 uL of this was added to ethyl 2-methylquinoline-6-carboxylate (0.200 g, 0.929 mmol), followed by a minimum amount of MeOH (<0.1 mL) in order to allow the mixture to stir. The reaction mixture was then heated to 50° C. for 110 min, and then at rt for 2 h, diluted with water, and washed with diethyl ether (2×). The aqueous phase was made basic with 1 M NaOH, then extracted with EtOAc (2×). This organic phase was washed with brine (1×), dried (Na$_2$SO$_4$), filtered and concentrated. The crude material was purified by silica gel column chromatography using a gradient of 1 to 4.5% MeOH in DCM containing 1% 2 M NH$_3$ in MeOH to afford the title compound (39 mg, 31%) as a very pale yellow oil. $^1$H NMR (500 MHz, CDCl$_3$) δ 8.55 (d, J=1.8 Hz, 1H), 8.28 (dd, J=8.8, 1.9 Hz, 1H), 8.17 (d, J=8.4 Hz, 1H), 8.06 (d, J=8.8 Hz, 1H), 7.41 (d, J=8.4 Hz, 1H), 4.45 (q, J=7.1 Hz, 2H), 3.22-3.15 (m, 2H), 2.88-2.80 (m, 2H), 2.35 (s, 6H), 1.45 (t, J=7.1 Hz, 2H). HRMS (ESI$^+$): calcd for C$_{16}$H$_{21}$N$_2$O$_2$ (M+H)$^+$, 273.1598; found 273.1597.

Preparation of Compound 88, 2-(2-(dimethylamino)ethyl)quinoline-6-carboxylic acid hydrochloride LiOH (1.984 M, 0.108 mL, 0.215 mmol) was added to a solution of Compound 87 (0.039 g, 0.14 mmol) in THF (2.0 mL) and MeOH (1.0 mL) and the reaction mixture was stirred at rt for 24 hrs. Additional LiOH (1.984 M, 0.108 mL, 0.215 mmol) was added and the reaction mixture stirred at rt for 24 h, then water (1 mL) was added and the reaction mixture was stirred for a further 24 h. NaOH (3.0 M, 0.048 mL) was added and the reaction mixture stirred at rt for 24 h before additional NaOH (3.0 M, 0.010 mL) was added, and the reaction mixture was stirred at rt for 5.5 h, concentrated to remove organic solvent, diluted with water, washed with EtOAc (1×). The aqueous phase was acidified to pH 3 with 2 M HCl, then concentrated to afford the title compound as a paly yellow solid (contains LiCl and NaCl) and was used without further purification. HRMS (ESI$^+$): calcd for C$_{14}$H$_{17}$N$_2$O$_2$ (M+H)$^+$, 245.1284; found 245.1282.

Preparation of Compound 89, 6-(ethoxycarbonyl)-2-methylquinoline 1-oxide

3-Chloroperbenzoic acid (0.695 g, 3.02 mmol) was added to a solution of ethyl 2-methylquinoline-6-carboxylate (0.500 g, 2.323 mmol) in dry DCM (7 mL) at 0° C. The rxn mix was then allowed to warm to rt, stirred overnight, washed with 10% sodium sulfite (1×), saturated NaHCO$_3$ (1×), brine (1×), dried (MgSO4), filtered and concentrated. The crude material was purified by silica gel column chromatography using a gradient of 80 to 100% EtOAc in PE, and then from 0 to 10% MeOH in EtOAc to afford the title compound (463 mg, 86%) as a pale yellow solid. $^1$H NMR (500 MHz, CDCl$_3$) δ 8.82 (d, J=9.1 Hz, 1H), 8.58 (d, J=1.7

Hz, 1H), 8.33 (dd, J=9.1, 1.8 Hz, 1H), 7.74 (d, J=8.5 Hz, 1H), 7.39 (d, J=8.5 Hz, 1H), 4.46 (q, J=7.1 Hz, 2H), 2.74 (s, 3H), 1.45 (t, J=7.1 Hz, 3H). HRMS (ESI$^+$): calcd for $C_{13}H_{14}NO_3$ (M+H)$^+$, 232.0976; found 232.0976.

Preparation of Compound 90, ethyl 2-((tosyloxy)methyl)quinoline-6-carboxylate

To a solution of Compound 89 (0.274 g, 1.18 mmol) in dry acetonitrile (10 mL) at 0° C. was added $K_2CO_3$ (0.246 g, 1.78 mmol) followed by p-toluenesulfonyl chloride (0.271 g, 1.42 mmol). The reaction mixture was stirred at 0° C. for 5 hr 45 min, diluted with saturated NaHCO$_3$, extracted with EtOAc (2×). The organic phase was washed with water (1×), brine (1×), dried (MgSO$_4$), filtered and concentrated. The crude material was purified by silica gel column chromatography using a gradient of 14 to 28% EtOAc in PE to afford the title compound (186 mg, 41%) as an orange solid. $^1$H NMR (500 MHz, CDCl$_3$) δ 8.58 (d, J=1.9 Hz, 1H), 8.34-8.25 (m, 2H), 8.01 (d, J=8.8 Hz, 1H), 7.86 (d, J=8.4 Hz, 2H), 7.63 (d, J=8.5 Hz, 1H), 7.33 (d, J=8.1 Hz, 2H), 5.32 (s, 2H), 4.45 (q, J=7.1 Hz, 2H), 2.42 (s, 3H), 1.45 (t, J=7.1 Hz, 3H). HRMS (ESI$^+$): calcd for $C_{21}H_{20}NO_5S$ (M+H)$^+$, 386.1057; found 386.1071.

Preparation of Compound 91, ethyl 2-((4-methylpiperazin-1-yl)methyl)quinoline-6-carboxylate 1-Methylpiperazine (0.058 mL, 0.52 mmol) was added to a solution of Compound 90 (0.080 g, 0.21 mmol) in dry THF (1.5 mL). The reaction mixture was heated at reflux for 1 h 45 min, then at rt for 2 h, concentrated, added EtOAc, washed with water (1×), NaHCO$_3$ (1×). The aqueous phase was extracted with EtOAc (1×) and the combined organic phases were dried (MgSO$_4$), filtered and concentrated to afford the title compound (64 mg, 98%) as a pale yellow solid. $^1$H NMR (500 MHz, CDCl$_3$) δ 8.56 (d, J=1.9 Hz, 1H), 8.29 (dd, J=8.8, 1.9 Hz, 1H), 8.22 (d, J=8.5 Hz, 1H), 8.09 (d, J=8.8 Hz, 1H), 7.71 (d, J=8.5 Hz, 1H), 4.45 (q, J=7.1 Hz, 2H), 3.86 (s, 2H), 2.61 (br s, 4H), 2.49 (br s, 4H), 2.31 (s, 3H), 1.45 (t, J=7.1 Hz, 3H). HRMS (ESI$^+$): calcd for $C_{18}H_{24}N_3O_2$ (M+H)$^+$, 314.1863; found 314.1871.

Preparation of Compound 92, 2-((4-methylpiperazin-1-yl)methyl)quinoline-6-carboxylic acid dihydrochloride NaOH (0.82 M, 0.735 mL, 0.60 mmol) was added to a solution of Compound 91 (0.063 g, 0.20 mmol) in THF (1.0 mL). MeOH (0.25 mL) was then added and the reaction mixture was stirred at rt overnight, concentrate to remove organic solvents, diluted with water, washed with EtOAc (1×). The aqueous phase was acidified with 2 M HCl to pH 2-3, then concentrated to dryness to afford the title compound (contains NaCl) as a light brown solid. $^1$H NMR (500 MHz, DMSO) δ 13.33 (v br s, 1H), 11.77 (br s, 1H), 8.72 (d, J=1.9 Hz, 1H), 8.69 (d, J=8.5 Hz, 1H), 8.26 (dd, J=8.8, 1.9 Hz, 1H), 8.16 (d, J=8.9 Hz, 1H), 7.85 (d, J=8.5 Hz, 1H), 4.53 (br s, 2H), 3.83-3.45 (br m, 8H), 2.80 (s, 3H). HRMS (ESI$^+$): calcd for $C_{16}H_{20}N_3O_2$ (M+H)$^+$, 286.1550; found 286.1553.

Preparation of Compound 93, methyl 6-(thiazol-4-ylmethoxy)nicotinate 4-(Hydroxymethyl)-1,3-thiazole (0.187 mL, 2.17 mmol) was added to a suspension of NaH (60%, 0.054 g, 2.3 mmol) in dry THF (6 mL) at 0° C. After a few minutes, the reaction mixture was allowed to warm to rt, stirred for 20 min before methyl 6-chloropyridine-3-carboxylate (0.339 g, 1.97 mmol) was added and the reaction mixture was heated at reflux for 4.5 h, cooled, concentrated, added water and saturated NaHCO$_3$. The mixture was extracted with DCM (3×). The organic phase was dried (Na$_2$SO$_4$), filtered and concentrated. The crude material was purified by silica gel column chromatography using a gradient of 20 to 25% EtOAc in PE to afford the title compound (106 mg, 22%) as a white solid. $^1$H NMR (500 MHz, CDCl$_3$) δ 8.87-8.84 (m, 2H), 8.18 (dd, J=8.7, 2.4 Hz, 1H), 7.43 (dd, J=1.9, 0.9 Hz, 1H), 6.86 (dd, J=8.5, 0.8 Hz, 1H), 5.64 (d, J=0.7 Hz, 2H), 3.91 (s, 3H). HRMS (ESI$^+$): calcd for $C_{11}H_{11}N_2O_3S$ (M+H)$^+$, 251.0485; found 251.0487.

Preparation of Compound 94, 6-(thiazol-4-ylmethoxy)nicotinic acid

LiOH (1.42 M, 0.580 mL, 0.823 mmol) was added to a solution of Compound 93 (0.103 g, 0.412 mmol) in THF (2.5 mL), followed by MeOH (0.8 mL). The reaction mixture was stirred at rt overnight, concentrated to remove organic solvents, diluted with water, washed with EtOAc (1×). The aqueous phase was acidified to pH 2-3 with 2 M HCl and the resulting precipitate was isolated by filtration, washed with water to afford the title compound (85 mg, 87%) as a white solid. $^1$H NMR (500 MHz, DMSO) δ 13.08 (br s, 1H), 9.12 (d, J=1.9 Hz, 1H), 8.74 (d, J=2.5 Hz, 1H), 8.17 (dd, J=8.7, 2.4 Hz, 1H), 7.81-7.77 (m, 1H), 6.97 (dd, J=8.8, 0.6 Hz, 1H), 5.53 (s, 2H). HRMS (ESI$^+$): calcd for $C_{10}H_9N_2O_3S$ (M+H)$^+$, 237.0328; found 237.0329.

Preparation of Compound 95, ethyl 2-((dimethylamino)methyl)quinoline-6-carboxylate A solution of Compound 90 (0.062 g, 0.16 mmol) in dimethylamine (2.0 M in THF, 1 mL, 2.0 mmol) was heated in a microwave at 60° C. for 1 h, cooled, concentrated, diluted with EtOAc, washed with water (1×), NaHCO$_3$ (1×). The aqueous phase was extracted with EtOAc (1×). The combined organic phases were dried (Na$_2$SO$_4$), filtered and concentrated to afford the title compound (42 mg, 100%) as an orange oil. $^1$H NMR (500 MHz, CDCl$_3$) δ 8.57 (d, J=1.8 Hz, 1H), 8.29 (dd, J=8.8, 1.9 Hz, 1H), 8.23 (d, J=8.5 Hz, 1H), 8.11 (d, J=8.8 Hz, 1H), 7.67 (d, J=8.5 Hz, 1H), 4.45 (q, J=7.2 Hz, 2H), 3.79 (s, 2H), 2.35 (s, 6H), 1.45 (t, J=7.1 Hz, 3H).

Preparation of Compound 96, 2-((dimethylamino)methyl)quinoline-6-carboxylic acid hydrochloride NaOH (1.04 M, 0.304 mL, 0.317 mmol) was added to a solution of Compound 95 (0.041 g, 0.16 mmol) in THF (1 mL) and MeOH (0.3 mL). The reaction mixture was stirred at rt overnight, and then water (0.5 mL) and NaOH (1.15 M, 0.276 mL, 0.317 mmol) was added and the reaction mixture stirred at rt for 48 h, concentrated to remove organic solvents, diluted with water, washed with EtOAc (1×). The aqueous phase was acidified to pH 3 with 2 M and then concentrated to dryness to afford the title compound (contains NaCl) as a pale yellow solid. $^1$H NMR (500 MHz, DMSO) δ 8.70 (d, J=1.8 Hz, 1H), 8.65 (d, J=8.5 Hz, 1H), 8.25 (dd, J=8.9, 1.9 Hz, 1H), 8.10 (d, J=8.8 Hz, 1H), 7.84 (d, J=8.5 Hz, 1H), 4.42 (br s, 2H), 2.70 (s, 6H).

Preparation of Compound 97, 2-(4,4-difluoropiperidin-1-yl)ethanol

2-Bromoethanol (0.164 mL, 2.31 mmol) was added to a suspension of 4,4-difluoropiperidine hydrochloride (0.354 g, 2.25 mmol) and potassium carbonate (0.683 g, 4.94 mmol) in dry acetonitrile (5 mL) and the reaction mixture was as heated at reflux overnight, cooled to rt, filtered, and the filtrate concentrated. Added diethyl ether, extracted with 1 M HCl (2×). The aqueous phase was made basic (pH>12) with solid NaOH, then extracted with DCM (3×). This organic phase was dried over $K_2CO_3$, filtered and concentrated to afford the title compound (216 mg, 58%) as a colourless oil. $^1$H NMR (500 MHz, $CDCl_3$) δ 3.79 (br t, J=4.7 Hz, 2H), 2.92 (br s, 4H), 2.82 (br s, 2H), 2.23 (br s, 4H). HRMS (ESI$^+$): calcd for $C_7H_4F_2NO$ (M+H)$^+$, 166.1038; found 166.1041.

Preparation of Compound 98, 6-bromo-2-(2-(4,4-difluoropiperidin-1-yl)ethoxy)quinoline This was prepared as for Compound 3, substituting Compound 97 for (R)-(−)-1-methyl-3-hydroxypyrrolidine. The crude material was purified by silica gel column chromatography using a gradient of 5 to 9% MeOH in DCM to afford the title compound as an off-white solid. $^1$H NMR (500 MHz, $CDCl_3$) δ 7.91 (d, J=9.1 Hz, 1H), 7.87 (s, 1H), 7.71-7.66 (m, 2H), 6.94 (d, J=8.9 Hz, 1H), 4.63 (br s, 2H), 2.91 (br s, 4H), 2.73 (br s, 4H), 2.04 (br s, 4H). HRMS (ESI$^+$): calcd for $C_{16}H_{18}{}^{79}BrF_2N_2O$ (M+H)$^+$, 371.0565; found 371.0563.

Preparation of Compound 99, 2-(2-(4,4-difluoropiperidin-1-yl)ethoxy)quinoline-6-carboxylic acid hydrochloride This was prepared as for Compound 4, substituting Compound 98 for Compound 3 to afford the title compound as a white solid. $^1$H NMR (500 MHz, DMSO) δ 13.09 (br s, 1H), 11.93, (br s, 1H), 8.57 (d, J=2.0 Hz, 1H), 8.44 (d, J=8.9 Hz, 1H), 8.14 (dd, J=8.7, 2.0 Hz, 1H), 7.83 (d, J=8.7 Hz, 1H), 7.13 (d, J=8.9 Hz, 1H), 4.71 (br s, 2H), 3.63 (br s, 2H), 2.78 (br s, 4H), 2.10 (br s, 4H). HRMS (ESI$^+$): calcd for $C_{17}H_{19}F_2N_2O_3$(M+H)$^+$, 337.1358; found 337.1356.

Preparation of Compound 100,[9] 1-(pyrrolidin-1-yl)propan-2-ol

Pyrrolidine (0.517 mL, 6.20 mmol) was added to a solution of propylene oxide (0.361 mL, 5.17 mmol) in water (2.0 mL) at 0° C. The reaction mixture was stirred at this temp for a couple of minutes, then allowed to warm to rt, stirred overnight, diluted with a bit of water, extracted with EtOAc (2×). The organic phase was dried ($Na_2SO_4$), filtered and concentrated to afford the title compound (478 mg, 72%) as a colourless oil. H NMR (500 MHz, $CDCl_3$) δ 3.83-3.75 (m, 1H), 2.70-2.65 (m, 2H), 2.53 (dd, J=11.9, 10.5 Hz, 1H), 2.48-2.42 (m, 2H), 2.24 (dd, J=12.0, 2.9 Hz, 1H), 1.80-1.73 (m, 4H), 1.13 (d, J=6.2 Hz, 3H).

Preparation of Compound 101, 6-bromo-2-((1-(pyrrolidin-1-yl)propan-2-yl)oxy)quinoline This was prepared as for Compound 3, substituting Compound 100 for (R)-(−)-1-methyl-3-hydroxypyrrolidine. The crude material was purified by silica gel column chromatography using a gradient of 3 to 13% MeOH in DCM to afford the title compound as a pale yellow oil. $^1$H NMR (500 MHz, $CDCl_3$) δ 7.86 (d, J=8.9 Hz, 1H), 7.85-7.82 (m, 1H), 7.68-7.62 (m, 2H), 6.89 (d, J=8.9 Hz, 1H), 5.67-5.60 (m, 1H), 2.85 (dd, J=12.6, 7.0 Hz, 1H), 2.67 (dd, J=12.6, 5.0 Hz, 1H), 2.65-2.57 (m, 4H), 1.78-1.72 (m, 4H), 1.41 (d, J=6.2 Hz, 3H). HRMS (ESI$^+$): calcd for $C_{16}H_{20}{}^{79}BrN_2O$ (M+H)$^+$, 335.0754; found 335.0752.

Preparation of Compound 102, 2-((1-(pyrrolidin-1-yl)propan-2-yl)oxy)quinoline-6-carboxylic acid hydrochloride This was prepared as for Compound 4, substituting Compound 101 for Compound 3 to afford the title compound as a pale yellow solid. $^1$H NMR (500 MHz, DMSO) δ 10.70 (s, 1H), 8.58 (d, J=2.2 Hz, 1H), 8.46 (d, J=9.0 Hz, 1H), 8.15 (dd, J=8.9, 2.1 Hz, 1H), 7.83 (d, J=8.7 Hz, 1H), 7.14 (d, J=8.8 Hz, 1H), 5.79-5.72 (m, 1H), 3.60-3.48 (m, 4H), 3.15 (br s, 2H), 1.97 (br s, 2H), 1.89 (br s, 2H), 1.44 (d, J=6.2 Hz, 3H). HRMS (ESI$^+$): calcd for $C_{17}H_{21}N_2O_3$ (M+H)$^+$, 301.1547; found 301.1543.

Example 89—Preparation of 2-(2-aminoethoxy)-N-(5-(2,3-dihydrobenzo[b][1,4]dioxine-6-carboxamido)-2-methylphenyl)quinoline-6-carboxamide Trifluoroacetic acid (0.75 mL) was added to a solution of Example 21 (0.039 g, 0.065 mmol) in dry DCM (0.75 mL) and the reaction mixture was stirred at rt for 75 min, concentrated, added DCM and concentrated again. Diluted with a small amount of MeOH, then slowly added half saturated $NaHCO_3$. The resulting precipitate was isolated by filtration, washed with water. The crude material was purified by silica gel column chromatography using 10% MeOH in DCM then a gradient of 5 to 9% 2 M $NH_3$/MeOH to afford the title compound (22 mg, 68%) as an off-white solid. $^1$H NMR (500 MHz, DMSO) δ 10.07 (s, 2H), 8.57 (d, J=2.0 Hz, 1H), 8.39 (d, J=8.9 Hz, 1H), 8.22 (dd, J=8.7, 2.1 Hz, 1H), 7.89-7.84 (m, 2H), 7.58 (dd, J=8.3, 2.2 Hz, 1H), 7.54 (d, J=2.1 Hz, 1H), 7.51 (dd, J=8.5, 2.2 Hz, 1H), 7.24 (d, J=8.4 Hz, 1H), 7.12 (d, J=8.7 Hz, 1H), 6.98 (d, J=8.4 Hz, 1H), 4.42 (t, J=5.8 Hz, 2H), 4.33-4.28 (m, 4H), 2.99 (t, J=5.9 Hz, 2H), 2.24 (s, 3H). LRMS (ESI$^+$): 499.26

Preparation of Compound 103, methyl 4-(pyridin-2-ylmethoxy)benzoate

A mixture of methyl 4-hydroxybenzoate (0.200 g, 1.315 mmol), 2-(bromomethyl)pyridine hydrobromide (0.366 g, 1.45 mmol), and potassium carbonate (0.545 g, 3.94 mmol) in dry DMF (5.0 mL) was gradually heated to 60° C. for 2.5 h, cooled to rt, diluted with water and the resulting precipitate was isolated by filtration, washed with water and dried to afford the title compound (299 mg, 94%) as an off-white solid. $^1$H NMR (500 MHz, $CDCl_3$) δ 8.61 (ddd, J=4.7, 1.7, 0.9 Hz, 1H), 8.00 (d, J=8.9 Hz, 2H), 7.74 (td, J=7.8, 1.8 Hz, 1H), 7.51 (d, J=7.9 Hz, 1H), 7.28-7.24 (m, 1H), 7.01 (d, J=8.9 Hz, 2H), 5.27 (s, 2H), 3.88 (s, 3H). HRMS (ESI$^+$): calcd for $C_{14}H_{13}NO_3$ (M+H)$^+$, 244.0968; found 244.0965.

Preparation of Compound 104, 4-(pyridin-2-ylmethoxy)benzoic acid

LiOH (1.345 M, 1.803 mL, 2.425 mmol) was added to a solution of Compound 103 (0.295 g, 1.21 mmol) in THF (6.0 mL), followed by MeOH (3.0 mL) and the reaction mixture was stirred at rt for 3 days, concentrated to remove organic solvents, washed with EtOAc (1×). The aqueous phase was acidified with 2 M HCl to pH 3 and the resulting precipitate was isolated by filtration, washed with water and dried to afford the title compound (244 mg, 88%) as a white solid. $^1$H NMR (500 MHz, DMSO) δ 12.66 (br s, 1H), 8.59 (ddd, J=4.8, 1.7, 0.9 Hz, 1H), 7.89 (d, J=8.8 Hz, 2H), 7.84 (td, J=7.7, 1.7 Hz, 1H), 7.52 (br d, J=7.8 Hz, 2H), 7.36 (ddd, J=7.7, 4.8, 1.1 Hz, 1H), 7.11 (d, J=8.8 Hz, 2H), 5.26 (s, 2H). HRMS (ESI$^+$): calcd for $C_{13}H_{12}NO_3$ (M+H)$^+$, 230.0812; found 230.0811.

Preparation of Compound 105, methyl 4-(thiazol-5-ylmethoxy)benzoate

Diisopropyl azodicarboxylate (0.531 mL, 2.56 mmol) was added dropwise to a solution of methyl 4-hydroxybenzoate (0.300 g, 1.97 mmol), 5-(hydroxymethyl)-1,3-thiazole (0.172 mL, 1.97 mmol), and triphenylphosphine (0.672 g, 2.56 mmol) in dry THF (5.5 mL) at 0° C. The reaction mixture was then allowed to warm to rt, stirred overnight concentrated, diluted with EtOAc, washed with 1 M NaOH (1×), brine (1×), dried (Na$_2$SO$_4$), filtered and concentrated. The crude material was purified by silica gel column chromatography using a gradient of 28 to 40% EtOAc in PE to afford the title compound (436 mg, 89%) as a white solid. $^1$H NMR (500 MHz, CDCl$_3$) δ 8.88 (s, 1H), 8.02 (d, J=8.8 Hz, 2H), 7.95-7.94 (m, 1H), 6.99 (d, J=8.8 Hz, 2H), 5.35 (d, J=1.1 Hz, 2H), 3.89 (s, 3H). HRMS (ESI$^+$): calcd for $C_{12}H_{12}NO_3S$ (M+H)$^+$, 250.0532; found 250.0533.

Preparation of Compound 106, 4-(thiazol-5-ylmethoxy)benzoic acid

LiOH (1.345 M, 2.51 mL, 3.38 mmol) was added to a solution of Compound 105 (0.421 g, 1.69 mmol) in THF (8.0 mL), followed by MeOH (2.5 mL) and the reaction mixture was stirred at rt for 22 h, concentrated to remove organic solvents, diluted with a bit of water, and washed with EtOAc (1×). The aqueous phase was acidified to pH 2 with 2 M HCl and the resulting precipitate was isolated by filtration, washed with water and dried to afford the title compound (335 mg, 84%) as a white solid. $^1$H NMR (500 MHz, DMSO) δ 12.68 (s, 1H), 9.13 (s, 1H), 8.04 (s, 1H), 7.90 (d, J=8.8 Hz, 2H), 7.12 (d, J=8.8 Hz, 2H), 5.48 (s, 2H). HRMS (ESI$^+$): calcd for $C_{11}H_{10}NO_3S$ (M+H)$^+$, 236.0376; found 236.0375.

Preparation of Compound 107, methyl 2-chloro-4-methoxyquinoline-6-carboxylate mCPBA (0.185 g, 0.802 mmol) was added to a solution of Compound 82 (0.134 g, 0.617 mmol) in dry DCM (2.0 mL) at 0° C. The reaction mixture was then warmed to rt and stirred for 20 h diluted with DCM, washed with 10% sodium sulfite (1×). The aqueous phase was extracted with DCM (1×). The organic phases were washed with NaHCO$_3$ (1×), brine (1×), dried (MgSO$_4$), filtered and concentrated to afford the 4-methoxy-6-(methoxycarbonyl)quinoline 1-oxide intermediate as a yellow solid. The N-oxide intermediate was dissolved in dry DCM (2.0 mL), and to this was added phosphorus oxychloride (0.765 mL, 8.20 mmol) slowly while cooling flask in a water bath (exotherm). The reaction mixture was then heated to 50° C. for 17 h, and then at 55° C. for 6 h before additional POCl$_3$ (0.29 mL, 3.1 mmol) was added and the reaction mixture was heated to 50° C. for 18 h, cooled to rt, diluted with EtOAc, washed with NaHCO$_3$ (3×). The aqueous phase was made basic with 1 M NaOH, then extracted with EtOAc (1×). The combined organic phases were washed with brine (1×), dried (MgSO$_4$), filtered and concentrated. The crude material was purified by silica gel column chromatography using a gradient of 11 to 17% EtOAc in PE to afford the title compound (99 mg, 64%) as a white solid. $^1$H NMR (500 MHz, CDCl$_3$) δ 8.89 (d, J=1.6 Hz, 1H), 8.30 (dd, J=8.8, 2.0 Hz, 1H), 7.96 (dd, J=8.8, 0.6 Hz, 1H), 6.80 (s, 1H), 4.10 (s, 3H), 3.99 (s, 3H). HRMS (ESI$^+$): calcd for $C_{12}H_{11}{}^{35}ClNO_3$ (M+H)$^+$, 252.0422; found 252.0428.

Preparation of Compound 108, 4-methoxy-2-(2-methoxyethoxy)quinoline-6-carboxylic acid NaH (60% in mineral oil, 0.014 g, 0.60 mmol) was added to 2-methoxyethanol (0.75 ml, 9.5 mmol) at 0° C. The reaction mixture was stirred at 0° C. for a few minutes, then at rt for 20-25 min before Compound 107 (0.050 g, 0.20 mmol) was added. The resulting suspension was then heated to 70° C. for 24 h, cooled to rt, diluted with water, acidified to pH 3 with 2 M HCl. The resulting solid was isolated by filtration, washed with water and dried. The crude material was purified by silica gel column chromatography using a gradient of 2 to 5% MeOH in DCM to afford the title compound (16 mg, 29%) as a white solid. $^1$H NMR (500 MHz, CDCl$_3$) δ 8.88 (d, J=2.0 Hz, 1H), 8.24 (dd, J=8.8, 2.1 Hz, 1H), 7.78 (d, J=8.7 Hz, 1H), 6.36 (s, 1H), 4.70-4.64 (m, 2H), 4.02 (s, 3H), 3.83-3.78 (m, 2H), 3.47 (s, 3H). HRMS (ESI$^+$): calcd for $C_{14}H_{16}NO_5$(M+H)$^+$, 278.1023; found 278.1024.

Preparation of Compound 109, 6-carboxyquinoline 1-oxide

NaOH (0.92 M, 1.605 mL, 1.48 mmol) was added to a solution of 6-(methoxycarbonyl)quinoline 1-oxide (0.1 g, 0.492 mmol, synthesised as described for Compounds 56 and 57) in THF (3 mL), followed by MeOH (0.5 mL) and the reaction mixture was stirred overnight at rt, concentrated to remove organic solvents, diluted with water, washed with EtOAc (1×). The aqueous phase was acidified with 2 M HCl to pH 2-3, and the resulting solid was isolated by filtration, washed with water and dried to afford the title compound (79 mg, 85%) as an off-white solid. $^1$H NMR (500 MHz, DMSO) δ 13.53 (br s, 1H), 8.75 (d, J=1.7 Hz, 1H), 8.68 (dd, J=6.2, 0.9 Hz, 1H), 8.60 (d, J=9.1 Hz, 1H), 8.24 (dd, J=9.1, 1.8 Hz, 1H), 8.13 (d, J=8.5 Hz, 1H), 7.56 (dd, J=8.5, 6.1 Hz, 1H). HRMS (ESI$^+$): calcd for $C_{10}H_8NO_3$ (M+H)$^+$, 190.0499; found 190.0506.

Preparation of Compound 110, methyl 4-cyanoquinoline-6-carboxylate

A mixture of Compound 57 (0.200 g, 0.902 mmol), Zn(CN)$_2$ (0.212 g, 1.80 mmol), and Pd(PPh$_3$)$_4$(0.104 g, 0.0900 mmol) in dry DMF (2.3 mL) was heated in a microwave reactor to 160° C. for 30 min, cooled to rt, diluted with EtOAc, filtered through celite, diluted further with toluene, washed with water (2×), brine (1×), dried (MgSO$_4$), filtered and concentrated. Added heptane and concentrated (2×) to remove residual DMF. The crude material was combined with the crude from a separate reaction (0.23 mmol scale) and purified by silica gel column chromatography using a gradient of 22 to 25% EtOAc in PE to afford the title compound (213 mg, 89%) as an off-white solid. $^1$H NMR (500 MHz, CDCl$_3$) δ 9.14 (d, J=4.2 Hz, 1H), 8.92 (d, J=1.9 Hz, 1H), 8.46 (dd, J=8.8, 1.8 Hz, 1H), 8.28 (d, J=8.7 Hz, 1H), 7.81 (d, J=4.3 Hz, 1H), 4.04 (s, 3H). HRMS (ESI⁺): calcd for $C_{12}H_9N_2O_2(M+H)^+$, 213.0658; found 213.0663.

Preparation of Compound 111, 4-cyanoquinoline-6-carboxylic acid

A solution of LiOH (0.93 M), 2.05 ml, 1.91 mmol) was added to a solution of Compound 110 (0.207 g, 0.975 mmol) in THF (7 mL), followed by MeOH (3 mL) and the reaction mixture was stirred at rt overnight. Additional LiOH (0.769M, 2.7 ml, 2.1 mmol) was added and reaction mixture was stirred at rt for 4 h, concentrated to remove organic solvents, and washed with EtOAc (1×). The aqueous phase was acidified to pH 2-3 with 2 M HCl, and the resulting precipitate was isolated by filtration, washed with water and dried. The crude material was suspended in hot MeOH, cooled, and the solid isolated by filtration, and washed with MeOH and dried to afford the title compound, as a mixture with the amide from nitrile hydrolysis. This mixture was used in the following step without further purification. HRMS (ESI⁺): calcd for $C_{11}H_7N_2O_2(M+H)^+$, 199.0502; found 199.0502.

Preparation of Compound 112, methyl 6-(pyridin-2-ylmethoxy)nicotinate 2-(Hydroxymethyl)pyridine (0.169 mL, 1.75 mmol) was added to a suspension of NaH (60% in mineral oil, 0.044 g, 1.8 mmol) in dry THF (4.5 mL) at 0° C. After a few minutes, the reaction mixture was allowed to warm to rt, stirred for 20 min before methyl 6-chloropyridine-3-carboxylate (0.250 g, 1.46 mmol) was added and the reaction mixture was heated at reflux for 4 h (shortly after heating, an additional 3 mL of THF was added to help the thick reaction mixture to be stirred efficiently). The reaction mixture was cooled to rt, concentrated, added water and saturated NaHCO₃ and the mixture was extracted with DCM (3×). The organic phase was dried (Na₂SO₄), filtered and concentrated. The crude material was purified by silica gel column chromatography using a gradient of 25 to 50% EtOAc in PE to afford the title compound (104 mg, 29%) as a white solid. ¹H NMR (500 MHz, CDCl₃) δ 8.83 (dd, J=2.5, 0.8 Hz, 1H), 8.62 (ddd, J=4.8, 1.8, 1.0 Hz, 1H), 8.19 (dd, J=8.7, 2.4 Hz, 1H), 7.70 (td, J=7.7, 1.7 Hz, 1H), 7.44 (d, J=7.9 Hz, 1H), 7.24 (ddd, J=7.6, 4.8, 0.8 Hz, 1H), 6.90 (dd, J=8.7, 0.6 Hz, 1H), 5.58 (s, 2H), 3.91 (s, 3H). HRMS (ESI⁺): calcd for $C_{13}H_{13}N_2O_3$ (M+H)⁺, 245.0921; found 245.0922.

Preparation of Compound 113, 6-(pyridin-2-ylmethoxy)nicotinic acid

LiOH (1.345 M, 0.615 mL, 0.827 mmol) was added to a solution of Compound 112 (0.101 g, 0.414 mmol) in THF (2 mL), followed by MeOH (0.6 mL) and the reaction mixture was stirred at rt for 26 h, concentrated to remove organic solvents, diluted with water, and washed with EtOAc (1×). The aqueous phase was acidified to pH 2-3 with 2 M HCl, and the resulting precipitate was isolated by filtration, washed with water and dried to afford the title compound (79 mg, 83%) as a white solid. ¹H NMR (500 MHz, DMSO) δ 13.07 (s, 1H), 8.71 (dd, J=2.5, 0.8 Hz, 1H), 8.56 (ddd, J=5.0, 1.8, 1.1 Hz, 1H), 8.19 (dd, J=8.6, 2.4 Hz, 1H), 7.81 (td, J=7.7, 1.7 Hz, 1H), 7.46 (br d, J=7.8 Hz, 1H), 7.34 (dd, J=7.6, 4.8, 1.1 Hz, 1H), 7.04 (dd, J=8.6, 0.8 Hz, 1H), 5.50 (s, 2H). HRMS (ESI⁺): calcd for $C_{12}H_{11}N_2O_3(M+H)^+$, 231.0764; found 231.0760.

Preparation of Compound 114, 6-bromo-2-(4-methylpiperazin-1-yl)quinoline

A solution of 6-bromo-2-chloroquinoline (0.200 g, 0.825 mmol) and 1-methylpiperazine (0.459 mL, 4.12 mmol) in dry dioxane (4 mL) was heated at reflux for 19 h, cooled to rt, concentrated, diluted with EtOAc, washed with water (1×), brine (1×), dried (Na₂SO₄), filtered and concentrated. The crude material was purified by silica gel column chromatography using a gradient of 2 to 4% MeOH in DCM to afford the title compound (236 mg, 93%) as a pale yellow solid. ¹H NMR (500 MHz, CDCl₃) δ 7.79 (d, J=9.2 Hz, 1H), 7.72 (d, J=2.0 Hz, 1H), 7.58 (dd, J=8.9, 2.1 Hz, 1H), 7.55 (d, J=8.9 Hz, 1H), 6.99 (d, J=9.2 Hz, 1H), 3.79-3.73 (m, 4H), 2.58-2.51 (m, 4H), 2.36 (s, 3H). HRMS (ESI⁺): calcd for $C_{14}H_{17}{}^{79}BrN_3$ (M+H)⁺, 306.0600; found 306.0587.

Preparation of Compound 115, 2-(4-methylpiperazin-1-yl)quinoline-6-carboxylic acid hydrochloride This was prepared as for Compound 4, substituting Compound 114 for Compound 3. After acidification of the aqueous phase this was loaded onto a flash-NH₂ column, eluted first with water, and then 1 M HCl. The HCl fractions were concentrated to afford the title compound (13 mg, 9%) as a yellow-brown film. ¹H NMR (500 MHz, DMSO) δ 11.56 (br s, 1H), 8.43 (d, J=2.1 Hz, 1H), 8.31 (br d, J=9.1 Hz, 1H), 8.09-8.02 (m, 1H), 7.68 (br s, 1H), 7.42 (br d, J=9.2 Hz, 1H), 4.72 (br d, J=14.1 Hz, 2H), 3.16 (s, 3H), 3.14-3.05 (m, 2H), 2.79-2.75 (m, 4H). HRMS (ESI⁺): calcd for $C_{15}H_{17}N_3O_2$ (M+H)⁺, 272.1394; found 272.1393.

Preparation of Compound 116, 4-(6-bromoquinolin-2-yl)morpholine

A solution of 6-bromo-2-chloroquinoline (0.200 g, 0.825 mmol) and morpholine (0.719 mL, 8.25 mmol) in dry dioxane (3.5 mL) was heated at reflux overnight, cooled to rt, concentrated, diluted with EtOAc, washed with water (2×), brine (1×), dried (Na₂SO₄), filtered and concentrated. The crude material was purified by a silica gel column chromatography using a gradient of 25 to 33% EtOAc in PE to afford the title compound (231 mg, 96%) as a pale orange solid. ¹H NMR (500 MHz, CDCl₃) δ 7.82 (d, J=9.1 Hz, 1H), 7.75 (d, J=2.1 Hz, 1H), 7.60 (dd, J=8.9, 2.1 Hz, 1H), 7.57 (d, J=8.9 Hz, 1H), 6.97 (d, J=9.2 Hz, 1H), 3.88-3.82 (m, 4H), 3.73-3.69 (m, 4H). HRMS (ESI⁺): calcd for $C_{13}H_{14}{}^{79}BrN_2O$ (M+H)⁺, 293.0284; found 293.0283.

Preparation of Compound 117, 2-morpholinoquinoline-6-carboxylic acid

This was prepared as for Compound 4, substituting Compound 116 for Compound 3. After acidification of the aqueous phase, it was extracted with DCM (3×). The organic phases were dried (MgSO₄), filtered and concentrated. The crude material was purified by silica gel column chromatography using 1:1 PE:EtOAc+0.5% AcOH to afford the title compound as a pale yellow solid. LRMS (ESI⁺): 259.21

Preparation of Compound 118, methyl 6-(methylcarbamoyl)nicotinate

A suspension of dimethyl 2,5-pyridinedicarboxylate (0.500 g, 2.56 mmol) and MgCl₂ (0.122 g, 1.28 mmol) in dry THF (10 mL) was stirred at rt for 5 min, then methylamine (2.0 M in THF, 2.56 mL, 5.1 mmol) was added dropwise over 10 min. The reaction mixture was stirred at rt for 3.5 h, after which time water (5 mL) and then 1 M HCl (2.6 mL) were added. The pH was adjusted to 6 with 1 M NaOH, and the mixture extracted with EtOAc (3×). The organic phase was washed with brine (1×), dried (MgSO$_4$), filtered and concentrated to afford the title compound (485 mg, 97%) as a white solid. $^1$H NMR (500 MHz, CDCl$_3$) δ 9.13 (dd, J=2.0, 0.8 Hz, 1H), 8.44 (dd, J=8.1, 2.0 Hz, 1H), 8.28 (dd, J=8.1, 0.8 Hz, 1H), 8.05 (br s, 1H), 3.98 (s, 3H), 3.06 (d, J=5.1 Hz, 3H). LRMS (ESI$^+$): 195.09

Preparation of Compound 119, 6-(methylcarbamoyl)nicotinic acid

LiOH (1.984 M, 3.13 mL, 6.22 mmol) was added to a solution of Compound 118 (0.483 g, 2.49 mmol) in THF (13 mL) and MeOH (3 mL). The reaction mixture was stirred at rt overnight, concentrated to remove organic solvents, diluted with water, and washed with EtOAc (1×). The aqueous phase was acidified to pH 3 with 2 M HCl, and the resulting precipitate was isolated by filtration, washed with water and dried to afford the title compound (321 mg, 72%) as a white solid. $^1$H NMR (500 MHz, DMSO) δ 13.67 (br s, 1H), 9.07 (dd, J=2.1, 0.7 Hz, 1H), 8.95-8.91 (m, 1H), 8.43 (dd, J=8.1, 2.1 Hz, 1H), 8.13 (dd, J=8.1, 0.7 Hz, 1H), 2.83 (d, J=4.9 Hz, 3H). HRMS (ESI$^+$): calcd for C$_3$H$_9$N$_2$O$_3$(M+H)$^+$, 181.0608; found 181.0608.

Preparation of Compound 120, tert-butyl (3-((6-bromoquinolin-2-yl)oxy)propyl)carbamate This was prepared as for Compound 3, substituting tert-butyl N-(3-hydroxypropyl)carbamate for (R)-(−)-1-methyl-3-hydroxypyrrolidine. The crude material was purified by silica gel column chromatography using a gradient of 15 to 25% MeOH in DCM to afford the title compound as an off-white solid. $^1$H NMR (500 MHz, CDCl$_3$) δ 7.90 (d, J=8.8 Hz, 1H), 7.86 (d, J=2.2 Hz, 1H), 7.73 (d, J=8.9 Hz, 1H), 7.68 (dd, J=8.9, 2.1 Hz, 1H), 6.91 (d, J=8.9 Hz, 1H), 4.56 (t, J=6.1 Hz, 2H), 3.30 (br s, 2H), 2.01 (p, J=6.3 Hz, 2H), 1.45 (s, 9H). HRMS (ESI$^+$): calcd for C$_{17}$H$_{22}$$^{79}$BrN$_2$O$_3$(M+H)$^+$, 381.0808; found 381.0786.

Preparation of Compound 121, 2-(3-((tert-butoxycarbonyl)amino)propoxy)quinoline-6-carboxylic acid This was prepared as for Compound 4, substituting Compound 120 for Compound 3. After acidification of the aqueous phase, it was extracted with DCM (3×), dried (MgSO$_4$), filtered and concentrated to afford the title compound as a white solid. $^1$H NMR (500 MHz, CDCl$_3$) δ 8.52 (s, 1H), 8.25 (d, J=7.8 Hz, 1H), 8.08 (d, J=9.0 Hz, 1H), 7.91-7.84 (m, 2H), 6.96 (d, J=9.1 Hz, 1H), 4.63-4.58 (m, 2H), 3.32 (t, J=6.5 Hz, 2H), 2.03 (p, J=6.3 Hz, 2H), 1.46 (s, 9H). HRMS (ESI$^+$): calcd for C$_{18}$H$_{23}$N$_2$O$_5$ (M+H)$^+$, 347.1602; found 347.1607.

Example 90—Preparation of N-(5-(2,3-dihydrobenzo[b][1,4]dioxine-6-carboxamido)-2-methylphenyl)-2-(trifluoromethyl)-1H-benzo[d]imidazole-6-carboxamide A solution of HATU (122 mg, 0.32 mmol) in DMA (1 mL) was added to a stirred mixture of Compound 2 (70 mg, 0.25 mmol), 2-(trifluoromethyl)-3H-benzimidazole-5-carboxylic acid (0.49 mmol) and DIPEA (0.172 mL, 0.98 mmol) in DMA (1 mL) at ambient temperature. The resulting mixture was stirred at ambient temperature for 1 hour and then at 60° C. for 2 hours before being allowed to cool. The crude product was purified by preparative HPLC. Fractions containing the desired compound were evaporated to dryness to afford the desired material as a solid (67 mg, 55%). $^1$H NMR (400 MHz, DMSO) δ 14.24 (s, 1H), 10.02 (m, 2H), 8.42 (s, 1H), 8.03 (d, J=8.7 Hz, 1H), 7.86 (s, 1H), 7.44-7.67 (m, 4H), 7.24 (d, J=8.6 Hz, 1H), 6.98 (d, J=8.4 Hz, 1H), 4.2-4.42 (m, 4H), 2.24 (s, 3H). m/z (ES+) (M+H)+=497.37.

Examples 91 to 100

The following compounds were synthesised according to the procedure for Example 90, by substituting the appropriate carboxylic acid for 2-(trifluoromethyl)-3H-benzimidazole-5-carboxylic acid.

Example 91, 2-amino-N-(5-(2,3-dihydrobenzo[b][1,4]dioxine-6-carboxamido)-2-methylphenyl)benzo[d]thiazole-6-carboxamide Example 92, N-(5-(2,3-dihydrobenzo[b][1,4]dioxine-6-carboxamido)-2-methylphenyl)-3H-imidazo[4,5-b]pyridine-6-carboxamide Example 93, N-(3-(4-hydroxybenzamido)-4-methylphenyl)-2,3-dihydrobenzo[b][1,4]dioxine-6-carboxamide Example 94, N-(5-(2,3-dihydrobenzo[b][1,4]dioxine-6-carboxamido)-2-methylphenyl)-6-(phenylamino)nicotinamide Example 95, 2-amino-N-(5-(2,3-dihydrobenzo[b][1,4]dioxine-6-carboxamido)-2-methylphenyl)-4-methoxybenzo[d]thiazole-6-carboxamide Example 96, N-(5-(2,3-dihydrobenzo[b][1,4]dioxine-6-carboxamido)-2-methylphenyl)-2-(1H-1,2,4-triazol-1-yl)isonicotinamide Example 97, N-(5-(2,3-dihydrobenzo[b][1,4]dioxine-6-carboxamido)-2-methylphenyl)-1H-indazole-5-carboxamide Example 98, N-(5-(2,3-dihydrobenzo[b][1,4]dioxine-6-carboxamido)-2-methylphenyl)-2-morpholinoisonicotinamide Example 99, N-(5-(2,3-dihydrobenzo[b][1,4]dioxine-6-carboxamido)-2-methylphenyl)-2-methyl-1H-pyrrolo[2,3-b]pyridine-5-carboxamide Example 100, N-(5-(2,3-dihydrobenzo[b][1,4]dioxine-6-carboxamido)-2-methylphenyl)-1H-pyrrolo[2,3-b]pyridine-5-carboxamide Table C

TABLE C

| | 1H NMR | Mass Spec |
|---|---|---|
| Example 91 | $^1$H NMR (400 MHz, DMSO) δ 10.03 (s, 1H), 9.73 (s, 1H), 8.30 (s, 1H), 7.89 (dd, J = 1.9, 8.4 Hz, 1H), 7.83 (d, J = 2.2 Hz, 1H), 7.77 (s, 1H), 7.47-7.62 (m, 2H), 7.41 (d, J = 8.4 Hz, 1H), 7.21 (d, J = 8.4 Hz, 1H), 6.97 (dd, J = 8.3, 11.0 Hz, 1H), 4.14-4.47 m, 4H), 1.99 (s, 3H). | m/z (ES−) (M − H)− = 459.55 |

TABLE C-continued

| | 1H NMR | Mass Spec |
|---|---|---|
| Example 92 | $^1$H NMR (400 MHz, DMSO) δ 13.20 (s, 1H), 10.04 (d, J = 4.8 Hz, 2H), 9.00 (s, 1H), 8.60 (s, 2H), 7.87 (d, J = 2.1 Hz, 1H), 7.60 (dd, J = 2.2, 8.3 Hz, 1H), 7.47-7.58 (m, 2H), 7.24 (d, J = 8.5 Hz, 1H), 6.98 (d, J = 8.4 Hz, 1H), 4.23-4.4 (m, 4H), 2.25 (s, 3H). | m/z (ES+) (M + H)+ = 430.4 |
| Example 93 | $^1$H NMR (400 MHz, DMSO) δ 10.01 (s, 1H), 9.61 (s, 1H), 7.84-7.91 (m, 2H), 7.80 (d, J = 2.5 Hz, 1H), 7.42-7.61 (m, 4H), 7.20 (d, J = 8.5 Hz, 1H), 6.98 (d, J = 8.4 Hz, 1H), 6.82-6.91 (m, 2H), 4.25-4.41 (m, 4H), 2.19 (s, 3H). | m/z (ES+) (M + H)+ = 405.41 |
| Example 94 | $^1$H NMR (400 MHz, DMSO) δ 10.03 (s, 1H), 9.71 (s, 1H), 9.45 (s, 1H), 8.82 (d, J = 2.4 Hz, 1H), 8.11 (dd, J = 2.5, 8.8 Hz, 1H), 7.84 (d, J = 2.3 Hz, 1H), 7.66-7.8 (m, 2H), 7.48-7.65 (m, 3H), 7.28-7.38 (m, 2H), 7.22 (d, J = 8.5 Hz, 1H), 6.98 (m, 1H), 6.91 (d, J = 8.8 Hz, 1H), 4.32 (m, 4H), 2.22 (s, 3H). | m/z (ES+) (M + H)+ = 481.44 |
| Example 95 | $^1$H NMR (400 MHz, DMSO) δ 10.02 (s, 1H), 9.75 (s, 1H), 7.95 (d, J = 1.24 Hz, 1H), 7.82 (d, J = 2.21 Hz, 1H), 7.68 (s, 2H), 7.43-7.61 (m, 4H), 7.21 (d, J = 8.5 Hz, 1H), 6.98 (d, J = 8.4 Hz, 1H), 4.18-4.42 (m, 4H), 3.92 (s, 3H), 2.21 (s, 3H). | m/z (ES−) (M − H)− = 489 |
| Example 96 | $^1$H NMR (400 MHz, DMSO) δ 10.44 (s, 1H), 10.06 (s, 1H), 9.45 (s, 1H), 8.76 (d, J = 5.0 Hz, 1H), 8.38 (s, 1H), 7.99 (d, J = 5.21 Hz, 1H), 7.87 (s, 1H), 7.60 (dd, J = 2.2, 8.3 Hz, 1H), 7.44-7.55 (m, 3H), 7.25 (d, J = 8.4 Hz, 1H), 6.98 (d, J = 8.4 Hz, 1H), 4.31 (m, 4H), 2.22 (s, 3H). | m/z (ES−) (M − H)− = 455 |
| Example 97 | $^1$H NMR (400 MHz, DMSO) δ 13.31 (s, 1H), 10.03 (s, 1H), 9.88 (s, 1H), 9.68 (s, 1H), 8.51 (s, 1H), 8.26 (s, 1H), 7.94-8.06 (d, 1H), 7.85 (d, J = 2.3 Hz, 1H), 7.63 (d, J = 8.78 Hz, 1H), 7.55-7.6 (m, 1H), 7.51-7.54 (m, 1H). 7.23 (d, J = 8.6 Hz, 1H), 6.97 (dd, J = 8.3, 11.9 Hz, 1H), 4.23-4.45 (m, 4H), 2.24 (s, 3H). | m/z (ES−) (M − H)− = 427 |
| Example 98 | $^1$H NMR (400 MHz, DMSO) δ 10.03 (m, 2H), 8.30 (d, J = 5.2 Hz, 1H), 7.83 (t, J = 2.7, 2.7 Hz, 1H), 7.58 (dd, J = 2.2, 8.3 Hz, 1H), 7.44-7.55 (m, 2H), 7.31 (s, 1H), 7.24 (d, J = 8.5 Hz, 1H), 7.16 (d, J = 5.1 Hz, 1H), 6.98 (d, J = 8.3 Hz, 1H), 4.32 (m, 4H), 3.65-3.85 (m, 4H), 3.49-3.63 (m, 4H), 2.19 (s, 3H). | m/z (ES−) (M − H)− = 473 |
| Example 99 | $^1$H NMR (400 MHz, DMSO) δ 11.77 (s, 1H), 10.03 (s, 1H), 9.84 (s, 1H), 8.75 (d, J = 2.1 Hz, 1H), 8.41 (d, J = 2.0 Hz, 1H), 7.85 (d, J = 2.4 Hz, 1H), 7.45-7.66 (m, 3H), 7.22 (d, J = 8.6 Hz, 1H), 6.98 (d, J = 8.4 Hz, 1H), 6.30 (s, 1H), 4.16-4.43 (m, 4H), 2.43 (s, 3H), 2.24 (s, 3H). | m/z (ES−) (M − H)− = 442 |
| Example 100 | $^1$H NMR (400 MHz, DMSO) δ 11.95 (s, 1H), 10.04 (s, 1H), 9.90 (s, 1H), 8.86 (d, J = 2.1 Hz, 1H), 8.59 (d, J = 2.1 Hz, 1H), 7.86 (d, J = 2.4 Hz, 1H), 7.38-7.69 (m, 4H), 7.23 (d, J = 8.5 Hz, 1H), 7.0 (d, J = 8.4 Hz, 1H), 6.55-6.65 (m, 1H), 4.26-4.39 (m, 4H), 2.24 (s, 3H). | m/z (ES−) (M − H)− = 427 |

Example 101—Preparation of N-(4-methyl-3-(4-(thiazol-4-ylmethoxy)benzamido)phenyl)-2,3-dihydrobenzo[b][1,4]dioxine-6-carboxamide HATU (0.321 g, 0.840 mmol) and DIPEA (0.368 mL, 2.11 mmol) were added to a solution of 4-(thiazol-4-ylmethoxy) benzoic acid (0.199 g, 0.840 mmol) in DMA (3 mL) under an inert atmosphere and the reaction allowed to stir for 15 minutes. Compound 2 (0.200 g, 0.700 mmol) was added and the reaction mixture was stirred at ambient temperature overnight. The reaction was diluted with water and the solids filtered. The solids were dissolved in DMF and purified by preparative HPLC. Fractions containing the desired compound were evaporated to dryness to afford the desired material as a white solid (0.184 g, 52%). $^1$H NMR (400 MHz, DMSO) δ 10.02 (s, 1H), 9.73 (s, 1H), 9.14 (d, J=2.00 Hz, 1H), 8.06-7.94 (m, 2H), 7.82 (dd, J=2.1, 11.8 Hz, 2H), 7.64-7.43 (m, 3H), 7.26-7.10 (m, 3H), 6.97 (d, J=8.4 Hz, 1H), 5.32 (s, 2H), 4.45-4.13 (m, 4H), 2.19 (s, 3H). m/z (ES+) (M+H)+=502.

Examples 102 to 112

The following compounds were synthesised according to the procedure for Example 101, by substituting the appropriate carboxylic acid for 4-(thiazol-4-ylmethoxy)benzoic acid.

Example 102, N-(5-(2,3-dihydrobenzo[b][1,4]dioxine-6-carboxamido)-2-methylphenyl)-6-(ethylamino)nicotinamide Example 103, N-(5-(2,3-dihydrobenzo[b][1,4]dioxine-6-carboxamido)-2-methylphenyl)-2-oxo-1,2,3,4-tetrahydroquinoline-6-carboxamide Example 104, 6-amino-N-(5-(2,3-dihydrobenzo[b][1,4]dioxine-6-carboxamido)-2-methylphenyl)nicotinamide Example 105, 2-amino-N-(5-(2,3-dihydrobenzo[b][1,4]dioxine-6-carboxamido)-2-methylphenyl)isonicotinamide Example 106, N-(5-(2,3-dihydrobenzo[b][1,4]dioxine-6-carboxamido)-2-methylphenyl)-6-(1H-pyrazol-1-yl)nicotinamide Example 107, N-(3-(4-(1H-pyrazol-1-yl)benzamido)-4-methylphenyl)-2,3-dihydrobenzo[b][1,4]dioxine-6-carboxamide Example 108, N-(4-methyl-3-(6-methyl-2-naphthamido)phenyl)-2,3-dihydrobenzo[b][1,4]dioxine-6-carboxamide Example 109, N-(5-(2,3-dihydrobenzo[b][1,4]dioxine-6-carboxamido)-2-methylphenyl)-3-methyl-4-oxo-3,4-dihydroquinazoline-6-carboxamide Example 110, N-(5-(2,3-dihydrobenzo[b][1,4]dioxine-6-carboxamido)-2-methylphenyl)-4-(2-(dimethylamino)ethylamino)-2-methylquinoline-6-carboxamide Example 111, N-(5-(2,3-dihydrobenzo[b][1,4]dioxine-6-carboxamido)-2-methylphenyl)-4-(3-(dimethylamino)propylamino)-2-methylquinoline-6-carboxamide Example 112, N-(5-(2,3-dihydrobenzo[b][1,4]dioxine-6-carboxamido)-2-methylphenyl)-2-methyl-4-(methyl(1-methylpyrrolidin-3-yl)amino)quinoline-6-carboxamide

TABLE D

| | 1H NMR | Mass Spec |
|---|---|---|
| Example 102 | $^1$H NMR (400 MHz, DMSO) δ 10.00 (s, 1H), 9.51 (s, 1H), 8.66 (d, J = 2.4 Hz, 1H), 7.91 (dd, J = 2.4, 8.8 Hz, 1H), 7.80 (d, J = 2.2 Hz, 1H), 7.61-7.45 (m, 3H), 7.19 (d, J = 8.5 Hz, 1H), 7.10 (t, J = 5.4, 5.4 Hz, 1H), 6.97 (d, J = 8.4 Hz, 1H), 6.49 (d, J = 8.8 Hz, 1H), 4.4-4.2 (m, 4H), 3.40-3.20 (m, 2H), 2.18 (s, 3H), 1.16 (t, J = 7.2, 7.2 Hz, 3H). | m/z (ES+) (M + H)+ = 433 |
| Example 103 | $^1$H NMR (400 MHz, DMSO) δ 10.32 (s, 1H), 10.02 (s, 1H), 9.71 (s, 1H), 7.92-7.71 (m, 3H), 7.65-7.44 (m, 3H), 7.20 (d, J = 8.5 Hz, 1H), 7.02-6.88 (m, 2H), 4.41-4.18 (m, 4H), 2.97 (t, J = 7.5, 7.5 Hz, 2H), 2.57-2.45 (m, 2H), 2.18 (s, 3H). | m/z (ES+) (M + H)+ = 458 |
| Example 104 | $^1$H NMR (400 MHz, DMSO) δ 10.00 (s, 1H), 9.53 (s, 1H), 8.60 (d, J = 2.16 Hz, 1H), 7.93 (dd, J = 2.5, 8.7 Hz, 1H), 7.79 (d, J = 2.2 Hz, 1H), 7.60-7.40 (m, 3H), 7.19 (d, J = 8.5 Hz, 1H), 6.97 (d, J = 8.4 Hz, 1H), 6.54 (s, 2H), 6.48 (d, J = 8.39 Hz, 1H), 4.39-4.19 (m, 4H), 2.18 (s, 3H). | m/z (ES+) (M + H)+ = 405 |
| Example 105 | $^1$H NMR (400 MHz, DMSO) δ 10.03 (s, 1H), 9.90 (s, 1H), 8.05 (d, J = 5.2 Hz, 1H), 7.79 (d, J = 2.1 Hz, 1H), 7.58 (dd, J = 2.1, 8.3 Hz, 1H), 7.54-7.45 (m, 2H), 7.21 (d, J = 8.5 Hz, 1H), 7.07-6.75 (m, 3H), 6.16 (s, 2H), 4.24-4.36 (m, 4H), 2.18 (s, 3H). | m/z (ES+) (M + H)+ = 405 |
| Example 106 | $^1$H NMR (400 MHz, DMSO) δ 9.90 (s, 1H), 9.83 (s, 1H), 8.83 (d, J = 1.8 Hz, 1H), 8.47-8.54 (m, 1H), 8.31 (dd, J = 2.3, 8.6 Hz, 1H), 7.85 (d, J = 9.1 Hz, 1H), 7.69 (d, J = 1.0 Hz, 1H), 7.66 (d, J = 2.2 Hz, 1H), 7.37 (dd, J = 2.2, 8.3 Hz, 1H), 7.25-7.34 (m, 2H), 7.03 (d, J = 8.5 Hz, 1H), 6.76 (d, J = 8.4 Hz, 1H), 6.43 (dd, J = 1.7, 2.6 Hz, 1H), 4.05-4.15 (m, 4H), 2.01 (s, 3H). | m/z (ES+), (M + H)+ = 456 |
| Example 107 | $^1$H NMR (400 MHz, DMSO) δ 10.04 (s, 1H), 9.95 (s, 1H), 8.64 (d, J = 2.5 Hz, 1H), 8.1-8.15 (m, 2H), 7.98-8.05 (m, 2H), 7.85 (d, J = 2.2 Hz, 1H), 7.83 (d, J = 1.7 Hz, 1H), 7.59 (dd, J = 2.1, 8.3 Hz, 1H), 7.49-7.56 (m, 2H), 7.24 (d, J = 8.5 Hz, 1H), 6.98 (d, J = 8.4 Hz, 1H), 6.62 (dd, J = 1.8, 2.4 Hz, 1H), 4.28-4.35 (m, 4H), 2.23 (s, 3H). | m/z (ES+), (M + H)+ = 455 |
| Example 108 | $^1$H NMR (400 MHz, DMSO) δ 10.10 (s, 1H), 10.08 (s, 1H), 8.62 (s, 1H), 7.98-8.12 (m, 3H), 7.93 (d, J = 2.2 Hz, 1H), 7.85 (s, 1H), 7.65 (d, J = 2.2, 8.3 Hz, 1H), 7.5-7.62 (m, 3H), 7.30 (d, J = 8.4 Hz, 1H), 7.04 (d, J = 8.4 Hz, 1H), 4.34-4.42 (m, 4H), 2.58 (s, 3H), 2.31 (s, 3H). | m/z (ES+), (M + H)+ = 453 |
| Example 109 | $^1$H NMR (400 MHz, DMSO) δ 10.27 (s, 1H), 10.07 (s, 1H), 8.83 (d, J = 2.1 Hz, 1H), 8.49 (s, 1H), 8.37 (dd, J = 2.1, 8.5 Hz, 1H), 7.89-7.75 (m, 2H), 7.59 (dd, J = 2.2, 8.3 Hz, 1H), 7.56-7.44 (m, 2H), 7.23 (d, J = 8.5 Hz, 1H), 6.98 (d, J = 8.4 Hz, 1H), 4.40-4.21 (m, 4H), 3.54 (s, 3H), 2.21 (s, 3H). | m/z (ES+) (M + H)+ = 471 |
| Example 110 | $^1$H NMR (400 MHz, DMSO) δ 10.08 (s, 1H), 9.92 (s, 1H), 8.76 (d, J = 1.60 Hz, 1H), 8.10 (dd, J = 1.82, 8.76 Hz, 1H), 7.90 (d, J = 2.18 Hz, 1H), 7.77 (d, J = 8.75 Hz, 1H), 7.45-7.62 (m, 3H), 7.24 (d, J = 8.53 Hz, 1H), 7.10 (t, J = 5.25, 5.25 Hz, 1H), 6.99 (d, J = 8.39 Hz, 1H), 6.46 (s, 1H), 4.27-4.37 (m, 4H), 3.36-3.43 (m, 2H), 3.32 (s, 3H), 2.58 (t, J = 6.74, 6.74 Hz, 2H), 2.24 (s, 3H), 2.23 (s, 6H). | m/z (ES+) (M + H)+ = 540 |
| Example 111 | $^1$H NMR (400 MHz, DMSO) δ 10.04 (s, 1H), 9.87 (s, 1H), 8.75 (d, J = 1.7 Hz, 1H), 8.10 (dd, J = 1.8, 8.7 Hz, 1H), 7.88 (d, J = 2.2 Hz, 1H), 7.76 (d, J = 8.7 Hz, 1H), 7.63-7.43 (m, 4H), 7.24 (d, J = 8.5 Hz, 1H), 6.98 (d, J = 8.4 Hz, 1H), 6.42 (s, 1H), 4.39-4.18 (m, 4H), 3.42-3.27 (m, 2H), 2.49 (s, 3H), 2.38 (t, J = 6.7, 6.7 Hz, 2H), 2.24 (s, 3H), 2.19 (s, 6H), 1.83 (q, J = 6.7, 6.7, 6.7, 6.7 Hz, 2H). | m/z (ES+) (M + H)+ = 554 |
| Example 112 | $^1$H NMR (400 MHz, DMSO) δ 10.04 (d, J = 2.8 Hz, 2H), 10.04 (d, J = 2.8 Hz, 2H), 8.61 (d, J = 1.7 Hz, 1H), 8.16 (dd, J = 1.9, 8.7 Hz, 1H), 7.99-7.79 (m, 2H), 7.59 (dd, J = 2.1, 8.3 Hz, 1H), 7.56-7.47 (m, 2H), 7.24 (d, J = 8.4 Hz, 1H), 6.98 (d, J = 8.4 Hz, 1H), 6.89 (s, 1H), 4.44-4.17 (m, 5H), 2.96 (s, 3H), 2.79 (dd, J = 4.4, 9.7 Hz, 2H), 2.76-2.69 (m, 1H), 2.64-2.60 (m, 1H), 2.59 (s, 3H), 2.26 (s, 6H), 2.22-2.10 (m, 1H), 1.91-2.05 (m, 1H). | m/z (ES+) (M + H)+ = 566 |

Preparation of Compound 122, N-(3-Nitrophenyl)-2,3-dihydro-1,4-benzodioxine-7-carboxamide 2,3-Dihydrobenzo[b][1,4]dioxine-6-carboxylic acid (3.13 g, 17.38 mmol) was dissolved in DMA (25 mL) and (7.57 mL, 43.44 mmol) and HATU (6.61 g, 17.38 mmol) added under an inert atmosphere. The reaction was allowed to stir for 15 minutes then 3-nitroaniline (2.0 g, 14.48 mmol) was added and the reaction stirred at ambient temperature overnight. The reaction was heated for a further 16 hours at 40° C. then concentrated in vacuo and water added. The solids were isolated by filtration, washed with water and dried in a vacuum oven. The solids were stirred in EtOAc for an hour and then filtered. The filtrate was evaporated down and the solids were triturated with DCM then filtered. The collected solids were combined to afford the desired material as a cream solid (3.44 g, 79%). $^1$H NMR (400 MHz, DMSO, 30° C.) d 4.33 (4H, tq), 7.03 (1H, d), 7.53-7.59 (2H, m), 7.65 (1H, t), 7.95 (1H, ddd), 8.20 (1H, ddd), 8.78-8.82 (1H, m), 10.48 (1H, s). m/z (ES+) (M+H)+=301.

Preparation of Compound 123, N-(3-Aminophenyl)-2,3-dihydro-1,4-benzodioxine-7-carboxamide A mixture of Compound 122 (2.75 g, 9.15 mmol), palladium (10% on charcoal, 0.487 g) in ethanol (25 mL)/EtOAc (25 mL)/THF (25 mL) were stirred under an atmosphere of hydrogen at ambient temperature overnight. The reaction mixture was filtered through celite and the celite was washed with THF. The filtrate and washings were combined and evaporated to afford the desired material as a light brown foam (2.62 g, 106%). ¹H NMR (400 MHz, DMSO, 30° C.) d 4.28-4.35 (4H, m), 5.02 (2H, s), 6.30 (1H, ddd), 6.85 (1H, ddd), 6.96 (2H, dt), 7.09 (1H, t), 7.49 (2H, qd), 9.72 (1H, s). m/z (ES+) (M+H)+=271.

Example 113, N-(3-(2,3-dihydrobenzo[b][1,4]dioxine-6-carboxamido)phenyl)-2-methylquinoline-6-carboxamide 2-Methylquinoline-6-carboxylic acid (0.291 g, 1.55 mmol) was dissolved in DMA (3 mL) and put under an inert atmosphere. DIPEA (0.677 mL, 3.88 mmol) and HATU (0.591 g, 1.55 mmol) were added and the reaction stirred for 15 minutes. Compound 123 (0.350 g, 1.29 mmol) was added and the reaction was stirred at ambient temperature overnight. The reaction was cooled, diluted with water and the solids filtered. The solids were dissolved in DMF and purified by preparative HPLC. Fractions containing the desired compound were evaporated to dryness to afford the desired material as a solid (0.117 g, 21%). ¹H NMR (400 MHz, DMSO) δ 10.51 (s, 1H), 10.14 (s, 1H), 8.59 (d, J=2.0 Hz, 1H), 8.41 (d, J=8.5 Hz, 1H), 8.38-8.30 (m, 1H), 8.22 (dd, J=2.0, 8.8 Hz, 1H), 8.02 (d, J=8.8 Hz, 1H), 7.62-7.41 (m, 5H), 7.32 (t, J=8.1, 8.1 Hz, 1H), 6.99 (d, J=8.4 Hz, 1H), 4.37-4.22 (m, 4H), 2.70 (s, 3H). m/z (ES+) (M+H)+=440.

Example 114—Preparation of N-(5-(2,3-dihydrobenzo[b][1,4]dioxine-6-carboxamido)-2-methylphenyl)benzo[d]thiazole-6-carboxamide HATU (695 mg, 1.83 mmol) was added to Compound 2 (400 mg, 1.41 mmol), benzo[d]thiazole-6-carboxylic acid (290 mg, 1.62 mmol) and DIPEA (0.737 mL, 4.22 mmol) in DMA (15 mL) and the resultant mixture stirred at ambient temperature for 16 hours under an inert atmosphere. The reaction mixture was diluted with EtOAc (300 mL), and washed with water (2×200 mL). The organic layer was dried over Na₂SO₄, filtered and evaporated to afford crude product. The crude product was purified by flash silica chromatography, elution gradient 20 to 100% EtOAc in isohexane. The pure fractions were evaporated to a yellow solid which was triturated with DCM and filtered to afford the desired material as a white solid (287 mg, 46%). ¹H NMR (400 MHz, DMSO) δ 10.05 (s, 2H), 9.57 (s, 1H), 8.82 (d, J=1.5 Hz, 1H), 8.23 (d, J=8.5 Hz, 1H), 8.15 (dd, J=1.74, 8.6 Hz, 1H), 7.87 (d, J=2.1 Hz, 1H), 7.58-7.65 (m, 1H), 7.47-7.57 (m, 2H), 7.24 (d, J=8.42 Hz, 1H), 6.98 (d, J=8.37 Hz, 1H), 4.32 (m, 4H), 2.24 (s, 3H). m/z (ES+), (M+H)+=446.

Example 115—Preparation of N-(5-(2,3-dihydrobenzo[b][1,4]dioxine-6-carboxamido)-2-methylphenyl)-2-(methylamino)benzo[d]thiazole-6-carboxamide Compound 2 (98 mg, 0.34 mmol) and 4-(4,6-dimethoxy-1,3,5-triazin-2-yl)-4-methylmorpholin-4-ium (173 mg, 0.620 mmol) were added to a solution of 2-(methylamino)benzo[d]thiazole-6-carboxylic acid (65 mg, 0.31 mmol) in DMF (4 mL) and the resultant solution stirred at ambient temperature overnight. The reaction was diluted with water and the solids filtered. The solids were dissolved in DMF and purified by preparative HPLC. Fractions containing the desired compound were evaporated to dryness to afford the desired material as a white solid (19 mg, 13%). ¹H NMR (400 MHz, DMSO) δ 10.06 (s, 1H), 9.78 (s, 1H), 8.32 (d, J=1.7 Hz, 1H), 8.27 (q, J=4.6 Hz, 1H), 7.89 (dd, J=1.9, 8.4 Hz, 1H), 7.82 (d, J=2.1 Hz, 1H), 7.57 (dd, J=2.2, 8.3 Hz, 1H), 7.51-7.55 (m, 2H), 7.47 (d, J=8.4 Hz, 1H), 7.21 (d, J=8.5 Hz, 1H), 6.98 (d, J=8.4 Hz, 1H), 4.27-4.36 (m, 4H), 2.99 (d, J=4.7 Hz, 3H), 2.21 (s, 3H). m/z (ES+), (M+H)+=475.

Example 116, 2-amino-N-(5-(2,3-dihydrobenzo[b][1,4]dioxine-6-carboxamido)-2-methylphenyl)benzo[d]thiazole-7-carboxamide HATU (0.201 g, 0.53 mmol) and DIPEA (0.230 mL, 1.32 mmol) were added to a solution of 2-aminobenzo[d]thiazole-7-carboxylic acid (102 mg, 0.53 mmol) in DMA (3 mL) under an inert atmosphere and the reaction allowed to stir for 15 minutes. Compound 2 (0.125 g, 0.440 mmol) was added and the reaction stirred at ambient temperature for approximately 24 hours and then at 40° C. overnight. No product was observed. Additional 2-aminobenzo[d]thiazole-7-carboxylic acid (102 mg, 0.53 mmol) was converted to the acid chloride by treatment with oxalyl chloride (approximately 1.2 equivalents) and DMF (a few drops) in DCM and the acid chloride added to the reaction mixture. The reaction was diluted with water and the solids filtered. The solids were dissolved in DMF and purified by preparative HPLC. Fractions containing the desired compound were evaporated to dryness to afford the desired material as a white solid (0.043 g, 21%). ¹H NMR (400 MHz, DMSO) δ 10.05 (s, 1H), 10.04 (s, 1H), 7.87 (d, J=7.1 Hz, 1H), 7.82 (d, J=2.2 Hz, 1H), 7.62 (dd, J=2.2, 8.3 Hz, 1H), 7.49-7.56 (m, 3H), 7.47 (s, 2H), 7.39 (t, J=7.8 Hz, 1H), 7.25 (d, J=8.5 Hz, 1H), 6.98 (d, J=8.4 Hz, 1H), 4.28-4.35 (m, 4H), 2.21 (s, 3H). m/z (ES+), (M+H)+=461.

Preparation of Compound 124, ethyl 4-(2-dimethylaminoethylamino)-2-methylquinoline-6-carboxylate Ethyl 4-chloro-2-methylquinoline-6-carboxylate (0.355 g, 1.42 mmol), N,N-dimethylethane-1,2-diamine (0.783 mL, 7.11 mmol) and DIPEA (2.476 mL, 14.22 mmol) were combined in NMP (8 mL) and sealed in a microwave tube. The reaction was heated at 200° C. for 1 hour. The crude product was purified by preparative HPLC. Fractions containing the desired compound were evaporated to dryness to afford the desired material as a gum (0.163 g, 38%). ¹H NMR (400 MHz, CDCl3, 30° C.) d 1.38 (3H, t), 2.27 (6H, s), 2.57 (3H, s), 2.59-2.68 (2H, t), 3.26 (2H, q), 4.37 (2H, q), 6.06 (1H, s), 6.26 (1H, s), 7.84 (1H, d), 8.12 (1H, dd), 8.55 (1H, d). m/z (ES+) (M+H)+=302.

Preparation of Compound 125, 4-(2-dimethylaminoethylamino)-2-methylquinoline-6-carboxylic acid Sodium hydroxide (2.00 M, 5.13 mL, 10.3 mmol) was added to a solution of Compound 124 (0.163 g, 0.54 mmol) in dioxane (5 mL) and stirred at 40° C. overnight. The reaction was neutralized to pH 7 with 2M hydrochloric acid and the solvent removed in vacuo to afford the desired material as a solid (0.148 g) which was used without further purification. ¹H NMR (400 MHz, DMSO, 30° C.) d 2.60 (9H, bd), 3.06 (2H, bt), 3.71 (2H, bs), 6.75 (1H, s), 7.89 (1H, d), 8.12-8.20 (1H, m), 8.61 (1H, bs), 9.02 (1H, s), 13.21 (1H, bs). m/z (ES+) (M+H)+=274.

Preparation of Compound 126, ethyl 4-(3-dimethylaminopropylamino)-2-methylquinoline-6-carboxylate Ethyl 4-chloro-2-methylquinoline-6-carboxylate (0.352 g, 1.41 mmol), N,N-dimethylpropane-1,3-diamine (0.719 mL, 7.04 mmol) and DIPEA (2.452 mL, 14.08 mmol) were combined in NMP (8 mL) and sealed in a microwave tube. The reaction was heated at 200° C. for 1 hour. The crude product was purified by preparative HPLC. Fractions containing the desired compound were evaporated to dryness to afford the desired material as a gum (0.205 g, 46%). $^1$H NMR (400 MHz, CDCl3, 30° C.) d 1.31 (3H, t), 1.73-1.81 (2H, m), 2.31 (6H, s), 2.44-2.48 (2H, m), 2.49 (3H, s), 3.20-3.27 (2H, m), 4.28-4.35 (2H, q), 6.09 (1H, s), 7.74-7.79 (1H, m), 8.06 (1H, dd), 8.38 (1H, d), 8.45 (1H, s). m/z (ES+) (M+H)+=316.

Preparation of Compound 127, 4-(3-dimethylaminopropylamino)-2-methylquinoline-6-carboxylic acid Sodium hydroxide (2.00M, 6.16 mL, 12.3 mmol) was added to a solution of Compound 126 (0.205 g, 0.650 mmol) in dioxane (5 mL) and stirred at 40° C. overnight. The reaction was neutralized to pH 7 with 2M hydrochloric acid and the solvent removed in vacuo to afford the desired material as a solid (0.186 g) which was used without further purification. $^1$H NMR (400 MHz, DMSO, 30° C.) d 2.06 (2H, q), 2.62 (9H, bd), 3.00 (2H, t), 3.54 (2H, d), 6.69 (1H, s), 7.92 (1H, d), 8.21 (1H, t), 8.86 (1H, bs), 9.11 (1H, s), 12.39-13.53 (1H, bs). m/z (ES+) (M+H)+=288.

Preparation of Compound 128, ethyl 2-methyl-4-[methyl-(1-methylpyrrolidin-3-yl)amino]quinoline-6-carboxylate Ethyl 4-chloro-2-methylquinoline-6-carboxylate (0.270 g, 1.08 mmol), N,1-dimethylpyrrolidin-3-amine (0.702 mL, 5.41 mmol) and DIPEA (1.883 mL, 10.81 mmol) were combined in NMP (8 mL) and sealed in a microwave tube. The reaction was heated at 200° C. for 1 hour. The crude product was purified by preparative HPLC. Fractions containing the desired compound were evaporated to dryness to afford the desired material as a gum (0.066 g, 19%). $^1$H NMR (400 MHz, CDCl3, 30° C.) d 1.43 (3H, t), 2.06 (1H, tt), 2.18-2.30 (1H, m), 2.35 (3H, d), 2.40-2.49 (1H, m), 2.63-2.67 (3H, m), 2.67-2.87 (4H, m), 2.98 (3H, d), 4.42 (2H, q), 6.67 (1H, d), 7.94 (1H, dd), 8.16 (1H, dt), 8.76 (1H, d). m/z (ES+) (M+H)+=328.

Preparation of Compound 129, 2-methyl-4-[methyl-(1-methylpyrrolidin-3-yl)amino]quinoline-6-carboxylic acid Sodium hydroxide (1.924 mL, 3.85 mmol) was added to a solution of Compound 128 (0.066 g, 0.20 mmol) in dioxane (5 mL) and stirred at 40° C. overnight. The reaction was neutralized to pH 7 with 2M hydrochloric acid and the solvent removed in vacuo to afford the desired material as a solid (0.061 g) which was used without further purification. $^1$H NMR (400 MHz, DMSO, 30° C.) d 2.09-2.21 (1H, m), 2.28 (1H, m), 2.62 (6H, d), 2.97 (3H, s), 3.22 (4H, m), 4.41-4.52 (1H, m), 6.98 (1H, s), 7.90 (1H, d), 8.10 (1H, dd), 8.65 (1H, d), 12.27-12.75 (1H, bs). m/z (ES+) (M+H)+=277.

Preparation of Compound 130, 4-chloro-2-methylquinoline-6-carboxylic acid hydrochloride A mixture of Compound 57 (0.500 g, 2.12 mmol) in HCl (37%, 9.5 mL) was heated to 95° C. for 1 hr, then concentrated to afford the title compound (519 mg, 95%) as a pale purple solid. $^1$H NMR (500 MHz, DMSO) δ 8.77 (d, J=1.7 Hz, 1H), 8.32 (dd, J=8.8, 1.9 Hz, 1H), 8.15 (d, J=8.8 Hz, 1H), 7.91 (s, 1H), 2.75 (s, 3H). HRMS (ESI+): calcd for $C_{11}H_9NO_2$ (M+H)+, 222.0322; found 222.0312.

Preparation of Compound 131, N-[5-(2,3-Dihydro-1,4-benzodioxine-7-carbonylamino)-2-methylphenyl]-2-methyl-4-(triazolo[5,4-b]pyridin-3-yloxy) quinoline-6-carboxamide HATU (1.384 g, 3.64 mmol) was added to a stirred solution of Compound 130 (783 mg, 3.03 mmol) and DIPEA (1.585 mL, 9.10 mmol) in DMF (8 mL). After 2-3 minutes a thick suspension formed and Compound 2 (863 mg, 3.03 mmol) was added followed by DMF (8 mL). The resulting suspension was stirred at ambient temperature overnight then the reaction quenched with water (50 mL) and the precipitate was collected by filtration. The solid was washed with water (10 mL) and dried under vacuum to afford the crude desired material as a brown solid (2.14 g) which was used in subsequent reactions without further purification. $^1$H NMR (400 MHz, DMSO, 20° C.) 2.25 (3H, s), 2.55 (3H, s), 4.21-4.38 (4H, m), 6.85 (1H, s), 6.98 (1H, d), 7.25 (1H, d), 7.5-7.57 (2H, m), 7.60 (1H, dd), 7.73 (1H, dd), 7.88 (1H, d), 7.95 (1H, s), 8.18 (1H, d), 8.44 (1H, dd), 8.81-8.89 (1H, m), 9.10 (1H, d), 10.09 (1H, s), 10.42 (1H, s). m/z (ES+) (M+H)+=588.

Example 117, N-(5-(2,3-dihydrobenzo[b][1,4]dioxine-6-carboxamido)-2-methylphenyl)-2-methyl-4-(2-(pyrrolidin-1-yl)ethylamino)quinoline-6-carboxamide Compound 131 (160 mg, 0.27 mmol) and 2-pyrrolidin-1-ylethanamine (0.82 mmol) were suspended in DMA (2 mL) and sealed into a microwave tube. The reaction was heated to 120° C. for 30 minutes in the microwave reactor and cooled to RT. The reaction mixtures were purified by preparative HPLC. Fractions containing the desired compound were evaporated to dryness to afford the desired material as a solid (9 mg, 6%). $^1$H NMR (700 MHz, DMSO) δ 10.05 (s, 1H), 9.87 (s, 1H), 8.78 (d, J=1.8 Hz, 1H), 8.11 (dd, J=1.9, 8.7 Hz, 1H), 7.90 (s, 1H), 7.77 (d, J=8.7 Hz, 1H), 7.56 (d, J=8.4 Hz, 1H), 7.54 (s, 1H), 7.5-7.54 (m, 1H), 7.25 (d, J=8.5 Hz, 1H), 7.18 (s, 1H), 6.98 (d, J=8.4 Hz, 1H), 4.28-4.35 (m, 4H), 3.42-3.46 (m, 3H), 2.78 (t, J=6.9 Hz, 2H), 2.55-2.60 (m, 4H), 2.55 (s, 3H), 2.25 (s, 3H), 1.69-1.75 (m, 4H). m/z (ES+) (M+H)+=566.

Example 118—Preparation of N-(5-(2,3-dihydrobenzo[b][1,4]dioxine-6-carboxamido)-2-methylphenyl)-2-methyl-4-(2-morpholinoethylamino) quinoline-6-carboxamide This was prepared as for Example 117, substituting 2-morpholinoethanamine for 2-pyrrolidin-1-ylethanamine. $^1$H NMR (700 MHz, DMSO) δ 10.05 (s, 1H), 9.91 (s, 1H), 8.80 (d, J=1.8 Hz, 1H), 8.13 (dd, J=1.8, 8.7 Hz, 1H), 7.91 (d, J=2.1 Hz, 1H), 7.79 (d, J=8.7 Hz, 1H), 7.57 (dd, J=2.2, 8.2 Hz, 1H), 7.54 (d, J=2.2 Hz, 1H), 7.52 (dd, J=2.2, 8.4 Hz, 1H), 7.30 (s, 1H), 7.25 (d, J=8.5 Hz, 1H), 6.98 (d, J=8.4 Hz, 1H), 6.52 (s, 1H), 4.27-4.35 (m, 4H), 3.6-3.63 (m, 4H), 3.46

(t, J=6.3 Hz, 2H), 2.67 (t, J=6.9 Hz, 2H), 2.52 (s, 3H), 2.49-2.52 (m, 4H), 2.26 (s, 3H). m/z (ES+) (M+H)+=582.

Example 119, N-(5-(2,3-dihydrobenzo[b][1,4]dioxine-6-carboxamido)-2-methylphenyl)-4-((2-(dimethylamino)ethyl)(methyl)amino)-2-methylquinoline-6-carboxamide This was prepared as for Example 117, substituting $N^1,N^1,N^2$-trimethylethane-1,2-diamine for 2-pyrrolidin-1-ylethanamine. $^1$H NMR (700 MHz, DMSO) δ 10.04 (s, 2H), 8.68 (d, J=1.8 Hz, 1H), 8.16 (dd, J=2.0, 8.7 Hz, 1H), 7.91 (d, J=8.7 Hz, 1H), 7.88 (d, J=2.3 Hz, 1H), 7.58 (dd, J=2.1, 8.2 Hz, 1H), 7.54 (d, J=2.2 Hz, 1H), 7.52 (dd, J=2.2, 8.5 Hz, 1H), 7.24 (d, J=8.5 Hz, 1H), 6.98 (d, J=8.4 Hz, 1H), 6.91 (s, 1H), 4.28-4.35 (m, 4H), 3.43 (t, J=7.0 Hz, 2H), 3.03 (s, 4H), 2.72 (t, J=6.9 Hz, 2H), 2.60 (s, 3H), 2.24 (s, 3H), 2.19 (s, 6H). m/z (ES+) (M+H)+=554.

Example 120—Preparation of N-(5-(2,3-dihydrobenzo[b][1,4]dioxine-6-carboxamido)-2-methylphenyl)-2-methyl-4-(2-(pyrrolidin-1-yl)ethoxy)quinoline-6-carboxamide 2-(Pyrrolidin-1-yl)ethanol (0.090 mL, 0.77 mmol) was added to a stirred suspension of sodium hydride (60% in mineral oil, 30.6 mg, 0.77 mmol) in DMA (2 mL) under an inert atmosphere and the resulting solution stirred at ambient temperature for 5 minutes. Compound 131 (150 mg, 0.26 mmol) was added and the mixture stirred at 70° C. for 1 hour. The reaction was quenched with water (2 mL) and the mixture purified by ion exchange chromatography, using an SCX column with the desired product eluted from the column using 7M NH$_3$/MeOH. Pure fractions were evaporated to dryness to afford a brown gum which was further purified by preparative HPLC. Fractions containing the desired compound were evaporated to dryness to afford the desired material as a white solid (20 mg, 14%). $^1$H NMR (400 MHz, DMSO) δ 10.11 (s, 1H), 10.04 (s, 1H), 8.74 (d, J=1.9 Hz, 1H), 8.23 (dd, J=2.0, 8.8 Hz, 1H), 7.95 (d, J=8.8 Hz, 1H), 7.89 (d, J=2.1 Hz, 1H), 7.60 (dd, J=2.2, 8.3 Hz, 1H), 7.48-7.57 (m, 2H), 7.25 (d, J=8.5 Hz, 1H), 7.06 (s, 1H), 6.99 (d, J=8.4 Hz, 1H), 4.40 (t, J=5.7 Hz, 2H), 4.24-4.36 (m, 4H), 3.01 (t, J=5.7 Hz, 2H), 2.58-2.67 (m, 7H), 2.25 (s, 3H), 1.65-1.76 (m, 4H). m/z (ES+) (M+H)+=567.

Preparation of Compound 132, 6-chloro-N-[5-(2,3-dihydro-1,4-benzodioxine-7-carbonylamino)-2-methylphenyl]pyridine-3-carboxamide 6-Chloronicotinoyl chloride (201 mg, 1.14 mmol) was added to Compound 2 (295 mg, 1.04 mmol) and pyridine (0.126 mL, 1.56 mmol) in DCM (20 mL) under an inert atmosphere and the resulting solution stirred at ambient temperature for 2 hours. The reaction mixture was washed sequentially with water (2×20 mL) and a saturated solution of sodium bicarbonate (20 mL), the organic layer was dried over MgSO$_4$, filtered and evaporated. The solid was triturated with diethyl ether and filtered to afford the desired material as a solid (348 mg, 79%). $^1$H NMR (400 MHz, DMSO, 30° C.) d 2.21 (3H, s), 4.31 (4H, q), 6.98 (1H, d), 7.24 (1H, d), 7.42-7.64 (3H, m), 7.72 (1H, d), 7.86 (1H, d), 8.37 (1H, dd), 8.98 (1H, d), 10.05 (1H, s), 10.16 (1H, s). m/z (ES+) (M+H)+=424.

Preparation of Example 121, N-(5-(2,3-dihydrobenzo[b][1,4]dioxine-6-carboxamido)-2-methylphenyl)-6-(3-(1-methylpiperidin-4-yloxy)phenylamino)nicotinamide A mixture of Compound 132 (50 mg, 0.12 mmol), 3-(1-methylpiperidin-4-yloxy)aniline (36.5 mg, 0.18 mmol), (9,9-dimethyl-9H-xanthene-4,5-diyl)bis(diphenylphosphine) (4.10 mg, 0.0071 mmol), tris(dibenzylideneacetone)dipalladium (0) (3.24 mg, 0.0035 mmol), sodium 2-methylpropan-2-olate (17 mg, 0.18 mmol) in toluene (2 mL) and isopropyl alcohol (0.5 mL) was degassed with nitrogen and heated at reflux for 18 hours. The reaction mixture was diluted with EtOAc (100 mL), washed with water (100 mL), the organic layer dried over Na$_2$SO$_4$, filtered and evaporated to afford crude product. The crude product was purified by flash silica chromatography, elution gradient 0 to 30% MeOH/7M NH$_3$ in EtOAc to give crude material which was further purified by preparative HPLC. Fractions containing the desired compound were evaporated to dryness to afford the desired material as a cream solid (23 mg, 33%). $^1$H NMR (400 MHz, DMSO) δ 10.02 (s, 1H), 9.71 (s, 1H), 9.41 (s, 1H), 8.82 (d, J=2.4 Hz, 1H), 8.10 (dd, J=2.5, 8.8 Hz, 1H), 7.83 (d, J=2.3 Hz, 1H), 7.39-7.65 (m, 5H), 7.14-7.25 (m, 2H), 6.97 (d, J=8.4 Hz, 1H), 6.89 (d, J=8.8 Hz, 1H), 6.56 (dd, J=2.2, 2.2, 6.9 Hz, 1H), 4.31 (m, 4H), 2.58-2.71 (m, 4H), 2.20 (s, 3H), 2.18 (s, 3H), 1.96 (m, 2H), 1.66 (m, 2H). m/z (ES+) (M+H)+=594.

Example 122, N-(5-(2,3-dihydrobenzo[b][1,4]dioxine-6-carboxamido)-2-methylphenyl)-6-(3-(4-methylpiperazin-1-yl)propylamino)nicotinamide A mixture of Compound 132 (50 mg, 0.12 mmol), 3-(4-methylpiperazin-1-yl)propan-1-amine (27.8 mg, 0.18 mmol), (9,9-dimethyl-9H-xanthene-4,5-diyl)bis(diphenylphosphine) (4.10 mg, 0.0071 mmol), tris(dibenzylideneacetone)dipalladium (O) (3.24 mg, 0.0035 mmol), sodium 2-methylpropan-2-olate (17 mg, 0.18 mmol) in toluene (2 mL) and isopropyl alcohol (0.5 mL) was degassed with nitrogen and heated at reflux for 18 hours. The reaction mixture was diluted with EtOAc (100 mL), washed with water (100 mL), the organic layer dried over Na$_2$SO$_4$, filtered and evaporated to afford crude product. The crude product was purified by preparative HPLC. Fractions containing the desired compound were evaporated to dryness to afford the desired material as a colourless gum (2 mg, 3%). $^1$H NMR (400 MHz, CDCl$_3$) δ 8.62 (s, 1H), 8.10 (d, J=9.32 Hz, 2H), 7.92 (d, J=6.46 Hz, 1H), 7.75 (s, 1H), 7.69 (d, J=8.28 Hz, 1H), 7.55 (s, 1H), 7.43 (d, J=2.15 Hz, 1H), 7.36 (dd, J=2.20, 8.44 Hz, 1H), 7.21 (d, J=8.32 Hz, 1H), 6.94 (d, J=8.41 Hz, 1H), 6.50 (d, J=8.80 Hz, 1H), 4.50-4.13 (m, 4H), 3.59-3.47 (m, 2H), 3.04-2.84 (m, 6H), 2.83-2.64 (m, 2H), 2.55 (s, 3H), 2.31 (s, 3H), 2.00-1.87 (m, 2H), 0.96-0.71 (m, 2H). m/z (ES+) (M+H)+=545.

Example 123, N-(5-(2,3-dihydrobenzo[b][1,4]dioxine-6-carboxamido)-2-methylphenyl)-6-(3-((4-methylpiperazin-1-yl)methyl)phenylamino)nicotinamide This was prepared as for Example 122, substituting 3-((4-methylpiperazin-1-yl)methyl)aniline for 3-(4-methylpiperazin-1-yl)propan-1-amine. $^1$H NMR (400 MHz, DMSO) δ 10.02 (s, 1H), 9.70 (s, 1H), 9.44 (s, 1H), 8.81 (d, J=2.4 Hz, 1H), 8.09 (dd, J=2.5, 8.8 Hz, 1H), 7.83 (d, J=2.2 Hz, 1H), 7.71 (d, J=9.3 Hz, 1H), 7.42-7.6 (m, 5H), 7.26 (d, J=7.8 Hz, 1H), 7.17-7.23 (m, 1H), 6.97 (d, J=8.4 Hz, 1H), 6.89 (d, J=8.7 Hz, 1H), 4.23-4.42 (m, 4H), 3.44 (s, 2H), 3.28 (m, 8H), 2.21 (s, 3H), 2.16 (s, 3H). m/z (ES+) (M+H)+=593.

Example 124, N-(5-(2,3-dihydrobenzo[b][1,4]dioxine-6-carboxamido)-2-methylphenyl)-6-(3-((dimethylamino)methyl)phenylamino)nicotinamide This was prepared as for Example 122, substituting 3-((dimethylamino)methyl)aniline for 3-(4-methylpiperazin-1-yl)propan-1-amine. $^1$H NMR (400 MHz, DMSO) δ 10.02 (s, 1H), 9.70 (s, 1H), 9.43 (s, 1H), 8.82 (d, J=2.4 Hz, 1H), 8.09 (dd, J=2.5, 8.8 Hz, 1H), 7.95 (s, 1H), 7.83 (d, J=2.2 Hz, 1H), 7.68 (dd, J=8.0 Hz, 1H), 7.47-7.64 (m, 4H), 7.18-7.24 (m, 2H), 6.97 (d, J=8.4 Hz, 1H), 6.89 (d, J=8.3 Hz, 1H), 4.22-4.38 (m, 4H), 3.0 (s, 2H), 2.33 (s, 3H), 2.23 (s, 6H). m/z (ES+) (M+H)+=538.

Example 125, N-(5-(2,3-dihydrobenzo[b][1,4]dioxine-6-carboxamido)-2-methylphenyl)-6-(3-(3-(dimethylamino)pyrrolidin-1-yl)phenylamino)nicotinamide This was prepared as for Example 122, substituting 1-(3-aminophenyl)-N,N-dimethylpyrrolidin-3-amine for 3-(4-methylpiperazin-1-yl)propan-1-amine. $^1$H NMR (400 MHz, DMSO) δ 10.02 (s, 1H), 9.71 (s, 1H), 9.25 (s, 1H), 8.82 (d, J=2.4 Hz, 1H), 8.10 (dd, J=2.5, 8.8 Hz, 1H), 7.83 (d, J=2.3 Hz, 1H), 7.39-7.65 (m, 5H), 7.14-7.25 (m, 2H), 6.97 (d, J=8.4 Hz, 1H), 6.89 (d, J=8.8 Hz, 1H), 6.22 (dd, J=2.2, 2.2, 6.9 Hz, 1H), 4.31 (m, 4H), 3.28 (m, 6H), 2.28-2.40 (s, 3H), 2.20 (s, 3H), 2.18 (s, 3H). m/z (ES+) (M+H)+=593.

Example 126, N-(3-(2,3-dihydrobenzo[b][1,4]dioxine-6-carboxamido)phenyl)-1H-pyrrolo[2,3-b]pyridine-5-carboxamide 1H-Pyrrolo[2,3-b]pyridine-5-carboxylic acid (0.200 g, 1.23 mmol) was dissolved in DMA (3 mL) and put under an inert atmosphere. DIPEA (0.537 mL, 3.09 mmol) and HATU (0.469 g, 1.23 mmol) were added and the reaction stirred for 15 minutes. Compound 2 (0.278 g, 1.03 mmol) was added and the reaction was stirred at ambient temperature for approximately 24 hours then at 40° C. overnight. The reaction was cooled, diluted with water and the solids filtered. The solids were dissolved in DMF and purified by preparative HPLC. Fractions containing the desired compound were evaporated to dryness to afford the desired material as a solid (0.163 g, 38%). $^1$H NMR (400 MHz, DMSO) δ 11.93 (s, 1H), 10.29 (s, 1H), 10.08 (s, 1H), 8.84 (d, J=2.1 Hz, 1H), 8.58 (d, J=2.1 Hz, 1H), 8.32 (t, J=2.0, 2.0 Hz, 1H), 7.71-7.38 (m, 5H), 7.30 (t, J=8.1, 8.1 Hz, 1H), 6.99 (d, J=8.4 Hz, 1H), 6.61 (d, J=3.5 Hz, 1H), 4.38-4.25 (m, 4H). m/z (ES+) (M+H)+=415.

Preparation of Compound 133, N-(4-Fluoro-3-nitrophenyl)-2,3-dihydro-1,4-benzodioxine-7-carboxamide 2,3-Dihydrobenzo[b][1,4]dioxine-6-carboxylic acid (2.77 g, 15.37 mmol) was dissolved in DMA (25 mL) and DIPEA (6.69 mL, 38.43 mmol) and HATU (5.85 g, 15.37 mmol) added under an inert atmosphere. The reaction was allowed to stir for 15 minutes then 4-fluoro-3-nitroaniline (2.000 g, 12.81 mmol) was added and the reaction stirred at ambient temperature overnight. The reaction was heated for a further 16 hours at 40° C. then concentrated in vacuo and water added. The solids were isolated by filtration, washed with water and dried in a vacuum oven. The solids were stirred in EtOAc for an hour and then filtered. The filtrate was evaporated down and the solids were triturated with DCM then filtered. The collected solids were combined to afford the desired material as a cream solid (3.50 g, 86%). $^1$H NMR (400 MHz, DMSO, 30° C.) d 4.29-4.36 (4H, m), 7.02 (1H, d), 7.50-7.63 (3H, m), 8.15 (1H, ddd), 8.69 (1H, dd), 10.46 (1H, s). m/z (ES+) (M+H)+=319.

Preparation of Compound 134, N-(3-Amino-4-fluorophenyl)-2,3-dihydro-1,4-benzodioxine-7-carboxamide A mixture of Compound 133 (2.96 g, 9.31 mmol) and palladium (10% on charcoal, 0.495 g) in ethanol (25 mL)/EtOAc (25 mL)/THF (25 mL) were stirred under an atmosphere of hydrogen at ambient temperature overnight. The reaction mixture was filtered through celite and the celite was washed with THF. The filtrate and washings were combined and evaporated to afford the desired material as an off white solid (2.70 g, 101%). $^1$H NMR (400 MHz, DMSO, 30° C.) d 4.27-4.35 (4H, m), 5.10 (2H, d), 6.84 (1H, ddd), 6.92 (1H, dd), 6.95-6.98 (1H, m), 7.26-7.32 (1H, m), 7.48 (2H, dt), 9.80 (1H, s). m/z (ES+) (M+H)+=289.

Example 127, N-(5-(2,3-dihydrobenzo[b][1,4]dioxine-6-carboxamido)-2-fluorophenyl)-1H-pyrrolo[2,3-b]pyridine-5-carboxamide 1H-Pyrrolo[2,3-b]pyridine-5-carboxylic acid (0.200 g, 1.23 mmol) was dissolved in DMA (3 mL) and put under nitrogen. DIPEA (0.537 mL, 3.09 mmol) and HATU (0.469 g, 1.23 mmol) were added and the reaction stirred for 15 minutes. Compound 134 (0.296 g, 1.03 mmol) was added and the reaction was stirred at ambient temperature for approximately 24 hours then at 40° C. overnight. The reaction was cooled, diluted with water and the solids filtered. The solids were dissolved in DMF and purified by preparative HPLC. Fractions containing the desired compound were evaporated to dryness to afford the desired material as a solid (0.074 g, 17%). $^1$H NMR (400 MHz, DMSO) δ 10.00 (s, 1H), 8.83 (d, J=2.1 Hz, 1H), 8.56 (d, J=2.1 Hz, 1H), 8.22 (d, J=2.6 Hz, 1H), 7.69-7.57 (m, 2H), 7.57-7.45 (m, 2H), 7.07 (d, J=9.0 Hz, 1H), 6.97 (d, J=8.4 Hz, 1H), 6.61 (d, J=3.5 Hz, 1H), 4.23-4.37 (m, 4H). (2 exchangeable protons not observed) m/z (ES+) (M+H)+=433.

Example 128—Preparation of N-(5-(2,3-dihydrobenzo[b][1,4]dioxine-6-carboxamido)-2-fluorophenyl)-2-methylquinoline-6-carboxamide This was prepared as for Example 127, substituting 2-Methylquinoline-6-carboxylic acid for 1H-pyrrolo[2,3-b]pyridine-5-carboxylic acid. $^1$H NMR (400 MHz, DMSO) δ 10.33 (s, 1H), 10.15 (s, 1H), 8.61 (d, J=1.93 Hz, 1H), 8.41 (d, J=8.52 Hz, 1H), 8.23 (dd, J=2.04, 8.77 Hz, 1H), 8.18-8.08 (m, 1H), 8.03 (d, J=8.79 Hz, 1H), 7.73-7.59 (m, 1H), 7.57-7.48 (m, 3H), 7.34-7.19 (m, 1H), 6.99 (d, J=8.38 Hz, 1H), 4.39-4.20 (m, 4H), 2.71 (s, 3H). m/z (ES+) (M+H)+=458.

Preparation of Compound 135, tert-butyl N-[3-amino-4-(trifluoromethyl)phenyl]carbamate tert-Butyl 3-nitro-4-(trifluoromethyl)phenylcarbamate (680 mg, 2.22 mmol) and palladium (59.1 mg, 0.56 mmol) in ethanol (7 mL) was stirred at ambient temperature under an atmosphere of hydrogen for 16 hours. The reaction mixture was filtered through a pad of celite and concentrated in vacuo to afford the desired material as a yellow oil which crystallised on standing (613 mg, 100%). $^1$H NMR (400

MHz, DMSO, 30° C.) 1.47 (9H, s), 5.42 (2H, s), 6.63 (1H, d), 7.06-7.25 (2H, m), 9.36 (1H, s).

Preparation of Compound 136, tert-butyl N-[3-[(2-methylquinoline-6-carbonyl)amino]-4-(trifluoromethyl)phenyl]carbamate Phosphorus oxychloride (0.454 mL, 4.87 mmol) was added dropwise to a stirred suspension of Compound 135 (0.612 g, 2.22 mmol), 6-carboxy-2-methylquinolinium chloride (0.495 g, 2.22 mmol) and DIPEA (1.929 mL, 11.08 mmol) in DCM (5 mL) at 0° C. The reaction mixture was then warmed to ambient temperature and stirred for 30 minutes. A saturated solution of sodium bicarbonate (50 mL) was added carefully over 30 mins then the mixture was extracted with DCM (2×50 mL). The combined organics were washed with brine, passed through a phase separating cartridge and concentrated in vacuo to give a yellow solid. The crude product was purified by flash silica chromatography, elution gradient 0 to 4% MeOH in DCM, to afford the desired material as a white solid (0.431 g, 44%). $^1$H NMR (400 MHz, DMSO, 30° C.) 1.50 (9H, s), 3.29 (3H, s), 7.49-7.60 (2H, m), 7.65-7.78 (2H, m), 8.04 (1H, d), 8.20 (1H, dt), 8.41 (1H, d), 8.56 (1H, d), 9.86 (1H, s), 10.27 (1H, s).

Preparation of Compound 137, N-[5-Amino-2-(trifluoromethyl)phenyl]-2-methylquinoline-6-carboxamide TFA (2.5 mL) was added to a stirred solution of Compound 136 (426 mg, 0.96 mmol) in DCM (5 mL) and the reaction stirred at ambient temperature for 1 hour. The crude product was purified by ion exchange chromatography, using an SCX column, and the desired product eluted from the column using 7M $NH_3$/MeOH. The pure fractions were evaporated to dryness to afford the desired material as a yellow solid (330 mg, 100%). $^1$H NMR (400 MHz, DMSO, 30° C.) 2.70 (3H, d), 5.89 (2H, s), 6.60 (1H, dd), 6.68 (1H, d), 7.38 (1H, d), 7.44-7.58 (1H, m), 7.96-8.04 (1H, m), 8.12-8.22 (1H, m), 8.39 (1H, t), 8.53 (1H, dd), 9.98 (1H, s). m/z (ES+) (M+H)+=346.21.

Example 129, N-(5-(2,3-dihydrobenzo[b][1,4]dioxine-6-carboxamido)-2-(trifluoromethyl)phenyl)-2-methylquinoline-6-carboxamide Phosphorus oxychloride (0.196 mL, 2.10 mmol) was added dropwise to a stirred suspension of 2,3-dihydrobenzo[b][1,4]dioxine-6-carboxylic acid (172 mg, 0.96 mmol), Compound 137 (330 mg, 0.96 mmol) and DIPEA (0.832 mL, 4.78 mmol) in DCM (5 mL) at 0° C. The reaction mixture was allowed to come to ambient temperature and stirred for 4 days. A saturated aqueous solution of sodium bicarbonate (50 mL) was added carefully over 30 mins then the mixture was extracted with DCM (2×50 mL). The combined organics were washed with brine, passed through a phase separating cartridge and concentrated in vacuo to give a yellow solid. The crude product was purified by preparative HPLC. Fractions containing the desired compound were evaporated to dryness to afford the desired material as a white solid (26 mg, 5%). $^1$H NMR (400 MHz, DMSO) δ 10.42 (s, 1H), 10.32 (s, 1H), 8.56 (d, J=1.9 Hz, 1H), 8.41 (d, J=8.5 Hz, 1H), 8.21 (dd, J=2.0, 8.8 Hz, 1H), 8.09-8.01 (m, 2H), 7.97 (d, J=8.7 Hz, 1H), 7.78 (d, J=8.9 Hz, 1H), 7.64-7.44 (m, 3H), 7.01 (d, J=8.4 Hz, 1H), 4.39-4.24 (m, 4H), 2.71 (s, 3H). m/z (ES+) (M+H)+=508.4.

Preparation of Compound 138, tert-butyl N-(4-methyl-3-nitrophenyl)carbamate

Di-tert-butyl dicarbonate (25.9 g, 118.90 mmol) in THF (50 mL) was added dropwise to 4-methyl-3-nitroaniline (18.09 g, 118.90 mmol) in tetrahydrofuran (70 mL) at 65° C. over a period of 20 minutes under air. The resulting solution was stirred at 65° C. for 16 hours. The solvents were removed in vacuo to give a brown oil which was dissolved in 200 mL of 20% Ethyl acetate/isohexane and 80 g silica gel added. The mixture was stirred for 15 mins then the silica filtered off and washed with 500 mL of 20% Ethyl acetate/isohexane and the filtrates combined and concentrated. The crude product was purified by flash silica chromatography, elution gradient 0 to 20% EtOAc in isohexane to afford the desired material as a yellow solid (26.7 g, 89%). $^1$H NMR (400 MHz, CDCl3, 30° C.) d 1.52 (9H, s), 2.52 (3H, s), 6.61 (1H, s), 7.23 (1H, d), 7.48 (1H, dt), 8.03 (1H, d). m/z (ES+) (M−H)−=251.47.

Preparation of Compound 139, tert-butyl N-(3-amino-4-methylphenyl)carbamate

Compound 138 (30.5 g, 120.90 mmol) and palladium on carbon (5% JM Type87L, 6.1 g) in MeOH (300 mL) were stirred under an atmosphere of hydrogen at 5 bar and 25° C. for 3 hours. The catalyst was filtered off through a pad of celite, washed with methanol and filtrate concentrated in vacuo to give an orange oil. The crude product was purified by flash silica chromatography, elution gradient 0 to 2% MeOH in DCM, to afford the desired material as a white solid (22.60 g, 96%). $^1$H NMR (400 MHz, DMSO, 30° C.) d 1.45 (9H, s), 1.96 (3H, s), 6.49 (1H, dd), 6.74 (1H, d), 6.82 (1H, d), 8.85 (1H, s). m/z (ES+) (M+H)+=223.5.

Preparation of Compound 140, tert-butyl N-[4-methyl-3-[(2-methylquinoline-6-carbonyl)amino]phenyl]carbamate HATU (20.12 g, 52.91 mmol) was added portionwise to Compound 139 (9.80 g, 44.09 mmol), 2-methylquinoline-6-carboxylic acid (8.67 g, 46.29 mmol) and DIPEA (23.04 mL, 132.26 mmol) in DMA (197 mL) at ambient temperature under an inert atmosphere and the resulting solution stirred overnight. The reaction mixture was concentrated, diluted with DCM (50 mL), and washed sequentially with a saturated solution of sodium bicarbonate (50 mL), saturated brine (50 mL), and water (50 mL). The organic layer was dried over $MgSO_4$, filtered and evaporated to afford a dark solid. The crude product was purified by flash silica chromatography, elution gradient 0 to 5% MeOH in DCM, to afford the desired material as an off white solid (8.25 g, 48%). $^1$H NMR (400 MHz, DMSO, 30° C.) d 1.37 (9H, d), 2.18 (3H, s), 2.61-2.85 (3H, m), 7.14 (1H, d), 7.23 (1H, dd), 7.52 (1H, d), 7.56 (1H, d), 8.02 (1H, d), 8.22 (1H, dd), 8.39 (1H, d), 8.58 (1H, d), 9.28 (1H, s), 10.04 (1H, s). m/z (ES+) (M+H)+=392.56.

Preparation of Compound 141, N-(5-amino-2-methylphenyl)-2-methylquinoline-6-carboxamide TFA (80 mL) was added to Compound 140 (8.25 g, 21.07 mmol) in DCM (2 mL) at ambient and the reaction stirred for 1 hour. The crude product was purified by ion exchange chromatography, using an SCX column, and the desired product eluted from the column using 7 M NH$_3$/MeOH. The pure fractions were evaporated to dryness and the residue triturated in diethyl ether, filtered and dried to afford the desired material as a solid (5.42 g, 88%). $^1$H NMR (400 MHz, DMSO, 21° C.) d 2.09 (3H, s), 2.65-2.74 (3H, m), 4.94 (2H, s), 6.41 (1H, dd), 6.64 (1H, d), 6.91 (1H, d), 7.51 (1H, d), 8.00 (1H, d), 8.21 (1H, dd), 8.39 (1H, d), 8.56 (1H, d), 9.86 (1H, s). m/z (ES+) (M+H)+=292.51.

Example 130, N-(5-(7-fluoro-2,3-dihydrobenzo[b] [1,4]dioxine-6-carboxamido)-2-methylphenyl)-2-methylquinoline-6-carboxamide Oxalyl chloride (0.065 mL, 0.76 mmol) was added dropwise to 6-fluoro-2,3-dihydro-1,4-benzodioxine-7-carboxylic acid (100 mg, 0.50 mmol), and DMF (a couple of drops) in DCM (10 mL) at ambient temperature for 4 hours. The reaction mixture was evaporated to afford 6-fluoro-2,3-dihydro-1,4-benzodioxine-7-carbonyl chloride as a colourless gum (110 mg) which was used without further purification. A solution of 6-fluoro-2,3-dihydro-1,4-benzodioxine-7-carbonyl chloride (108 mg, 0.5 mmol) in DCM (10 mL) was added dropwise to a stirred suspension of Compound 141 (146 mg, 0.50 mmol) and pyridine (0.040 mL, 0.50 mmol) in DCM (30 mL) and the resulting mixture stirred at ambient temperature for 3 hours. The reaction mixture was evaporated to dryness and redissolved in a mixture of DMSO/MeCN/H$_2$O (7:2:1.4 mL) and purified by preparative HPLC. Fractions containing the desired compound were evaporated to dryness to afford the desired material as a yellow solid (50.0 mg, 21%). $^1$H NMR (DMSO, 400 MHz) δ 10.15 (1H, s), 10.11 (1H, s), 8.61 (1H, d, J=1.9 Hz), 8.41 (1H, d, J=8.4 Hz), 8.25 (1H, dd, J=8.8, 2.0 Hz), 8.03 (1H, d, J=8.8 Hz), 7.83 (1H, d, J=2.0 Hz), 7.47-7.57 (2H, m), 7.25 (1H, d, J=8.5 Hz), 7.17 (1H, d, J=7.0 Hz), 6.92 (1H, d, J=11.0 Hz), 4.31-4.36 (2H, m), 4.21-4.3 (2H, m), 2.72 (3H, s), 2.25 (3H, s). m/z (ES+) (M+H)+=472.

Example 131—Preparation of N-(5-(benzo[d][1,3] dioxole-5-carboxamido)-2-methylphenyl)quinoline-6-carboxamide HATU (891 mg, 2.34 mmol) was added to 1,3-benzodioxole-5-carboxylic acid (344 mg, 2.07 mmol), N-(5-amino-2-methylphenyl)quinoline-6-carboxamide (500 mg, 1.80 mmol) and DIPEA (0.945 mL, 5.41 mmol) in DMA (15 mL) and the mixture stirred at ambient temperature under an inert atmosphere for 3 days. The reaction mixture was diluted with EtOAc (300 mL), and washed with water (2×150 mL). The organic layer was dried over Na$_2$SO$_4$, filtered and evaporated to afford crude product. The crude product was purified by flash silica chromatography, elution gradient 20 to 100% EtOAc in isohexane. The pure fractions were evaporated to dryness, triturated in DCM and the solid filtered to afford the desired material as a white solid (290 mg, 38%). $^1$H NMR (400 MHz, DMSO) δ 10.16 (s, 1H), 10.07 (s, 1H), 9.03 (dd, J=1.7, 4.2 Hz, 1H), 8.68 (d, J=1.9 Hz, 1H), 8.49-8.6 (m, 1H), 8.30 (dd, J=2.0, 8.8 Hz, 1H), 8.2 (d, J=8.8 Hz, 1H), 7.89 (s, 1H), 7.5-7.7 (m, 4H), 7.26 (d, J=8.48 Hz, 1H), 7.06 (d, J=8.16 Hz, 1H), 6.14 (s, 2H), 2.26 (s, 3H). m/z (ES+) (M+H)+=426.

Preparation of Compound 142, 2-amino-4-methoxy-1,3-benzothiazole-6-carboxylic acid[10]

Methyl 2-amino-4-methoxy-1,3-benzothiazole-6-carboxylate (2 g) was added to hydrogen bromide (48% in acetic acid, 50 mL) and the mixture stirred for 1 hour. Water (~5 mL) was added dropwise to ensure material was in solution and the material stirred at ambient temperature for 16 hours then heated at reflux for 5 hours. The mixture was allowed to cool and the solid removed by filtration to give the desired material (2.37 g) which was used without further purification. $^1$H NMR (300 MHz, DMSO) δ 8.07 (1H, s), 7.48 (1H, s), 3.93 (3H, s).

Preparation of Compound 143, 3-Methyl-4-oxo-3,4-dihydroquinazoline-6-carboxylate 4-Oxo-3,4-dihydroquinazoline-6-carboxylic acid (0.875 g, 4.60 mmol) and potassium carbonate (3.18 g, 23.01 mmol) were suspended in dry acetone (40 mL) and dimethyl sulfate (0.873 mL, 9.20 mmol) was added. The reaction was stirred at reflux for several hours and then allowed to cool, the suspension filtered and the filtrate concentrated in vacuo to give the desired product as a solid (0.823 g, 82%). $^1$H NMR (400 MHz, DMSO) δ 8.72 (1H, d), 8.51 (1H, s), 8.30 (1H, dt), 7.78 (1H, d), 3.92 (3H, s), 3.53 (3H, s). m/z (ES+) (M+H)+=219.

Preparation of Compound 144, 3-methyl-4-oxo-3,4-dihydroquinazoline-6-carboxylic acid Compound 143 (0.550 g, 2.52 mmol) and lithium hydroxide (0.302 g, 12.60 mmol) were dissolved in THF (8 mL) and water (2.0 mL) then heated to 50° C. for an hour. The reaction was cooled, water was added and the pH adjusted to ~3. DCM was added and the resultant precipitation removed by filtration. The organic layer was dried over MgSO$_4$, filtered and concentrated in vacuo to yield the desired material, ~65% pure based on HPLC data, as a solid (0.30 g, 58%) which was used in the subsequent reaction without further purification. $^1$H NMR (400 MHz, DMSO) δ 12.84-11.95 (1H, m), 8.71 (1H, d), 8.50 (1H, s), 8.28 (1H, dt), 7.76 (1H, dd), 3.52 (3H, s). m/z (ES+) (M+H)+=205.

Example 132, N-(5-(3,4-dihydro-2H-benzo[b][1,4] dioxepine-7-carboxamido)-2-methylphenyl)-2-methylquinoline-6-carboxamide HATU (0.082 g, 0.22 mmol) was added to a solution of 3,4-dihydro-2H-1,5-benzodioxepin-7-carboxylic acid and N,N-diisopropylethylamine (0.075 mL, 0.43 mmol) in dry DMF (1.2 mL). The reaction mixture was stirred for 4 min, before Compound 141 (0.050 g, 0.17 mmol) was added. The reaction mixture was stirred at rt for 23 h, diluted with water and the resulting precipitate was isolated by filtration, washed with water and dried. The crude material was purified by silica gel column chromatography using a gradient of 1 to 5% MeOH in DCM to afford the title compound (55 mg, 68%) as a white solid. $^1$H NMR (500 MHz, DMSO) δ 10.13 (s, 1H), 10.13 (s, 1H), 8.61 (d, J=2.0 Hz, 1H), 8.41 (d, J=8.5 Hz, 1H), 8.24 (dd, J=8.8, 2.0 Hz, 1H), 8.03 (d, J=8.8 Hz, 1H), 7.88 (d, J=2.2 Hz, 1H), 7.63 (d, J=2.2 Hz, 1H), 7.61-7.57 (m, 2H), 7.53 (d, J=8.4 Hz, 1H), 7.25 (d, J=8.3 Hz, 1H), 7.07 (d, J=8.3 Hz, 1H), 4.24-4.18 (m, 4H), 2.71 (s, 3H), 2.24 (s, 3H), 2.15 (p, J=5.6 Hz, 2H). HRMS (ESI$^+$): calcd for C$_{28}$H$_{26}$N$_3$O$_4$ (M+H)$^+$, 468.1918; found 468.1918.

Example 133, N-(5-(2,3-dihydrobenzo[b][1,4]dioxine-6-carboxamido)-2-ethylphenyl)quinoline-6-carboxamide A solution of B(Et)$_3$ (60 µL, 0.18 mmol, 3.0 eq) in dry 1,4 dioxane (0.12 ml) was added to a mixture of Example 138

(30 mg, 0.060 mmol, 1.0 eq), $Cs_2CO_3$ (20 mg, 0.060 mmol, 1.0 eq) and $Pd(dppf)C_{12}$ (0.3 mg, 0.0004 mmol). The mixture was stirred under argon at 70° C. for 3 h. After cooling to r.t., the mixture was dropped into water and extracted with DCM. The organic phase was dried over $Na_2SO_4$ and concentrated. The crude was purified by preparative TLC (DCM/MeOH 97:3) to afford the title compound (8 mg). $^1$H NMR (500 MHz, DMSO) δ 10.19 (s, 1H), 10.09 (s, 1H), 9.04-9.00 (m, 1H), 8.66 (s, 1H), 8.55 (d, J=8.0 Hz, 1H), 8.29 (d, J=8.8 Hz, 1H), 8.15 (d, J=8.8 Hz, 1H), 7.83 (s, 1H), 7.67-7.63 (m, 2H), 7.54 (d, J=2.3 Hz, 1H), 7.51 (dd, J=8.5, 2.2 Hz, 1H), 7.28 (d, J=8.4 Hz, 1H), 6.98 (d, J=8.4 Hz, 1H), 4.34-4.28 (m, 4H), 2.63 (q, J=7.7 Hz, 2H), 1.15 (t, J=7.5 Hz, 3H).

HRMS: calcd for $C_{27}H_{24}N_3O_4$ $(M+H)^+$, 454.1761; found 454.1755.

Preparation of Compound 145, N-(2-methyl-5-nitrophenyl)-2-(2-(pyrrolidin-1-yl)ethoxy)quinoline-6-carboxamide Oxalyl chloride (10.7 g, 84.3 mmol) was added to a suspension of Compound 70 (2.26 g, 7.00 mmol) in DCM (12 mL) and DMF (0.014 mL) and the reaction mixture was stirred at rt for 3 days, concentrated, dissolved in DCM (15 mL) and added dropwise to a solution of 2-methyl-5-nitroaniline (1.07 g, 7.03 mmol) and pyridine (2.3 mL) in DCM (10 mL). The reaction mixture was stirred at rt for 6 h, and then concentrated. The residue was suspended in MeOH, and the solid isolated by filtration. The crude material was purified by silica gel column chromatography using 4% MeOH in DCM and then 6% 2 M $NH_3$/MeOH in DCM to afford the title compound (1.20 g, 41%) as a white solid. $^1$H NMR (500 MHz, DMSO) δ 10.30 (s, 1H), 8.59 (d, J=2.1 Hz, 1H), 8.43-8.37 (m, 2H), 8.23 (dd, J=8.7, 2.1 Hz, 1H), 8.05 (dd, J=8.5, 2.5 Hz, 1H), 7.88 (d, J=8.7 Hz, 1H), 7.60 (d, J=8.5 Hz, 1H), 7.13 (d, J=8.8 Hz, 1H), 4.57 (t, J=5.8 Hz, 2H), 2.88 (t, J=6.0 Hz, 2H), 2.56 (br s, 4H), 2.43 (s, 3H), 1.72-1.67 (m, 4H). HRMS: calcd for $C_{23}H_{25}N_4O_4$ $(M+H)^+$, 421.1870; found 421.1864.

Preparation of Compound 146, N-(5-amino-2-methylphenyl)-2-(2-(pyrrolidin-1-yl)ethoxy)quinoline-6-carboxamide A suspension of Compound 145 (85 mg, 2.0 mmol) and 10% Pd/C (84 mg) in EtOAc (12 ml), EtOH (12 ml) and DCM (4 ml) was stirred under an atmosphere of hydrogen gas at rt for 3.5 h, filtered through a celite pad and concentrated under vacuum to afford the title compound as a yellow solid that was used without any further purification. $^1$H NMR (500 MHz, $CDCl_3$) δ 8.28 (d, J=2.1 Hz, 1H), 8.07 (d, J=8.8 Hz, 1H), 8.04 (dd, J=8.7, 2.1 Hz, 1H), 7.90 (d, J=8.7 Hz, 1H), 7.75 (s, 1H), 7.59-7.53 (m, 1H), 7.03 (d, J=8.9 Hz, 1H), 7.01 (d, J=8.1 Hz, 1H), 6.47 (dd, J=8.1, 2.5 Hz, 1H), 4.70 (t, J=5.8 Hz, 2H), 3.67 (br s, 2H), 3.04 (t, J=5.8 Hz, 2H), 2.76 (br s, 4H), 1.90-1.85 (m, 4H). HRMS: calcd for $C_{23}H_{26}N_4O_2$ $(M+H)^+$, 391.2129; found 391.2122.

Example 134, N-(4-methyl-3-(2-(2-(Pyrrolidin-1-yl)ethoxy)quinoline-6-carboxamido)phenyl)-2,3-dihydro-[1,4]dioxino[2,3-b]pyridine-7-carboxamide To a solution of 2,3-dihydro-[1,4]dioxino[2,3-b]pyridine-7-carboxylic acid (0.015 g, 0.085 mmol) and DIEA (0.030 mL, 0.17 mmol) in dry DMF (0.4 mL) was added HATU (0.037 g, 0.096 mmol) and the reaction mixture was stirred at rt for 5 min before Compound 146 (0.030 g, 0.077 mmol) was added. The reaction mixture was stirred at rt overnight, diluted with water and the resulting solid was isolated by filtration, washed with water and dried. The crude material was purified by silica gel column chromatography using a gradient of 5 to 15% MeOH in DCM to afford the title compound (0.013 g, 30%) as a white solid. $^1$H NMR (500 MHz, DMSO) δ 10.23 (s, 1H), 10.09 (s, 1H), 8.58 (d, J=2.0 Hz, 1H), 8.40 (d, J=8.8 Hz, 1H), 8.38 (d, J=2.1 Hz, 1H), 8.23 (dd, J=8.8, 2.1 Hz, 1H), 7.90-7.85 (m, 2H), 7.84 (d, J=2.1 Hz, 1H), 7.57 (dd, J=8.2, 2.2 Hz, 1H), 7.26 (d, J=8.4 Hz, 1H), 7.13 (d, J=8.8 Hz, 1H), 4.62 (t, J=5.8 Hz, 2H), 4.51-4.47 (m, 2H), 4.34-4.29 (m, 2H), 3.09 (br s, 2H), 2.78 (br s, 4H), 2.25 (s, 3H), 1.77 (br s, 4H). HRMS calcd for $C_{31}H_{32}N_5O_5$ $(M+H)^+$, 554.2398; found 554.2380.

Example 135, N-(4-methyl-3-(2-methylquinoline-6-carboxamido)phenyl)-2,3-dihydro-[1,4]dioxino[2,3-b]pyridine-7-carboxamide This was prepared as for Example 134, substituting Compound 141 for Compound 146. $^1$H NMR (500 MHz, DMSO) δ 10.23 (s, 1H), 10.14 (s, 1H), 8.61 (d, J=2.0 Hz, 1H), 8.41 (d, J=8.4 Hz, 1H), 8.38 (d, J=2.1 Hz, 1H), 8.24 (dd, J=8.7, 2.0 Hz, 1H), 8.03 (d, J=8.8 Hz, 1H), 7.87 (d, J=2.2 Hz, 1H), 7.84 (d, J=2.1 Hz, 1H), 7.59 (dd, J=8.2, 2.2 Hz, 1H), 7.53 (d, J=8.4 Hz, 1H), 7.26 (d, J=8.3 Hz, 1H), 4.52-4.45 (m, 2H), 4.35-4.29 (m, 2H), 2.71 (s, 3H), 2.25 (s, 3H). HRMS: calcd for $C_{31}H_{33}N_5O_5$ $(M+H)^+$, 455.1714; found 455.1713.

Preparation of Compound 147, ethyl 2-formylquinoline-6-carboxylate

To a stirring suspension of selenium dioxide (359 mg, 3.23 mmol) in 1,4-dioxane (4.5 mL) under argon was added ethyl 2-methylquinoline-6-carboxylate (633 mg, 2.94 mmol). The reaction mixture was heated to 80° C. and left to stir for 23 h. Further selenium dioxide (80 mg, 0.72 mmol, 0.24 eq.) was added and the reaction heated for 3 h, the reaction mixture was allowed to cool and was filtered through celite (eluting with DCM). The filtrate was concentrated in vacuo to afford the crude title compound as an orange solid (674 mg, quantitative). This material was used directly in the next reaction without further purification. $^1$H NMR (500 MHz, Chloroform-d) δ 10.26 (d, J=0.8 Hz, 1H), 8.68 (d, J=1.8 Hz, 1H), 8.48-8.41 (m, 2H), 8.32 (d, J=8.8 Hz, 1H), 8.11 (d, J=8.4 Hz, 1H), 4.55-4.45 (m, 4H), 1.51-1.46 (m, 3H).

Preparation of Compound 148, ethyl 2-(hydroxymethyl)quinoline-6-carboxylate

To a stirring suspension of Compound 147 (213 mg, 0.929 mmol) in ethanol (6.5 mL) and water (3.25 mL) at 0° C. was added sodium borohydride (176 mg, 4.65 mmol) and the reaction left to stir at 0° C. for 2.5 h. The reaction mixture was diluted with water (30 ml) and extracted with EtOAc (2×30 ml)—brine was added to clear. The combined organic layer was washed with brine (30 ml), dried ($MgSO_4$) and concentrated in vacuo. The crude material was purified by biotage chromatography using a gradient of 5 to 40% EtOAc in DCM to afford the title compound as a yellow solid (132 mg, 61%). $^1$H NMR (500 MHz, Chloroform-d) δ 8.62 (d, J=1.9 Hz, 1H), 8.35 (dd, J=8.8, 1.9 Hz, 1H), 8.27 (d, J=8.3 Hz, 1H), 8.14 (d, J=8.8 Hz, 1H), 7.38 (d, J=8.5 Hz, 1H), 4.98

(s, 1H), 4.49 (q, J=7.1 Hz, 2H), 4.39 (s, 1H), 1.48 (t, J=7.1 Hz, 3H). HRMS (ESI$^+$): calcd for $C_{13}H_{14}NO_3$ (M+H)$^+$, 232.0974; found 232.0972.

Preparation of Compound 149, ethyl 2-(((tert-butyldimethylsilyl)oxy)methyl)quinoline-6-carboxylate To a solution of Compound 148 (75 mg, 0.324 mmol) in anhydrous DCM (3.0 mL) under argon was added imidazole (33.1 mg, 0.486 mmol), followed by tert-butyldimethylsilyl chloride (56.2 mg, 0.373 mmol). The reaction was stirred at room temperature for 4 days, then diluted with DCM (10 ml) and washed with water (1×10 ml), 0.25 M HCl aq. (1×10 ml), brine (1×10 ml), dried (Na$_2$SO$_4$), concentrated and dried in vacuo to afford the title compound as a yellow oil (103 mg, 92%). $^1$H NMR (500 MHz, Chloroform-d) δ 8.60 (d, J=1.8 Hz, 1H), 8.31 (dd, J=8.8, 2.1 Hz, 2H), 8.05 (d, J=8.8 Hz, 1H), 7.79 (d, J=8.5 Hz, 1H), 5.03 (s, 2H), 4.47 (q, J=7.2 Hz, 2H), 1.47 (t, J=7.1 Hz, 3H), 1.00 (s, 9H), 0.17 (s, 6H). HRMS (ESI$^+$): calcd for $C_{19}H_{27}NO_3Si$ (M+H)$^+$, 347.1859; found 347.1853.

Preparation of Compound 150, 2-(((tert-butyldimethylsilyl)oxy)methyl)quinoline-6-carboxylic acid To a stirring solution of Compound 149 (39 mg, 0.113 mmol) in THF (0.9 mL) and methanol (0.3 mL) was added 2M NaOH aq. (0.113 mL, 0.226 mmol). The reaction was left to stir at room temperature for 2 days. Further 2M NaOH aq. (0.113 mL, 0.226 mmol) was added and the reaction was heated to 50° C. for 5 h. Further 2M NaOH aq. (0.113 mL, 0.226 mmol) was added and the reaction left to stir at room temperature for 18.5 h. The reaction mixture was diluted with water (10 ml) and the aqueous layer acidified by the addition of 1M HCl aq. (to ~pH 3). The aqueous layer was extracted with EtOAc (2×20 ml) and the combined organic layer dried (MgSO$_4$). LCMS (ESI$^+$): showed a 2.7:1 mixture of 2-(hydroxymethyl)quinoline-6-carboxylic acid (-TBDMS) and the title compound. This mixture was used directly in the next reaction without further purification. HRMS (ESI$^+$): calcd for $C_{17}H_{23}NO_3Si$ (M+H)$^+$, 318.1525; found 318.1518.

Preparation of Compound 151, 2-(((tert-butyldimethylsilyl)oxy)methyl)-N-(5-(2,3-dihydrobenzo[b][1,4]dioxine-6-carboxamido)-2-methylphenyl)quinoline-6-carboxamide To a stirring solution of crude Compound 150 (36 mg, 0.113 mmol, theoretical yield used) in DMF (1.2 mL) at room temperature under argon was added DIEA (0.043 mL, 0.249 mmol), followed by HATU (56.1 mg, 0.147 mmol). The reaction mixture was allowed to stir for 5 min before Compound 2 (38.7 mg, 0.136 mmol) was added. The mixture was allowed to stir at room temperature for 16 h then it was diluted with water (10 ml) and extracted with EtOAc (2×25 ml)—brine was added to clear. The combined organic layer was washed with brine (25 ml), dried (Na$_2$SO$_4$) and concentrated in vacuo. The crude residue was purified by biotage chromatography using a gradient of 10 to 80% EtOAc in DCM to afford the title compound as an off-white solid (9.5 mg, 44% based on percentage of starting material in crude mixture).

Preparation of Compound 152, N-(5-(2,3-dihydrobenzo[b][1,4]dioxine-6-carboxamido)-2-methylphenyl)-2-(hydroxymethyl)quinoline-6-carboxamide To a stirring solution of Compound 151 (9.5 mg, 0.016 mmol) in THF (0.5 mL) at room temperature under argon was slowly added TBAF (1M in THF, 0.024 mL, 0.024 mmol). The reaction mixture was allowed to stir for 3 h. The reaction mixture was diluted with water (20 ml) and the aqueous layer extracted with EtOAc (2×20 ml). The combined organic layer was washed with brine (10 ml), dried Na$_2$SO$_4$ and concentrated in vacuo to afford the crude product as a cream solid. This material was purified by column chromatography using a gradient of 20 to 33% EtOAc/DCM, then 10% MeOH/DCM to afford the title compound as a pale yellow solid (4.4 mg, 58%). $^1$H NMR (500 MHz, DMSO-d6) δ 10.18 (s, 1H), 10.10 (s, 1H), 8.65 (d, J=1.8 Hz, 1H), 8.54 (d, J=8.5 Hz, 1H), 8.27 (dd, J=8.8, 2.0 Hz, 1H), 8.07 (d, J=8.8 Hz, 1H), 7.89 (d, J=2.1 Hz, 1H), 7.77 (d, J=8.5 Hz, 1H), 7.60 (dd, J=8.3, 2.1 Hz, 1H), 7.55 (d, J=2.1 Hz, 1H), 7.52 (dd, J=8.4, 2.2 Hz, 1H), 7.26 (d, J=8.5 Hz, 1H), 6.99 (d, J=8.4 Hz, 1H), 4.78 (s, 2H), 4.41-4.23 (m, 10H), 2.26 (s, 3H). HRMS (ESI$^+$): calcd for $C_{27}H_{24}NO_3O_5$ (M+H)$^+$, 470.1710; found 470.1691.

Preparation of Compound 153, butyl 8-fluoroquinoline-6-carboxylate

To a stirring suspension of 6-bromo-8-fluoroquinoline (72 mg, 0.319 mmol), Hermann's palladacycle (14.9 mg, 0.016 mmol) and tri-t-butylphosphonium tetrafluoroborate (18.5 mg, 0.064 mmol) in butanol (1.0 mL) was added molybdenum hexacarbonyl (168 mg, 0.637 mmol) followed by DBU 1.0M in THF (0.96 ml, 0.956 mmol). The reaction was heated to 130° C. in a microwave for 1 h. The reaction mixture was filtered through celite then concentrated in vacuo. The resulting residue was dry-loaded onto silica and purified by column chromatography using a gradient of 10 to 20% EtOAc/petroleum ether to afford the title compound as a yellow solid (60 mg, 70%). $^1$H NMR (500 MHz, Chloroform-d) δ 9.08 (dd, J=4.2, 1.6 Hz, 1H), 8.42 (s, 1H), 8.33 (dt, J=8.4, 1.5 Hz, 1H), 8.01 (dd, J=10.9, 1.7 Hz, 1H), 7.57 (dd, J=8.4, 4.2 Hz, 1H), 4.42 (t, J=6.6 Hz, 2H), 1.91-1.75 (m, 2H), 1.53 (dq, J=14.8, 7.4 Hz, 2H), 1.03 (t, J=7.4 Hz, 3H). HRMS (ESI$^+$): calcd for $C_{14}H_{15}FNO_2$ (M+H)$^+$, 248.1081; found 248.1080.

Preparation of Compound 154, 8-fluoroquinoline-6-carboxylic acid

To a stirring solution of Compound 153 (53 mg, 0.214 mmol) in THF (1.5 mL) and MeOH (0.5 mL) was added 2M NaOH aq. (0.536 mL, 1.072 mmol) and the reaction mixture left to stir for 16 h. The reaction mixture was diluted with water (20 ml) and acidified using 1 M HCl aq. (to ~pH 3) The aqueous layer was extracted with DCM (3×15 ml) and the combined organic layer dried with (Na$_2$SO$_4$) then concentrated in vacuo to afford the title compound as an orange solid (34 mg, 83%). This material was used directly in the next reaction without further purification. $^1$H NMR (500 MHz, Methanol-d4) b 8.96 (dd, J=4.2, 1.5 Hz, 1H), 8.38 (s, 3H), 8.30 (d, J=8.4 Hz, 1H), 7.96 (dd, J=10.9, 1.5 Hz, 1H), 7.54 (dd, J=8.4, 4.3 Hz, 3H). HRMS (ESI$^+$): calcd for $C_{10}H_7FNO_2$ (M+H)$^+$, 192.0461; found 192.0462.

Example 136, N-(5-(2,3-dihydrobenzo[b][1,4]dioxine-6-carboxamido)-2-methylphenyl)-8-fluoroquinoline-6-carboxamide To a stirring solution of Compound 154 (30 mg, 0.157 mmol) in DMF (1.0 mL) at room temperature under argon was added DIEA (0.087 mL, 0.502 mmol), followed by HATU (78 mg, 0.204 mmol). The reaction mixture was allowed to stir for 5 min before Compound 2 (53.5 mg, 0.188 mmol) was added. The reaction mixture was allowed to stir at room temperature for 16 h. The reaction mixture was diluted with water (20 ml) and extracted with EtOAc (3×15 ml)—brine was added to clear. The combined organic layer was washed with brine (15 mL), dried $Na_2SO_4$ and concentrated in vacuo. The resulting residue was purified by column chromatography using a gradient of 5 to 25% EtOAc/DCM to afford an off-white solid (25 mg). However, this material required further purification. Therefore 15 mg of this material was purified by SCX chromatography eluting with MeOH followed by 5, then 10% 2M $NH_3$ in MeOH/MeOH to afford the title compound as an off-white solid (10.8 mg, 15%). $^1$H NMR (500 MHz, DMSO-d6) δ 10.23 (s, 1H), 10.09 (s, 1H), 9.08 (dd, J=4.2, 1.6 Hz, 1H), 8.63 (d, J=8.4 Hz, 1H), 8.55 (d, J=1.4 Hz, 1H), 8.11 (dd, J=11.5, 1.7 Hz, 1H), 7.88 (d, J=2.1 Hz, 1H), 7.76 (dd, J=8.4, 4.2 Hz, 1H), 7.59 (dd, J=8.3, 2.2 Hz, 1H), 7.57-7.46 (m, 2H), 7.25 (d, J=8.5 Hz, 1H), 6.98 (d, J=8.4 Hz, 1H), 4.33-4.29 (m, 4H), 2.69 (s, 2H), 2.24 (s, 3H). HRMS (ESI$^+$): calcd for $C_{26}H_{21}FN_3O_2(M+H)^+$, 458.1511; found 458.1505.

Preparation of Compound 155,
6-bromoquinoline-2-carbaldehyde

To a stirring suspension of selenium dioxide (412 mg, 3.71 mmol) in 1,4-dioxane (5.5 mL) under argon was added 6-bromo-2-methylquinoline (750 mg, 3.38 mmol). The reaction was heated to 80° C. and left to stir for 23 h. The reaction mixture was then filtered through celite and concentrated in vacuo. The resulting residue was purified by column chromatography using a gradient of 5 to 15% EtOAc/petroleum ether to afford the title compound as a pale yellow solid (551 mg, 69%). $^1$H NMR (500 MHz, Chloroform-d) δ 10.22 (s, 1H), 8.25 (d, J=8.5 Hz, 1H), 8.14 (d, J=9.0 Hz, 1H), 8.10 (d, J=2.1 Hz, 1H), 8.07 (d, J=8.5 Hz, 1H), 7.91 (dd, J=9.0, 2.2 Hz, 1H). HRMS (ESI$^+$): calcd for $C_{10}H_7^{79}BrNO$ (M+H)$^+$, 235.9711; found 235.9704.

Preparation of Compound 156,
(6-bromoquinolin-2-yl)methanol

To a stirring suspension of Compound 155 (1.36 g, 5.76 mmol) in ethanol (41 mL) and water (20.5 mL) at 0° C. was added sodium borohydride (1.090 g, 28.8 mmol) and the reaction left to stir at 0° C. for 18 h. The solvents were removed in vacuo and the resulting residue diluted with water (30 ml) and extracted with EtOAc (3×20 ml). The combined organic layer as washed with brine (20 ml), dried ($MgSO_4$) and concentrated in vacuo to afford the title product as a yellow solid (1.27 g, 93%). $^1$H NMR (500 MHz, Methanol-d4) δ 7.35 (d, J=8.5 Hz, 1H), 7.21 (d, J=2.0 Hz, 1H), 7.10 (d, J=9.0 Hz, 1H), 6.99 (dd, J=9.0, 2.1 Hz, 1H), 6.80 (d, J=8.5 Hz, 1H), 6.60 (s, 0.5H, OH), 4.07 (s, 2H). HRMS (ESI$^+$): calcd for $C_{10}H_9^{79}BrNO$ (M+H)$^+$, 237.9868; found 237.9865.

Preparation of Compound 157,
6-bromo-2-(methoxymethyl)quinoline

To a stirring suspension of sodium hydride (101 mg, 2.52 mmol) in DMF (20 mL) at 0° C. under argon was slowly added Compound 156 (500 mg, 2.100 mmol) portion-wise. The reaction mixture was allowed to stir at 0° C. for 0.5 h before the addition of methyl iodide (0.314 mL, 5.04 mmol). The reaction was allowed to warm gradually to room temperature and allowed to stir for 19 h. The reaction mixture was then poured into water (100 ml) and extracted with EtOAc (3×75 ml)—brine was added to clear. The combined organic layer was washed with brine (75 ml), dried ($MgSO_4$) and concentrated in vacuo (last traces of DMF were removed by co-evaporation with heptane) to afford a yellow solid. The crude material was purified by biotage chromatography using a gradient of 5 to 80% EtOAc/DCM to afford the title compound as a pale yellow solid (451 mg, 85%). $^1$H NMR (500 MHz, Chloroform-d) δ 8.11 (d, J=8.5 Hz, 1H), 8.00 (d, J=2.2 Hz, 1H), 7.96 (d, J=9.0 Hz, 1H), 7.80 (dd, J=9.0, 2.2 Hz, 1H), 7.62 (d, J=8.5 Hz, 1H), 4.76 (s, 2H), 3.54 (s, 3H). HRMS (ESI$^+$): calcd for $C_{11}H_{11}^{79}BrNO$ (M+H)$^+$, 252.0024; found 252.0016.

Preparation of Compound 158,
2-(trimethylsilyl)ethyl
2-(methoxymethyl)quinoline-6-carboxylate To a stirring suspension of Compound 157 (173 mg, 0.686 mmol), Hermann's palladacycle (32.2 mg, 0.034 mmol) and tri-t-butylphosphonium tetrafluoroborate (39.8 mg, 0.137 mmol) in 2-(trimethylsilyl)-ethanol (3.0 mL) was added molybdenum hexacarbonyl (362 mg, 1.372 mmol) followed by DBU (1.0 M in THF, 2.06 ml, 2.06 mmol). The reaction mixture was heated to 130° C. in a microwave for 1 h. The reaction mixture was filtered through celite then concentrated in vacuo. The resulting residue was dry-loaded onto silica and purified by column chromatography using a gradient of 10 to 20% EtOAc/petroleum ether to afford the title compound as a yellow solid (60 mg, 70%). $^1$H NMR (500 MHz, Chloroform-d) δ 8.59 (d, J=1.8 Hz, 1H), 8.35-8.27 (m, 2H), 8.13 (d, J=8.5 Hz, 1H), 7.67 (d, J=8.5 Hz, 1H), 4.81 (s, 2H), 4.64-4.36 (m, 2H), 3.55 (s, 3H), 1.59 (s, OH), 1.27-1.11 (m, 2H), 0.13 (s, 9H). HRMS (ESI$^+$): calcd for $C_{17}H_{24}NO_3Si$ (M+H)$^+$, 318.1520; found 318.1530.

Preparation of Compound 159,
2-(methoxymethyl)quinoline-6-carboxylic acid

To a stirring solution of Compound 158 (213 mg, 0.671 mmol) in THF (5.0 mL) at room temperature under argon was slowly added TBAF 1.0M in THF (1.006 mL, 1.006 mmol) the reaction mixture was allowed to stir for 5 h. Water (10 ml) was added and the reaction mixture concentrated to remove THF. The aqueous layer was then acidified (to ~pH 3) using 1M HCl aq. and extracted with EtOAc (3×15 ml)—brine was added to clear. The combined organic layer was washed with brine (10 ml), dried ($Na_2SO_4$) and concentrated in vacuo to afford the crude product as a pale yellow solid. This material was used directly in the next reaction without further purification.

Example 137, N-(5-(2,3-dihydrobenzo[b][1,4]diox-
ine-6-carboxamido)-2-methylphenyl)-2-(methoxym-
ethyl)quinoline-6-carboxamide To a stirring solution of crude Compound 159 (148 mg, 0.477 mmol) and DIEA (0.249 mL, 1.431 mmol) in DMF (4 mL) under argon was added HATU (218 mg, 0.572 mmol). The reaction was allowed to stir for 3 min before the addition of Compound 2 (129 mg, 0.453 mmol). The reaction mixture was allowed to stir at room temperature for 16 h. The reaction was diluted with water, the resulting precipitate isolated by filtration and washed with water. The pale green precipitate obtained was purified by biotage chromatography using a gradient of 12 to 100% EtOAc/DCM to afford the title compound as a cream solid (114 mg, 49%). $^1$H NMR (500 MHz, DMSO-d6) δ 10.17 (s, 1H), 10.08 (s, 1H), 8.66 (d, J=1.9 Hz, 1H), 8.55 (d, J=8.5 Hz, 1H), 8.28 (dd, J=8.8, 2.0 Hz, 1H), 8.09 (d, J=8.8 Hz, 1H), 7.88 (d, J=2.1 Hz, 1H), 7.69 (d, J=8.5 Hz, 1H), 7.59 (dd, J=8.3, 2.2 Hz, 1H), 7.54 (d, J=2.1 Hz, 1H), 7.51 (dd, J=8.4, 2.2 Hz, 1H), 7.25 (d, J=8.5 Hz, 1H), 6.98 (d, J=8.4 Hz, 1H), 4.72 (s, 2H), 4.37-4.19 (m, 4H), 3.43 (s, 3H), 2.25 (s, 3H). HRMS (ESI$^+$): calcd for $C_{28}H_{26}NO_5$ (M+H)$^+$, 484.1867; found 484.1861.

Preparation of Compound 160, N-(4-bromo-3-nitrophenyl)-2,3-dihydrobenzo[b][1,4]dioxine-6-carboxamide Oxalyl chloride (0.282 mL, 3.33 mmol) was added drop-wise to a solution of 1,4-benzodioxane-6-carboxylic acid (500 mg, 2.78 mmol) and DMF (5.37 µL, 0.069 mmol) in dry DCM (7 mL). The reaction was allowed to stir at room temperature for 2 h before the reaction mixture was concentrated, anhydrous DCM (7 mL) was added and concentrated again. The resulting residue was re-dissolved in anhydrous DCM (3+3+1 mL) and added drop-wise to a solution of 4-bromo-3-nitroaniline (602 mg, 2.78 mmol) and pyridine (0.449 mL, 5.55 mmol) in dry DCM (7 mL). The reaction was left to stir at room temperature for 18 h. The reaction mixture was concentrated and the resulting solid suspended in MeOH, diluted with water and then isolated by filtration. The solid was washed with water to afford the title compound as a pale yellow solid (1.01 g, 96%). $^1$H NMR (500 MHz, DMSO-d6) δ 10.54 (s, 1H), 8.55 (d, J=2.5 Hz, 1H), 7.97 (dd, J=8.8, 2.5 Hz, 1H), 7.88 (d, J=8.8 Hz, 1H), 7.55 (d, J=2.1 Hz, 1H), 7.52 (dd, J=8.5, 2.2 Hz, 1H), 7.02 (d, J=8.4 Hz, 1H), 4.40-4.19 (m, 4H). HRMS (ESI$^+$): calcd for $C_{15}H_{12}{}^{79}BrN_2O_5$(M+H)$^+$, 378.9930; found 378.9920.

Preparation of Compound 161, N-(3-amino-4-bromophenyl)-2,3-dihydrobenzo[b][1,4]dioxine-6-carboxamide To a stirring solution of Compound 160 (750 mg, 1.978 mmol) in ethanol (12 mL) and water (4.0 mL) was added iron powder (773 mg, 13.85 mmol) followed by ammonium chloride (741 mg, 13.85 mmol). The reaction mixture was heated to reflux for 23 h, then filtered through celite (eluting with EtOH/EtOAc) and the solvents removed in vacuo. The resulting residue was partitioned between water (50 mL) and EtOAc (50 mL). The organic layer was washed with sat. NaHCO$_3$ aq. (50 mL), water (50 mL), brine (30 mL) and dried (Na$_2$SO$_4$), then concentrated in vacuo to afford the crude product as a beige solid (575 mg, 83%). $^1$H NMR (500 MHz, DMSO-d6) δ 9.89 (s, 1H), 7.55-7.43 (m, 2H), 7.37 (d, J=2.5 Hz, 1H), 7.25 (d, J=8.6 Hz, 1H), 6.97 (d, J=8.4 Hz, 1H), 6.85 (dd, J=8.7, 2.5 Hz, 1H), 5.30 (s, 2H), 4.30 (td, J=5.2, 3.7 Hz, 4H). HRMS (ESI$^+$): calcd for $C_{15}H_{14}{}^{79}BrN_2O_3$(M+H)$^+$, 349.0188; found 349.0187.

Example 138, N-(2-bromo-5-(2,3-dihydrobenzo[b][1,4]dioxine-6-carboxamido)phenyl)quinoline-6-carboxamide Oxalyl chloride (0.116 mL, 1.375 mmol) was added dropwise to a suspension of 6-quinoline carboxylic acid (198 mg, 1.146 mmol) and DMF (2.217 µL, 0.029 mmol) in dry DCM (7 mL). Anhydrous dioxane (3 mL) was added to the reaction in an attempt to fully solubilise all reagents, however this was not entirely successful. The reaction mixture was stirred at room temperature for 2 h. Pyridine (0.278 mL, 3.44 mmol) was added to the reaction followed by Compound 161 (400 mg, 1.146 mmol) in anhydrous dioxane (7 ml). DMF (3 ml) was added in order to dissolve the solids formed. The reaction was left to stir for 48 h, then concentrated in vacuo to remove solvents. The resulting residue was diluted with water and extracted with EtOAc (3×20 ml). A solid precipitate was observed to form in the aqueous layer. The aqueous layer was ensured basic by addition of sat. NaHCO$_3$ aq. and the beige precipitate collected. The combined organic layer was washed with brine (25 ml), then dried (Na$_2$SO$_4$) to afford the crude product as a brown oil. LCMS showed that both the precipitate and oil contained product, therefore the two were combined and purified by biotage chromatography using a gradient of 0 to 10% MeOH/DCM to afford the title compound as a white solid (236 mg, 41%). $^1$H NMR (500 MHz, DMSO-d6) δ 10.34 (s, 1H), 10.27 (s, 1H), 9.03 (dd, J=4.2, 1.7 Hz, 1H), 8.69 (d, J=2.0 Hz, 1H), 8.56 (dd, J=8.2, 1.3 Hz, 2H), 8.30 (dd, J=8.8, 2.0 Hz, 1H), 8.16 (d, J=8.8 Hz, 1H), 8.11 (d, J=1.5 Hz, 1H), 7.70-7.69 (m, 2H), 7.66 (dd, J=8.3, 4.2 Hz, 1H), 7.58-7.48 (m, 2H), 7.00 (d, J=8.4 Hz, 1H), 4.39-4.21 (m, 6H). HRMS (ESI$^+$): calcd for $C_{25}H_{19}{}^{79}BrN_3O_4$(M+H)$^+$, 504.0559; found 504.0554.

Example 139, N-(2-bromo-5-(2,3-dihydrobenzo[b][1,4]dioxine-6-carboxamido)phenyl)-2-(2-(pyrrolidin-1-yl)ethoxy)quinoline-6-carboxamide Oxalyl chloride (0.029 mL, 0.344 mmol) was added drop-wise to a solution of Compound 70 (118 mg, 0.315 mmol) and DMF (0.554 µL, 7.16 µmol) in dry DCM (3 mL) under argon. The reaction mixture was stirred at room temperature for 2.5 h. Compound 161 (100 mg, 0.286 mmol) was then added, followed by pyridine (0.046 mL, 0.573 mmol). The reaction mixture was not very homogeneous therefore anhydrous dioxane (2 mL), followed by anhydrous DMF (2 mL) were added. The reaction was allowed to stir at room temperature for 18 h. The reaction mixture was poured into water and the aqueous layer washed with EtOAc (1×20 ml). The aqueous layer was made basic with sat. NaHCO$_3$ aq. (to ~pH 8/9) and then extracted with EtOAc (3×15 ml), the combined organic layer was washed with brine (15 ml), dried (Na$_2$SO$_4$) and concentrated in vacuo. Purification by biotage chromatography using a gradient of 1 to 10% MeOH/DCM afforded the title compound as a beige solid (44 mg, 25%). $^1$H NMR (500 MHz, DMSO-d6) δ 10.26 (s, 1H), 10.22 (s, 1H) 8.59 (d, J=2.0 Hz, 1H), 8.40 (d, J=8.9 Hz, 1H), 8.23 (dd, J=8.7, 2.0 Hz, 1H), 8.10 (s, 1H), 7.88 (d, J=8.7 Hz, 1H), 7.69-7.67 (m, 2H), 7.59-7.47 (m, 4H), 7.13 (d, J=8.8 Hz, 3H), 7.00 (d, J=8.4 Hz, 3H), 4.62-4.56 (br m, 2H), 4.35-4.25 (m, 4H), 3.05-2.85 (br m, 2H), 2.80-2.50 (br m, 4H), 1.80-1.65 (br m, 4H). HRMS (ESI$^+$): calcd for $C_{31}H_{30}{}^{79}BrN_4O_5$(M+H)$^+$, 617.1394; found 617.1399.

Example 140, N-(2-cyano-5-(2,3-dihydrobenzo[b][1,4]dioxine-6-carboxamido)phenyl)quinoline-6-carboxamide To a solution of Example 138 (150 mg, 0.297 mmol) in anhydrous NMP (2 mL) was added copper(I) cyanide (53.1 mg, 0.593 mmol) and the reaction mixture heated to 140° C. in a microwave for 2 h.

The crude reaction mixture was filtered, eluting with EtOAc. The EtOAc was removed in vacuo and the resulting residue poured into water. A green precipitate formed. This precipitate was collected by filtration and washed with water. Half of the precipitate was taken and purified by preparative HPLC to afford the product as a beige solid (4 mg, 3%). $^1$H NMR (500 MHz, DMSO-d6) δ 10.93 (s, 1H), 10.53 (s, 1H), 9.13 (br s, 1H), 8.72 (s, 1H), 8.58 (d, J=8.2 Hz, 1H), 8.30 (d, J=6.4 Hz, 2H), 8.20 (s, 2H), 7.84 (q, J=8.6 Hz, 2H), 7.69 (d, J=8.0 Hz, 1H), 7.59-7.48 (m, 2H), 7.02 (d, J=8.4 Hz, 1H), 4.42-4.22 (m, 4H). HRMS (ESI$^+$): calcd for $C_{26}H_{19}N_4O_4$ (M+H)$^+$, 451.1401; found 451.1397.

Preparation of Compound 162, 5,6,7,8-tetrahydroquinoline-3-carboxylic acid

To a stirring solution of 3-quinoline carboxylic acid (500 mg, 2.89 mmol) in trifluoroacetic acid (5.80 mL) was added Adam's catalyst (58 mg, 0.255 mmol). The reaction mixture was purged with hydrogen (3× vacuum/hydrogen cycles) and left to stir for 24 h. Further Adam's catalyst (58 mg, 0.255 mmol) was added and the reaction was allowed to stir for 22.5 h. The reaction mixture was filtered through celite and the celite pad washed with DCM. The organic solvents were removed in vacuo to afford a dark yellow oil. The oil was triturated with diethyl ether to afford a precipitate that was collected by filtration and dried under vacuum to afford the title compound as an off-white solid (323 mg, 63%). $^1$H NMR (500 MHz, DMSO-d6) δ 8.86 (d, J=1.9 Hz, 2H), 8.13 (s, 1H), 2.93 (t, J=6.4 Hz, 2H), 2.84 (t, J=6.2 Hz, 2H), 1.88-1.82 (m, 2H), 1.81-1.70 (m, 3H). HRMS (ESI$^+$): calcd for $C_{10}H_{12}NO_2$ (M+H)$^+$, 178.0868; found 178.0874.

Example 141, N-(5-(2,3-dihydrobenzo[b][1,4]dioxine-6-carboxamido)-2-methylphenyl)-5,6,7,8-tetrahydroquinoline-3-carboxamide To a stirring solution of Compound 162 (37.4 mg, 0.211 mmol) in DMF (1.5 mL) at room temperature under argon was added DIEA (0.098 mL, 0.563 mmol), followed by HATU (87 mg, 0.229 mmol). The reaction mixture was allowed to stir for 5 min before Compound 2 (50 mg, 0.176 mmol) was added. The reaction mixture was allowed to stir for 16.5 h. The reaction was diluted with water and the resulting precipitate collected by filtration, washed with water and dried under vacuum to afford the crude product as a beige solid. Purification by column chromatography using 20% EtOAc/DCM, 5% MeOH/DCM, then 10% MeOH/DCM+2% 2M NH$_3$ in MeOH to afford the title compound as a yellow glass (64 mg, 82%). $^1$H NMR (500 MHz, DMSO-d6) δ 10.05 (s, 1H), 9.99 (s, 1H), 8.86 (d, J=1.9 Hz, 1H), 8.01 (d, J=1.9 Hz, 1H), 7.81 (d, J=2.1 Hz, 1H), 7.57 (dd, J=8.3, 2.2 Hz, 1H), 7.55-7.46 (m, 2H), 7.22 (d, J=8.4 Hz, 1H), 6.98 (d, J=8.4 Hz, 1H), 4.36-4.20 (m, 4H), 2.90-2.87 (m, 2H), 2.83 (t, J=6.2 Hz, 2H), 2.19 (s, 3H), 1.85-1.82 (m, 2H), 1.82-1.74 (m, 2H). HRMS (ESI$^+$): calcd for $C_{26}H_{26}N_3O_4$ (M+H)$^+$, 444.1918; found 444.1907.

Preparation of Compound 163, 1-(6-bromoquinolin-2-yl)ethanol

To a stirring suspension of Compound 155 (200 mg, 0.847 mmol) in dry THF (2.5 mL) at 0° C. was drop-wise added methylmagnesium bromide (3.0 M in diethyl ether, 0.367 mL, 1.101 mmol). The reaction was allowed to warm gradually to room temperature over 1.5 h. The reaction was partitioned between sat. NH$_4$Cl aq. (30 ml) and EtOAc (30 ml). The aqueous layer was extracted with a further portion of EtOAc (30 ml). The combined organic layers were washed with brine (30 ml), dried Na$_2$SO$_4$ and concentrated in vacuo. Purification by biotage chromatography using a gradient of 6 to 80% EtOAc/cyclohexane gave the title compound as a brown oil (148 mg, 69%). $^1$H NMR (500 MHz, Chloroform-d) δ 8.09 (d, J=8.5 Hz, 1H), 8.01 (d, J=2.2 Hz, 1H), 7.96 (d, J=8.9 Hz, 1H), 7.81 (dd, J=8.9, 2.2 Hz, 1H), 7.40 (d, J=8.5 Hz, 1H), 5.12-4.97 (m, 1H), 4.92-4.75 (br s, 1H), 1.59 (d, J=6.6 Hz, 3H). HRMS (ESI$^+$): calcd for $C_{11}H_{11}^{79}BrNO$ (M+H)$^+$, 252.0015; found 252.0019.

Preparation of Compound 164, 6-bromo-2-(1-((tert-butyldimethylsilyl)oxy)ethyl)quinoline To a solution of Compound 163 (64 mg, 0.254 mmol) in anhydrous DCM (3.0 mL) was added imidazole (25.9 mg, 0.381 mmol) followed by tert-butyldimethylsilyl chloride (44.0 mg, 0.292 mmol). The reaction mixture was allowed to stir at room temperature for 19.5 h. The reaction had not reached completion. Further portions of imidazole (25.9 mg, 0.381 mmol) and tert-butyldimethylsilyl chloride (44.0 mg, 0.292 mmol) were added (×3) over a 48 h period and finally the reaction was warmed to 35° C. in an attempt to drive the reaction to completion. The reaction mixture was diluted with DCM (10 mL) washed with water (1×10 mL), 0.25 M HCl (1×10 mL), brine (1×10 mL), dried (MgSO$_4$), and concentrated in vacuo. Purification by column chromatography (5% EtOAc/petroleum ether) gave the title compound as a pale yellow oil (64 mg, 69%). $^1$H NMR (500 MHz, Chloroform-d) δ 8.10 (d, J=8.6 Hz, 1H), 7.99 (d, J=2.2 Hz, 1H), 7.92 (d, J=9.0 Hz, 1H), 7.80-7.74 (m, 3H), 5.12 (q, J=6.5 Hz, 1H), 1.54 (d, J=6.5 Hz, 3H), 0.94 (s, 9H), 0.12 (s, 3H), 0.02 (s, 3H). HRMS (ESI$^+$): calcd for $C_{17}H_{25}^{79}BrNOSi$ (M+H)$^+$, 366.0889; found 366.0885.

Preparation of Compound 165, 2-(1-((tert-butyldimethylsilyl)oxy)ethyl)quinoline-6-carboxylic acid To a stirring solution of Compound 164 (62 mg, 0.169 mmol) in dry THF (1.5 mL) at −78° C. was drop-wise added freshly titrated n-BuLi (0.168 mL, 0.372 mmol). The reaction was allowed to stir at −78° C. for 40 min before solid CO$_2$ was added. The reaction was stirred at −78° C. for a further 30 min before it was allowed to warm to room temperature over 17 h. The reaction mixture was diluted with water (10 ml). The aqueous layer was washed with one portion of DCM (15 ml) (an emulsion was produced which gradually separated). The aqueous layer was then acidified using 1 M HCl aq. (to ~pH 2/3) and extracted with DCM (3×15 ml). The combined organic layer was dried (MgSO$_4$) and concentrated in vacuo to afford the crude product as a yellow oil (29 mg, 57%). This material was used in the next reaction without further purification.

Preparation of Compound 166, 2-(1-((tert-butyldimethylsilyl)oxy)ethyl)-N-(5-(2,3-dihydrobenzo[b][1,4]dioxine-6-carboxamido)-2-methylphenyl)quinoline-6-carboxamide To a stirring solution of Compound 165 (28 mg, 0.084 mmol) in DMF (1.0 mL) at room temperature under argon was added DIEA (0.032 mL, 0.186 mmol), followed by HATU (41.8 mg, 0.110 mmol). The reaction was allowed to stir for 5 min before Compound 2 (28.8 mg, 0.101 mmol) was added and the reaction allowed to stir for 16.5 h. The reaction mixture was diluted with water (15 ml) and extracted with EtOAc (3×15 ml)—brine was added to clear. The combined organic layer was washed with brine (15 ml), dried (Na$_2$SO$_4$) and concentrated in vacuo. Remaining traces of DMF were removed by co-evaporation with heptane to afford the crude product as a brown oil. Purification by biotage chromatography using a gradient of 10 to 100% EtOAc/cyclohexane afforded the title compound as a white solid (14 mg, 28%). $^1$H NMR (500 MHz, Chloroform-d) δ 8.42 (s, 1H), 8.32 (d, J=8.6 Hz, 1H), 8.18-8.15 (m, 3H), 7.90 (br s, 1H), 7.87 (br s, 1H), 7.85 (d, J=8.6 Hz, 1H), 7.72 (dd, J=8.3, 2.2 Hz, 1H), 7.46 (d, J=2.2 Hz, 1H), 7.40 (dd, J=8.4, 2.2 Hz, 1H), 7.26 (d, J=8.5 Hz, 1H), 6.96 (d, J=8.4 Hz, 1H), 5.18 (q, J=6.5 Hz, 1H), 4.40-4.23 (m, 4H), 2.38 (s, 3H), 1.60 (s, 3H), 1.58 (d, J=6.5 Hz, 3H), 0.96 (s, 9H), 0.15 (s, 3H), 0.05 (s, 3H). HRMS (ESI$^+$): calcd for $C_{34}H_{36}N_3O_5Si$ (M+H)$^+$, 598.2732; found 598.2724.

Example 142, N-(5-(2,3-dihydrobenzo[b][1,4]dioxine-6-carboxamido)-2-methylphenyl)-2-(1-hydroxyethyl)quinoline-6-carboxamide To a stirring solution of Compound 166 (14 mg, 0.023 mmol) in THF (0.5 mL) at room temperature under argon was slowly added TBAF (1M in THF, 0.035 mL, 0.035 mmol). The reaction mixture was allowed to stir for 3 h. The reaction was diluted with water (20 ml) and the aqueous layer extracted with EtOAc (3×20 ml). The combined organic layer was washed with brine, dried ($Na_2SO_4$) and concentrated in vacuo. Purification by column chromatography using a gradient of 100% DCM then 2.5% to 5% MeOH in DCM afforded the title compound as a yellow solid (9.3 mg, 82%). $^1$H NMR (500 MHz, Chloroform-d) δ 8.43 (s, 1H), 8.29 (d, J=8.5 Hz, 1H), 8.21-8.16 (m, 3H), 8.14 (d, J=2.0 Hz, 1H), 7.97 (s, 1H), 7.91 (s, 1H), 7.66 (dd, J=8.3, 2.2 Hz, 1H), 7.48 (d, J=8.5 Hz, 1H), 7.45 (d, J=2.2 Hz, 1H), 7.39 (dd, J=8.4, 2.2 Hz, 1H), 7.24 (d, J=8.4 Hz, 1H), 6.95 (d, J=8.4 Hz, 1H), 5.10 (d, J=6.4 Hz, 1H), 4.89 (s, 1H), 4.37-4.27 (m, 4H), 2.37 (s, 3H), 1.64 (d, J=6.7 Hz, 3H). HRMS (ESI$^+$): calcd for $C_{28}H_{26}N_3O_5$ (M+H)$^+$, 484.1867; found 484.1853.

Preparation of Compound 167, methyl 1,2,3,4-tetrahydroquinoline-6-carboxylate

A two-necked 250 mL round bottomed flask was charged with methyl 6-quinolinecarboxylate (0.500 g, 2.67 mmol) and $Pt_2O$ (0.030 g, 0.13 mmol), evacuated and backfilled with argon. TFA (9 mL) was added and the flask was evacuated and backfilled with hydrogen, then sealed and heated to 60° C. for 5 h, cooled to room temperature, carefully quenched with sat. $NaHCO_3$ aq. while cooling the flask in a water bath. The mixture was extracted with DCM (3×) and the organic phases were dried ($MgSO_4$), filtered and concentrated. The crude material was purified by silica gel column chromatography using a gradient of 14 to 20% EtOAc in petroleum ether to afford the title compound as a white solid (232 mg, 45%). $^1$H NMR (500 MHz, $CDCl_3$) δ 7.66-7.62 (m, 2H), 6.39 (d, J=8.9 Hz, 1H), 4.29 (br s, 1H), 3.83 (s, 3H), 3.38-3.33 (m, 2H), 2.77 (t, J=6.3 Hz, 2H), 1.97-1.89 (m, 2H). HRMS (ESI$^+$): calcd for $C H_{14}NO_2$ (M+H)$^+$, 192.1019; found 192.1027.

Preparation of Compound 168, methyl 1-methyl-1,2,3,4-tetrahydroquinoline-6-carboxylate To a stirring suspension of NaH (31.8 mg, 0.795 mmol) in anhydrous DMF (4 mL) at 0° C. under argon was portion-wise added Compound 167 (76 mg, 0.397 mmol). The reaction was allowed to stir at 0° C. for 0.5 h and then allowed to warm to room temperature for 0.5 h. The flask was cooled to 0° C. and iodomethane (0.037 mL, 0.596 mmol) added. The reaction was allowed to warm to room temperature and left to stir 19.5 h. The reaction mixture was poured into water (50 ml) and extracted with EtOAc (2×25 ml)—brine was added to clear. The combined organic layer was washed with brine (20 ml), dried ($Na_2SO_4$) and concentrated in vacuo. Purification by biotage chromatography using a gradient of 1 to 10% EtOAc/cyclohexane afforded the title compound as a pale pink solid (54 mg, 66%). $^1$H NMR (500 MHz, Methanol-d4) δ 7.68 (dd, J=8.8, 2.2 Hz, 1H), 7.56-7.50 (m, 2H), 6.56 (d, J=8.7 Hz, 1H), 3.81 (s, 3H), 3.37-3.33 (m, 2H), 2.97 (s, 3H), 2.75 (t, J=6.3 Hz, 2H), 2.01-1.91 (m, 2H). HRMS (ESI$^+$): calcd for $C_{12}H_{16}NO_2$ (M+H)$^+$, 206.1176; found 206.1186.

Preparation of Compound 169, 1-methyl-1,2,3,4-tetrahydroquinoline-6-carboxylic acid To a stirring solution of Compound 168 (41 mg, 0.200 mmol) in THF (1.8 mL) and MeOH (0.6 mL) was added 2M NaOH aq. (0.200 mL, 0.400 mmol). The reaction was left to stir for 20 h. Further 2M NaOH aq. (0.400 mL, 0.800 mmol) was added and the reaction allowed to stir for 6 h, then heated to 50° C. and left to stir for 21 h. The solvents were removed in vacuo. The resulting residue was taken up in water (25 ml) and acidified using 1 M HCl aq. (to ~pH 4). The aqueous layer was extracted with EtOAc (2×20 ml). The organic layer was washed with 1 M NaOH aq. (2×20 ml) and once with water (10 ml). The combined aqueous layer was acidified (to ~pH 2/3) and extracted with EtOAc (2×20 ml) and the combined organic layer was washed with brine (20 ml) and dried ($Na_2SO_4$) to afford the title compound as an off-white solid (37 mg, 97%). This material was used without further purification. $^1$H NMR (500 MHz, Methanol-d4/$CDCl_3$, 1.5:1) δ 7.70 (dd, J=8.6, 2.1 Hz, 1H), 7.58-7.53 (m, 1H), 6.53 (d, J=8.7 Hz, 1H), 3.39-3.33 (m, 2H), 2.97 (s, 2H), 2.76 (t, J=6.3 Hz, 2H), 2.03-1.89 (m, 2H). HRMS (ESI$^+$): calcd for $C_{11}H_{14}NO_2$ (M+H)$^+$, 192.1025; found 192.1019.

Example 143, N-(5-(2,3-dihydrobenzo[b][1,4]dioxine-6-carboxamido)-2-methylphenyl)-1-methyl-1,2, 3,4-tetrahydroquinoline-6-carboxamide To a stirring solution of Compound 169 (34 mg, 0.178 mmol) in DMF (1.4 mL) at room temperature under argon was added DIEA (0.108 mL, 0.622 mmol), followed by HATU (73.2 mg, 0.193 mmol). The reaction was allowed to stir for 5 min before Compound 2 (42.1 mg, 0.148 mmol) was added. The reaction was allowed to stir for 18 h. Further HATU (73.2 mg, 0.193 mmol) and DIEA (0.108 mL, 0.622 mmol) were added and left to stir for a further 28.5 h. The reaction was poured into water (50 ml) and extracted with EtOAc (3×20 ml)—brine was added to clear. The organic layer was washed with a further portion of brine (20 ml), dried ($Na_2SO_4$) and concentrated in vacuo to afford a dark pink semi-solid. Purification by biotage chromatography using a gradient of 5% to 40% EtOAc in DCM afforded the title compound as an off-white solid (6 mg, 9%). $^1$H NMR (500 MHz, DMSO-d6) δ 10.01 (s, 1H), 9.42 (s, 1H), 7.77 (d, J=2.1 Hz, 1H), 7.69 (dd, J=8.6, 2.2 Hz, 1H), 7.59-7.47 (m, 4H), 7.18 (d, J=8.3 Hz, 1H), 6.97 (d, J=8.4 Hz, 1H), 6.60 (d, J=8.7 Hz, 1H), 4.36-4.23 (m, 4H), 3.32-3.25 (m, 2H), 2.92 (s, 3H), 2.74 (t, J=6.3 Hz, 2H), 2.16 (s, 3H), 1.95-1.85 (m, 2H). HRMS (ESI$^+$): calcd for $C_{27}H_{27}N_3O_4$ (M+H)$^+$, 458.2080; found 458.2069.

Preparation of Compound 170, 2-(6-bromoquinolin-2-yl)ethyl 4-methylbenzenesulfonate To a stirring solution of Compound 6 (400 mg, 1.587 mmol) and DABCO (356 mg, 3.17 mmol) in DCM (2.0 mL) at 0° C. under argon was added toluenesulfonyl chloride (454 mg, 2.380 mmol). The reaction was allowed to warm to RT and left to stir for 18.5 h, then concentrated in vacuo. The resulting residue was partitioned between EtOAc (25 ml) and 5% NaHCO$_3$ aq. (30 ml). The aqueous layer was extracted with a further portion of EtOAc (25 ml). The combined organic layer was washed with water (25 ml), dried Na$_2$SO$_4$ and concentrated in vacuo to afford the crude product as a yellow solid. This solid was suspended in a small amount of EtOAc (3 ml) then heptane was added (15 ml) and the solid triturated for 2 h. The reaction mixture was left to stand in the fridge overnight.

The precipitated material was isolated by filtration, washed with heptane and dried under vacuum to afford the product as an off-white solid (363 mg, 56%). $^1$H NMR (500 MHz, Chloroform-d) δ 7.98-7.94 (m, 2H), 7.75-7.73 (m, 2H), 7.61 (d, J=8.3 Hz, 2H), 7.29 (d, J=8.4 Hz, 1H), 7.14 (d, J=8.0 Hz, 2H), 4.58 (t, J=6.4 Hz, 2H), 3.29 (t, J=6.4 Hz, 2H), 2.36 (s, 3H).

Preparation of Compound 171, 4-(2-(6-bromoquinolin-2-yl)ethyl)morpholine

To a stirring solution of Compound 170 (100 mg, 0.246 mg) in anhydrous acetonitrile (2.5 mL) was added K$_2$CO$_3$ (112 mg, 0.812 mmol) followed by morpholine (0.033 mL, 0.369 mmol). The reaction was heated to 60° C. and allowed to stir for 14 h. The reaction was concentrated in vacuo, then partitioned between EtOAc (25 ml) and 5% NaHCO$_3$ aq (25 ml). The organic layer was washed with brine (25 ml). However, there was concern that some of the product has gone into the aqueous layer. Therefore it was ensured that the aqueous layer was basic by addition of further NaHCO$_3$ aq. This layer was re-extracted with EtOAc (25 ml) and solid NaCl was added to the aqueous layer followed by re-extraction with EtOAc (25 ml). The combined organic layer was dried (Na$_2$SO$_4$) and concentrated in vacuo. Purification by column chromatography using a gradient of 1 to 5% 2M NH$_3$ in MeOH/EtOAc afforded the title compound as an off-white solid (40 mg, 51%). $^1$H NMR (500 MHz, Chloroform-d) δ 8.00 (d, J=8.4 Hz, 1H), 7.96 (d, J=2.2 Hz, 1H), 7.91 (d, J=9.0 Hz, 1H), 7.76 (dd, J=9.0, 2.2 Hz, 1H), 7.37 (d, J=8.5 Hz, 1H), 3.81-3.65 (m, 4H), 3.24-3.09 (m, 2H), 2.95-2.78 (m, 2H), 2.64-2.48 (m, 4H).

Example 144, N-(5-(2,3-dihydrobenzo[b][1,4]dioxine-6-carboxamido)-2-methylphenyl)-2-(2-morpholinoethyl)quinoline-6-carboxamide n-Butyllithium (2.01 M in hexanes, 0.139 mL, 0.280 mmol) was added drop-wise to a solution of Compound 171 (75 mg, 0.233 mmol) in dry THF (2.0 mL) at −78° C. under argon.

The reaction was allowed to stir at −78° C. for 0.5 h, then solid lumps of CO$_2$ were added. The reaction was allowed to warm gradually to room temperature with stirring overnight, after which time the reaction mixture quenched with MeOH and the solvents removed in vacuo to afford the intermediate 2-(2-morpholinoethyl)quinoline-6-carboxylic acid. HATU (116 mg, 0.304 mmol) was added to a solution of the crude 2-(2-morpholinoethyl)quinoline-6-carboxylic acid (67 mg, 0.234 mmol) and DIEA (0.090 mL, 0.515 mmol) in dry DMF (2.0 mL). The reaction was stirred for 5 min, then Compound 2 (73.2 mg, 0.257 mmol) was added and the reaction allowed to stir at room temperature for 17 h. The reaction mixture was poured into water (30 ml) and extracted with EtOAc (2×30 ml)—brine was added to clear. The combined organic layer was washed with brine (30 ml), dried (Na$_2$SO$_4$) and concentrated in vacuo. The initial purification was carried out using an SCX column, eluting with MeOH then 10% 2M NH$_3$ in MeOH/MeOH. The material was further purified by biotage chromatography using a gradient of 0 to 2% MeOH in DCM to afford the title compound as a yellow semi-solid (12 mg, 9.5%). $^1$H NMR (500 MHz, DMSO-d6) δ 10.13 (s, 1H), 10.07 (s, 1H), 8.61 (d, J=2.0 Hz, 1H), 8.42 (d, J=8.4 Hz, 1H), 8.24 (dd, J=8.8, 2.0 Hz, 1H), 8.05 (d, J=8.7 Hz, 1H), 7.90-7.83 (m, 1H), 7.62-7.50 (m, 4H), 7.24 (d, J=8.3 Hz, 1H), 6.98 (d, J=8.4 Hz, 1H), 4.35-4.26 (m, 4H), 3.62-3.51 (m, 1H), 3.16-3.10 (m, 2H), 2.86-2.76 (m, 2H), 2.49-2.44 (m, 4H), 2.24 (s, 3H). HRMS (ESI$^+$): calcd for C$_{32}$H$_{33}$N$_4$O$_5$ (M+H)$^+$, 553.2451; found 553.2444.

Preparation of Compound 172, methyl 2-(hydroxymethyl)quinoline-6-carboxylate To a stirring suspension of Compound 13 (256 mg, 1.190 mmol) in ethanol (8 mL) and water (4 mL) at 0° C. was added sodium borohydride (225 mg, 5.95 mmol) and the reaction left to stir at 0° C. for 40 min. The reaction was diluted with water (30 ml) and extracted with EtOAc (3×20 ml). The combined organic layer as washed with brine (20 ml), dried (MgSO$_4$) and concentrated in vacuo to afford the title compound as a yellow solid (248 mg, 96%). $^1$H NMR (500 MHz, Chloroform-d) δ 8.62 (d, J=1.9 Hz, 1H), 8.34 (dd, J=8.8, 1.9 Hz, 1H), 8.26 (d, J=8.4 Hz, 1H), 8.13 (d, J=8.8 Hz, 1H), 7.38 (d, J=8.5 Hz, 1H), 4.97 (s, 2H), 4.35 (br s, 1H, OH), 4.02 (s, 3H). HRMS (ESI$^+$): calcd for C$_{12}$H$_{13}$NO$_4$ (M+H)$^+$, 218.0817; found 218.0823.

Preparation of Compound 173, methyl 2-(((methylsulfonyl)oxy)methyl)quinoline-6-carboxylate To a stirring solution of Compound 172 (145 mg, 0.668 mmol) and DMAP (8.15 mg, 0.067 mmol) in DCM (10 mL) at 0° C. under argon was added triethylamine (0.279 mL, 2.003 mmol), followed by methanesulfonic anhydride (174 mg, 1.001 mmol). The reaction was allowed to stir at 0° C. for 2 h, the reaction was diluted with DCM (20 ml) and washed with sat. NH$_4$Cl (aq.) (2×10 ml), sat. NaHCO$_3$ aq. (1×10 ml), water (1×10 ml) and dried (Na$_2$SO$_4$) to afford the title compound as a cream solid (169 mg, 86%). $^1$H NMR (500 MHz, Chloroform-d) δ 8.64 (d, J=1.8 Hz, 1H), 8.39-8.32 (m, 2H), 8.12 (d, J=8.8 Hz, 1H), 7.69 (d, J=8.5 Hz, 1H), 5.54 (s, 2H), 4.02 (s, 3H), 3.17 (s, 3H). HRMS (ESI$^+$): calcd for C$_{13}$H$_{14}$NO$_5$S (M+H)$^+$, 296.0586; found 296.0589.

Preparation of Compound 174, methyl 2-(isopropoxymethyl)quinoline-6-carboxylate Compound 173 (40 mg, 0.135 mmol) was dissolved in isopropanol (3 mL) and heated to 80° C. in a sealed tube for 15 h. The reaction was diluted with water (20 ml) and extracted with EtOAc (3×20 ml). The combined organic layer was washed with brine (20 ml), dried (Na$_2$SO$_4$) and concentrated in vacuo to afford the crude product as a yellow/brown oil. Purification by biotage chromatography using a gradient of 5 to 40% EtOAc in DCM afforded the title compound as a yellow solid (25 mg, 80% pure, 60% yield). $^1$H NMR (500 MHz, Chloroform-d) δ 8.60 (d, J=1.9 Hz, 1H), 8.32-8.26 (m, 2H), 8.08 (d, J=8.8 Hz, 1H), 7.75 (d, J=8.5 Hz, 1H), 4.84 (s, 2H), 4.01 (s, 3H), 3.87-3.73 (m, 1H), 1.30 (d, J=6.1 Hz, 6H). HRMS (ESI$^+$): calcd for $C_{15}H_{18}NO_3$ (M+H)$^+$, 260.1287; found 260.1285.

Preparation of Compound 175, 2-(isopropoxymethyl)quinoline-6-carboxylic acid

To a stirring solution of Compound 174 (25 mg, 0.096 mmol) in THF (0.6 mL) and MeOH (0.2 mL) was added 2M NaOH aq. (0.096 mL, 0.193 mmol). The reaction was allowed to stir for 18 h at room temperature. Further 2M NaOH aq. (0.096 mL, 0.193 mmol) was added and the reaction heated to 50° C. for 48 h. Finally, LiOH (11.55 mg, 0.482 mmol) was added to the reaction mixture and the reaction allowed to stir at room temperature for 2.5 h. The reaction mixture was poured into water (20 ml). The aqueous layer was acidified using 1M HCl aq. (to ~pH 3) and extracted with EtOAc (3×15 ml). The combined organic layer was dried (Na$_2$SO$_4$) and concentrated in vacuo to afford the crude title compound as a dark yellow solid. This material was used directly in the next reaction without further purification.

Example 145, N-(5-(2,3-dihydrobenzo[b][1,4]dioxine-6-carboxamido)-2-methylphenyl)-2-(isopropoxymethyl)quinoline-6-carboxamide To a stirring solution of Compound 175 (24 mg, 0.098 mmol) in DMF (1.2 mL) at room temperature under argon was added DIEA (0.037 mL, 0.215 mmol), followed by HATU (48.4 mg, 0.127 mmol). The reaction was allowed to stir for 5 min before Compound 2 (33.4 mg, 0.117 mmol) was added. The reaction was allowed to stir for 21 h, then diluted with water (20 ml) and extracted with EtOAc (3×10 ml)—brine was added to clear. The combined organic layer was washed with brine (10 mL), dried (Na$_2$SO$_4$) and concentrated in vacuo to afford the crude product as a yellow gum. Purification by biotage chromatography using a gradient of 30% to 50% EtOAc in DCM (it was necessary to carry out two biotage purifications to afford sufficiently pure material) afforded the title compound as a peach solid (10 mg, 20%). $^1$H NMR (500 MHz, Methanol-d4) δ 8.62 (d, J=1.6 Hz, 1H), 8.53 (d, J=8.5 Hz, 1H), 8.32 (dd, J=8.8, 1.9 Hz, 1H), 8.14 (d, J=8.8 Hz, 1H), 7.85-7.78 (m, 2H), 7.56 (dd, J=8.3, 2.2 Hz, 1H), 7.52-7.45 (m, 2H), 7.32 (d, J=8.4 Hz, 1H), 6.96 (d, J=8.4 Hz, 1H), 4.84 (s, 2H), 4.38-4.24 (m, 4H), 3.86 (hept, J=6.4 Hz, 1H), 2.35 (s, 3H), 1.31 (d, J=6.1 Hz, 6H). HRMS (ESI$^+$): calcd for $C_{30}H_{29}N_3O_5$ (M+H)$^+$, 512.2180; found 512.2174.

Preparation of Compound 176, methyl 2-(((tetrahydrofuran-2-yl)methoxy)methyl)quinoline-6-carboxylate Compound 173 (50 mg) was dissolved in tetrahydrofurfuryl alcohol (3 mL) and heated to 80° C. for 3 days. The reaction was diluted with water (20 ml) and extracted with EtOAc (3×20 ml). The combined organic layer was washed with brine (20 ml) and dried (Na$_2$SO$_4$) to afford the crude product as a yellow/brown oil. Initial purification was carried out by SCX chromatography, eluting with MeOH and then MeOH+2M NH$_3$ in MeOH. The resulting residue was further purified by biotage chromatography using a gradient of 8% to 100% EtOAc in DCM to afford the title compound as a yellow/brown solid (14 mg, 27%). $^1$H NMR (500 MHz, Chloroform-d) δ 8.60 (d, J=1.8 Hz, 1H), 8.34-8.26 (m, 2H), 8.09 (d, J=8.8 Hz, 1H), 7.76 (d, J=8.5 Hz, 1H), 4.93 (d, J=14.0 Hz, 1H), 4.89 (d, J=14.0 Hz, 1H), 4.19 (qd, J=7.0, 4.0 Hz, 1H), 4.01 (s, 3H), 3.97-3.91 (m, 1H), 3.88-3.78 (m, 1H), 3.71-3.57 (m, 2H), 2.07-1.85 (m, 3H), 1.75-1.63 (m, 1H). HRMS (ESI$^+$): calcd for $C_{17}H_{20}NO_4$ (M+H)$^+$, 302.1392; found 302.1387.

Example 146, N-(5-(2,3-dihydrobenzo[b][1,4]dioxine-6-carboxamido)-2-methylphenyl)-2-(((tetrahydrofuran-2-yl)methoxy)methyl)quinoline-6-carboxamide To a stirring solution of Compound 176 (14 mg, 0.046 mmol) in THF (0.3 mL) and methanol (0.1 mL) was added a solution of LiOH (11.13 mg, 0.465 mmol) in water (0.1 mL) The reaction was allowed to stir at room temperature for 4 h. The reaction was diluted with water (20 ml) and the aqueous layer made acidic by addition of 1 M HCl aq. (to ~pH 3). The aqueous layer was extracted with EtOAc (3×10 ml). The combined organic layer was dried (Na$_2$SO$_4$) and concentrated in vacuo to afford 2-(((tetrahydrofuran-2-yl)methoxy)methyl)quinoline-6-carboxylic acid as a brown oil. To a stirring solution of 2-(((tetrahydrofuran-2-yl)methoxy)methyl)quinoline-6-carboxylic acid (14 mg, 0.049 mmol) in DMF (0.75 mL) at room temperature under argon was added DIEA (0.019 mL, 0.107 mmol), followed by HATU (24.09 mg, 0.063 mmol). The reaction was allowed to stir for 5 min before Compound 2 (16.62 mg, 0.058 mmol) was added. The reaction was allowed to stir for 21 h, then diluted with water (20 ml) and extracted with EtOAc (3×10 ml)—brine was added to clear. The combined organic layer was washed with brine (10 mL), dried (Na$_2$SO$_4$) and concentrated in vacuo to afford the crude product as a yellow/orange gum. Purification by column chromatography using a gradient of 25% to 75% EtOAc in DCM afforded the title compound as a yellow solid (10.5 mg, 39%). $^1$H NMR (500 MHz, Methanol-d4) δ 8.61 (d, J=1.6 Hz, 1H), 8.50 (d, J=8.5 Hz, 1H), 8.31 (dd, J=8.8, 1.8 Hz, 1H), 8.13 (d, J=8.8 Hz, 1H), 7.86-7.75 (m, 2H), 7.54 (dd, J=8.3, 2.2 Hz, 1H), 7.52-7.43 (m, 2H), 7.30 (d, J=8.4 Hz, 1H), 6.94 (d, J=8.4 Hz, 1H), 4.89 (s, 2H), 4.36-4.28 (m, 4H), 4.21 (qd, J=7.0, 3.7 Hz, 1H), 3.96-3.88 (m, 1H), 3.87-3.78 (m, 1H), 3.73-3.60 (m, 2H), 3.33 (dt, J=3.3, 1.4 Hz, 2H), 2.35 (s, 3H), 2.11-1.88 (m, 3H), 1.78-1.70 (m, 1H). HRMS (ESI$^+$): calcd for $C_{32}H_{32}N_3O_6$ (M+H)$^+$, 554.2286; found 554.2279.

Preparation of Compound 177, methyl 2-((2-hydroxyethoxy)methyl)quinoline-6-carboxylate A solution of Compound 173 (200 mg, 0.677 mmol) in ethylene glycol (4.5 mL, 82 mmol) was warmed to 80° C. for 24 h. The reaction was allowed to cool to room temperature then diluted with water (40 ml) and extracted with EtOAc (3×15 ml)—brine was added to clear. The combined organic layer was washed with water (30 ml), brine (30 ml) and dried (Na$_2$SO$_4$), then concentrated in vacuo to afford the crude product as a brown oil (123 mg). Purification by column chromatography using a gradient of 8% to 100% EtOAc in DCM afforded the title compound as a beige solid (72 mg, 41%). $^1$H NMR (500 MHz, Chloroform-d) δ 8.62 (d, J=1.8 Hz, 1H), 8.33 (dd, J=8.8, 1.9 Hz, 1H), 8.30 (d, J=8.5 Hz, 1H), 8.13 (d, J=8.8 Hz, 4H), 7.59 (d, J=8.5 Hz, 4H), 4.94 (s, 2H), 4.02 (s, 3H), 3.90-3.86 (m, 2H), 3.85-3.82

(m, 2H), 3.54 (br s, 1H, OH). HRMS (ESI+): calcd for $C_{14}H_{16}NO_4$ (M+H)+, 262.1079; found 262.1074.

Preparation of Compound 178, methyl 2-((2-(pyrrolidin-1-yl)ethoxy)methyl)quinoline-6-carboxylate To a stirring solution of Compound 177 (68 mg, 0.260 mmol) in DCM (2.5 mL) at 0° C. under argon was added DMAP (3.18 mg, 0.026 mmol) followed by triethylamine (0.109 mL, 0.781 mmol) and methanesulfonic anhydride (68.0 mg, 0.390 mmol). The reaction was left to stir at 0° C. for 3 h. The reaction was diluted with DCM (20 ml) and washed with sat. NH$_4$Cl (aq.) (2×10 mL), NaHCO$_3$ aq. (1×10 mL), water (1×10 mL), brine (1×10 mL) and dried (Na$_2$SO$_4$), then concentrated in vacuo to afford methyl 2-((2-((methylsulfonyl)oxy)ethoxy)methyl)quinoline-6-carboxylate as a brown oil. To a stirring solution of methyl 2-((2-((methylsulfonyl)oxy)ethoxy)methyl)quinoline-6-carboxylate (88 mg, 0.259 mmol) in dry DCM (2.5 mL) at 0° C. under argon was added pyrrolidine (0.216 mL, 2.59 mmol). The reaction was then allowed to warm gradually to room temperature and allowed to stir for 22 h. The reaction was diluted with sat. NaHCO$_3$ aq. (20 ml) and extracted with EtOAc (3×15 ml). The combined organic layer was washed with brine (20 ml), dried Na$_2$SO$_4$ and concentrated in vacuo to afford the crude product as a green oil. Purification by biotage chromatography with a KP-NH column and using a gradient of 8% to 100% EtOAc in cyclohexane afforded the title compound as a waxy yellow/brown solid (41 mg, 50%). $^1$H NMR (500 MHz, Chloroform-d) δ 8.61 (d, J=1.8 Hz, 1H), 8.35-8.25 (m, 2H), 8.10 (d, J=8.8 Hz, 1H), 7.73 (d, J=8.5 Hz, 1H), 4.89 (s, 2H), 4.02 (s, 3H), 3.76 (t, J=5.9 Hz, 2H), 2.81 (t, J=5.9 Hz, 2H), 2.64-2.57 (m, 4H), 1.84-1.78 (m, 4H). HRMS (ESI+): calcd for $C_{18}H_{23}N_2O_3$ (M+H)+, 315.1709; found 315.1702.

Preparation of Compound 179, 2-((2-(pyrrolidin-1-yl)ethoxy)methyl)quinoline-6-carboxylic acid To a stirring solution of Compound 178 (36 mg, 0.115 mmol) in THF (1.5 mL) and MeOH (0.5 mL) was added 2M NaOH aq. (0.286 mL, 0.573 mmol) and the reaction left to stir for 19 h at room temperature. Further 2M NaOH aq. (0.286 mL, 0.573 mmol) was added and the reaction heated to 50° C. for 4 h. The reaction mixture was diluted with water (20 ml) and acidified with 1 M maleic acid aq. (to ~pH 3). The aqueous layer was washed twice with EtOAc (2×15 mL) and concentrated in vacuo to afford the crude product as a pale brown solid. Purification of this material by SCX chromatography eluting with a gradient of 0 to 10% 2M NH$_3$ in MeOH/MeOH gave the title compound as a brown oil (27 mg, 79%). HRMS (ESI+): calcd for $C_{17}H_{21}N_2O_3$ (M+H)+, 301.1552; found 301.1548.

Example 147, N-(5-(2,3-dihydrobenzo[b][1,4]dioxine-6-carboxamido)-2-methylphenyl)-2-((2-(pyrrolidin-1-yl)ethoxy)methyl)quinoline-6-carboxamide To a stirring solution of Compound 179 (27 mg, 0.090 mmol) in DMF (1.0 mL) at room temperature under argon was added DIEA (0.050 mL, 0.288 mmol), followed by HATU (44.4 mg, 0.117 mmol). The reaction was allowed to stir for 5 min before Compound 2 (30.7 mg, 0.108 mmol) was added. The reaction was allowed to stir for 15 h, then the reaction was diluted with water (20 ml) and extracted with EtOAc (3×15 ml)—brine was added to clear. Some solids were deposited around the side of the separating flask—these were dissolved in a small amount MeOH and added to the organic layer. The combined organic layer was washed with brine (20 ml), dried (Na$_2$SO$_4$) and concentrated in vacuo. Purification by column chromatography using initially 50% EtOAc/DCM, followed by using a gradient of 2% to 10% MeOH/DCM+1% 2M NH$_3$ in MeOH afforded a pale grey solid that was unfortunately insufficiently pure by $^1$H NMR. An attempt to further purify this material by SCX chromatography failed. Finally the material was purified by preparative TLC (eluting with 2×10% MeOH/DCM) to afford the title compound as an off-white solid (3.2 mg, 6%). $^1$H NMR (500 MHz, Methanol-d4) b 8.66-8.61 (m, 1H), 8.56 (d, J=8.5 Hz, 1H), 8.34 (dd, J=8.8, 1.8 Hz, 1H), 8.16 (d, J=8.8 Hz, 1H), 7.88-7.78 (m, 2H), 7.55 (dd, J=8.3, 2.2 Hz, 1H), 7.51-7.47 (m, 2H), 7.33 (d, J=8.4 Hz, 1H), 6.96 (d, J=8.4 Hz, 1H), 4.42-4.23 (m, 4H), 3.88 (t, J=5.5 Hz, 2H), 3.14-3.08 (m, 2H), 3.01-2.92 (m, 4H), 2.36 (s, 3H), 1.98-1.93 (m, 4H). HRMS (ESI+): calcd for $C_{33}H_{34}N_4O_5$ (M+H)+, 567.2602; found 567.2594.

Preparation of Compound 180, ethyl 5-((2-(pyrrolidin-1-yl)ethyl)amino)quinoline-3-carboxylate Ethyl 5-chloroquinoline-3-carboxylate (50 mg, 0.212 mmol), BrettPhos (22.8 mg, 0.042 mmol), Pd(OAc)$_2$ (4.7 mg, 0.021 mmol), K$_2$CO$_3$ (58.6 mg, 0.424 mmol) and 1-(2-aminoethyl)-pyrrolidine (0.022 mL, 0.170 mmol) were combined in anhydrous t-butanol (2.0 mL), degassed by 3× vacuum/argon cycles and heated to 80° C. for 18 h. The solvent was removed in vacuo and the resulting residue was partitioned between water (25 ml) and EtOAc (25 ml). The aqueous layer was acidified using 1 M HCl aq. (to ~pH 4.0). The aqueous and organic layers were separated and the aqueous layer washed with a further portion of EtOAc (25 ml). The aqueous layer was then concentrated in vacuo to afford the crude product as a red solid. Purification by biotage chromatography with a KP-NH column using a gradient of 0 to 60% EtOAc/cyclohexane afforded the title compound as a yellow oil (20 mg, 30%). $^1$H NMR (500 MHz, Chloroform-d) δ 9.39 (d, J=2.0 Hz, 1H), 8.95 (dd, J=1.9, 0.7 Hz, 1H), 7.67 (t, J=8.1 Hz, 1H), 7.48 (d, J=8.4 Hz, 1H), 6.65 (d, J=7.7 Hz, 1H), 5.50 (br s, 1H, NH), 4.49 (q, J=7.1 Hz, 2H), 3.43-3.27 (m, 2H), 3.02-2.82 (m, 2H), 2.70-2.50 (m, 4H), 1.91-1.78 (m, 4H), 1.48 (t, J=7.1 Hz, 3H). HRMS (ESI+): calcd for $C_{18}H_{23}N_3O_2$ (M+H)+, 314.1869; found 314.1847.

Example 148, N-(5-(2,3-dihydrobenzo[b][1,4]dioxine-6-carboxamido)-2-methylphenyl)-5-((2-(pyrrolidin-1-yl)ethyl)amino)quinoline-3-carboxamide To a stirring solution of Compound 180 (20 mg, 0.064 mmol) in THF (1.5 mL) and MeOH (0.5 mL) was added 2M NaOH aq. (0.22 mL, 0.447 mmol). The reaction was allowed to stir at room temperature for 17 h. The reaction mixture was concentrated in vacuo and the resulting residue was diluted with water (20 ml) and the aqueous layer acidified with 1M HCl aq. (to ~pH 2/3). The aqueous layer was washed with EtOAc (20 ml) and then concentrated in vacuo to afford 5-((2-(pyrrolidin-1-yl)ethyl)amino)quinoline-3-carboxylic acid as a red solid. To a stirring solution of 5-((2-(pyrrolidin-1-yl)ethyl)amino)quinoline-3-carboxylic acid (21 mg, 0.065 mmol) in DMF (0.5 mL) at room temperature under argon was added DIEA (0.040 mL, 0.228 mmol), followed by HATU (26.9 mg, 0.071 mmol). The reaction was allowed to stir for 5 min before Compound 2 (15.46 mg, 0.054 mmol) was added. The reaction was left to stir for 16 h, then diluted with water and the resulting precipitate collected by filtration and washed well with water, air dried and further dried under vacuum to afford the crude product as a yellow solid. Purification by column chromatography using a gradient of 5% to 10% MeOH in DCM+2% 2M NH$_3$ in MeOH afforded the title compound as a bright yellow solid (5 mg, 17%). $^1$H NMR (500 MHz, Methanol-d4) δ 9.33 (br s, 2H), 7.89 (d, J=2.2 Hz, 1H), 7.75 (t, J=8.1 Hz, 1H), 7.55-7.42 (m, 4H), 7.32 (d, J=8.4 Hz, 1H), 6.96 (d, J=8.4 Hz, 1H), 6.85 (d, J=7.9 Hz, 1H) 4.47-4.13 (m, 4H), 3.69 (t, J=6.1 Hz, 1H), 3.39-3.35 (m, 2H), 3.24-3.17 (m, 4H), 2.36 (s, 3H), 2.06-2.01 (m, 4H). HRMS (ESI$^+$): calcd for C$_{32}$H$_{33}$N$_5$O$_4$ (M+H)$^+$, 552.2605; found 552.2591.

Preparation of Compound 181, N-(4-chloro-3-nitrophenyl)-2,3-dihydrobenzo[b][1,4]dioxine-6-carboxamide Oxalyl chloride (0.141 mL, 1.665 mmol) was added dropwise to a solution of 1,4-benzodioxane-6-carboxylic acid (250 mg, 1.388 mmol) and DMF (2.69 μL, 0.035 mmol) in dry DCM (7 mL). The reaction was allowed to stir at room temperature for 2 h. The reaction mixture was concentrated, a further portion of dry DCM (7 ml) was added and concentrated again. This residue was re-dissolved in dry DCM (3+3+1 mL) and added drop-wise to a solution of 4-chloro-3-nitroaniline (239 mg, 1.388 mmol) and pyridine (0.224 mL, 2.78 mmol) in dry DCM (7 mL). The reaction was allowed to stir for 3 h at room temperature. The solvent was removed in vacuo and the resulting residue was suspended in MeOH and a solid precipitated by addition of water. The precipitate was isolated by filtration and washed with water, then dried under high vacuum to afford the title compound as a dark yellow solid (417 mg, 90%). $^1$H NMR (500 MHz, DMSO-d6) δ 10.54 (s, 1H), 8.59 (d, J=2.5 Hz, 1H), 8.05 (dd, J=8.9, 2.5 Hz, 1H), 7.75 (d, J=8.9 Hz, 1H), 7.59-7.46 (m, 2H), 7.02 (d, J=8.4 Hz, 1H), 4.35-4.28 (m, 6H). HRMS (ESI$^+$): calcd for C$_{15}$H$_{12}$ClN$_2$O$_5$ (M+H)$^+$, 335.0435; found 335.0437.

Preparation of Compound 182, N-(3-amino-4-chlorophenyl)-2,3 dihydrobenzo[b][1,4]dioxine-6-carboxamide To a stirring suspension of Compound 181 (200 mg, 0.598 mmol) in EtOH (3 mL) and water (1.0 mL) was added Fe powder (234 mg, 4.18 mmol) and NH$_4$Cl (224 mg, 4.18 mmol). The reaction mixture was then heated to reflux for 15 h. The reaction was filtered through celite (eluting with EtOH/EtOAc). The solvents were removed in vacuo and the resulting residue partitioned between water (30 ml) and EtOAc (30 ml). The organic layer was washed with sat. NaHCO$_3$ aq. (30 ml), water (30 ml), brine (30 ml) and dried (Na$_2$SO$_4$), then concentrated in vacuo to afford the crude product as a dark orange solid (143 mg, 79%). $^1$H NMR (500 MHz, DMSO-d6) δ 9.88 (s, 1H), 7.51-7.44 (m, 2H), 7.36 (d, J=2.4 Hz, 1H), 7.10 (d, J=8.6 Hz, 1H), 6.97 (d, J=8.4 Hz, 1H), 6.89 (dd, J=8.7, 2.5 Hz, 1H), 5.34 (s, 2H, NH$_2$), 4.31-4.27 (m, 4H). HRMS (ESI$^+$): calcd for C$_{15}$H$_{14}$ClN$_2$O$_3$ (M+H)$^+$, 305.0693; found 305.0705.

Example 149, N-(2-chloro-5-(2,3-dihydrobenzo[b][1,4]dioxine-6-carboxamido)phenyl)quinoline-6-carboxamide Oxalyl chloride (0.025 mL, 0.295 mmol) was added drop-wise to a solution of 6-quinoline carboxylic acid (46.9 mg, 0.271 mmol) and DMF (0.476 μL, 6.15 μmol) in dry DCM (2.5 mL). Dioxane (3 ml) was added in an attempt to further solubilise the material but this was ineffective. The reaction allowed to stir at room temperature for 3 h. The reaction was concentrated in vacuo, a further portion of anhydrous DCM (2.5 mL) was added and concentrated again. This residue was re-suspended in anhydrous DCM (2.0 mL). A solution of Compound 182 (75 mg, 0.246 mmol) and pyridine (0.060 mL, 0.738 mmol) in dry DCM (2 mL) and dioxane (1 mL) was prepared and added slowly to the acid chloride suspension. The reaction was allowed to stir for 18 h, then the solvents were removed in vacuo. The resulting residue was suspended in MeOH and diluted with water. The precipitate formed was isolated by filtration, washed with water and dried under high vacuum to afford the crude product as a yellow solid. Purification by preparative HPLC gave the title compound as a white solid (10 mg, 9%). $^1$H NMR (500 MHz, DMSO-d6) δ 10.37 (1H, s), 10.28 (1H, s), 9.03 (dd, J=4.2, 1.7 Hz, 1H), 8.69 (d, J=1.8 Hz, 1H), 8.56 (br d, J=7.5 Hz, 1H), 8.29 (dd, J=8.8, 2.0 Hz, 1H), 8.20-8.10 (m, 2H), 7.75 (dd, J=8.8, 2.5 Hz, 1H), 7.66 (dd, J=8.3, 4.2 Hz, 1H), 7.58-7.48 (m, 2H), 7.00 (d, J=8.4 Hz, 1H), 4.41-4.24 (m, 4H). HRMS (ESI$^+$): calcd for C$_{25}$H$_{19}$ClN$_3$O$_4$ (M+H)$^+$, 460.1056; found 460.1056.

Preparation of Compound 183, 6-bromo-2-chloro-3-iodoquinoline

To a stirring suspension of 6-bromo-2-chloroquinoline (1 g, 4.12 mmol) at −78° C. in dry THF (35 ml) was drop-wise added LDA (2.0 M in THF/Heptane/Ethyl benzene, 2.062 mL, 4.12 mmol). The reaction was allowed to stir at −78° C. for 2 h before the addition of iodine (1.047 g, 4.12 mmol) in THF (5 ml). The reaction was stirred at −78° C. for a further 2.5 h before 20% water/THF (10 ml) was added to quench the reaction. The reaction was diluted with further water (20 ml) at −10° C. The THF was removed in vacuo and the resulting aqueous layer extracted with EtOAc (1×10) and ether (2×10). Some solids which formed around the sides of the separating funnel could be dissolved using a small amount of DCM and were added to the organic layer. The combined organic layer was washed twice with 10% sodium thiosulfate (2×15 ml), water (20 ml), brine (20 ml) and dried (Na$_2$SO$_4$). Purification by short column chromatography (19:1 cyclohexane/EtOAc) gave the title compound as a pale yellow solid (627 mg, 41%). $^1$H NMR (500 MHz, Chloroform-d) δ 8.60 (s, 1H), 7.90 (d, J=2.0 Hz, 1H), 7.87 (d, J=9.0 Hz, 1H), 7.83 (dd, J=9.0, 2.1 Hz, 1H). HRMS (ESI$^+$): calcd for C$_9$H$_5$BrClIN (M+H)$^+$, 367.8333; found 367.8330.

Preparation of Compound 184, 6-bromo-3-iodo-2-(2-(pyrrolidin-1-yl)ethoxy)quinoline To a stirring suspension of NaH (37.5 mg, 0.936 mmol) in THF (3.0 mL) at 0° C. under argon was slowly added 1-(2-hydroxyethyl)pyrrolidine (0.114 mL, 0.977 mmol). The reaction mixture was allowed to stir for 5 min at 0° C., then allowed to warm to room temperature for 30 min. Compound 183 (300 mg, 0.814 mmol) was then added and the reaction heated to reflux for 16 h. The reaction was concentrated in vacuo and the resulting residue diluted with water (20 ml) and sat. NaHCO$_3$ aq. (10 ml). The aqueous layer was extracted with DCM (3×15 ml) and the combined organic layer was washed with water (20 ml) and dried (MgSO$_4$). Purification by biotage chromatography using a gradient of 2% to 10% MeOH/DCM afforded the title compound as an off-white solid (323 mg, 89%). $^1$H NMR (500 MHz, Chloroform-d) δ 8.44 (s, 1H), 7.78 (d, J=1.8 Hz, 1H), 7.71-7.68 (m, 2H), 4.69 (t, J=6.0 Hz, 2H), 3.04 (t, J=6.0 Hz, 2H), 2.80-2.75 (m, 4H), 1.89-1.83 (m, 4H). HRMS (ESI$^+$): calcd for $C_{15}H_{16}{}^{79}BrIN_2O$ (M+H)$^+$, 446.9563; found 446.9559.

Preparation of Compound 185, 6-bromo-N-(2-methoxyethyl)-2-(2-(pyrrolidin-1-yl)ethoxy)quinolin-3-amine Compound 184 (201 mg, 0.450 mmol), cesium carbonate (293 mg, 0.899 mmol), 2-methoxyethylamine (0.586 mL, 6.74 mmol) and 2-isobutyrylcyclohexanone (15.13 mg, 0.090 mmol) were combined in a microwave vial in anhydrous DMF (2.2 mL) and degassed by 3× vacuum/argon cycles. Copper(I) iodide (4.28 mg, 0.022 mmol) was added, the reaction degassed again via the same procedure and heated to 125° C. for 4 h. The reaction was poured into water (20 ml) and extracted with EtOAc (3×20 ml)—brine was added to clear. The combined organic layer was washed with brine (20 mL), dried $Na_2SO_4$ and concentrated in vacuo. Remaining traces of DMF were removed by co-evaporation with heptane. Purification by column chromatography using a gradient of 2% to 10% MeOH/DCM gave the title compound as a 2:1 mixture with the corresponding des-iodo compound (97 mg, 36% title compound). HRMS (ESI$^+$): calcd for $C_{18}H_{25}{}^{79}BrN_3O_2$ (M+H)$^+$, 394.1130; found 394.1125.

Preparation of Compound 186, butyl 3-((2-methoxyethyl)amino)-2-(2-(pyrrolidin-1-yl)ethoxy)quinoline-6-carboxylate To a stirring solution of crude Compound 185 (94 mg, 0.238 mmol) in 1-butanol (0.75 ml) was added Hermann's catalyst (11.18 mg, 0.012 mmol) and tri-t-butylphosphonium tetrafluoroborate (13.83 mg, 0.048 mmol), followed by molybdenum hexacarbonyl (126 mg, 0.477 mmol) and DBU (1.0M in THF, 0.715 mL, 0.715 mmol). The reaction was heated to 130° C. in a microwave for 1 h, then filtered through celite and the solvent removed in vacuo. Purification by column chromatography using a gradient of 2% to 8% MeOH/DCM gave the title compound as a dark yellow oil as a 2:1 mixture with the des-iodo compound from the previous step (80 mg, 53% title compound). HRMS (ESI$^+$): calcd for $C_{23}H_{33}N_3O_4$ (M+H)$^+$, 416.2549; found 416.2550.

Preparation of Compound 187, 3-((2-methoxyethyl)amino)-2-(2-(pyrrolidin-1-yl)ethoxy)quinoline-6-carboxylic acid To a stirring solution of crude Compound 186 (72 mg, 0.173 mmol) in THF (1.5 mL) and MeOH (0.5 mL) was added 2M NaOH aq. (0.433 mL, 0.866 mmol) and the reaction left to stir at room temperature for 18 h. Further 2M NaOH aq. (0.433 mL, 0.866 mmol) was added and the reaction heated to 50° C. for 4 h. The reaction was diluted with water (20 ml) and acidified with 1 M HCl aq. (to ~pH 3). The aqueous layer was washed with DCM (2×20 ml), then concentrated in vacuo to afford the title compound as a brown semi-solid, still as a 2:1 mixture with the des-iodo analogue carried through from the previous steps. This material was used directly in the next reaction without further purification. HRMS (ESI$^+$): calcd for $C_{19}H_{26}N_3O_4$ (M+H)$^+$, 360.1923; found 360.1922.

Example 150, N-(5-(2,3-dihydrobenzo[b][1,4]dioxine-6-carboxamido)-2-methylphenyl)-3-((2-methoxyethyl)amino)-2-(2-(Pyrrolidin-1-yl)ethoxy) quinoline-6-carboxamide To a stirring solution of crude Compound 187 (62 mg, 0.173 mmol) in DMF (1.5 mL) at room temperature under argon was added DIEA (0.096 mL, 0.552 mmol), followed by HATU (85 mg, 0.224 mmol). The reaction was allowed to stir for 5 min before Compound 2 (58.9 mg, 0.207 mmol) was added. The reaction was left to stir for 2 days, then diluted with water (20 ml) and the aqueous layer extracted with EtOAc (3×15 ml). The combined organic layer was washed with brine (2×10 ml), then concentrated in vacuo. Remaining traces of DMF were removed by co-evaporation with heptane (×2). Purification by column chromatography initially using 4:1 DCM/EtOAc, then using a gradient of 2.5% to 10% MeOH/DCM gave the title compound as a pale yellow solid (16 mg, 15%). $^1$H NMR (500 MHz, Chloroform-d) δ 8.12 (d, J=2.1 Hz, 1H), 8.09 (s, 1H), 8.01 (br s, 1H), 7.96 (br s, 1H), 7.79-7.72 (m, 3H), 7.46 (d, J=2.1 Hz, 1H), 7.40 (dd, J=8.4, 2.2 Hz, 1H), 7.23 (d, J=8.4 Hz, 1H), 6.94 (d, J=8.4 Hz, 1H), 6.89 (s, 2H), 5.21 (br s, 1H, NH), 4.73 (t, J=5.8 Hz, 2H), 4.34-4.28 (m, 4H), 3.75-3.71 (m, 2H), 3.44 (s, 3H), 3.43-3.38 (m, 2H), 3.04 (t, J=5.8 Hz, 2H), 2.75-2.70 (m, 4H), 2.35 (s, 3H), 1.89-1.82 (m, 4H). HRMS (ESI$^+$): calcd for $C_{35}H_{39}N_5O_6$ (M+H)$^+$, 626.2973; found 626.2969.

Preparation of Compound 188, methyl 2-(isobutoxymethyl)quinoline-6-carboxylate

Compound 173 (100 mg, 0.339 mmol) was combined with 2-methoxy-1-propanol and heated to 80° C. for 2 days. The reaction was diluted with water (25 ml) and extracted with EtOAc (3×20 ml). The combined organic layer was washed with brine (25 ml), dried ($Na_2SO_4$) and concentrated in vacuo. Purification by biotage chromatography using a gradient of 1% to 10% EtOAc/DCM gave the title compound as a yellow solid (39 mg, 42%). $^1$H NMR (500 MHz, Chloroform-d) δ 8.61 (d, J=1.8 Hz, 1H), 8.33-8.29 (m, 2H), 8.10 (d, J=8.8 Hz, 1H), 7.74 (d, J=8.5 Hz, 1H), 4.84 (s, 2H), 4.02 (s, 3H), 3.40 (d, J=6.6 Hz, 2H), 2.06-1.97 (m, 1H), 1.00 (d, J=6.7 Hz, 6H). HRMS (ESI$^+$): calcd for $C_{16}H_{20}NO_3$ (M+H)$^+$, 274.1443; found 274.1443.

Preparation of Compound 189, 2-(isobutoxymethyl)quinoline-6-carboxylic acid

To a stirring solution of Compound 188 (36 mg, 0.132 mmol) in THF (0.9 mL) and MeOH (0.3 mL) was added a solution of LiOH (31.5 mg, 1.317 mmol) in water (0.3 mL). The reaction was stirred at room temperature for 2.5 h. The reaction mixture was diluted with water (20 ml) and acidified using 1M HCl aq. (to ~pH3). The aqueous layer was extracted with EtOAc (3×15 ml). The combined organic layer was dried ($Na_2SO_4$) and concentrated in vacuo to afford the title compound as a pale yellow solid. This crude material was used directly in the next reaction without further purification. HRMS (ESI⁺): calcd for C₁₅H₁₈N0₃ (M+H)⁺, 260.1287; found 260.1288.

Example 151, N-(5-(2,3-dihydrobenzo[b][1,4]dioxine-6-carboxamido)-2-methylphenyl)-2-(isobutoxymethyl)quinoline-6-carboxamide To a stirring solution of Compound 189 (35 mg, 0.135 mmol) in DMF (2.0 mL) at room temperature under argon was added DIEA (0.052 mL, 0.297 mmol), followed by HATU (66.7 mg, 0.175 mmol). The reaction was allowed to stir for 5 min before Compound 2 (46.1 mg, 0.162 mmol) was added. The reaction was left to stir at room temperature for 23 h, then diluted with water (25 ml) and extracted with EtOAc (3×20 ml)—brine was added to clear. The combined organic layer was washed with brine (20 ml), dried (MgSO₄) and concentrated in vacuo. Co-evaporation with heptane was used to remove remaining traces of DMF. Purification by column chromatography using a gradient of 20% to 50% EtOAc/DCM gave the title compound as an off-white solid (41 mg, 58%). ¹H NMR (500 MHz, DMSO-d6) δ 10.17 (s, 1H), 10.08 (s, 1H), 8.66 (d, J=1.8 Hz, 1H), 8.56 (d, J=8.5 Hz, 1H), 8.28 (dd, J=8.8, 1.9 Hz, 1H), 8.09 (d, J=8.8 Hz, 1H), 7.88 (d, J=2.1 Hz, 1H), 7.70 (d, J=8.5 Hz, 1H), 7.59 (dd, J=8.3, 2.2 Hz, 1H), 7.55-7.50 (m, 2H), 7.25 (d, J=8.5 Hz, 2H), 6.98 (d, J=8.4 Hz, 1H), 4.76 (s, 2H), 4.35-4.27 (m, 4H), 2.69 (s, 3H), 2.25 (s, 3H), 1.98-1.87 (m, 1H), 0.93 (d, J=6.7 Hz, 6H). HRMS (ESI⁺): calcd for C₃₁H₃₁N₃O₅(M+H)⁺, 526.2336; found 526.2327.

Preparation of Compound 190, 2-methyl-1,2,3,4-tetrahydroquinoline-6-carboxylic acid To a stirring solution of 2-methylquinoline-6-carboxylic acid (250 mg, 1.336 mmol) in MeOH (10 mL) under argon was added palladium on carbon (10% wt, 35 mg), followed by ammonium formate (842 mg, 13.36 mmol). The reaction was heated to reflux and left to stir for 2 days (further portions of palladium on carbon (×1) and ammonium formate (×2) were added in order to drive the reaction to completion). The reaction mixture was filtered through celite and the solvents removed in vacuo. The resulting residue was taken up in water (30 ml) and made acidic by the addition of 1M HCl aq. (to ~pH 3). The aqueous layer was extracted with DCM (3×15 ml), the combined organic layer was dried (Na₂SO₄) and concentrated in vacuo to afford the title compound as a white solid (170 mg, 67%). ¹H NMR (500 MHz, DMSO-d6) δ 11.86 (s, 1H), 7.47-7.43 (m, 2H), 6.46-6.42 (m, 2H), 3.43-3.32 (m, 2H), 2.76-2.62 (m, 2H), 1.90-1.83 (m, 1H), 1.46-1.36 (m, 1H), 1.16 (d, J=6.3 Hz, 3H).

Preparation of Compound 191, 1-(((9H-fluoren-9-yl)methoxy)carbonyl)-2-methyl-1,2,3,4-tetrahydroquinoline-6-carboxylic acid Fmoc chloride (82 mg, 0.316 mmol) was added to a stirring solution of Compound 190 (55 mg, 0.288 mmol) and NaOH aq. 0.5 M (1.2 ml, 0.600 mmol) in dioxane (1.2 mL) at room temperature. The reaction was allowed to stir at room temperature for 19 h, then partitioned between DCM (20 ml) and 1M HCl aq. (20 ml). The aqueous layer was extracted with further DCM (20 ml) and the combined organic layer was washed with water (20 ml), brine (20 ml), dried (Na₂SO₄) and concentrated in vacuo to afford the crude material as a colourless oil (45 mg, 39%). ¹H NMR (500 MHz, DMSO-d6) δ 12.67 (br s, 1H), 7.90 (dd, J=12.1, 7.5 Hz, 2H), 7.66-7.61 (m, 3H), 7.50-7.29 (m, 5H), 7.14 (br d, J=8.3 Hz, 1H), 4.80 (dd, J=10.8, 5.1 Hz, 1H), 4.62 (dd, J=10.8, 5.1 Hz, 1H), 4.35 (t, J=5.0 Hz, 1H), 4.32-4.26 (m, 2H), 2.73-2.66 (m, 1H), 2.58-2.50 (m, 1H), 2.01-1.93 (m, 1H), 1.47-1.39 (m, 1H), 0.89 (d, J=6.5 Hz, 3H). HRMS (ESI⁺): calcd for C₂₆H₂₃N₃O₄ (M+H)⁺, 414.1692; found 414.1687.

Preparation of Compound 192, (9H-fluoren-9-yl)methyl 6-((5-(2,3-dihydrobenzo[b][1,4]dioxine-6-carboxamido)-2-methylphenyl)carbamoyl)-2-methyl-3,4-dihydroquinoline-1(2H)-carboxylate To a stirring solution of Compound 191 (31 mg, 0.075 mmol) in DMF (1.0 mL) at room temperature under argon was added DIEA (0.042 mL, 0.240 mmol), followed by HATU (37.1 mg, 0.097 mmol). The reaction was allowed to stir for 5 min before Compound 2 (25.6 mg, 0.090 mmol) was added. The reaction was allowed to stir at room temperature for 16 h, then diluted with water (10 ml) and extracted with EtOAc (3×10 ml)—brine was added to clear. The combined organic layer was washed with brine (10 ml), dried (MgSO₄) and concentrated in vacuo. Co-evaporation with heptane was used to remove remaining traces of DMF. Purification by column chromatography using a gradient of 10% to 80% EtOAc/DCM gave the title compound as a pale yellow solid (32 mg, 63%). ¹H NMR (500 MHz, Chloroform-d) δ 8.11 (d, J=2.1 Hz, 1H), 7.89 (s, 1H), 7.79 (t, J=7.6 Hz, 2H), 7.74 (dd, J=8.2, 2.2 Hz, 1H), 7.70 (s, 1H), 7.65 (d, J=1.8 Hz, 1H), 7.56 (dd, J=11.6, 7.5 Hz, 2H), 7.50-7.37 (m, 5H), 7.36-7.30 (m, 2H), 7.24 (d, J=8.4 Hz, 1H), 6.95 (d, J=8.4 Hz, 1H), 4.74 (dd, J=10.8, 5.7 Hz, 1H), 4.68 (dd, J=10.8, 5.8 Hz, 1H), 4.56-4.49 (m, 1H), 4.35-4.27 (m, 5H), 2.83-2.75 (m, 1H), 2.71-2.64 (m, 1H), 2.34 (s, 3H), 2.19-2.12 (m, 1H), 1.62-1.53 (m, 1H), 1.09 (d, J=6.6 Hz, 2H). HRMS (ESI⁺): calcd for C₄₂H₃₇N₃O₆ (M+H)⁺, 680.2761; found 680.2740.

Example 152, N-(5-(2,3-dihydrobenzo[b][1,4]dioxine-6-carboxamido)-2-methylphenyl)-2-methyl-1,2, 3,4-tetrahydroquinoline-6-carboxamide To a stirring solution of Compound 192 (32 mg, 0.047 mmol) in DMF (1.0 mL) was added piperidine (0.05 mL, 0.505 mmol). The reaction was allowed to stir at room temperature for 21 h. Further piperidine (0.05 mL, 0.505 mmol) was added and the reaction stirred for 26 h. The reaction was diluted with water (15 ml) and extracted with EtOAc (2×15 ml). The combined organic layer was washed with brine (15 ml), dried (Na₂SO₄) and concentrated in vacuo. Purification by biotage chromatography using a gradient of 8% to 48% EtOAc/DCM gave the title compound as a white solid (16 mg, 74.3%). ¹H NMR (500 MHz, DMSO-d6) δ 10.01 (s, 1H), 9.34 (s, 1H), 7.77 (d, J=2.2 Hz, 1H), 7.56 (s, 1H), 7.55-7.54 (m, 1H), 7.53 (d, J=2.1 Hz, 1H), 7.50 (dd, J=8.4, 2.2 Hz, 1H), 7.17 (d, J=8.5 Hz, 1H), 6.97 (d, J=8.4 Hz, 1H), 6.49 (d, J=8.2 Hz, 1H), 6.28 (s, 1H), 4.35-4.25 (m, 4H), 3.42-3.36 (m, 1H), 2.81-2.66 (m, 2H), 2.16 (s, 3H), 1.92-1.86 (m, 1H), 1.49-1.39 (m, 1H), 1.17 (d, J=6.3 Hz, 3H). HRMS (ESI⁺): calcd for C₂₇H₂₇N₃O₄ (M+H)⁺, 458.2060; found 458.2074.

Preparation of Compound 193, 6-bromo-2-(1-methoxyethyl)quinoline

To a stirring solution of Compound 163 (75 mg, 0.297 mmol) in dry DMF (3 mL) at 0° C. under argon was added sodium hydride (14.28 mg, 0.357 mmol). The reaction was allowed to warm gradually to room temperature over 40 min, then cooled back to 0° C. and iodomethane (0.093 mL, 1.487 mmol) was added drop-wise. The reaction was allowed to warm to room temperature and left to stir for 2 days. The reaction was cooled back to 0° C. and a further portion of sodium hydride (14.28 mg, 0.357 mmol) and iodomethane (0.093 mL, 1.487 mmol) added following the same procedure as previously. The flask was allowed to warm to room temperature and left to stir for 5 h. The reaction was diluted with water (25 ml) and extracted with EtOAc (3×15 ml)—brine was added to clear. The combined organic layer was washed with brine (25 ml), dried ($Na_2SO_4$) and concentrated in vacuo to afford the crude product as a yellow oil (45 mg, 57%). $^1$H NMR (500 MHz, Chloroform-d) δ 8.13 (d, J=8.6 Hz, 1H), 8.01 (d, J=2.2 Hz, 1H), 7.96 (d, J=9.0 Hz, 1H), 7.80 (dd, J=9.0, 2.2 Hz, 1H), 7.63 (d, J=8.6 Hz, 1H), 4.61 (q, J=6.6 Hz, 1H), 3.36 (s, 3H), 1.56 (d, J=6.6 Hz, 3H). HRMS (ESI$^+$): calcd for $C_{12}H_{13}{}^{79}BrNO$ (M+H)$^+$, 266.0181; found 266.0174.

Preparation of Compound 194, 2-(1-methoxyethyl)quinoline-6-carboxylic acid

To a stirring solution of Compound 193 (40 mg, 0.150 mmol) in dry THF (1 mL) at −78° C. was drop-wise added freshly titrated n-BuLi (0.150 mL, 0.331 mmol). The reaction was allowed to stir at −78° C. for 40 min before solid $CO_2$ was added. The reaction was left to stir at −78° C. for 30 min before being allowed to warm to room temperature over 2 h. The reaction mixture was diluted with water (15 ml) and the aqueous layer acidified with 1 M HCl aq. (to ~pH 2/3) and the aqueous layer was extracted with DCM (3×10 ml). The combined organic layer was dried ($MgSO_4$) and concentrated in vacuo to afford the title compound as an orange oil. This material was used directly in the next reaction without further purification. HRMS (ESI$^+$): calcd for $C_{13}H_{14}NO_3$ (M+H)$^+$, 232.0974; found 232.0975.

Example 153, N-(5-(2,3-dihydrobenzo[b][1,4]dioxine-6-carboxamido)-2-methylphenyl)-2-(1-methoxyethyl)quinoline-6-carboxamide To a stirring solution of Compound 194 (35 mg, 0.151 mmol) in DMF (1.5 mL) at room temperature under argon was added DIEA (0.058 mL, 0.333 mmol), followed by HATU (74.8 mg, 0.197 mmol). The reaction was allowed to stir for 5 min before Compound 2 (51.6 mg, 0.182 mmol) was added. The reaction was allowed to stir at room temperature for 7 h. Further DIEA (0.058 mL, 0.333 mmol), followed by HATU (74.8 mg, 0.197 mmol) and Compound 2 (51.6 mg, 0.182 mmol) was added and allowed to stir for 18 h, then the reaction mixture was heated to 40° C. for 23 h. The reaction was diluted with water (15 ml) and extracted with EtOAc (3×15 ml)—brine was added to clear. The combined organic layer was washed with brine (15 ml), dried ($Na_2SO_4$) and concentrated in vacuo. Remaining traces of DMF were removed by co-evaporation with heptane. An initial attempt to purify the crude product by biotage chromatography using a gradient of 0 to 20% EtOAc/DCM failed. Therefore the material was purified by 2× preparative HPLC to afford the title compound as a formate salt (formic acid was used in the HPLC solvent system). The free amine was obtained via SCX chromatography eluting with MeOH, then 10% 2M $NH_3$ in MeOH to afford the title compound as a pale yellow solid (7 mg, 9%). $^1$H NMR (500 MHz, Methanol-d4) δ 8.63 (d, J=1.7 Hz, 1H), 8.56 (d, J=8.6 Hz, 1H), 8.34-8.32 (m, 1H), 8.17 (d, J=8.8 Hz, 1H), 7.82 (d, J=2.1 Hz, 1H), 7.77 (d, J=8.5 Hz, 1H), 7.56 (dd, J=8.3, 2.2 Hz, 1H), 7.51-7.47 (m, 2H), 7.33 (d, J=8.4 Hz, 1H), 6.96 (d, J=8.4 Hz, 1H), 4.66 (q, J=6.6 Hz, 1H), 4.35-4.29 (m, 4H), 3.37 (s, 3H), 2.36 (s, 3H), 1.56 (d, J=6.6 Hz, 3H). HRMS (ESI$^+$): calcd for $C_{29}H_{28}N_3O_5$(M+H)$^+$, 498.2006; found 498.2023.

Example 154, (S)—N-(5-(2,3-dihydrobenzo[b][1,4]dioxine-6-carboxamido)-2-methylphenyl)-2-methyl-1,2,3,4-tetrahydroquinoline-6-carboxamide To a stirring suspension of Example 39 (124 mg, 0.273 mmol) in ethanol (9.6 mL) and ethyl acetate (7.2 mL) was added 10 drops glacial AcOH. The reaction was flushed with argon and 10% Pd on activated carbon (60 mg, 0.273 mmol) was added. The reaction flask was flushed with $H_2$, heated to 50° C. and left to stir under 1 atm. $H_2$ for 24 h. Further glacial AcOH (5 drops) was added and the reaction allowed to stir for 48 h. The reaction mixture was filtered through celite and the filtrate concentrated in vacuo. The resulting residue was purified by column chromatography using a gradient of 13 to 25% EtOAc/DCM to afford the racemic product as an off-white solid (69 mg). This material was then separated into individual enantiomers by chiral HPLC to afford the title compound as a pale yellow solid (11 mg, 9%). $^1$H NMR (500 MHz, DMSO-d6) δ 10.01 (s, 1H), 9.34 (s, 1H), 7.77 (d, J=2.2 Hz, 1H), 7.56 (s, 1H), 7.55-7.54 (m, 1H), 7.53 (d, J=2.1 Hz, 1H), 7.50 (dd, J=8.4, 2.2 Hz, 1H), 7.17 (d, J=8.5 Hz, 1H), 6.97 (d, J=8.4 Hz, 1H), 6.49 (d, J=8.2 Hz, 1H), 6.28 (s, 1H), 4.35-4.25 (m, 4H), 3.42-3.36 (m, 1H), 2.81-2.66 (m, 2H), 2.16 (s, 3H), 1.92-1.86 (m, 1H), 1.49-1.39 (m, 1H), 1.17 (d, J=6.3 Hz, 3H). HRMS (ESI$^+$): calcd for $C_{27}H_{28}N_3O_4$ (M+H)$^+$, 458.2074; found 458.2058. As measured by chiral HPLC 95.7% pure, >99% ee. Absolute stereochemistry unknown.

Example 155, (R)—N-(5-(2,3-dihydrobenzo[b][1,4]dioxine-6-carboxamido)-2-methylphenyl)-2-methyl-1,2,3,4-tetrahydroquinoline-6-carboxamide Following the same procedure outlined for Example 154, the opposite enantiomer was also isolated by chiral HPLC to afford the title compound as a pale yellow solid (11 mg, 9%). $^1$H NMR (500 MHz, DMSO-d6) δ 10.01 (s, 1H), 9.34 (s, 1H), 7.77 (d, J=2.2 Hz, 1H), 7.56 (s, 1H), 7.55-7.54 (m, 1H), 7.53 (d, J=2.1 Hz, 1H), 7.50 (dd, J=8.4, 2.2 Hz, 1H), 7.17 (d, J=8.5 Hz, 1H), 6.97 (d, J=8.4 Hz, 1H), 6.49 (d, J=8.2 Hz, 1H), 6.28 (s, 1H), 4.35-4.25 (m, 4H), 3.42-3.36 (m, 1H), 2.81-2.66 (m, 2H), 2.16 (s, 3H), 1.92-1.86 (m, 1H), 1.49-1.39 (m, 1H), 1.17 (d, J=6.3 Hz, 3H). HRMS (ESI$^+$): calcd for $C_{27}H_{28}N_3O_4$ (M+H)$^+$, 458.2074; found 458.2055. As measured by chiral HPLC 99% pure, 97.4% ee. Absolute stereochemistry unknown.

Preparation of Compound 195, 6-bromo-3-(2-(pyrrolidin-1-yl)ethoxy)isoquinoline

To a stirring suspension of sodium hydride (142 mg, 3.56 mmol) in anhydrous THF (10 mL) at 0° C. under argon was drop-wise added 1-(2-hydroxyethyl)pyrrolidine (0.434 mL, 3.71 mmol). The reaction was allowed to stir at 0° C. for 10 min, then allowed to warm to room temperature over 30 min. 6-Bromo-3-chloroisoquinoline (750 mg, 3.09 mmol) was added and the reaction heated to 70° C. for 18 h. The reaction was diluted with sat. $NaHCO_3$ aq. (30 ml) and the THF removed in vacuo. The aqueous layer was extracted with EtOAc (3×20 ml). The combined organic layer was washed with brine (20 ml), dried (Na$_2$SO$_4$) and concentrated in vacuo. Purification by biotage chromatography using a gradient of 3 to 30% MeOH/DCM afforded the title compound as a waxy brown solid (300 mg, 30%). $^1$H NMR (500 MHz, Chloroform-d) δ 8.90 (s, 1H), 7.87 (d, J=1.4 Hz, 1H), 7.74 (d, J=8.8 Hz, 1H), 7.45 (dd, J=8.8, 1.8 Hz, 1H), 6.96 (s, 1H), 4.57 (t, J=5.8 Hz, 2H), 3.03 (t, J=5.8 Hz, 2H), 2.79-2.73 (m, 4H), 1.89-1.85 (m, 4H). HRMS (ESI$^+$): calcd for C$_{15}$H$_{18}$$^{79}$BrN$_2$O (M+H)$^+$, 321.0603; found 321.0597.

Example 156, N-(5-(2,3-dihydrobenzo[b][1,4]dioxine-6-carboxamido)-2-methylphenyl)-3-(2-(pyrrolidin-1-yl)ethoxy)isoquinoline-6-carboxamide Tetraethylammonium chloride (25.8 mg, 0.156 mmol) and molybdenum hexacarbonyl (41.1 mg, 0.156 mmol) were combined in anhydrous dioxane (0.5 mL). The reaction was heated to 140° C. for 2 min to form the active catalyst. Compound 2 (89 mg, 0.311 mmol) and Example 155 (50 mg, 0.156 mmol) were then added and the reaction heated to 130° C. for 4 h in a MW. The reaction mixture was taken up in a mixture of EtOAc and MeOH and the solvents removed in vacuo to afford a black solid. The crude material was taken up in DCM/MeOH and dry-loaded onto silica. Purification by column chromatography using a gradient of 2 to 10% MeOH/DCM afforded the title compound as a yellow solid (24 mg, 28%). $^1$H NMR (500 MHz, DMSO-d6) δ 10.21 (s, 1H), 10.10 (s, 1H), 9.21 (s, 1H), 8.49 (s, 1H), 8.21 (d, J=8.7 Hz, 1H), 7.96 (dd, J=8.6, 1.3 Hz, 1H), 7.90 (d, J=2.0 Hz, 1H), 7.58 (dd, J=8.3, 2.2 Hz, 1H), 7.55 (d, J=2.1 Hz, 1H), 7.52 (dd, J=8.4, 2.2 Hz, 1H), 7.42 (s, 1H), 7.26 (d, J=8.5 Hz, 1H), 6.99 (d, J=8.4 Hz, 1H), 4.63 (t, J=4.9 Hz, 3H), 4.35-4.29 (m, 4H), 3.18-3.06 (m, 4H), 2.25 (s, 3H), 1.93-1.85 (m, 4H) (Note: 1 CH$_2$ hidden under water peak). HRMS (ESI$^+$): calcd for C$_{32}$H$_{33}$N$_4$O$_5$ (M+H)$^+$, 553.2445; found 553.2435.

Preparation of Compound 196, ethyl 5-allylquinoline-3-carboxylate

Tetrakis(triphenylphosphine) palladium(O) (1165 mg, 1.008 mmol) was added to a stirring, degassed (3× vacuum/argon cycles) solution of ethyl 5-chloroquinoline-3-carboxylate (950 mg, 4.03 mmol), allyl tributylstannane (3.75 mL, 12.09 mmol) and lithium chloride (514 mg, 12.09 mmol) in DMF (40 mL) and the reaction heated to 110° C. for 23 h. The reaction mixture was concentrated under high vacuum to remove most of the DMF. The residue was then poured into water (100 ml) and extracted with EtOAc (50 ml). The organic layer was washed with water (50 ml), brine (50 ml) and dried (Na$_2$SO$_4$). Purification by column chromatography using a gradient of 0 to 40% EtOAc/cyclohexane afforded the title compound as a yellow oil (520 mg, 54%). $^1$H NMR (500 MHz, Chloroform-d) δ 9.45 (d, J=2.0 Hz, 1H), 9.07 (dd, J=2.0, 0.8 Hz, 2H), 8.06 (d, J=8.5 Hz, 1H), 7.77 (dd, J=8.5, 7.1 Hz, 1H), 7.49 (d, J=6.7 Hz, 1H), 6.11 (ddt, J=16.5, 10.2, 6.3 Hz, 1H), 5.18 (dq, J=10.1, 1.4 Hz, 2H), 5.10 (dq, J=17.1, 1.6 Hz, 1H), 4.50 (q, J=7.1 Hz, 2H), 3.91 (d, J=6.2 Hz, 3H), 1.48 (t, J=7.1 Hz, 3H).

Preparation of Compound 197, ethyl 5-(2,3-dihydroxypropyl)quinoline-3-carboxylate To a stirring solution of compound 196 (397 mg, 1.645 mmol) and osmium tetroxide (20.91 mg, 0.082 mmol) in acetone (14 mL) and water (1.4 mL) was added NMO (N-Methyl morpholine N-oxide) (289 mg, 2.468 mmol). The reaction was left to stir for 18 h. Saturated sodium sulfate aq. was added to the solution (10 ml) and the reaction allowed to stir for 1.5 h. A precipitate formed. The aqueous layer was extracted with EtOAc (3×30 ml) and the combined organic layer washed with brine (20 ml), dried (Na$_2$SO$_4$) and concentrated in vacuo to afford the title compound as a yellow semi-solid (282 mg, 62%). This material was used as crude directly in the next reaction. HRMS (ESI$^+$): calcd for C$_5$H$_{17}$NO$_4$ (M+H)$^+$, 276.1236; found 276.1248.

Preparation of Compound 198, ethyl 5-(2-oxoethyl)quinoline-3-carboxylate

To a stirring solution of Compound 197 (277 mg, 1.006 mmol) in MeOH (8.6 mL) and THF (3.5 mL) at 0° C. was added a solution of sodium periodate (323 mg, 1.509 mmol) in water (8.60 mL). The reaction was allowed to warm to room temperature and left to stir for 1.25 h. The reaction was diluted with EtOAc (50 ml), washed with water (30 ml)—brine was added to clear, extracted with a further portion of EtOAc (30 ml). The combined organic layer was washed with brine (30 ml), dried (Na$_2$SO$_4$) and concentrated in vacuo to afford the crude product as a yellow oil (245 mg, 100%). $^1$H NMR (500 MHz, Chloroform-d) δ 9.89 (t, J=1.9 Hz, 1H), 9.49 (d, J=2.0 Hz, 1H), 8.89 (dd, J=1.9, 0.8 Hz, 1H), 8.17 (d, J=8.5 Hz, 2H), 7.83 (dd, J=8.5, 7.1 Hz, 1H), 7.54 (d, J=7.0 Hz, 1H), 4.51 (q, J=7.1 Hz, 2H), 4.25 (d, J=1.8 Hz, 2H), 1.48 (t, J=7.2 Hz, 3H). HRMS (ESI$^+$): calcd for C$_{14}$H$_{14}$NO$_4$ (M+H)$^+$, 244.0794; found 244.0972.

Preparation of Compound 199, ethyl 5-(2-hydroxypropyl)quinoline-3-carboxylate

To a stirring solution of Compound 198 (245 mg, 1.007 mmol) in ethanol (6.5 mL) and water (3.25 mL) at 0° C. was added sodium borohydride (191 mg, 5.04 mmol) and the reaction left to stir at 0° C. for 2.5 h. The reaction mixture was diluted with water (30 ml), and extracted with EtOAc (2×25 ml)—brine was added to clear. The combined organic layer was washed with brine (20 ml), dried (Na$_2$SO$_4$) and concentrated in vacuo. Purification by biotage chromatography using a gradient of 6 to 80% EtOAc/DCM afforded the title compound as a pale orange solid (99 mg, 40%). $^1$H NMR (500 MHz, Chloroform-d) δ 9.42 (d, J=2.0 Hz, 1H), 9.09 (dd, J=2.0, 0.8 Hz, 2H), 8.03 (d, J=8.5 Hz, 1H), 7.76 (dd, J=8.5, 7.1 Hz, 1H), 7.55 (br d, J=7.0 Hz, 1H), 4.52 (q, J=7.1 Hz, 2H), 4.05 (t, J=6.4 Hz, 2H), 3.51 (s, 1H, OH), 3.43 (t, J=6.6 Hz, 2H), 1.49 (t, J=7.1 Hz, 3H). HRMS (ESI$^+$): calcd for C$_{14}$H$_{16}$NO$_3$ (M+H)$^+$, 246.1130; found 246.1142.

Preparation of Compound 200, ethyl 5-(2-((tert-butyldimethylsilyl)oxy)ethyl)quinoline-3-carboxylate To a solution of Compound 199 (89 mg, 0.363 mmol) in anhydrous DCM (3.5 mL) was added imidazole (37.1 mg, 0.544 mmol) followed by tert-butyldimethylsilyl chloride (62.9 mg, 0.417 mmol). The reaction was stirred at room temperature for 2 h, then diluted with DCM (10 mL) and washed with water (1×10 mL), 0.25 M HCl (1×10 mL), brine (1×10 mL), dried (MgSO$_4$) and concentrated in vacuo. Purification by biotage chromatography using a gradient of 2 to 20% EtOAc/cyclohexane gave the title compound as a colourless oil (33 mg, 25%). $^1$H NMR (500 MHz, Chloroform-d) δ 9.44 (d, J=2.0 Hz, 1H), 9.10 (dd, J=2.0 Hz, 2H), 8.04 (d, J=8.5 Hz, 1H), 7.75 (dd, J=8.5, 7.1 Hz, 1H), 7.49 (d, J=6.5 Hz, 1H), 4.49 (q, J=7.1 Hz, 2H), 3.94 (t, J=6.7 Hz, 2H), 3.34 (t, J=6.7 Hz, 2H), 1.47 (t, J=7.1 Hz, 3H), 0.80 (s, 9H), −0.10 (s, 6H). HRMS (ESI$^+$): calcd for $C_{20}H_{30}NO_3Si$ (M+H)$^+$, 360.1995; found 360.2009.

Preparation of Compound 201, 5-(2-((tert-butyldimethylsilyl)oxy)ethyl)quinoline-3-carboxylic acid To a stirring solution of Compound 200 (30 mg, 0.083 mmol) in THF (0.6 mL) and MeOH (0.2 mL) was added a solution of 2M NaOH aq. (0.083 mL, 0.167 mmol). The reaction was left to stir for 15.5 h, then diluted with water (15 ml) and the solution made acidic by the addition of 1 M HCl aq. (to ~pH 3). The aqueous layer was extracted with EtOAc (2×15 ml). The combined organic layer was washed with water (15 ml), brine (15 ml) and dried (Na$_2$SO$_4$), then concentrated in vacuo to afford the title compound as a white solid (25.5 mg, 92%). $^1$H NMR (500 MHz, Chloroform-d) δ 9.59 (s, 1H), 9.29 (s, 1H), 8.17 (d, J=8.4 Hz, 1H), 7.83 (dd, J=8.4, 7.1 Hz, 1H), 7.56 (d, J=6.9 Hz, 1H), 4.00 (t, J=6.6 Hz, 2H), 3.40 (t, J=6.6 Hz, 2H), 0.82 (s, 9H), −0.08 (s, 6H). HRMS (ESI$^+$): calcd for $C_{18}H_{25}NO_3Si$ (M+H)$^+$, 332.1682; found 332.1680.

Preparation of Compound 202, 5-(2-((tert-butyldimethylsilyl)oxy)ethyl)-N-(5-(2,3-dihydrobenzo[b][1,4]dioxine-6-carboxamido)-2-methylphenyl)quinoline-3-carboxamide To a stirring solution of Compound 201 (23 mg, 0.069 mmol) in DMF (0.7 mL) at room temperature under argon was added DIEA (0.039 mL, 0.222 mmol), followed by HATU (34.3 mg, 0.090 mmol). The reaction was allowed to stir for 5 min before Compound 2 (23.67 mg, 0.083 mmol) was added. The reaction was allowed to stir at room temperature for 15.5 h, then poured into water (20 ml) and extracted with EtOAc (20 ml)—brine was added to clear. The organic layer was washed with a further portion of brine (20 ml), dried (Na$_2$SO$_4$) and concentrated in vacuo to afford a yellow oil. Purification by column chromatography using a gradient of 10 to 50% EtOAc/DCM gave the title compound as a pale yellow foam (34 mg, 82%). $^1$H NMR (500 MHz, Chloroform-d) δ 9.36 (d, J=2.0 Hz, 1H), 9.02-8.99 (br s, 1H), 8.13-8.11 (br s, 1H), 8.06 (d, J=8.5 Hz, 1H), 7.98 (s, 1H), 7.85 (s, 1H), 7.76 (dd, J=8.5, 7.1 Hz, 1H), 7.66 (dd, J=8.3, 2.2 Hz, 1H), 7.53 (br d, J=7.1 Hz, 1H), 7.43 (d, J=2.2 Hz, 1H), 7.37 (dd, J=8.4, 2.2 Hz, 1H), 7.24 (d, J=8.4 Hz, 1H), 6.93 (d, J=8.4 Hz, 1H), 4.35-4.26 (m, 4H), 3.97 (t, J=6.5 Hz, 2H), 3.35 (t, J=6.5 Hz, 2H), 2.35 (s, 3H), 0.77 (s, 9H), −0.14 (s, 6H). HRMS (ESI$^+$): calcd for $C_{34}H_{40}N_3O_5Si$ (M+H)$^+$, 598.2737; found 598.2715.

Example 157, N-(5-(2,3-dihydrobenzo[b][1,4]dioxine-6-carboxamido)-2-methylphenyl)-5-(2-hydroxyethyl)quinoline-3-carboxamide To a stirring solution of Compound 202 (31 mg, 0.052 mmol) in THF (1.5 mL) at room temperature under argon was slowly added TBAF (1M in THF, 0.078 mL, 0.078 mmol). The reaction was allowed to stir for 3.75 h. The reaction was diluted with water (20 ml) and the resulting precipitate was collected by filtration, washed with water and dried under vacuum to afford the title compound as a white solid (9 mg, 36%). $^1$H NMR (500 MHz, DMSO-d6) δ 10.36 (s, 1H), 10.10 (s, 1H), 9.39 (d, J=1.8 Hz, 1H), 9.15 (s, 1H), 7.99 (d, J=8.4 Hz, 1H), 7.93 (d, J=1.8 Hz, 1H), 7.82 (dd, J=8.4, 7.2 Hz, 1H), 7.64-7.58 (m, 2H), 7.55 (d, J=2.1 Hz, 1H), 7.53 (dd, J=8.4, 2.1 Hz, 1H), 7.28 (d, J=8.4 Hz, 1H), 7.00 (d, J=8.4 Hz, 1H), 4.82 (t, J=5.3 Hz, 1H), 4.35-4.29 (m, 4H), 3.79 (q, J=6.7 Hz, 2H), 2.27 (s, 3H). HRMS (ESI$^+$): calcd for $C_{28}H_{26}N_3O_5$ (M+H)$^+$, 484.1867; found 484.1851.

Preparation of Compound 203, ethyl 5-(2-(pyrrolidin-1-yl)ethyl)quinoline-3-carboxylate To a stirring solution of Compound 198 (45 mg, 0.185 mmol) in CHCl$_3$ (2 mL) at room temperature under nitrogen was added acetic acid (10.58 µL, 0.185 mmol), followed by pyrrolidine (0.020 mL, 0.240 mmol). Sodium triacetoxyborohydride (43.1 mg, 0.203 mmol) was then added and the reaction left to stir at room temperature for 16.5 h. The reaction was diluted with CHCl$_3$ (30 ml) and washed with brine (20 ml). The aqueous layer was extracted with a further portion of CHCl$_3$ (20 ml) and the combined organic layer dried (Na$_2$SO$_4$) and concentrated in vacuo. Purification by column chromatography using a gradient of 2 to 10% MeOH/DCM+2% 2M NH$_3$ in MeOH gave the title compound as a yellow oil (10 mg, 18%). $^1$H NMR (500 MHz, Chloroform-d) δ 9.46 (d, J=2.0 Hz, 1H), 9.10-9.08 (m, 1H), 8.08 (d, J=8.5 Hz, 1H), 7.77 (dd, J=8.5, 7.2 Hz, 1H), 7.57 (d, J=7.0 Hz, 1H), 4.51 (q, J=7.2 Hz, 2H), 3.61-3.54 (m, 2H), 3.15-3.06 (m, 3H), 3.05-2.95 (s, 4H), 2.04-2.00 (m, 4H), 1.49 (t, J=7.1 Hz, 3H). HRMS (ESI$^+$): calcd for $C_{18}H_{22}N_2O_2$ (M+H)$^+$, 299.1760; found 299.1757.

Example 158, N-(5-(2,3-dihydrobenzo[b][1,4]dioxine-6-carboxamido)-2-methylphenyl)-5-(2-(pyrrolidin-1-yl)ethyl)quinoline-3-carboxamide To a stirring solution of Compound 203 (10 mg, 0.034 mmol) in THF (0.3 mL) and MeOH (0.1 mL) was added 2M NaOH aq. (0.034 mL, 0.067 mmol). The reaction was left to stir at room temperature for 17.5 h, then the solvents were removed in vacuo. The resulting residue was taken up in water (15 ml) and made acidic using 1M HCl aq. (to ~pH 3). The organic layer was washed with EtOAc (10 ml) and the aqueous layer was concentrated in vacuo to afford 5-(2-(pyrrolidin-1-yl)ethyl)quinoline-3-carboxylic acid as a brown solid. To a stirring solution of 5-(2-(pyrrolidin-1-yl) ethyl)quinoline-3-carboxylic acid (11 mg, 0.036 mmol) in DMF (0.4 mL) at room temperature under argon was added DIEA (0.026 mL, 0.151 mmol), followed by HATU (17.72 mg, 0.047 mmol). The reaction was allowed to stir for 5 min before Compound 2 (11.21 mg, 0.039 mmol) was added. The reaction was allowed to stir for 24 h. Further HATU (17.72 mg, 0.047 mmol) and DIEA (0.026 mL, 0.151 mmol) were added and the reaction left to stir for a 5.5 h. The reaction mixture was diluted with water (20 ml) and extracted with EtOAc (2×20 ml)—brine was added to clear. The combined organic layer was washed with brine (20 ml), dried (Na$_2$SO$_4$) and concentrated in vacuo. Purification by column chromatography using a gradient of 0 to 10% MeOH/DCM+0.5% 2M NH$_3$ in MeOH gave the title compound as a yellow glass (8 mg, 42%). $^1$H NMR (500 MHz, DMSO-d6) δ 10.34 (s, 1H), 10.10 (s, 1H), 9.41 (br s, 1H), 9.12 (br s, 1H), 8.04 (d, J=8.4 Hz, 1H), 7.99 (s, 1H), 7.88-7.83 (m, 1H), 7.66 (d, J=7.1 Hz, 1H), 7.55-7.47 (m, 3H), 7.27 (d, J=8.4 Hz, 1H), 6.99 (d, J=8.4 Hz, 1H), 4.34-4.28 (m, 4H), 3.58-3.46 (m, 2H), 2.94-2.86 (m, 2H), 2.28 (s, 3H) 2.00-1.80 (4H, m). Note: 4H under H$_2$O peak. HRMS (ESI$^+$): calcd for $C_{32}H_{32}N_4O_4$ (M+H)*, 537.2502; found 537.2485.

Example 159, N-(5-(2,3-dihydrobenzo[b][1,4]diox-ine-6-carboxamido)-2-methylphenyl)-1,2-dimethyl-1,2,3,4-tetrahydroquinoline-6-carboxamide To a stirring suspension of Example 39 (125 mg, 0.276 mmol) in MeOH (9.6 mL) and ethyl acetate (7.2 mL) was added glacial AcOH (10 drops). The reaction mixture was sonicated and to dissolve all solids. The flask was flushed with argon and 10% Pd on activated carbon (0.060 g, 0.276 mmol) was added. The flask was then purged with $H_2$ and the reaction heated to 40° C. under 1 atm $H_2$ for 4 days. Over this time period two further portions of 10% Pd on activated carbon (0.060 g, 0.276 mmol) and glacial AcOH (5 drops) were added to drive the reaction to completion. The reaction mixture was filtered through celite and concentrated in vacuo. Purification by biotage chromatography using a gradient of 6 to 100% EtOAc/DCM afforded the title compound as a white solid (25 mg, 19%). $^1$H NMR (500 MHz, DMSO-d6) δ 10.04 (s, 1H), 9.44 (s, 1H), 7.78 (d, J=2.1 Hz, 1H), 7.72 (dd, J=8.6, 2.2 Hz, 1H), 7.63 (d, J=1.9 Hz, 1H), 7.57-7.53 (m, 3H), 7.52 (d, J=2.2 Hz, 1H), 7.51 (dd, J=8.4, 2.2 Hz, 1H), 7.19 (d, J=8.5 Hz, 1H) 6.99 (d, J=8.4 Hz, 1H), 6.57 (d, J=8.8 Hz, 1H), 4.35-4.28 (m, 4H), 3.58-3.52 (m, 1H), 2.94 (s, 3H), 2.88-2.79 (m, 1H), 2.74-2.67 (m, 1H), 2.18 (s, 3H), 1.92-1.74 (m, 2H), 1.12 (d, J=6.5 Hz, 3H). HRMS (ESI$^+$): calcd for $C_{28}H_{30}N_3O_4$ (M+H)$^+$, 472.2231; found 472.2210.

Example 160, N-(5-(2,3-dihydrobenzo[b][1,4]diox-ine-6-carboxamido)-2-methylphenyl)-8-(2-methoxy-ethoxy)quinoline-6-carboxamide To a stirring suspension of NaH (55.8 mg, 1.395 mmol) in NMP (2.0 mL) in a microwave vial at 0° C. under argon was slowly added 2-methoxyethanol (0.114 mL, 1.456 mmol). The reaction was allowed to warm slowly to room temperature over 1 h. Compound 153 (100 mg, 0.404 mmol) was added and the reaction mixture heated to 140° C. for 15 min. The reaction was diluted with water (30 ml) and acidified with 1 M HCl aq. (to ~pH 3). The aqueous layer was extracted with DCM (3×15 ml) and the combined organic layer washed with water (2×15 ml), dried (Na$_2$SO$_4$) and concentrated in vacuo to afford the crude product as a yellow oil. The crude material was purified by SCX chromatography (eluting with MeOH then 10% 2M NH$_3$ in MeOH) to afford 8-(2-methoxyethoxy)quinoline-6-carboxylic acid as a pale yellow solid. HATU (200 mg, 0.525 mmol) was added to a stirring solution of 8-(2-methoxyethoxy)quinoline-6-carboxylic acid (100 mg, 0.404 mmol) and DIEA (0.225 mL, 1.293 mmol) in DMF (4.0 mL) at room temperature under argon. The reaction was allowed to stir for 5 min before Compound 2 (115 mg, 0.404 mmol) was added. The reaction was allowed to stir at room temperature for 22 h, then diluted with water (30 ml) and extracted with EtOAc (3×15 ml)—brine was added to clear. The combined organic layer was washed with brine (2×20 ml), dried (Na$_2$SO$_4$) and concentrated in vacuo. Purification by column chromatography using a gradient of 20 to 50% EtOAc/DCM, then 10% MeOH/DCM gave the title compound as a pale yellow solid (41 mg, 20%). $^1$H NMR (500 MHz, Methanol-d4) δ 8.92 (dd, J=4.3, 1.7 Hz, 1H), 8.47 (dd, J=8.4, 1.6 Hz, 1H), 8.18 (d, J=1.4 Hz, 1H), 7.81 (d, J=2.2 Hz, 1H), 7.73 (br s, 1H), 7.66 (dd, J=8.3, 4.3 Hz, 1H), 7.52 (dd, J=8.3, 2.2 Hz, 1H), 7.48-7.44 (m, 2H), 7.29 (d, J=8.4 Hz, 1H), 6.93 (d, J=8.4 Hz, 1H), 4.48-4.44 (m, 2H), 4.32- 4.26 (m, 4H), 3.99-3.95 (m, 2H), 3.48 (s, 3H), 2.32 (s, 3H). HRMS (ESI$^+$): calcd for $C_{29}H_{28}N_3O_6$ (M+H)$^+$, 514.1973; found 514.1965.

Preparation of Compound 204, 5-allylquinoline-3-carboxylic acid

To a stirring solution of Compound 196 (73 mg, 0.303 mmol) in THF (1.8 mL) and MeOH (0.6 mL) was added 2M NaOH aq. (0.303 mL, 0.605 mmol). The reaction was allowed to stir at room temperature for 19 h, then the solvents were removed in vacuo. The resulting residue was taken up in water (25 ml) and acidified with 1 M HCl aq. (to ~pH2/3). The aqueous layer was extracted with EtOAc (2×20 ml) and the organic layer was washed with 1 M NaOH (2×20 ml) and once with water (10 ml). The combined aqueous layer was acidified (to ~pH 2/3) and extracted with EtOAc (2×20 ml). The combined organic layer was washed with brine (20 ml) and dried (Na$_2$SO$_4$) to afford the title compound as a yellow/brown oil (32 mg, 50%). This material was used without any further purification. HRMS (ESI$^+$): calcd for $C_{13}H_{12}NO$ (M+H)$^+$, 214.0868; found 214.0866.

Example 161, 5-allyl-N-(5-(2,3-dihydrobenzo[b][1,4]dioxine-6-carboxamido)-2-methylphenyl)quinoline-3-carboxamide To a stirring solution of Compound 204 (29 mg, 0.136 mmol) in DMF (1.2 mL) at room temperature under argon was added DIEA (0.047 mL, 0.272 mmol), followed by HATU (61.1 mg, 0.161 mmol). The reaction was allowed to stir for 5 min before Compound 2 (35.2 mg, 0.124 mmol) was added. The reaction was allowed to stir for 18.5 h, then diluted with water and the resulting precipitate collected by filtration and washed with water. The sample was air dried for 1 h, then dried under vacuum to afford the title compound as a beige solid (39 mg, 66%). $^1$H NMR (500 MHz, DMSO-d6) δ 10.34 (s, 1H), 10.10 (s, 1H), 9.41 (d, J=1.7 Hz, 1H), 9.12 (br s, 1H), 8.01 (d, J=8.4 Hz, 1H), 7.94-7.91 (m, 1H), 7.84 (dd, J=8.3, 7.2 Hz, 1H), 7.63-7.51 (m, 5H), 7.28 (d, J=8.4 Hz, 1H), 7.00 (d, J=8.4 Hz, 1H), 6.21-6.11 (m, 1H), 5.16-5.10 (m, 2H), 4.35-4.29 (m, 4H), 4.00-3.96 (m, 2H), 2.27 (s, 3H). HRMS (ESI$^+$): calcd for $C_{28}H_{26}N_3O_4$ (M+H)$^+$, 480.1918; found 480.1895.

Preparation of Compound 205, butyl 8-((2-(dimethylamino)ethyl)(methyl)amino)quinoline-6-carboxylate To a stirring solution of Compound 153 (119 mg, 0.481 mmol) in anhydrous NMP (3.0 mL) was added N,N,N'-trimethylenediamine (0.320 mL, 2.406 mmol). The reaction was heated to 140° C. in a microwave for 10.75 h. The reaction mixture was partitioned between EtOAc (30 ml) and sat. NaHCO$_3$ aq. (30 ml). The aqueous layer was extracted with further EtOAc (2×20 ml) and the combined organic layer was washed with water (2×20 ml), brine (20 ml), dried Na$_2$SO$_4$ and concentrated in vacuo to afford the crude product as a yellow/brown oil. Purification by column chromatography using a gradient of 5 to 10% MeOH/DCM+5% 2M NH$_3$ in MeOH gave the title compound as a yellow oil (60 mg, 38%). $^1$H NMR (500 MHz, Chloroform-d) b 8.96-8.92 (m, 1H), 8.21 (dd, J=8.3, 1.8 Hz, 1H), 8.11 (d, J=1.7 Hz, 1H), 7.70 (d, J=1.7 Hz, 1H), 7.44 (dd, J=8.3, 4.2 Hz, 1H), 4.40 (t, J=6.7 Hz, 2H), 3.76-3.67 (m, 2H), 3.12 (s, 3H), 2.75-2.66 (m, 2H), 2.29 (s, 3H), 1.85-1.79 (m, 2H), 1.58-1.49 (m, 2H), 1.03 (t, J=7.4 Hz, 4H). HRMS (ESI$^+$): calcd for $C_{19}H_{28}N_3O_2$ (M+H)$^+$, 330.2183; found 330.2195.

Preparation of Compound 206, 8-((2-(dimethylamino)ethyl)(methyl)amino)quinoline-6-carboxylic acid hydrochloride salt A solution of Compound 205 (55 mg, 0.167 mmol) in 6M HCl aq. (1.0 mL, 0.167 mmol) was heated to 80° C. for 5 h, after this time the starting material had been consumed as indicated by LCMS. Therefore the solvents were removed in vacuo and remaining traces of water were removed by co-evaporation with MeCN, then toluene to afford the title compound as a yellow solid. This material was used in the next reaction without further purification. $^1$H NMR (500 MHz, Methanol-d4) δ 9.33-9.28 (m, 2H), 8.81 (br s, 1H), 8.45 (br s, 1H), 8.23-8.18 (m, 1H), 3.69 (t, J=5.6 Hz, 1H), 3.61 (t, J=5.5 Hz, 1H), 2.95 (s, 6H), 2.94 (s, 3H). HRMS (ESI$^+$): calcd for $C_{15}H_{20}N_3O_2$ (M+H)$^+$, 274.1556; found 274.1555.

Example 162, N-(5-(2,3-dihydrobenzo[b][1,4]dioxine-6-carboxamido)-2-methylphenyl)-8-((2-(dimethylamino)ethyl)(methyl)amino)quinoline-6-carboxamide To a stirring solution of Compound 206 (51.7 mg, 0.167 mmol) in DMF (2.0 mL) at room temperature under argon was added DIEA (0.151 mL, 0.868 mmol), followed by HATU (82 mg, 0.217 mmol). The reaction was allowed to stir for 5 min before Compound 2 (47.4 mg, 0.167 mmol) was added. The reaction was allowed to stir for 15.5 h. The reaction mixture was partitioned between water (20 ml) and EtOAc (20 ml). Brine (10 ml) was added to the aqueous layer which was further extracted with EtOAc (2×20 ml). The combined organic layer was washed with brine (20 ml), dried Na$_2$SO$_4$ and concentrated in vacuo. Traces of DMF were removed by co-evaporation with heptane, to afford the crude product as a yellow/brown oil. Purification by column chromatography using a gradient of 3 to 10% MeOH/DCM, then 10% MeOH/DCM+2 to 5% 2M NH$_3$ in MeOH gave the title compound as a pale orange solid (56 mg, 62%). $^1$H NMR (500 MHz, DMSO-d6) δ 10.10 (s, 1H), 10.07 (s, 1H), 8.94-8.90 (m, 1H), 8.44 (d, J=8.3 Hz, 1H), 8.09 (s, 1H), 7.88 (d, J=1.6 Hz, 1H), 7.62-7.55 (m, 3H), 7.54 (d, J=2.1 Hz, 1H), 7.51 (dd, J=8.4, 2.1 Hz, 1H), 7.25 (d, J=8.4 Hz, 1H), 6.98 (d, J=8.4 Hz, 1H), 4.34-4.28 (m, 4H), 3.75 (t, J=6.4 Hz, 2H), 3.07 (s, 3H), 2.78 (m, 2H), 2.33 (br s, 6H), 2.24 (s, 3H). HRMS (ESI$^+$): calcd for $C_{31}H_{33}N_5O_4$ (M+H)$^+$, 541.2636; found 541.2628.

Preparation of Compound 207, 3-((6-bromoquinolin-2-yl)(methyl)amino)propanenitrile 6-Bromo-2-chloroquinoline (250 mg, 1.031 mmol) and N-methyl-beta-alanine nitrile (0.482 mL, 5.15 mmol) in NMP (10 mL) were heated to 140° C. in the microwave for 5 h. The reaction mixture was poured into sat. NaHCO$_3$ aq. (50 ml) and extracted with EtOAc (3×50 ml)—further water and brine had to be added in order to clear the aqueous layer. The combined organic layer was washed with water (2×50 ml), brine (50 ml) and concentrated in vacuo to give a pale brown semi-solid. Purification by biotage chromatography using a gradient of 5 to 40% MeOH/DCM gave the title compound as a yellow solid (193 mg, 32%). $^1$H NMR (500 MHz, Chloroform-d) δ 7.86 (d, J=9.1 Hz, 1H), 7.78 (d, J=2.2 Hz, 1H), 7.62 (dd, J=8.9, 2.2 Hz, 1H), 7.57 (d, J=8.9 Hz, 1H), 6.93 (d, J=9.1 Hz, 1H), 4.05 (t, J=6.5 Hz, 2H), 3.31 (s, 3H), 2.86 (t, J=6.5 Hz, 2H). HRMS (ESI$^+$): calcd for $C_{13}H_{13}{}^{79}BrN_3$ (M+H)$^+$, 290.0287; found 290.0283.

Preparation of Compound 208, 2-(trimethylsilyl)ethyl 2-((2-cyanoethyl)(methyl)amino)quinoline-6-carboxylate To a stirring suspension of Compound 207 (100 mg, 0.345 mmol), Hermann's palladacycle (16.2 mg, 0.017 mmol) and tri-t-butylphosphonium tetrafluoroborate (20 mg, 0.069 mmol) in 2-(trimethylsilyl)-ethanol (3.0 mL) was added molybdenum hexacarbonyl (182 mg, 0.689 mmol) followed by DBU (1.0M in THF, 1.03 ml, 1.03 mmol). The reaction mixture was heated to 130° C. in a microwave for 1 h. The reaction mixture was diluted with EtOAc, filtered through celite and concentrated in vacuo. The crude reaction was loaded onto an SCX column and eluted with MeOH, 1% 2M NH$_3$ in MeOH/MeOH, then 10% 2M NH$_3$ in MeOH/MeOH to afford a brown oil. Purification of this oil by biotage chromatography using a gradient of 5 to 40% EtOAc/cyclohexane afforded the title compound as a white solid (84 mg, 69%). $^1$H NMR (500 MHz, Chloroform-d) δ 8.40 (br s, 1H), 8.17 (d, J=8.6 Hz, 1H), 8.02 (d, J=9.1 Hz, 1H), 7.68 (s, 1H), 6.95 (d, J=9.1 Hz, 1H), 4.54-4.39 (m, 2H), 4.13-4.05 (m, 2H), 3.34 (s, 3H), 2.94-2.84 (m, 2H), 1.26-1.07 (m, 2H), 0.12 (s, 9H). HRMS (ESI$^+$): calcd for $C_{19}H_{25}N_3NaO_2Si$ (M+Na)+, 379.1632; found 379.1626.

Preparation of Compound 209, 2-((2-cyanoethyl)(methyl)amino)quinoline-6-carboxylic acid To a stirring solution of Compound 208 (81 mg, 0.228 mmol) in THF (2.5 mL) at room temperature under argon was slowly added TBAF (1.0M in THF, 0.342 mL, 0.342 mmol) and the reaction was allowed to stir for 20.5 h. Water (10 ml) was added and the reaction mixture concentrated to remove THF. The aqueous layer was acidified using 1 M HCl aq. (to ~pH 3) and extracted with EtOAc (3×15 ml)—brine was added to clear. The combined organic layer was washed with brine (10 ml), dried (Na$_2$SO$_4$) and concentrated in vacuo to afford the title compound as a white solid (31 mg, 53%). $^1$H NMR (500 MHz, DMSO-d6) δ 12.77 (s, 1H), 8.38 (d, J=2.0 Hz, 1H), 8.21 (d, J=9.2 Hz, 1H), 8.00 (dd, J=8.7, 2.0 Hz, 1H), 7.58 (d, J=8.7 Hz, 1H), 7.21 (d, J=9.2 Hz, 1H), 3.99 (t, J=6.7 Hz, 2H), 3.23 (s, 3H), 2.89 (t, J=6.7 Hz, 2H).

Preparation of Compound 210, 2-((2-cyanoethyl)(methyl)amino)-N-(5-(2,3-dihydrobenzo[b][1,4]dioxine-6-carboxamido)-2-methylphenyl)quinoline-6-carboxamide To a stirring solution of Compound 209 (27 mg, 0.091 mmol) and DIEA (0.048 mL, 0.273 mmol) in DMF (1 mL) under argon was added HATU (41.5 mg, 0.109 mmol). The reaction was allowed to stir for 3 min before the addition of Compound 2 (31.0 mg, 0.109 mmol). The reaction was allowed to stir at room temperature for 22 h. The reaction mixture was poured into water (25 ml) and the aqueous layer extracted with EtOAc (3×15 ml)—brine was added to clear. The combined organic layer was washed with brine (15 ml) and dried (Na$_2$SO$_4$) to afford the crude product as a beige solid. The solid was dry-loaded onto silica using DCM/MeOH and purified by column chromatography using a gradient of 0 to 10% EtOAc/DCM, then 5 to 10% MeOH/DCM afforded the title compound as a beige solid (44 mg, 93%). ¹H NMR (500 MHz, DMSO-d6) δ 10.06 (s, 1H), 9.93 (s, 1H), 8.42 (d, J=2.0 Hz, 1H), 8.19 (d, J=9.1 Hz, 1H), 8.11 (dd, J=8.8, 2.1 Hz, 1H), 7.85 (d, J=2.1 Hz, 1H), 7.65 (d, J=8.8 Hz, 1H), 7.58 (dd, J=8.3, 2.2 Hz, 1H), 7.54 (d, J=2.1 Hz, 1H), 7.51 (dd, J=8.5, 2.2 Hz, 1H), 7.23 (dd, J=8.8, 3.6 Hz, 2H), 6.98 (d, J=8.4 Hz, 1H), 4.33-4.28 (m, 4H), 4.01 (t, J=6.6 Hz, 2H), 3.24 (s, 3H), 2.91 (t, J=6.7 Hz, 2H), 2.23 (s, 3H). HRMS (ESI⁺): calcd for $C_{30}H_{28}N_5O_4$ (M+H)⁺, 522.2136; found 522.2140.

Example 163, 3-((6-((5-(2,3-dihydrobenzo[b][1,4]dioxine-6-carboxamido)-2-methylphenyl)carbamoyl)quinolin-2-yl)(methyl)amino)propanoic acid To a stirring solution of Compound 210 (20 mg, 0.038 mmol) in THF (0.6 mL) was added hydrogen peroxide (35%, 0.3 mL, 0.038 mmol) and 1 M NaOH aq. (0.3 mL, 0.038 mmol). The reaction was allowed to stir at room temperature for 28.5 h. Further 1 M NaOH aq. (0.3 mL, 0.038 mmol) was added and left to stir for 2 more days. The reaction was diluted with water (10 ml) and the aqueous layer washed with EtOAc (5 ml). The aqueous layer was acidified using 1 M HCl aq. (to ~pH 2) and extracted with EtOAc (3×10 ml)—brine was added to clear. The combined organic layer was washed with brine (10 ml), dried ($Na_2SO_4$) and concentrated in vacuo to afford the product as a beige solid. This material was triturated with ether to afford the title compound as a pale yellow solid (1.6 mg, 8%). ¹H NMR (500 MHz, DMSO-d6) δ 10.07 (s, 1H), 9.92 (s, 1H), 8.39 (d, J=1.9 Hz, 1H), 8.14 (d, J=9.3 Hz, 1H), 8.10 (dd, J=8.7, 2.0 Hz, 1H), 7.85 (d, J=1.9 Hz, 1H), 7.61 (d, J=8.8 Hz, 1H), 7.59 (dd, J=8.1, 1.9 Hz, 1H), 7.55 (d, J=2.1 Hz, 1H), 7.52 (dd, J=8.4, 2.1 Hz, 1H), 7.23 (d, J=8.5 Hz, 1H), 7.18 (d, J=9.2 Hz, 1H), 6.99 (d, J=8.4 Hz, 1H), 4.35-4.29 (m, 4H), 3.91 (t, J=7.2 Hz, 3H), 3.19 (s, 3H), 2.61 (t, J=7.4 Hz, 2H), 2.24 (s, 3H). HRMS (ESI⁺): calcd for $C_{30}H_{29}N_4O_6$ (M+H)⁺, 541.2082; found 541.2075.

Preparation of Compound 211, tert-butyl (4-((6-bromoquinolin-2-yl)oxy)butyl)carbamate NaH (60%) (0.095 g, 2.378 mmol) was added to a solution of 4-(Boc-amino)-1-butanol (0.432 mL, 2.378 mmol) in dry THF (7 mL) at 0° C. The reaction mixture was stirred for 5 min, then allowed to warm to room temperature and stirred for 30 min. 6-Bromo-2-chloroquinoline (0.481 g, 1.981 mmol) was added and the reaction mixture was heated to reflux for 4.5 h. The reaction was allowed to cool, concentrated to remove THF and diluted with water (10 mL) and sat. $NaHCO_3$ aq. (10 mL). The aqueous layer was extracted with DCM (3×10 mL) and the organic phase dried ($MgSO_4$), filtered and concentrated. Purification by biotage chromatography using a gradient of 3 to 30% EtOAc/cyclohexane afforded the title compound as an off-white solid (484 mg, 62%). ¹H NMR (500 MHz, Chloroform-d) δ 7.89 (d, J=8.9 Hz, 1H), 7.86 (d, J=2.0 Hz, 1H), 7.71 (d, J=8.8 Hz, 1H), 7.68 (dd, J=8.9, 2.1 Hz, 1H), 6.91 (d, J=8.9 Hz, 1H), 4.68 (br s, 1H), 4.48 (t, J=6.5 Hz, 2H), 3.24 (q, J=6.0 Hz, 2H), 1.92-1.82 (m, 2H), 1.70 (p, J=7.3 Hz, 2H), 1.46 (s, 9H). HRMS (ESI⁺): calcd for $C_{18}H_{24}^{79}BrN_2O_3$(M+H)⁺, 395.0970; found 395.0695.

Preparation of Compound 212, 2-(4-((tert-butoxycarbonyl)amino)butoxy)quinoline-6-carboxylic acid n-BuLi (2.1 M in hexanes, 0.632 mL, 1.328 mmol) was added drop-wise to a solution of Compound 211 (250 mg, 0.632 mmol) in dry THF (7.5 mL) at −78° C. The reaction was stirred at −78° C. for 40 min before solid $CO_2$ was added. After stirring for few min, the reaction mixture was allowed to warm nearly to room temperature. The reaction mixture was quenched with water (5 mL), then concentrated to remove THF, diluted with water (10 mL), washed with EtOAc (1×10 mL)—with brine was added to clear. The aqueous phase was acidified with 2 M HCl aq. (~to pH 2-3) then extracted with DCM (2×10 mL) and EtOAc (2×10 mL). The combined organic phase was dried ($Na_2SO_4$) and concentrated in vacuo to afford the title compound as a white solid (90 mg, 40%). ¹H NMR (500 MHz, DMSO-d6) δ 13.07 (br s, OH), 8.56 (d, J=1.9 Hz, 1H), 8.41 (d, J=8.8 Hz, 1H), 8.13 (dd, J=8.7, 2.0 Hz, 1H), 7.81 (d, J=8.7 Hz, 1H), 7.09 (d, J=8.9 Hz, 1H), 6.87 (t, J=5.6 Hz, 1H), 4.44 (t, J=6.6 Hz, 2H), 3.00 (q, J=6.7 Hz, 2H), 1.77 (p, J=6.6 Hz, 2H), 1.55 (p, J=7.2 Hz, 2H), 1.38 (s, 9H). HRMS (ESI⁺): calcd for $C_{19}H_{25}N_2O_5$ (M+H)⁺, 361.1763; found 361.1767.

Example 164, tert-butyl (4-((6-((5-(2,3-dihydrobenzo[b][1,4]dioxine-6-carboxamido)-2-methylphenyl)carbamoyl)quinolin-2-yl)oxy)butyl)carbamate HATU (108 mg, 0.283 mmol) was added to a solution of Compound 212 (85 mg, 0.236 mmol) and DIEA (0.123 mL, 0.708 mmol) in dry DMF (2.0 mL). The reaction was allowed to stir for 3 min before Compound 2 (79 mg, 0.236 mmol) was added and the reaction left to stir at room temperature for 19 h. The reaction mixture was diluted with water (20 ml) and the aqueous layer extracted with EtOAc (3×15 ml)—brine was added to clear. The combined organic layer was washed with brine (15 ml), dried ($MgSO_4$) and concentrated in vacuo, remaining traces of DMF were removed by co-evaporation with heptane. Purification by biotage chromatography using a gradient of 5 to 40% EtOAc/DCM afforded a brown gum. The product although otherwise clean, still contained DMF therefore the sample was re-dissolved in EtOAc (15 ml) and washed with water (1×15 ml) and brine (2×15 ml). The organic layer was dried ($MgSO_4$) and concentrated in vacuo. Heptane was used in an attempt to remove any remaining DMF and dried under vacuum to afford the title compound as a brown tacky solid (60 mg, 41%). ¹H NMR (500 MHz, Methanol-d4) δ 8.48 (d, J=1.9 Hz, 1H), 8.26 (d, J=8.9 Hz, 1H), 8.21 (dd, J=8.7, 2.0 Hz, 1H), 7.92 (d, J=8.7 Hz, 1H), 7.80 (d, J=2.2 Hz, 1H), 7.55 (dd, J=8.3, 2.2 Hz, 1H), 7.50 (d, J=2.0 Hz, 1H), 7.49 (d, J=2.2 Hz, 1H), 7.47 (d, J=2.2 Hz, 1H), 7.31 (d, J=8.4 Hz, 1H), 7.05 (d, J=8.9 Hz, 1H), 6.95 (d, J=8.4 Hz, 1H), 4.54 (t, J=6.5 Hz, 2H), 4.34-4.29 (m, 4H), 3.37 (s, 3H), 3.17 (t, J=7.0 Hz, 2H), 2.34 (s, 3H), 1.94-1.86 (m, 2H), 1.74-1.66 (m, 2H), 1.46 (s, 9H). HRMS (ESI⁺): calcd for $C_{35}H_{38}N_4O_7$ (M+H)⁺, 627.2813; found 627.2800.

Preparation of Compound 213, 1-(4-bromo-2-nitrophenyl)-N,N-dimethylmethanamine

To a solution of 4-bromo-2-nitrobenzaldehyde (228 mg, 0.991 mmol) in dichloromethane (10 mL) at room temperature was added dimethylamine (2.0 M in THF, 0.743 mL, 1.487 mmol). The reaction was allowed to stir at room temperature for 1.5 h before $NaBH(OAc)_3$ (315 mg, 1.487 mmol) was added. The reaction mixture was allowed to stir 16 h. Further dimethylamine (2.0 M in THF, 0.743 mL, 1.487 mmol) was added. The reaction was allowed to stir at room temperature for 2.0 h before additional $NaBH(OAc)_3$ (315 mg, 1.487 mmol) was added. The reaction was allowed to stir overnight for 16 h, then diluted with DCM (10 mL), washed with NaHCO$_3$ (1×10 mL) and the aqueous phase extracted with DCM (1×10 mL). The combined organic phase was dried (MgSO$_4$) and concentrated to afford the crude material as a yellow oil. Purification by biotage chromatography (KP-NH2 column) using a gradient of 0 to 40% EtOAc/cyclohexane afforded the required product as a yellow oil (179 mg, 70%). $^1$H NMR (500 MHz, Chloroform-d) δ 8.03 (br s, 1H), 7.76-7.63 (m, 2H), 3.78 (s, 2H), 2.32 (s, 6H). HRMS (ESI$^+$): calcd for C$_9$H$_{27}$$^{79}$BrN$_2$O$_2$ (M+H)$^+$, 259.0077; found 259.0074.

Preparation of Compound 214,
5-bromo-2-((dimethylamino)methyl)aniline

A mixture of Compound 213 (101 mg, 0.390 mmol) and SnCl$_2$.2H$_2$O (440 mg, 1.95 mmol) in EtOAc (3.0 mL) and DCM (1.0 mL) was stirred at rt for 24 h, and then carefully poured into sat. aq NaHCO$_3$ (30 ml), then filtered to remove solids. The aqueous layer was then extracted with DCM (3×15 ml). The combined organic layers were dried (Na$_2$SO$_4$) and concentrated in vacuo to afford the crude product as a yellow oil. This material as purified by SCX chromatography, eluting with MeOH then 10% 2M NH$_3$/MeOH to afford the title compound (55 mg, 62%). $^1$H NMR (500 MHz, DMSO-d6) δ 6.85 (d, J=7.9 Hz, 1H), 6.79 (d, J=2.1 Hz, 1H), 6.61 (dd, J=7.9, 2.1 Hz, 1H), 5.51 (br s, 2H), 3.24 (s, 2H), 2.10 (s, 6H). HRMS (ESI$^+$): calcd for C$_9$H$_{13}$$^{81}$BrN$_2$(M+H)$^+$, 231.0315; found 231.0318.

Preparation of Compound 215, N-(5-bromo-2-((dimethylamino)methyl)phenyl)-2-methylquinoline-6-carboxamide Oxalyl chloride (0.032 mL, 0.378 mmol) was added drop-wise to a solution of 2-methyl-6-quinoline carboxylic acid (62.5 mg, 0.334 mmol) and DMF (0.431 μL, 5.56 μmol) in dry DCM (2 mL). The reaction mixture was allowed to stir for 1.5 h. The solvent was removed in vacuo, a further portion of anhydrous DCM (2 ml) was added and then removed in vacuo. The resulting residue was re-dissolved in DCM (1 ml×2) and added to a solution of Compound 214 (51 mg, 0.223 mmol) and pyridine (0.090 mL, 1.113 mmol) in anhydrous DCM (2 ml). The reaction was left to stir for 19 h, then poured into sat. aq. NaHCO$_3$ aq. (20 mL) and the aqueous layer extracted with DCM (3×15 ml). The combined organic layer was washed with brine (15 ml), dried (Na$_2$SO$_4$) and concentrated in vacuo to afford the crude product as a green oil. Purification by biotage chromatography with a KP-NH column using a gradient of 0 to 100% EtOAc/cyclohexane afforded the required product as a green solid (45 mg, 51%). $^1$H NMR (500 MHz, Chloroform-d) δ 12.10 (s, 1H), 8.78 (s, 1H), 8.42 (s, 1H), 8.18-8.07 (m, 3H), 7.39 (d, J=8.4 Hz, 1H), 7.22-7.19 (m, 1H), 7.02 (d, J=8.0 Hz, 1H), 3.61 (s, 2H), 2.81 (s, 3H), 2.40 (s, 6H). HRMS (ESI$^+$): calcd for C$_{20}$H$_{20}$$^{79}$BrN$_3$O (M+H)$^+$, 398.0868; found 398.0858.

Preparation of Compound 216, N-(2-((dimethylamino)methyl)-5-((diphenylmethylene)amino)phenyl)-2-methylquinoline-6-carboxamide Palladium acetate (2.42 mg, 0.011 mmol) was added to a suspension of Compound 215 (43 mg, 0.108 mmol), xantphos (12.49 mg, 0.022 mmol), cesium carbonate (70.4 mg, 0.216 mmol) and benzophenone imine (21.5 mg, 0.119 mmol) in anhydrous dioxane (1.2 ml). The reaction was degassed by 4× vacuum/argon cycles and heated to 100° C. for 22 h. Further palladium(II) acetate (2.424 mg, 10.80 μmol) and xantphos (12.49 mg, 0.022 mmol) were added and the reaction allowed to heat at 100° C. for 24 h. The reaction was diluted with DCM (30 ml) and the solids were filtered off. The filtrate was washed with water (10 ml), brine (10 ml), dried Na$_2$SO$_4$ and concentrated in vacuo. Purification by biotage chromatography (KP-NH2 column) using a gradient of 8 to 100% EtOAc/cyclohexane gave the title compound as a pale yellow solid (16.5 mg, 31%). HRMS (ESI$^+$): calcd for C$_{33}$H$_{31}$N$_{40}$ (M+H)$^+$, 499.2498; found 499.2492.

Example 165, N-(5-amino-2-((dimethylamino)methyl)phenyl)-2-methylquinoline-6-carboxamide To a stirring solution of Compound 216 (17 mg, 0.034 mmol) in THF (0.5 mL) at room temperature was slowly added 2M HCl aq. (0.043 mL, 0.085 mmol). The reaction was allowed to stir at room temperature for 2.25 h. The solvents were removed in vacuo and traces of water removed by co-evaporation with toluene. The resulting residue was then taken up in DCM/MeOH and dried (Na$_2$SO$_4$), filtered and concentrated again to afford N-(5-amino-2-((dimethylamino)methyl)phenyl)-2-methylquinoline-6-carboxamide. Oxalyl chloride (4.73 μL, 0.056 mmol) was added drop-wise to a solution of 1,4-benzodioxane carboxylic acid (8.89 mg, 0.049 mmol) and DMF (0.064 μL, 0.822 μmol) in dry DCM (0.5 mL). The RM was allowed to stir for 1.5 h at room temperature. Further DMF (0.064 μL, 0.822 μmol) and oxalyl chloride (4.73 μL, 0.056 mmol) were added and the reaction stirred for 1.5 h. The DCM was then removed in vacuo. A further portion of anhydrous DCM (2 ml) was added and removed in vacuo. The resulting residue was re-dissolved in DCM (1 ml×2) and added to a solution of N-(5-amino-2-((dimethylamino)methyl)phenyl)-2-methylquinoline-6-carboxamide (11 mg, 0.033 mmol) and pyridine (0.027 mL, 0.329 mmol) in anhydrous DCM (0.5 ml). Dioxane (0.5 mL) and DMF (0.5 mL) were added in an attempt to solubilise all solids in the reaction. The reaction was left to stir for 17 h. Further acid chloride was prepared [to form 5 equivalents, using the same procedure as previously and oxalyl chloride (14.0 μL, 0.165 mmol), benzodioxane carboxylic acid (29.7 mg, 0.165 mmol) and DMF (0.32 μL, 4.11 μmol)]. The reaction was allowed to stir at room temperature for 22 h. The reaction was partitioned between DCM (10 mL) and 1M NaOH (10 ml). The aqueous layer was extracted with a further portion of DCM (10 mL) and the combined organic layer washed with brine (10 ml) and dried (Na$_2$SO$_4$). Then concentrated in vacuo to afford the crude product as a yellow oil (16 mg). Purification by column chromatography using a gradient of 0 to 6% MeOH/DCM afforded the title compound as a white solid (8.8 mg, 54%). $^1$H NMR (500 MHz, DMSO-d6) δ 12.08 (s, 1H), 10.18 (s, 1H), 8.74 (d, J=1.9 Hz, 1H), 8.45 (d, J=1.9 Hz, 1H), 8.44 (d, J=8.5 Hz, 1H), 8.17 (dd, J=8.8, 2.0 Hz, 1H), 8.08 (d, J=8.8 Hz, 1H), 7.60 (dd, J=8.2, 2.1 Hz, 1H), 7.58 (d, J=2.1 Hz, 1H), 7.54 (dd, J=8.4, 3.0 Hz, 3H), 7.20 (d, J=8.3 Hz, 1H), 6.99 (d, J=8.4 Hz, 1H), 4.34-4.29 (m, 4H), 3.66 (s, 2H), 2.71 (s, 3H), 2.34 (s, 6H). HRMS (ESI$^+$): calcd for C$_{29}$H$_{29}$N$_4$O$_4$ (M+H)$^+$, 497.2183; found 497.2171.

Preparation of Compound 217,
(4-bromo-2-nitrophenyl)methanol

To a stirring suspension of 4-bromo-2-nitrobenzaldehyde (550 mg, 2.391 mmol) in ethanol (14 mL) and water (7 mL)

at 0° C. was added sodium borohydride (452 mg, 11.96 mmol) and the reaction left to stir at 0° C. for 17.5 h. The reaction was diluted with water (30 ml), and extracted with EtOAc (2×30 ml)—brine was added to clear. The combined organic layer was washed with brine (30 ml), dried (MgSO$_4$) and concentrated in vacuo to afford the title compound as a yellow solid (536 mg, 97%). $^1$H NMR (500 MHz, Chloroform-d) δ 8.27 (d, J=2.0 Hz, 1H), 7.82 (dd, J=8.3, 2.0 Hz, 1H), 7.69 (d, J=8.3 Hz, 1H), 4.98 (s, 2H).

Preparation of Compound 218, 4-bromo-1-(methoxymethyl)-2-nitrobenzene

To a stirring solution of Compound 217 (313 mg, 1.349 mmol) in DCM (4.0 mL) was added a solution of sodium hydroxide (405 mg, 10.12 mmol) in water (4.0 mL). The reaction was allowed to stir for 10 min before tetrabutylammonium hydrogen sulfate (458 mg, 1.349 mmol) was added, followed by dimethyl sulfate (0.256 mL, 2.70 mmol). The reaction was left to stir at room temperature for 20 h, then diluted with DCM (20 ml) and washed with water (20 ml), brine (20 ml), dried (Na$_2$SO$_4$) and concentrated in vacuo to give the crude product as a yellow/brown oil. Purification by column chromatography using a gradient of 5 to 40% EtOAc/cyclohexane gave the title compound as a pale yellow solid (289 mg, 87%). $^1$H NMR (500 MHz, Chloroform-d) δ 8.24 (d, J=2.0 Hz, 1H), 7.79 (dd, J=8.4, 2.0 Hz, 1H), 7.70 (d, J=8.4 Hz, 1H), 4.80 (s, 2H), 3.51 (s, 3H).

Preparation of Compound 219, 5-bromo-2-(methoxymethyl)aniline

SnCl$_2$.2H$_2$O (702 mg, 3.11 mmol) was added to a stirring solution of Compound 218 (153 mg, 0.622 mmol) in ethyl acetate (4.5 mL) and DCM (1.5 mL). The reaction was allowed to stir at room temperature for 20 h. The reaction was carefully poured into sat. NaHCO$_3$ aq. (30 ml), then filtered. The aqueous layer was extracted with DCM (3×15 ml) and the combined organic layer dried (Na$_2$SO$_4$) and concentrated in vacuo to afford the title compound as a yellow oil (95 mg, 71%). $^1$H NMR (500 MHz, Chloroform-d) δ 6.93 (d, J=7.9 Hz, 1H), 6.89 (d, J=1.8 Hz, 1H), 6.86 (dd, J=7.9, 1.9 Hz, 1H), 4.44 (s, 2H), 3.34 (s, 3H).

Preparation of Compound 220, N-(5-bromo-2-(methoxymethyl)phenyl)-2-methylquinoline-6-carboxamide Oxalyl chloride (0.060 mL, 0.708 mmol) was added drop-wise to a solution of 2-methyl-6-quinoline carboxylic acid (117 mg, 0.625 mmol) and DMF (0.806 μL, 10.41 μmol) in anhydrous DCM (4 mL). The reaction was allowed to stir for 1 h. The solvent was removed in vacuo. Two further portions of anhydrous DCM (2 ml) were added and removed in vacuo. The resulting residue was re-dissolved in DCM (1 ml×2) and added to a solution of Compound 219 (90 mg, 0.417 mmol) and pyridine (0.168 mL, 2.083 mmol) in anhydrous DCM (2 ml). The reaction mixture was allowed to stir for 2 h at room temperature, then poured into sat. NaHCO$_3$ aq. and the aqueous layer extracted with DCM (3×15 ml). The combined organic layer was washed with brine (15 ml), dried (Na$_2$SO$_4$) and concentrated in vacuo to afford the crude product as a green semi-solid which was dry-loaded on to silica. Purification by biotage chromatography using a gradient of 6 to 50% EtOAc/cyclohexane gave the title compound as an off-white solid (83 mg, 52%). $^1$H NMR (500 MHz, Chloroform-d) δ 9.86 (s, 1H), 8.73 (d, J=1.9 Hz, 1H), 8.42 (d, J=1.8 Hz, 1H), 8.21 (d, J=8.4 Hz, 1H), 8.17 (d, J=8.8 Hz, 1H), 8.13 (dd, J=8.8, 2.0 Hz, 1H), 7.42 (d, J=8.4 Hz, 1H), 7.26 (dd, J=8.1, 2.0 Hz, 1H), 7.09 (d, J=8.0 Hz, 1H), 4.65 (s, 2H), 3.50 (s, 3H), 2.83 (s, 3H). HRMS (ESI$^+$): calcd for C$_{19}$H$_{18}$$^{79}$BrN$_2$O$_2$ (M+H)$^+$, 385.0552; found 385.0541.

Preparation of Compound 221, N-(5-(((diphenylmethylene)amino)-2-(methoxymethyl)phenyl)-2-methylquinoline-6-carboxamide Palladium acetate (4.72 mg, 0.210 mmol) was added to a suspension of Compound 220 (81 mg, 0.210 mmol), xantphos (24.33 mg, 0.231 mmol), cesium carbonate (137 mg, 0.421 mmol) and benzophenone imine (0.039 mL, 0.231 mmol) in anhydrous dioxane (2.0 ml). The reaction was degassed by 4× vacuum/argon cycles and heated to 100° C. for 23 h. Further palladium(II) acetate (4.72 mg, 0.210 mmol) and xantphos (24.33 mg, 0.231 mmol) were added and the reaction allowed to heat at 100° C. for 3 days. The reaction was diluted with DCM (30 ml) and filtered. The filtrate was washed with water (10 ml), brine (10 ml), dried (Na$_2$SO$_4$) and concentrated in vacuo. Purification by biotage chromatography using a gradient of 12 to 100% EtOAc/cyclohexane gave the title compound as a yellow solid (54 mg, 53%). HRMS (ESI$^+$): calcd for C$_{32}$H$_{28}$N$_3$O$_2$ (M+H)$^+$, 486.2182; found: 486.2192.

Example 166, N-(5-(2,3-dihydrobenzo[b][1,4]dioxine-6-carboxamido)-2-(methoxymethyl)phenyl)-2-methylquinoline-6-carboxamide To a stirring solution of Compound 221 (49 mg, 0.101 mmol) in THF (1.0 mL) at room temperature was slowly added 2M HCl aq. (0.126 mL, 0.252 mmol). The reaction was allowed to stir at room temperature for 3 h. The solvents were removed in vacuo and the remaining traces of water were removed by co-evaporation with toluene. The crude N-(5-amino-2-(methoxymethyl)phenyl)-2-methylquinoline-6-carboxamide was further dried under high vacuum.

Oxalyl chloride (0.015 mL, 0.171 mmol) was added dropwise to a solution of 1,4-benzodioxane carboxylic acid (27.2 mg, 0.151 mmol) and N,N-dimethylformamide (0.195 μL, 2.52 μmol) in anhydrous DCM (1.0 mL). The reaction was allowed to stir for 1.5 h. The solvent was removed in vacuo, a further portion of anhydrous DCM (2 ml) was added and concentrated again.

The resulting residue was re-dissolved in DCM (1 ml+0.5 ml) and added to a solution of N-(5-amino-2-(methoxymethyl)phenyl)-2-methylquinoline-6-carboxamide (32.4 mg, 0.101 mmol) and pyridine (0.082 mL, 1.008 mmol) in anhydrous DCM (2.0 ml) and anhydrous DMF (0.5 ml). The reaction was left to stir for 21 h, then diluted with DCM (10 ml) and washed with sat. NH$_4$Cl aq. (10 ml), water (2×10 ml), brine (10 ml) and dried (Na$_2$SO$_4$) to afford the crude product as a yellow oil. An attempt to purify the material by column chromatography using a gradient of 5 to 75% EtOAc/DCM failed to provide pure product. Therefore this material was further purified by preparative TLC (3:1 DCM/EtOAc) to afford the title compound as a white solid (2 mg, 4%). $^1$H NMR (500 MHz, DMSO-d6) δ 10.20 (s, 1H), 10.17 (s, 1H), 8.58 (br s, 1H), 8.43 (d, J=8.4 Hz, 1H), 8.23-8.20 (m, 1H), 8.15-8.13 (m, 1H), 8.06 (d, J=8.7 Hz, 1H), 7.71-7.68 (m, 1H), 7.58-7.52 (m, 3H), 7.39 (d, J=8.4 Hz, 1H), 7.00 (d, J=8.4 Hz, 1H), 4.52 (s, 2H), 4.35-4.29 (m, 4H), 3.33 (s, 3H), 2.72 (s, 3H). HRMS (ESI$^+$): calcd for C$_{28}$H$_{26}$N$_3$O$_5$ (M+H)$^+$, 484.1872; found: 484.1848.

Example 167, N-(5-(2,3-dihydrobenzo[b][1,4]diox-ine-6-carboxamido)-2-(hydroxymethyl)phenyl)-2-methylquinoline-6-carboxamide Following the same procedure as for Example 166, a side product was isolated by preparative TLC (1:1 EtOAc/DCM) to afford the title compound as a white solid (1.2 mg, 2.5%). $^1$H NMR (500 MHz, MeOD/CDCl$_3$, 6:1) δ 8.55 (d, J=2.0 Hz, 1H), 8.40 (d, J=8.4 Hz, 1H), 8.29-8.25 (m, 2H), 8.09 (d, J=8.8 Hz, 1H), 7.61 (dd, J=8.2, 2.2 Hz), 7.54 (d, J=8.5 Hz, 1H), 7.51 (d, J=2.1 Hz, 1H), 7.49 (dd, J=8.3, 2.2 Hz), 7.39 (d, J=8.3 Hz, 1H), 6.95 (d, J=8.4 Hz, 1H), 4.77 (s, 2H), 4.34-4.29 (m, 4H), 2.79 (s, 3H). HRMS (ESI$^+$): calcd for C$_{27}$H$_{24}$N$_3$O$_5$ (M+H)$^+$, 470.1710; found: 470.1690.

Preparation of Compound 222, 5-bromo-1-methyl-1,3-dihydrobenzo[c]isothiazole 2,2-dioxide Iodomethane (0.045 mL, 0.726 mmol) was added to a stirring suspension of 5-bromo-1,3-dihydrobenzo[c]isothiazole 2,2-dioxide (150 mg, 0.605 mmol) and potassium carbonate (125 mg, 0.907 mmol) in anhydrous DMF (6 mL) at room temperature under argon. The reaction was allowed to stir for 17.5 h. The reaction mixture was poured into brine (20 ml) and the aqueous layer extracted with DCM (2×20 ml). The combined organic layer was washed with brine (20 ml), dried (Na$_2$SO$_4$) and concentrated in vacuo, high vacuum was used to remove remaining traces of DMF. Purification by biotage chromatography using a gradient of 5 to 40% EtOAc/cyclohexane gave the title compound as an off-white solid (130 mg, 82%). $^1$H NMR (500 MHz, Chloroform-d) δ 7.49-7.45 (m, 1H), 7.41-7.39 (m, 1H), 6.63 (d, J=8.5 Hz, 1H), 4.34 (s, 2H), 3.14 (s, 3H).

Preparation of Compound 223, 2-(trimethylsilyl)ethyl 1-methyl-1,3-dihydrobenzo[c]isothiazole-5-carboxylate 2,2-dioxide To a stirring suspension of Compound 222 (116 mg, 0.443 mmol), Hermann's palladacycle (20.8 mg, 0.022 mmol) and tri-t-butylphosphonium tetrafluoroborate (25.7 mg, 0.089 mmol) in 2-(trimethylsilyl)-ethanol (3.5 mL) was added molybdenum hexacarbonyl (234 mg, 0.885 mmol) followed by DBU (0.20 ml, 1.328 mmol). The reaction mixture was heated to 130° C. in a microwave for 1 h. The reaction mixture was filtered to remove solids and the filtrate concentrated under high vacuum to remove the solvent. The resulting residue was taken up in DCM (20 ml) and washed with sat. NH$_4$Cl aq. (25 ml), water (25 ml—brine had to be added to clear) and brine (5 ml), dried (Na$_2$SO$_4$) and concentrated in vacuo to afford the crude product as a brown oil. Purification by biotage chromatography using a gradient of 5 to 40% EtOAc/cyclohexane gave the title compound as a pale yellow oil (25 mg, 17%). $^1$H NMR (500 MHz, Chloroform-d) δ 8.09-8.05 (m, 1H), 7.96-7.94 (m, 1H), 6.76 (d, J=8.4 Hz, 1H), 4.44-4.40 (m, 2H), 4.40 (s, 2H), 3.21 (s, 3H), 1.19-1.02 (m, 2H), 0.10 (s, 9H). HRMS (ESI$^+$): calcd for C$_{12}$H$_{17}$NO$_4$SSi (M−2×Me)+, 300.0720; found: 300.0722.

Example 168, N-(5-(2,3-dihydrobenzo[b][1,4]diox-ine-6-carboxamido)-2-methylphenyl)-1-methyl-1,3-dihydrobenzo[c]isothiazole-5-carboxamide 2,2-dioxide To a stirring solution of Compound 223 (24 mg, 0.073 mmol) in THF (1.0 mL) at room temperature under argon was slowly added TBAF (1.0M in THF, 0.110 mL, 0.110 mmol) the reaction mixture was allowed to stir for 3 h. Water (10 ml) was added and the reaction mixture concentrated to remove THE. The aqueous layer was acidified (to ~pH 3) using 1M HCl aq. and extracted with EtOAc (3×15 ml)—brine was added to clear. The combined organic layer was washed with brine (10 ml), dried (Na$_2$SO$_4$) and concentrated in vacuo to afford 1-methyl-1,3-dihydrobenzo[c]isothiazole-5-carboxylic acid 2,2-dioxide as a white semi-solid (31 mg). HATU (29.4 mg, 0.077 mmol) was added to a stirring solution of 1-methyl-1,3-dihydrobenzo[c]isothiazole-5-carboxylic acid 2,2-dioxide (17 mg, 0.064 mmol) and DIEA (0.034 mL, 0.193 mmol) in DMF (1 mL) at room temperature under argon. The reaction was allowed to stir for 3 min before the addition of Compound 2 (18.29 mg, 0.064 mmol). The reaction was left to stir at room temperature for 18 h, then diluted with water (10 ml) and extracted with EtOAc (3×15 ml). The combined organic layer was washed with brine (15 ml), dried (Na$_2$SO$_4$) and concentrated in vacuo. Purification by column chromatography using a gradient of 0 to 10% EtOAc/DCM gave the title compound as a white solid (18 mg, 57%). $^1$H NMR (500 MHz, DMSO-d6) δ 10.05 (s, 1H), 9.86 (s, 1H), 8.05 (dd, J=8.3, 1.7 Hz, 2H), 7.98 (br s, 1H), 7.80 (d, J=2.1 Hz, 1H), 7.57 (dd, J=8.3, 2.2 Hz, 1H), 7.53 (d, J=2.1 Hz, 1H), 7.50 (dd, J=8.4, 2.2 Hz, 1H), 7.21 (d, J=8.4 Hz, 1H), 7.08 (d, J=8.4 Hz, 1H), 6.98 (d, J=8.4 Hz, 1H), 4.79 (s, 2H), 4.34-4.28 (m, 4H)), 3.13 (s, 3H), 2.18 (s, 3H). HRMS (ESI$^+$): calcd for C$_{25}$H$_{24}$N$_3$O$_6$S (M+H)$^+$, 494.1386; found: 494.1364.

Compound 224, N-(2-fluoro-5-nitrophenyl)-2-methylquinoline-6-carboxamide

Oxalyl chloride (3.25 mL, 38.4 mmol) was added dropwise to a solution of 2-methylquinoline-6-carboxylic acid (6.59 g, 35.2 mmol) and DMF (0.0062 mL, 0.080 mmol) in dry DCM (80 mL). The reaction mixture was stirred at room temperature for 3 h, and then concentrated. The residue was dissolved in DCM and concentrated again. This residue was dissolved in pyridine (80 mL) and 2-fluoro-5-nitroaniline (5.00 g, 32.00 mmol) was added in one portion. The reaction mixture was stirred at room temperature for 18 h, and then poured onto water (100 mL). The green precipitate was filtered and washed several times with water, Et$_2$O and finally with a minimum amount of DCM to afford the title compound (10.42 g, 100%) as a light green solid which does not require further purification. $^1$H NMR (500 MHz, DMSO) δ 10.70 (s, 1H), 8.72 (dd, J=6.45, 2.93 Hz, 1H), 8.63 (d, J=2.02 Hz, 1H), 8.43 (d, J=8.46 Hz, 1H), 8.23 (dd, J=8.48, 2.02 Hz, 1H), 8.21-8.16 (m, 1H), 8.05 (d, J=8.86 Hz, 1H), 7.65 (app t, J=9.25 Hz, 1H), 7.54 (d, J=8.46 Hz, 1H), 2.71 (s, 3H). HRMS (ESI$^+$): Found [M+H]+ 326.0934 C$_{17}$H$_{13}$FN$_3$O$_3$ requires 326.0935.

Compound 225, N-(5-amino-2-fluorophenyl)-2-methylquinoline-6-carboxamide

To a solution of N-(2-fluoro-5-nitrophenyl)-2-methylquinoline-6-carboxamide (10.42 g, 32.00 mmol) in ethanol (120 mL) and water (40 mL), ammonium chloride (11.99 g, 224 mmol) and iron powder (12.52 g, 224 mmol) were added and the resulting suspension was allowed to stir at 90° C. for 1 hour. The reaction mixture was allowed to cool to room temperature, diluted with MeOH and DCM and filtered through a pad of Celite. The resulting filtrate was concentrated under vacuum to afford a light brown solid as crude product, which was taken directly onto the next step without any further purification (9.46 g, 100%). ¹H-NMR (500 MHz, DMSO) δ 10.05 (s, 1H), 8.57 (d, J=1.67 Hz, 1H), 8.39 (d, J=8.74 Hz, 1H), 8.19 (dd, J=8.74, 1.67 Hz, 1H), 8.01 (d, J=8.74 Hz, 1H), 7.52 (d, J=8.33 Hz, 1H), 6.94 (dd, J=9.78, 8.28 Hz, 1H), 6.89 (dd, J=6.58, 2.74 Hz, 1H), 6.46-6.39 (m, 1H), 5.05 (bs, 2H), 2.70 (s, 3H). HRMS (ESI$^+$): Found [M+H]$^+$ 296.1191 $C_{17}H_{15}FN_3O$ requires 296.1194.

Compound 226, N-(4-fluoro-3-nitrophenyl)-2,3-dihydrobenzo[b][1,4]dioxine-6-carboxamide 4-fluoro-3-nitroaniline (1.00 g, 6.41 mmol), 2,3-dihydrobenzo[b][1,4]dioxine-6-carboxylic acid (1.154 g, 6.41 mmol) and EDC (3.07 g, 16.01 mmol) were dissolved in dry DMF (45 mL), then pyridine was added dropwise and the resulting orange/brown mixture was allowed to stir at room temperature for 72 hours. The reaction mixture was then washed with water (2×50 mL) and extracted with a mixture of DCM/MeOH 9:1 (2×50 mL). The organic layers were dried over $Na_2SO_4$ and concentrated under reduced pressure to afford an orange solid as crude product, which was purified via flash column chromatography on silica gel in gradient (from 0 to 10% MeOH in DCM) to afford the title compound as a pale yellow solid (0.98 g, 48%). ¹H-NMR (500 MHz, DMSO): δ 10.47 (s, 1H), 8.69 (dd, J 6.48, 2.88 Hz, 1H), 8.13 (m, 1H), 7.58 (dd, J=11.12, 9.22 Hz, 1H), 7.55 (d, J=2.42 Hz, 1H), 7.52 (dd, J=8.08, 2.42 Hz, 1H), 7.02 (d, J=8.08 Hz, 1H), 4.36-4.29 (m, 4H). HRMS (ESI$^+$): Found [M+H]$^+$ 319.0729 $C_{15}H_{12}FN_2O_5$ requires 319.0725.

Compound 227, N-(3-amino-4-fluorophenyl)-2,3-dihydrobenzo[b][1,4]dioxine-6-carboxamide To a solution of N-(4-fluoro-3-nitrophenyl)-2,3-dihydrobenzo[b][1,4]dioxine-6-carboxamide (10.19 g, 32.00 mmol) in ethanol (100 mL) and water (33 mL), ammonium chloride (11.99 g, 224 mmol) and iron powder (12.52 g, 224 mmol) were added and the resulting suspension was allowed to stir at 90° C. for 1 hour. The reaction mixture was allowed to cool to room temperature, diluted with MeOH and DCM and filtered through a pad of Celite. The resulting filtrate was concentrated under vacuum to afford a light brown solid as crude product, which was taken directly onto the next step without any further purification (9.23 g, 100%). ¹H-NMR (500 MHz, DMSO): δ 9.81 (s, 1H), 7.52-7.48 (m, 1H), 7.46 (dd, J=8.51, 1.76 Hz, 1H), 7.28 (dd, J=8.51, 2.27 Hz, 1H), 6.96 (d, J=8.35 Hz, 1H), 6.91 (dd, J=10.60, 9.10 Hz, 1H), 6.86-6.79 (m, 1H), 5.14 (bs, 2H), 4.33-4.26 (m, 4H). HRMS (ESI$^+$): Found [M+H]$^+$ 289.0990 $C_{15}H_{14}FN_2O_3$ requires 289.0983.

Compound 228, N-(5-(2,3-dihydrobenzo[b][1,4]dioxine-6-carboxamido)-2-fluorophenyl)-2-methylquinoline-6-carboxamide Procedure A: N-(3-amino-4-fluorophenyl)-2,3-dihydrobenzo[b][1,4]dioxine-6-carboxamide (0.600 g, 2.081 mmol), 2-methylquinoline-6-carboxylic acid (0.468 g, 2.498 mmol) and EDC (0.998 g, 5.20 mmol) were dissolved in dry DMF (12 mL), then pyridine (0.84 mL, 10.41 mmol) was added dropwise and the resulting mixture was allowed to stir at room temperature for 48 hours. The reaction mixture was poured onto water (20 mL) and the precipitate was washed several times with water and $Et_2O$ to afford the crude product as a pale green solid, which was purified via flash column chromatography on silica gel in gradient (from 0 to 10% MeOH in DCM) to afford the title compound as a pale yellow solid (0.45 g, 47%).

Procedure B: To a suspension of 2,3-dihydrobenzo[b][1,4]dioxine-6-carboxylic acid (12.70 g, 70.5 mmol) in dry DCM (100 mL), DMF (6.16 μl, 0.080 mmol) and oxalyl chloride (6.51 mL, 77 mmol) were added dropwise and the resulting green solution was allowed to stir at 20° C. for 3 hours after which it was concentrated under vacuum to afford a dry pale green solid. The solid was dissolved in pyridine (100 mL) and N-(5-amino-2-fluorophenyl)-2-methylquinoline-6-carboxamide (9.46 g, 32.0 mmol) was added in one portion. The resulting dark yellow suspension was allowed to stir for 2 hours after which it was poured onto water (100 mL). The yellow precipitate was filtered and washed several times with water, $Et_2O$ and finally with a minimum amount of DCM to afford the crude product as a pale yellow solid which does not require further purification (12.5 g, 85%).

¹H-NMR (500 MHz, DMSO): δ 10.37 (s, 1H), 10.18 (s, 1H), 8.62 (d, J=1.65 Hz, 1H), 8.41 (d, J=8.77 Hz, 1H), 8.23 (dd, J=8.77, 2.19 Hz, 1H), 8.13 (dd, J=7.01, 2.63 Hz, 1H), 8.03 (d, J=8.51 Hz, 1H), 7.68-7.63 (m, 1H), 7.55-7.53 (m, 2H), 7.52 (dd, J=8.51, 2.09 Hz, 1H), 7.29 (dd, J=9.98, 8.69 Hz, 1H), 6.99 (d, J=8.51 Hz, 1H), 4.34-4.28 (m, 4H), 2.71 (s, 3H). HRMS (ESI$^+$): Found [M+H]$^+$ 458.1499 $C_{26}H_{21}FN_3O_4$ requires 458.1511.

Compound 229, N-(5-(2,3-dihydrobenzo[b][1,4]dioxine-6-carboxamido)-2-fluorophenyl)-2-formylquinoline-6-carboxamide A solution of N-(5-(2,3-dihydrobenzo[b][1,4]dioxine-6-carboxamido)-2-fluorophenyl)-2-methylquinoline-6-carboxamide (5.00 g, 10.93 mmol) and selenium dioxide (1.334 g, 12.02 mmol) in dry DMF (40.00 mL) and dioxane (120.00 mL) was heated at 152° C. for 1 h after which the reaction mixture was allowed to cool to room temperature, diluted with DCM and filtered through a pad of Celite. The filtrate was concentrated under vacuum to afford the crude product as a yellow solid which was taken directly onto the next step without any further purification (5.15 g, 100%). ¹H-NMR (500 MHz, DMSO): 510.54 (s, 1H), 10.19 (s, 1H), 10.17 (s, 1H), 8.81-8.77 (m, 1H), 8.39 (dd, J=8.73, 1.95 Hz, 1H), 8.36 (d, J=8.73 Hz, 1H), 8.17 (dd, J=6.93, 2.57 Hz, 1H), 8.09 (d, J=9.26 Hz, 1H), 7.69-7.64 (m, 1H), 7.55 (d, J=1.99 Hz, 1H), 7.52 (dd, J=8.30, 1.99 Hz, 1H), 7.31 (app t, J=9.97 Hz, 1H), 6.99 (d, J=8.30 Hz, 1H), 4.36-4.27 (m, 4H). HRMS (ESI$^+$): Found [M+H]$^+$ 472.1290 $C_{26}H_{19}FN_3O_5$ requires 472.1303.

Example 169, N-(5-(2,3-dihydrobenzo[b][1,4]dioxine-6-carboxamido)-2-fluorophenyl)-2-((4-ethylpiperazin-1-yl)methyl)quinoline-6-carboxamide A solution of N-(5-(2,3-dihydrobenzo[b][1,4]dioxine-6-carboxamido)-2-fluorophenyl)-2-formylquinoline-6-carboxamide (1.19 g, 2.52 mmol) and 1-ethylpiperazine in dry DCM (20 mL) was allowed to stir at 20° C. for 6 h, after which sodium triacetoxyborohydride (1.605 g, 7.57 mmol) was added in one portion and the resulting mixture was allowed to stir at 20° C. for 2 h. The reaction was quenched with $NaHCO_3$ saturated aqueous solution (20 mL) and extracted with a mixture DCM/MeOH 9/1 (3×20 mL). Purification via flash column chromatography on silica gel in gradient DCM/MeOH from 0 to 20%, followed by wash in water and trituration in $Et_2O$ afforded the desired product as a white solid (0.950 g, 66%). ¹H-NMR (500 MHz, DMSO): δ 10.41 (s, 1H), 10.20 (s, 1H), 8.66 (d, J=1.86 Hz, 1H), 8.49 (d, J=8.67 Hz, 1H), 8.26 (dd, J=8.67, 1.86 Hz, 1H), 8.14 (dd, J=7.14, 2.55 Hz, 1H), 8.08 (d, J=8.67 Hz, 1H), 7.73 (d, J=8.27 Hz, 1H), 7.69-7.62 (m, 1H), 7.55 (d, J=1.83 Hz, 1H), 7.53 (dd, J=8.53, 1.83 Hz, 1H), 7.29 (app t, J=9.16 Hz, 1H), 6.99 (d, J=8.53 Hz, 1H), 4.36-4.25 (m, 4H), 3.79 (s, 2H), 2.64-2.18 (m, 10H), 0.99 (t, J=6.41 Hz, 3H). HRMS (ESI$^+$): Found [M+H]$^+$ 570.2532 $C_{32}H_{33}FN_5O_4$ requires 570.2511.

The following compounds were synthesised according to the procedure for Example 169, by substituting the appropriate amine for 1-ethylpiperazine.

Example 170, N-(5-(2,3-dihydrobenzo[b][1,4]dioxine-6-carboxamido)-2-fluorophenyl)-2-(pyrrolidin-1-ylmethyl)quinoline-6-carboxamide Example 171, 2-(azetidin-1-ylmethyl)-N-(5-(2,3-dihydrobenzo[b][1,4]dioxine-6-carboxamido)-2-fluorophenyl)quinoline-6-carboxamide Example 172, N-(5-(2,3-dihydrobenzo[b][1,4]dioxine-6-carboxamido)-2-fluorophenyl)-2-(piperidin-1-ylmethyl)quinoline-6-carboxamide Example 173, N-(5-(2,3-dihydrobenzo[b][1,4]dioxine-6-carboxamido)-2-fluorophenyl)-2-((4-methylpiperazin-1-yl)methyl)quinoline-6-carboxamide Example 174, N-(5-(2,3-dihydrobenzo[b][1,4]dioxine-6-carboxamido)-2-fluorophenyl)-2-(piperazin-1-ylmethyl)quinoline-6-carboxamide Example 175, (S)—N-(5-(2,3-dihydrobenzo[b][1,4]dioxine-6-carboxamido)-2-fluorophenyl)-2-((2-methylpyrrolidin-1-yl)methyl)quinoline-6-carboxamide Example 176, (R)—N-(5-(2,3-dihydrobenzo[b][1,4]dioxine-6-carboxamido)-2-fluorophenyl)-2-((2-methylpyrrolidin-1-yl)methyl)quinoline-6-carboxamide Example 177, 2-((4-(tert-butyl)piperazin-1-yl)methyl)-N-(5-(2,3-dihydrobenzo[b][1,4]dioxine-6-carboxamido)-2-fluorophenyl)quinoline-6-carboxamide Example 178, 2-((4-cyclopropylpiperazin-1-yl)methyl)-N-(5-(2,3-dihydrobenzo[b][1,4]dioxine-6-carboxamido)-2-fluorophenyl)quinoline-6-carboxamide Example 179, 2-((4-(sec-butyl)piperazin-1-yl)methyl)-N-(5-(2,3-dihydrobenzo[b][1,4]dioxine-6-carboxamido)-2-fluorophenyl)quinoline-6-carboxamide Example 180, N-(5-(2,3-dihydrobenzo[b][1,4]dioxine-6-carboxamido)-2-fluorophenyl)-2-(((1S,4S)-5-ethyl-2,5-diazabicyclo[2.2.1]heptan-2-yl)methyl)quinoline-6-carboxamide Example 181, 2-(2-azaspiro[3.3]heptan-2-ylmethyl)-N-(5-(2,3-dihydrobenzo[b][1,4]dioxine-6-carboxamido)-2-fluorophenyl)quinoline-6-carboxamide Example 182, N-(5-(2,3-dihydrobenzo[b][1,4]dioxine-6-carboxamido)-2-fluorophenyl)-2-((3-methylazetidin-1-yl)methyl)quinoline-6-carboxamide Example 183, N-(5-(2,3-dihydrobenzo[b][1,4]dioxine-6-carboxamido)-2-fluorophenyl)-2-((3,3-dimethylazetidin-1-yl)methyl)quinoline-6-carboxamide Example 184, N-(5-(2,3-dihydrobenzo[b][1,4]dioxine-6-carboxamido)-2-fluorophenyl)-2-((4-ethyl-1,4-diazepan-1-yl)methyl)quinoline-6-carboxamide

TABLE E

| Compound | 1H NMR | Mass Spec |
| --- | --- | --- |
| Example 170 | $^1$H-NMR (500 MHz, DMSO): δ 10.39 (s, 1H), 10.18 (s, 1H), 8.64 (d, J = 1.77 Hz, 1H), 8.48 (d, J = 8.39 Hz, 1H), 8.24 (dd, J = 8.39, 1.77 Hz, 1H), 8.14 (dd, J 2.82 Hz, 7.33 Hz, 1H), 8.08 (1H, d, J 8.51 Hz, CH), 7.72 (d, J = 8.51 Hz, 1H), 7.68-7.63 (m, 1H), 7.54 (d, J 2.13 Hz, 1H), 7.52 (dd, J = 8.52, 2.13 Hz, 1H), 7.29 (app t, J = 9.39 Hz, 1H), 6.99 (d, J = 8.52 Hz, 1H), 4.34-4.27 (m, 4H), 3.92 (s, 2H), 2.63-2.50 (m, 4H), 1.80-1.69 (m, 4H). | Found [M + H]$^+$ 527.2074 $C_{30}H_{28}FN_4O_4$ requires 527.2089 |
| Example 171 | $^1$H-NMR (500 MHz, MeOD): δ 8.59 (d, J = 1.90 Hz, 1H), 8.48 (d, J = 8.87 Hz, 1H), 8.29 (dd, J = 8.87, 1.90 Hz, 1H), 8.19 (dd, J = 6.97, 3.17 Hz, 1H), 8.15 (d, J = 8.87 Hz, 1H), 7.66 (d, J = 8.87 Hz, 1H), 7.62-7.58 (m, 1H), 7.51 (d, J = 2.28 Hz, 1H), 7.49 (dd, J = 8.38, 2.28 Hz, 1H), 7.24 (dd, J = 9.90, 8.76 Hz, 1H), 6.96 (d, J = 8.38 Hz, 1H), 4.36-4.29 (m, 4H), 3.99 (s, 2H), 3.47 (t, J = 7.30 Hz, 4H), 2.21 (qn, J = 7.30 Hz, 2H). | Found [M + H]$^+$ 513.1930 $C_{29}H_{26}FN_4O_4$ requires 513.1933 |
| Example 172 | $^1$H-NMR (500 MHz, DMSO): δ 10.39 (s, 1H), 10.18 (s, 1H), 8.64 (s, 1H), 8.48 (d, J = 8.55 Hz, 1H), 8.24 (d, J = 8.55 Hz, 1H), 8.14 (dd, J = 7.08, 2.26 Hz, 1H), 8.08 (d, J = 8.55 Hz, 1 H), 7.74 (app d, J = 7.60 Hz, 1H), 7.68-7.63 (m, 1H), 7.54 (s, 1H), 7.52 (d, J = 8.55 Hz, 1H), 7.29 (app t, J = 8.93 Hz, 1H), 6.99 (d, J = 7.60 Hz, 1H), 4.37-4.28 (m, 4H), 3.75 (s, 2H), 2.48-2.37 (m, 4H), 1.63-1.48 (m, 4H), 1.47-1.36 (m, 2H). | Found [M + H]$^+$ 541.2242 $C_{31}H_{30}FN_4O_4$ requires 541.2246 |
| Example 173 | $^1$H-NMR (500 MHz, DMSO): δ 10.40 (s, 1H), 10.19 (s, 1H), 8.65 (d, J = 1.68 Hz, 1H), 8.49 (d, J = 8.40 Hz, 1H), 8.25 (dd, J = 8.40, 1.68 Hz, 1H), 8.14 (dd, J = 7.56, 2.52 Hz, 1H), 8.08 (d, J = 8.81 Hz, 1H), 7.72 (d, J = 8.40 Hz, 1H), 7.68-7.63 (m, 1H), 7.55 (d, J = 2.52 Hz, 1H), 7.52 (dd, J = 8.40, 1.68 Hz, 1H), 7.29 (app t, J = 9.24 Hz, 1H), 6.99 (d, J = 9.24 Hz, 1H), 4.37-4.27 (m, 4H), 3.79 (s, 2H), 2.54-2.27 (m, 8H), 2.16 (m, 3H). | Found [M + H]$^+$ 556.2329 $C_{31}H_{31}FN_5O_4$ requires 556.2355 |
| Example 174 | $^1$H-NMR (500 MHz, DMSO): δ 10.41 (s, 1H), 10.20 (s, 1H), 8.73 (bs, 1H), 8.67 (d, J = 1.66 Hz, 1H), 8.52 (d, J = 8.71 Hz, 1H), 8.27 (dd, J = 8.71, 1.66 Hz, 1H), 8.15 (dd, J = 7.08, 2.72 Hz, 1H), 8.09 (d, J = 8.71 Hz, 1H), 7.74 (d, J = 8.42 Hz, 1H), 7.66-7.61 (m, 1H), 7.54 (d, J = 2.11 Hz, 1H), 7.52 (dd, J = 8.42, 2.11 Hz, 1H), 7.30 (app t, J = 10.10 Hz, 1H), 6.99 (d, J = 8.42 Hz, 1H), 4.35-4.27 (m, 4H), 3.89 (s, 2H), 3.19-3.09 (m, 4H), 2.76-2.66 (m, 4H). | Found [M + H]$^+$ 542.2190 $C_{30}H_{29}FN_5O_4$ requires 542.2198 |

TABLE E-continued

| Compound | 1H NMR | Mass Spec |
| --- | --- | --- |
| Example 175 | $^1$H-NMR (500 MHz, DMSO): δ 10.38 (s, 1H), 10.18 (s, 1H), 8.64 (d, J = 1.79 Hz, 1H), 8.47 (d, J = 8.51 Hz, 1H), 8.24 (dd, J = 8.51, 1.79 Hz, 1H), 8.14 (dd, J = 7.17, 2.69 Hz, 1H), 8.08 (d, J = 8.51 Hz, 1H), 7.71 (d, J = 8.28 Hz, 1H), 7.68-7.63 (m, 1H), 7.54 (d, J = 2.07 Hz, 1H), 7.52 (dd, J = 8.28, 2.07 Hz, 1H), 7.29 (app t, J = 10.01 Hz, 1H), 6.99 (d, J = 8.28 Hz, 1H), 4.35-4.28 (m, 4H), 4.24 (d, J = 14.04 Hz, 1H), 3.54 (d, J = 14.04 Hz, 1H), 2.89-2.81 (m, 1H), 2.58-2.51 (m, 1H), 2.22 (dd, J = 9.56, 8.36 Hz, 1H), 2.00-1.91 (m, 1H), 1.72-1.58 (m, 2H), 1.44-1.33 (m, 1H), 1.12 (d, J = 6.04 Hz, 3H). | Found [M + H]$^+$ 541.2237 $C_{31}H_{30}FN_4O_4$ requires 541.2246 |
| Example 176 | $^1$H-NMR (500 MHz, DMSO): δ 10.38 (s, 1H), 10.18 (s, 1H), 8.64 (s, 1H), 8.47 (d, J = 8.54 Hz, 1H), 8.24 (d, J = 8.91 Hz, 1H), 8.14 (dd, J = 7.42, 2.60 Hz, 1H), 8.08 (d, J = 8.54 Hz, 1H), 7.71 (d, J = 8.27 Hz, 1H), 7.68-7.62 (m, 1H), 7.57-7.53 (m, 1H), 7.52 (d, J = 8.27 Hz, 1H), 7.29 (app t, J = 10.11 Hz, 1H), 6.99 (d, J = 8.27 Hz, 1H), 4.38-4.27 (m, 4H), 4.24 (d, J = 13.93 Hz, 1H), 3.54 (d, J = 13.93 Hz, 1H), 2.89-2.82 (m, 1H), 2.57-2.50 (m, 1H), 2.22 (dd, J = 9.56, 8.36 Hz, 1H), 1.99-1.90 (m, 1H), 1.72-1.59 (m, 2H), 1.43-1.33 (m, 1H), 1.12 (d, J = 6.03 Hz, 3H). | Found [M + H]$^+$ 541.2221 $C_{31}H_{30}FN_4O_4$ requires 541.2246 |
| Example 177 | $^1$H-NMR (500 MHz, DMSO): δ 10.50 (s, 1H), 10.29 (s, 1H), 8.69 (d, J = 1.53 Hz, 1H), 8.50 (d, J = 8.39 Hz, 1H), 8.27 (dd, J = 8.39, 1.53 Hz, 1H), 8.13 (dd, J = 7.29, 2.43 Hz, 1H), 8.09 (d, J = 8.51 Hz, 1H), 7.74 (d, J = 8.39 Hz, 1H), 7.61-7.66 (m, 1H), 7.57 (d, J = 2.22 Hz, 1H), 7.55 (dd, J = 8.51, 2.22 Hz, 1H), 7.28 (app t, J = 9.82 Hz, 1H), 6.98 (d, J = 8.51 Hz, 1H), 4.35-4.27 (m, 4H), 3.85 (s, 2H), 3.09-2.54 (m, 8H), 1.46-0.94 (bs, 9H). | Found [M + H]$^+$ 598.2809 $C_{34}H_{37}FN_5O_4$ requires 598.2824 |
| Example 178 | $^1$H-NMR (500 MHz, DMSO): δ 10.38 (s, 1H), 10.18 (s, 1H), 8.65 (d, J = 1.70 Hz, 1H), 8.49 (d, J = 8.50 Hz, 1H), 8.25 (dd, J = 9.05, 2.55 Hz, 1H), 8.14 (dd, J 6.80, 2.55 Hz, 1H), 8.08 (d, J = 9.05 Hz, 1H), 7.73 (d, J = 8.50 Hz, 1H), 7.68-7.63 (m, 1H), 7.54 (d, J = 1.70 Hz, 1H), 7.52 (dd, J = 7.65, 1.70 Hz, 1H), 7.30 (app t, J = 9.87 Hz, 1H), 6.99 (d, J = 8.50 Hz, 1H), 4.34-4.28 (m, 4H), 3.78 (s, 2H), 2.57 (bs, 4H), 2.57 (bs, 4H), 2.44 (bs, 4H), 1.61 (app heptet, J = 3.23 Hz, 1H), 0.42-0.37 (m, 2H), 0.29-0.25 (m, 2H). | Found [M + H]$^+$ 582.2487 $C_{33}H_{33}FN_5O_4$ requires 582.2511 |
| Example 179 | $^1$H-NMR (500 MHz, DMSO): δ 10.39 (s, 1H), 10.19 (s, 1H), 8.65 (d, J = 1.70 Hz, 1H), 8.49 (d, J = 8.50 Hz, 1H), 8.25 (dd, J = 8.50, 1.70 Hz, 1H), 8.14 (dd, J = 6.80, 2.55 Hz, 1H), 8.08 (d, J = 9.12 Hz, 1H), 7.73 (d, J = 8.50 Hz, 1H), 7.68-7.63 (m, 1H), 7.54 (d, J = 1.70 Hz, 1H), 7.52 (dd, J = 8.50, 2.55 Hz, 1H), 7.29 (app t, J = 9.92 Hz, 1H), 6.99 (d, J = 8.50 Hz, 1H), 4.36-4.27 (m, 4H), 3.79 (s, 2H), 2.61-2.28 (m, 9H), 1.55-1.38 (m, 1H), 1.35-1.16 (m, 1H), 0.91 (bs, 3H), 0.84 (t, J = 7.97 Hz, 3H). | Found [M + H]$^+$ 598.2808 $C_{34}H_{37}FN_5O_4$ requires 582.2824 |
| Example 180 | $^1$H-NMR (500 MHz, DMSO): δ 10.48 (s, 1H), 10.29 (s, 1H), 8.68 (d, J = 1.81 Hz, 1H), 8.48 (d, J = 9.06 Hz, 1H), 8.26 (dd, J = 9.06, 1.81 Hz, 1H), 8.13 (dd, J = 7.25, 2.72 Hz, 1H), 8.05 (d, J = 9.06 Hz, 1H), 7.76 (d, J = 8.16 Hz, 1H), 7.71-7.66 (m, 1H), 7.57 (d, J = 2.72 Hz, 1H), 7.55 (dd, J = 9.06, 2.72 Hz, 1H), 7.28 (app t, J = 9.97 Hz, 1H), 6.99 (d, J = 9.06 Hz, 1H), 4.34-4.27 (m, 5H), 4.03 (d, J = 14.59 Hz, 1H), 3.95 (d, J = 14.59 Hz, 1H), 2.87-2.57 (m, 6H), 1.78-1.58 (m, 3H), 1.01 (t, J = 6.48 Hz, 3H). | Found [M + H]$^+$ 582.2489 $C_{33}H_{33}FN_5O_4$ requires 582.2511 |
| Example 181 | $^1$H-NMR (500 MHz, DMSO): δ 10.39 (s, 1H), 10.18 (s, 1H), 8.64 (d, J = 1.67 Hz, 1H), 8.47 (d, J = 8.37 Hz, 1H), 8.24 (dd, J = 8.37, 1.67 Hz, 1H), 8.14 (dd, J = 6.69, 2.51 Hz, 1H), 8.06 (d, J = 8.37 Hz, 1H), 7.68-7.64 (m, 1H), 7.63 (d, J = 8.37 Hz, 1H), 7.55 (d, J = 2.51 Hz, 1H), 7.52 (dd, J = 8.37, 2.51 Hz, 1H), 7.29 (app t, J = 10.04 Hz, 1H), 6.99 (d, J = 8.37 Hz, 1H), 4.36-4.27 (m, 4H), 3.83 (s, 2H), 3.24 (s, 4H), 2.07 (t, J = 8.08 Hz, 4H), 1.76 (qn, J = 8.08 Hz, 2H). | Found [M + H]$^+$ 553.2266 $C_{32}H_{30}FN_4O_4$ requires 553.2251 |
| Example 182 | $^1$H-NMR (500 MHz, DMSO): δ 10.41 (s, 1H), 10.19 (s, 1H), 8.66 (d, J = 1.49 Hz, 1H), 8.50 (d, J = 8.20 Hz, 1H), 8.27 (dd, J = 8.20, 1.49 Hz, 1H), 8.14 (dd, J = 6.71, 2.24 Hz, 1H), 8.09 (d, J = 8.20 Hz, 1H), 7.67-7.64 (m, 1H), 7.64 (d, J = 8.20 Hz, 1H), 7.55 (d, J = 1.49 Hz, 1H), 7.52 (dd, J = 8.20, 1.49 Hz, 1H), 7.29 (app t, J = 9.69 Hz, 1H), 6.99 (d, J = 8.20 Hz, 1H), 4.35-4.28 (m, 4H), 4.11 (bs, 2H), 3.72-3.63 (m, 2H), 3.16-3.04 (m, 2H), 2.62 (oct, J = 7.43 Hz, 1H), 1.17 (d, J = 7.43 Hz, 3H). | Found [M + H]$^+$ 527.2102 $C_{30}H_{28}FN_4O_4$ requires 527.2095 |
| Example 183 | $^1$H-NMR (500 MHz, DMSO): δ 10.40 (s, 1H), 10.18 (s, 1H), 8.66 (d, J = 1.95 Hz, 1H), 8.51 (d, J = 8.47 Hz, 1H), 8.26 (dd, J = 8.47, 1.95 Hz, 1H), 8.14 (dd, J = 7.16, 2.60 Hz, 1H), 8.08 (d, J = 9.12 Hz, 1H), 7.67-7.63 (m, 2H), 7.54 (d, J = 1.95 Hz, 1H), 7.52 (dd, J = | Found [M + H]$^+$ 541.2240 $C_{31}H_{30}FN_4O_4$ requires 541.2246 |

TABLE E-continued

| Compound | 1H NMR | Mass Spec |
|---|---|---|
| Example 184 | 8.47, 2.60 Hz, 1H), 7.29 (app t, J = 9.77 Hz, 1H), 6.99 (d, J = 8.47 Hz, 1H), 4.35-4.28 (m, 4H), 4.08 (bs, 2H), 3.22 (bs, 4H), 1.24 (s, 6H).<br>$^1$H-NMR (500 MHz, MeOD): δ 8.58 (d, J = 1.88 Hz, 1H), 8.47 (d, J = 8.16 Hz, 1H), 8.27 (dd, J = 8.16, 1.88 Hz, 1H), 8.19 (dd, J = 6.28, 2.51 Hz, 1H), 8.12 (d, J = 8.16 Hz, 1H), 7.87 (d, J = 8.16 Hz, 1H), 7.60-7.56 (m, 1H), 7.49 (d, J = 1.88 Hz, 1H), 7.48 (dd, J = 8.16, 1.88 Hz, 1H), 7.22 (app t, J = 9.42 Hz, 1H), 6.94 (d, J = 8.16 Hz, 1H), 4.35-4.28 (m, 4H), 4.00 (s, 2H), 2.88-2.78 (m, 8H), 2.63 (q, J = 7.61 Hz, 2H), 1.92-1.85 (m, 2H), 1.11 (t, J = 7.61 Hz, 3H). | Found [M + H]$^+$ 584.2693<br>$C_{33}H_{34}FN_5O_4$ requires 584.2673 |

Example 185, N-(5-(2,3-dihydrobenzo[b][1,4]dioxine-6-carboxamido)-2-fluorophenyl)-2-((4-isopropylpiperazin-1-yl)methyl)quinoline-6-carboxamide N-(3-amino-4-fluorophenyl)-2,3-dihydrobenzo[b][1,4]dioxine-6-carboxamide (0.1009 g, 0.347 mmol), 2-((4-isopropylpiperazin-1-yl)methyl)quinoline-6-carboxylic acid hydrochloride (0.143 g, 0.763 mmol) and EDO (0.166 g, 0.867 mmol) were dissolved in dry DMF (2.5 mL), then pyridine (0.140 mL, 1.734 mmol) was added dropwise and the resulting mixture was allowed to stir at room temperature for 72 hours. The reaction mixture was poured onto water (5 mL) and the precipitate was washed several times with water and Et$_2$O to afford the crude product as a pale yellow solid, which was purified via flash column chromatography on silica gel in gradient (from 0 to 10% MeOH in DCM) to afford the title compound as an orange solid (0.050 g, 25%). $^1$H-NMR (500 MHz, DMSO): δ 10.41 (bs, 1H), 10.21 (bs, 1H), 8.65 (s, 1H), 8.49 (d, J=8.78 Hz, 1H), 8.25 (dd, J=8.78, 1.88 Hz, 1H), 8.14 (dd, J=6.90, 2.51 Hz, 1H), 8.08 (d, J=8.78 Hz, 1H), 7.73 (d, J=8.78 Hz, 1H), 7.68-7.63 (m, 1H), 7.55 (d, J=2.51 Hz, 1H), 7.52 (dd, J=8.78, 1.88 Hz, 1H), 7.29 (app t, J=9.28 Hz, 1H), 6.99 (d, J=8.78 Hz, 1H), 4.36-4.27 (m, 4H), 3.79 (bs, 2H), 3.15-2.34 (m, 9H), 0.99 (bs, 6H). HRMS (ESI$^+$): Found [M+H]$^+$ 584.2636 $C_{33}H_{35}N_5O_4$ requires 584.2668.

The following compounds were synthesised according to the procedure for Example 185, by substituting the appropriate carboxylic acid for 2-((4-isopropylpiperazin-1-yl)methyl)quinoline-6-carboxylic acid hydrochloride.

Example 186, N-(5-(2,3-dihydrobenzo[b][1,4]dioxine-6-carboxamido)-2-fluorophenyl)-2-(3-(piperidin-1-yl)propoxy)quinoline-6-carboxamide Example 187, N-(5-(2,3-dihydrobenzo[b][1,4]dioxine-6-carboxamido)-2-fluorophenyl)-2-(3-(pyrrolidin-1-yl)propoxy)quinoline-6-carboxamide Example 188, N-(5-(2,3-dihydrobenzo[b][1,4]dioxine-6-carboxamido)-2-fluorophenyl)-2-(2-(pyrrolidin-1-yl)ethoxy)quinoline-6-carboxamide Example 189, N-(2-chloro-5-(2,3-dihydrobenzo[b][1,4]dioxine-6-carboxamido)phenyl)-2-(3-(piperidin-1-yl)propoxy)quinoline-6-carboxamide Example 190, (rac)-N-(5-(2,3-dihydrobenzo[b][1,4]dioxine-6-carboxamido)-2-fluorophenyl)-2-((2-methylpyrrolidin-1-yl)methyl)quinoline-6-carboxamide

TABLE F

| Compound | 1H NMR | Mass Spec |
|---|---|---|
| Example 186 | $^1$H-NMR (500 MHz, DMSO): δ 10.32 (bs, 1H), 10.19 (bs, 1H), 8.59 (d, J = 1.76 Hz, 1H), 8.39 (d, J = 8.79 Hz, 1H), 8.22 (dd, J 8.79, 1.76 Hz, 1H), 8.13 (dd, J = 7.03 Hz, 2.34 Hz, 1H), 7.86 (d, J = 8.79 Hz, 1H), 7.67-7.62 (m, 1H), 7.55 (d, J = 1.76 Hz, 1H), 7.52 (dd, J = 8.21, 1.76 Hz, 1H), 7.28 (app t, J = 9.96 Hz, 1H), 7.11 (d, J = 8.90 Hz, 1H), 6.99 (d, J = 8.90 Hz, 1H), 4.51 (t, J = 6.29 Hz, 2H), 4.34-4.28 (m, 4H), 3.16-2.65 (m, 4H), 2.36-1.30 (m, 10H). | Found [M + H]$^+$ 585.2485<br>$C_{33}H_{34}FN_4O_5$ requires 585.2508. |
| Example 187 | $^1$H-NMR (500 MHz, DMSO): δ 10.32 (bs, 1H), 10.19 (bs, 1H), 8.59 (d, J = 2.21 Hz, 1H), 8.41 (d, J = 8.84 Hz, 1H), 8.23 (dd, J = 8.84, 2.21 Hz, 1H), 8.13 (dd, J = 8.84, 2.21 Hz, 1H), 7.87 (d, J = 8.84 Hz, 1H), 7.66-7.61 (m, 1H), 7.55 (d, J = 2.21 Hz, 1H), 7.52 (dd, J = 8.11, 2.21 Hz, 1H), 7.29 (app t, J = 10.23 Hz, 1H), 7.12 (d, J = 8.84 Hz, 1H), 6.99 (d, J = 8.84 Hz, 1H), 4.53 (t, J = 5.57 Hz, 2H), 4.34-4.28 (m, 4H), 3.41-2.66 (m, 6H), 2.21-2.09 (m, 2H), 1.93-1.80 (m, 4H). | Found [M + H]$^+$ 571.2321<br>$C_{32}H_{32}FN_4O_5$ requires 571.2351. |
| Example 188 | $^1$H-NMR (500 MHz, MeOD): δ 8.48 (d, J = 2.04 Hz, 1H), 8.29 (d, J = 8.85 Hz, 1H), 8.20 (dd, J = 8.17, 2.04 Hz, 1H), 8.17 (dd, J = 6.81, 2.72 Hz, 1H), 7.92 (d, J = 8.17 Hz, 1H), 7.62-7.56 (m, 1H), 7.50 (d, J = 2.04 Hz, 1H), 7.48 (dd, J = 8.17, 2.04 Hz, 1H), 7.23 (app t, J = 9.79 Hz, 1H), 7.09 (d, J = 8.85 Hz, 1H), 6.96 (d, J = 8.17 Hz, 1H), 4.70 (t, J = 5.32 Hz, 2H), 4.36-4.28 (m, 4H), 3.08 (t, J = 5.25 Hz, 2H), 2.84-2.76 (m, 4H), 1.91-1.85 (m, 4H). | Found [M + H]$^+$ 557.2196<br>$C_{31}H_{30}FN_4O_5$ requires 557.2195. |

TABLE F-continued

| Compound | 1H NMR | Mass Spec |
| --- | --- | --- |
| Example 189 | $^1$H-NMR (500 MHz, DMSO): δ 10.29 (s, 1H), 10.26 (s, 1H), 8.60 (bs, 1H), 8.41 (d, J = 9.19 Hz, 1H), 8.24 (d, J = 8.49 Hz, 1H), 8.13 (d, J = 2.12 Hz, 1H), 7.87 (d, J = 8.49 Hz, 1H), 7.74 (dd, J = 9.19, 2.12 Hz, 1H), 7.56 (d, J = 2.12 Hz, 1H), 7.55-7.50 (m, 2H), 7.11 (d, J = 8.49 Hz, 1H), 6.99 (d, J = 8.49 Hz, 1H), 4.51 (t, J = 6.52 Hz, 2H), 4.35-4.27 (m, 4H), 3.08 (t, J = 5.25 Hz, 2H), 2.28-1.96 (m, 4H), 1.84-1.32 (m, 8H). | Found [M + H]$^+$ 601.2200 $C_{33}H_{34}ClN_4O_5$ requires 601.2212. |
| Example 190 | $^1$H-NMR (500 MHz, DMSO): δ 10.39 (s, 1H), 10.19 (s, 1H), 8.64 (d, J = 1.48 Hz, 1H), 8.48 (d, J = 8.87 Hz, 1H), 8.24 (dd, J = 8.87, 2.22 Hz, 1H), 8.13 (dd, J = 6.65, 2.22 Hz, 1H), 8.08 (d, J = 8.87 Hz, 1H), 7.68-7.63 (m, 1H), 7.55 (d, J = 2.22 Hz, 1H), 7.48 (dd, J = 8.87, 2.22 Hz, 1H), 7.29 (app t, J = 9.61 Hz, 1H), 6.99 (d, J = 8.87 Hz, 1H), 4.34-4.28 (m, 4H), 4.24 (d, J = 13.83 Hz, 1H), 3.53 (d, J = 13.83 Hz, 1H), 2.89-2.83 (m, 1H), 2.57-2.48 (m, 1H), 2.22 (q, J = 8.80 Hz, 1H), 2.00-1.91 (m, 1H), 1.71-1.59 (m, 2H), 1.43-1.34 (m, 1H), 1.11 (d, J = 5.03 Hz, 3H). | Found [M + H]$^+$ 541.2236 $C_{31}H_{30}FN_4O_4$ requires 541.2246. |

Compound 230, methyl 2-formylquinoline-6-carboxylate

To a solution of 2-methylquinoline-6-carboxylic acid (1.5 g, 8.01 mmol) in dry methanol (18 mL) under argon at room temperature, HCl in dioxane (8.01 mL, 32.1 mmol) was added dropwise and the resulting mixture was heated at 85° C. for 7 hours. Then it was cooled, concentrated, diluted with ethyl acetate and washed with NaOH 1N (2×20 mL), water (1×20 mL) and brine (1×20 mL). Dried over $Na_2SO_4$, filtered and concentrated under vacuum to afford the crude product methyl-2-methylquinoline-6-carboxylate as a pink solid (1.44 g, 89%) which was carried onto the next step without purification. To a suspension of selenium dioxide (0.873 g, 7.87 mmol) in dry dioxane (11 mL) under argon at room temperature methyl-2-methylquinoline-6-carboxylate (1.44 g, 7.16 mmol) was added in one portion and the resulting suspension was allowed to stir at 80° C. for 18 hours. The reaction was allowed to cool to room temperature, filtered through Celite and concentrated under vacuum to afford an orange solid as crude product which was purified via flash column chromatography on silica gel in gradient from 10 to 20% ethyl acetate in petroleum ether to afford the clean product as a pale yellow solid (1.28 g, 83%). $^1$H-NMR (500 MHz, CDCl$_3$): δ 10.26 (d, J=0.58 Hz, 1H), 8.68 (d, J=1.62 Hz, 1H), 8.45 (d, J=8.71 Hz, 1H), 8.42 (dd, J=8.71, 1.62 Hz, 1H), 8.32 (d, J=8.71 Hz, 1H), 8.11 (d, J=8.23 Hz, 1H), 4.04 (s, 3H). HRMS (ESI$^+$): Found [M+H]$^+$ 216.0658 $C_{12}H_{10}NO_3$ requires 216.0660.

Compound 231, methyl 2-((4-isopropylpiperazin-1-yl)methyl)quinoline-6-carboxylate To a solution of methyl-2-formylquinoline-6-carboxylate (0.20 g, 0.929 mmol) in dry DCM, 1-isopropylpiperazine (0.399 mL, 2.79 mmol) was added dropwise at room temperature and the resulting mixture was allowed to stir under an inert argon atmosphere for 2.5 hours. Then sodium triacetoxyborohydride (0.591 g, 2.79 mmol) was added in one portion and the resulting mixture was allowed to stir overnight at room temperature. The reaction mixture was diluted with DCM (20 mL) and quenched with NaHCO$_3$ (20 mL). The aqueous phase was extracted with DCM (3×10 mL) and the combined organic layers were dried to afford a yellow-orange solid as crude product (322 mg, 106%) which was carried through the next step without purification. $^1$H-NMR (500 MHz, CDCl$_3$): δ 8.55 (d, J=1.93 Hz, 1H), 8.27 (dd, J=8.87, 1.93 Hz, 1H), 8.20 (d, J=8.87 Hz, 1H), 8.09 (d, J=8.87 Hz, 1H), 7.70 (d, J=8.87 Hz, 1H), 3.98 (s, 3H), 3.86 (s, 2H), 2.26 (heptet, J=6.75 Hz, 1H), 2.67-2.52 (m, 8H), 1.05 (d, J=6.75 Hz, 6H). HRMS (ESI$^+$): Found [M+H]$^+$ 328.2031 $C_{19}H_{26}N_3O_2$ requires 328.2020.

Compound 232, 2-((4-isopropylpiperazin-1-yl)methyl)quinoline-6-carboxylic acid

To a solution of methyl 2-((4-isopropylpiperazin-1-yl)methyl)quinolone-6-carboxylate (0.32 g, 0.977 mmol) in THF (6 mL), sodium hydroxide aqueous solution (2.443 mL, 4.89 mmol) was added dropwise at 20° C. and methanol (2.4 mL) was added to increase the miscibility of the two phases. The resulting red-brown solution was allowed to stir at room temperature for 2 hours after which it was concentrated under reduced pressure to remove the organic solvents and the aqueous layer was acidified with HCl 1N (pH 3) and then washed with ethyl acetate (3×5 mL). The aqueous phase is concentrated under reduced pressure to afford a salmon solid as crude product (0.306 g, 100%) which was carried onto the next step without purification. $^1$H-NMR (500 MHz, DMSO): δ$_H$ 11.99 (bs, 1H), 8.73 (d, J=1.47 Hz, 1H), 8.71 (d, J=8.01 Hz, 1H), 8.27 (dd, J=8.84, 1.97 Hz, 1H), 8.18 (d, J=8.84 Hz, 1H), 7.89 (d, J=8.35 Hz, 1H), 4.69 (bs, 2H), 2.79-2.46 (m, 9H), 1.29 (d, J=6.74 Hz, 6H). HRMS (ESI$^+$): Found [M+H]$^+$ 314.1868 $C_{18}H_{24}N_3O_2$ requires 314.1863.

Compound 233, N-(2-chloro-5-nitrophenyl)-2-methylquinoline-6-carboxamide

To a suspension of 2-methylquinoline-6-carboxylic acid (1.5 g, 8.01 mmol) in dry DCM (40 mL), DMF (1.401 μl, 0.018 mmol) and oxalyl chloride (0.740 mL, 8.74 mmol) were added dropwise and the resulting green solution was allowed to stir at 20° C. for 3 hours after which it was concentrated under vacuum to afford a dry pale green solid. The solid was dissolved in pyridine (40.0 mL) and 2-chloro-5-nitroaniline (1.257 g, 7.28 mmol) was added in one portion. The resulting dark yellow suspension was allowed to stir for 2 hours after which it was poured onto water and the yellow precipitate was filtered and washed several times with water, Et$_2$O and finally with a minimum amount of DCM to afford the crude product as a yellow solid which does not require further purification (2.20 g, 88%). $^1$H-NMR (500 MHz, DMSO): δ 10.59 (s, 1H), 8.65 (d, J=1.99 Hz, 1H), 8.60 (d, J=2.66 Hz, 1H), 8.44 (d, J=8.64 Hz, 1H), 8.25 (dd, J=8.64, 1.99 Hz, 1H), 8.15 (dd, J=8.64, 2.66 Hz, 1H), 8.06 (d, J=8.64 Hz, 1H), 7.91 (d, J=8.64 Hz, 1H), 7.55 (d, J=7.98 Hz, 1H), 2.71 (s, 3H). HRMS (ESI$^+$): Found [M+H]$^+$ 342.0646 $C_{17}H_{13}ClN_3O_3$ requires 342.0640.

Compound 234, N-(5-amino-2-chlorophenyl)-2-methylquinoline-6-carboxamide

To a solution of N-(2-chloro-5-nitrophenyl)-2-methylquinoline-6-carboxamide in water (7.00 mL) and EtOH (21 mL), ammonium chloride (2.410 g, 45.1 mmol) and iron powder (2.52 g, 45.1 mmol) were added and the resulting suspension was allowed to stir at 90° C. for 1 hour. The reaction mixture was allowed to warm to room temperature, diluted with MeOH and DCM and filtered through a pad of Celite. The resulting filtrate was concentrated under vacuum to afford a light brown solid as crude product, which was taken directly onto the next step without any further purification (2.00 g, 100%). $^1$H-NMR (500 MHz, DMSO): δ 9.96 (s, 1H), 8.58 (d, J=2.18 Hz, 1H), 8.41 (d, J=8.72 Hz, 1H), 8.21 (dd, J=8.72, 2.18 Hz, 1H), 8.02 (d, J=8.72 Hz, 1H), 7.53 (d, J=7.63 Hz, 1H), 7.15 (d, J=8.72 Hz, 1H), 6.87 (d, J=2.18 Hz, 1H), 6.50 (dd, J=8.72, 2.18 Hz, 1H), 5.41 (bs, 2H), 2.70 (s, 3H). HRMS (ESI$^+$): Found [M+H]$^+$ 312.0902 $C_{17}H_{15}ClN_3O$ requires 312.0898.

Compound 235, N-(2-chloro-5-(2,3-dihydrobenzo[b][1,4]dioxine-6-carboxamido)phenyl)-2-methylquinoline-6-carboxamide To a suspension of 2,3-dihydrobenzo[b][1,4]dioxine-6-carboxylic acid (1.271 g, 7.06 mmol) in dry DCM (20 mL), DMF (1.234 μl, 0.016 mmol) and oxalyl chloride (0.651 mL, 7.70 mmol) were added dropwise and the resulting green solution was allowed to stir at 20° C. for 3 hours after which it was concentrated under vacuum to afford a dry pale green solid. The solid was dissolved in pyridine (20.00 mL) and N-(5-amino-2-chlorophenyl)-2-methylquinoline-6-carboxamide (2.00 g, 6.42 mmol) was added in one portion. The resulting dark yellow suspension was allowed to stir for 2 hours after which it was poured onto water and the yellow precipitate was filtered and washed several times with water, Et$_2$O and finally with a minimum amount of DCM to afford the crude product as a pale yellow solid which does not require further purification (1.86 g, 61%). $^1$H-NMR (500 MHz, DMSO): δ 10.31 (s, 1H), 10.27 (s, 1H), 8.63 (d, J=1.47 Hz, 1H), 8.43 (d, J=8.81 Hz, 1H), 8.25 (dd, J=8.81, 2.20 Hz, 1H), 8.14 (d, J=2.20 Hz, 1H), 8.04 (d, J=8.81 Hz, 1H), 7.75 (dd, J=8.81, 2.94 Hz, 1H), 7.58-7.49 (m, 4H), 7.00 (d, J=8.81 Hz, 1H), 4.37-4.26 (m, 4H), 2.71 (s, 3H). HRMS (ESI$^+$): Found [M+H]$^+$ 474.1210 $C_{26}H_{21}ClN_3O_4$ requires 474.1215.

Compound 236, N-(2-chloro-5-(2,3-dihydrobenzo[b][1,4]dioxine-6-carboxamido)phenyl)-2-formylquinoline-6-carboxamide A solution of N-(2-chloro-5-(2,3-dihydrobenzo[b][1,4]dioxine-6-carboxamido)phenyl)-2-methylquinoline-6-carboxamide (0.500 g, 1.055 mmol) and selenium dioxide (0.129 g, 1.161 mmol) in dry DMF (12.00 mL) and dioxane (12.00 mL) was heated at 152° C. for 2 h after which a further portion of selenium dioxide (0.129 g, 1.161 mmol) was added and the reaction mixture was allowed to stir at 152° C. for 1 h. Then the reaction mixture was allowed to cool to room temperature and it was diluted with DCM and filtered through a pad of Celite. The filtrate was concentrated under vacuum to afford the crude product as a yellow solid which was taken directly onto the next step without any further purification (0.515 g, 100%). $^1$H-NMR (500 MHz, DMSO): δ 10.45 (s, 1H), 10.40 (s, 1H), 10.17 (s, 1H), 8.81-8.79 (m, 2H), 8.42-8.34 (m, 2H), 8.19 (app t, J=7.47 Hz, 1H), 8.09 (d, J=8.13 Hz, 1H), 7.79-7.74 (m, 2H), 7.55 (d, J=1.99 Hz, 1H), 7.52 (dd, J=8.13, 1.99 Hz, 1H), 6.99 (d, J=9.04 Hz, 1H), 4.36-4.26 (m, 4H). HRMS (ESI$^+$): Found [M+H]$^+$ 488.1012 $C_{26}H_{19}ClN_3O_5$ requires 488.1013.

Example 191, 2-((4-(tert-butyl)piperazin-1-yl)methyl)-N-(2-chloro-5-(2,3-dihydrobenzo[b][1,4]dioxine-6-carboxamido)phenyl)quinoline-6-carboxamide A solution of N-(2-chloro-5-(2,3-dihydrobenzo[b][1,4]dioxine-6-carboxamido)phenyl)-2-formylquinoline-6-carboxamide (0.300 g, 0.615 mmol) and 1-(tert-butyl)piperazine in dry DCM (5 mL) was allowed to stir at 20° C. for 12 h, after which sodium triacetoxyborohydride (0.391 g, 1.845 mmol) was added in one portion and the resulting mixture was allowed to stir at 20° C. for 2 h. The reaction was quenched with NaHCO$_3$ saturated aqueous solution (5 mL) and extracted with a DCM/MeOH 9/1 mixture (3×5 mL). The crude product (pale yellow solid) was purified via flash column chromatography on silica gel in gradient from 0 to 10% MeOH in DCM followed by water wash and Et$_2$O trituration to afford the desired product as a beige solid (0.060 g, 16%). $^1$H-NMR (500 MHz, DMSO): δ 10.34 (s, 1H), 10.29 (s, 1H), 8.66 (d, J=1.56 Hz, 1H), 8.50 (d, J=8.60 Hz, 1H), 8.26 (dd, J=8.60, 2.35 Hz, 1H), 8.14 (d, J=2.35 Hz, 1H), 8.09 (d, J=8.60 Hz, 1H), 7.77-7.72 (m, 2H), 7.56 (d, J=2.35 Hz, 1H), 7.54 (d, J=1.56 Hz, 1H), 7.53 (dd, J=7.82, 2.35 Hz, 1H), 7.00 (d, J=8.60 Hz, 1H), 4.35-4.27 (m, 4H), 3.79 (s, 2H), 2.79-2.29 (m, 8H), 1.03 (bs, 9H). HRMS (ESI$^+$): Found [M+H]$^+$ 614.2502 $C_{34}H_{37}ClN_5O_4$ requires 614.2529.

The following compounds were synthesised according to the procedure for Example 191, by substituting the appropriate amine for 1-(tert-butyl)piperazine.

Example 192, N-(2-chloro-5-(2,3-dihydrobenzo[b][1,4]dioxine-6-carboxamido)phenyl)-2-(piperazin-1-ylmethyl)quinoline-6-carboxamide Example 193, 2-((4-(sec-butyl)piperazin-1-yl)methyl)-N-(2-chloro-5-(2,3-dihydrobenzo[b][1,4]dioxine-6-carboxamido)phenyl)quinoline-6-carboxamide Example 194, N-(2-chloro-5-(2,3-dihydrobenzo[b][1,4]dioxine-6-carboxamido)phenyl)-2-((4-cyclopropylpiperazin-1-yl)methyl)quinoline-6-carboxamide Example 195, N-(2-chloro-5-(2,3-dihydrobenzo[b][1,4]dioxine-6-carboxamido)phenyl)-2-((4-methylpiperazin-1-yl)methyl)quinoline-6-carboxamide Example 196, N-(2-chloro-5-(2,3-dihydrobenzo[b][1,4]dioxine-6-carboxamido)phenyl)-2-((4-ethylpiperazin-1-yl)methyl)quinoline-6-carboxamide Example 197, N-(2-chloro-5-(2,3-dihydrobenzo[b][1,4]dioxine-6-carboxamido)phenyl)-2-((4-isopropylpiperazin-1-yl)methyl)quinoline-6-carboxamide Example 198, N-(2-chloro-5-(2,3-dihydrobenzo[b][1,4]dioxine-6-carboxamido)phenyl)-2-(pyrrolidin-1-ylmethyl)quinoline-6-carboxamide Example 199, 2-(azetidin-1-ylmethyl)-N-(2-chloro-5-(2,3-dihydrobenzo[b][1,4]dioxine-6-carboxamido)phenyl)quinoline-6-carboxamide Example 200, N-(2-chloro-5-(2,3-dihydrobenzo[b][1,4]dioxine-6-carboxamido)phenyl)-2-((3-methylazetidin-1-yl)methyl)quinoline-6-carboxamide Example 201, N-(2-chloro-5-(2,3-dihydrobenzo[b][1,4]dioxine-6-carboxamido)phenyl)-2-((3,3-dimethylazetidin-1-yl)methyl)quinoline-6-carboxamide

TABLE G

| Compound | 1H NMR | Mass Spec |
|---|---|---|
| Example 192 | $^1$H-NMR (500 MHz, DMSO): δ 10.38 (s, 1H), 10.33 (s, 1H), 9.01 (bs, 1H), 8.69 (d, J = 1.65 Hz, 1H), 8.53 (d, J = 8.27 Hz, 1H), 8.28 (dd, J = 8.27, 1.65 Hz, 1H), 8.16 (dd, J = 2.48 Hz, 1H), 8.10 (d, J = 8.27 Hz, 1H), 7.78-7.72 (m, 2H), 7.57 (d, J = 2.48 Hz, 1H), 7.54 (dd, J = 8.27, 2.48 Hz, 1H), 7.53 (d, J = 8.61 Hz, 1H), 6.99 (d, J = 8.27 Hz, 1H), 4.35-4.28 (m, 4H), 3.88 (s, 2H), 3.12-3.04 (m, 4H), 2.73-2.68 (m, 4H). | Found [M + H]$^+$ 558.1877 $C_{30}H_{29}ClN_5O_4$ requires 558.1903 |
| Example 193 | $^1$H-NMR (500 MHz, DMSO): δ 10.32 (s, 1H), 10.27 (s, 1H), 8.66 (d, J = 1.60 Hz, 1H), 8.50 (d, J = 8.43 Hz, 1H), 8.26 (dd, J = 8.43, 1.60 Hz, 1H), 8.15 (d, J = 2.36 Hz, 1H), 8.09 (d, J = 8.43 Hz, 1H), 7.75 (dd, J = 8.43, 2.36 Hz, 1H), 7.74 (d, J = 8.43 Hz, 1H), 7.55 (d, J = 2.36 Hz, 1H), 7.54 (d, J = 1.60 Hz, 1H), 7.52 (dd, J = 7.88, 2.36 Hz, 1H), 7.00 (d, J = 8.43 Hz, 1H), 4.35-4.27 (m, 4H), 3.81 (s, 2H), 2.87-2.17 (m, 9H), 1.51 (bs, 1H), 1.28 (bs, 1H), 0.95 (bs, 3H), 0.85 (t, J = 7.65 Hz, 3H). | Found [M + H]$^+$ 614.2495 $C_{34}H_{37}ClN_5O_4$ requires 614.2529 |
| Example 194 | $^1$H-NMR (500 MHz, DMSO): δ 10.32 (s, 1H), 10.27 (s, 1H), 8.65 (s, 1H), 8.50 (d, J = 7.87 Hz, 1H), 8.26 (d, J = 7.87 Hz, 1H), 8.15 (d, J = 1.83 Hz, 1H), 8.09 (d, J = 7.87 Hz, 1H), 7.77-7.71 (m, 2H), 7.57-7.49 (m, 3H), 7.00 (d, J = 7.87 Hz, 1H), 4.36-4.24 (m, 4H), 3.78 (s, 2H), 2.57 (bs, 4H), 2.43 (bs, 4H), 1.63-1.58 (m, 1H), 0.42-0.37 (m, 2H), 0.30-0.24 (m, 2H). | Found [M + H]$^+$ 598.2210 $C_{33}H_{33}ClN_5O_4$ requires 598.2216 |
| Example 195 | $^1$H-NMR (500 MHz, DMSO): δ 10.32 (s, 1H), 10.23 (s, 1H), 8.65 (s, 1H), 8.48 (d, J = 8.24 Hz, 1H), 8.29 (dd, J = 8.24 Hz, 1H), 8.14 (s, 1H), 8.07 (d, J = 8.24 Hz, 1H), 7.71 (d, J = 8.24 Hz, 2H), 7.57-7.43 (m, 3H), 7.00 (d, J = 8.24 Hz, 1H), 4.36-4.22 (m, 4H), 3.79 (s, 2H), 2.47-2.23 (m, 8H), 2.17 (s, 3H). | Found [M + H]$^+$ 572.2031 $C_{31}H_{31}ClN_5O_4$ requires 572.2059 |
| Example 196 | $^1$H-NMR (500 MHz, DMSO): δ 10.32 (s, 1H), 10.27 (s, 1H), 8.65 (s, 1H), 8.50 (d, J = 8.56 Hz, 1H), 8.26 (dd, J = 8.56, 1.56 Hz, 1H), 8.14 (d, J = 2.34 Hz, 1H), 8.09 (d, J = 8.56 Hz, 1H), 7.77-7.71 (m, 2H), 7.57-7.50 (m, 3H), 7.00 (d, J = 8.56 Hz, 1H), 4.35-4.28 (m, 4H), 3.80 (s, 2H), 2.49-2.18 (m, 10H), 0.99 (t, J = 6.97 Hz, 3H). | Found [M + H]$^+$ 586.2189 $C_{32}H_{33}ClN_5O_4$ requires 586.2216 |
| Example 197 | $^1$H-NMR (500 MHz, DMSO): δ 10.33 (bs, 1H), 10.27 (bs, 1H), 8.66 (d, J = 1.38 Hz, 1H), 8.50 (d, J = 8.25 Hz, 1H), 8.26 (dd, J = 8.25, 1.38 Hz, 1H), 8.15 (d, J = 2.75 Hz, 1H), 8.09 (d, J = 8.94 Hz, 1H), 7.76-7.61 (m, 2H), 7.56-7.50 (m, 3H), 7.00 (d, J = 8.25 Hz, 1H), 4.34-4.27 (m, 4H), 3.80 (bs, 2H), 2.76-2.40 (m, 9H), 0.99 (bs, 6H). | Found [M + H]$^+$ 600.2336 $C_{33}H_{35}ClN_5O_4$ requires 600.2372 |
| Example 198 | $^1$H-NMR (500 MHz, DMSO): δ 10.32 (s, 1H), 10.27 (s, 1H), 8.65 (s, 1H), 8.49 (d, J = 7.98 Hz, 1H), 8.26 (dd, J = 7.98, 2.28 Hz, 1H), 8.14 (d, J = 2.28 Hz, 1H), 8.09 (d, J = 7.98 Hz, 1H), 7.77-7.70 (m, 2H), 7.56-7.50 (m, 3H), 7.00 (d, J = 7.98 Hz, 1H), 4.35-4.28 (m, 4H), 3.92 (s, 2H), 2.57-2.52 (m, 4H), 1.77-1.70 (m, 4H). | Found [M + H]$^+$ 543.1778 $C_{30}H_{28}ClN_4O_4$ requires 543.1794 |
| Example 199 | $^1$H-NMR (500 MHz, DMSO): δ 10.35 (s, 1H), 10.31 (s, 1H), 8.66 (d, J = 2.16 Hz, 1H), 8.49 (d, J = 8.65 Hz, 1H), 8.27 (dd, J = 8.65, 2.16 Hz, 1H), 8.14 (d, J = 2.16 Hz, 1H), 8.08 (d, J = 8.65 Hz, 1H), 7.76 (dd, J = 8.65, 2.16 Hz, 1H), 7.65 (d, J = 7.62 Hz, 1H), 7.58-7.51 (m, 3H), 6.99 (d, J = 8.65 Hz, 1H), 4.35-4.27 (m, 4H), 3.91 (s, 2H), 3.39-3.27 (m, 4H), 2.06 (qn, J = 7.10 Hz, 2H). | Found [M + H]$^+$ 529.1616 $C_{29}H_{26}ClN_4O_4$ requires 529.1637 |
| Example 200 | $^1$H NMR (500 MHz, Chloroform-d) δ 8.63 (br s, 1H), 8.58 (d, J = 2.5 Hz, 1H), 8.41 (d, J = 1.8 Hz, 1H), 8.28 (d, J = 8.5 Hz, 1H), 8.20 (d, J = 8.8 Hz, 1H), 8.16 (dd, J = 8.8, 2.0 Hz, 1H), 7.98 (dd, J = 8.8, 2.4 Hz, 2H), 7.64 (d, J = 8.5 Hz, 1H), 7.46 (s, 1H), 7.45 (d, J = 7.2 Hz, 1H), 7.39 (dd, J = 8.4, 2.2 Hz, 1H), 6.96 (d, J = 8.4 Hz, 1H), 4.36-4.30 (m, 4H), 3.99 (s, 2H), 3.64 (t, J = 7.5 Hz, 2H), 2.95 (t, J = 7.2 Hz, 2H), 2.75-2.62 (m, 1H), 1.21 (d, J = 6.8 Hz, 3H). | Found [M + H]$^+$ 543.1769 $C_{30}H_{28}ClN_4O_4$ requires 543.1794 |
| Example 201 | $^1$H-NMR (500 MHz, DMSO): δ 10.35 (s, 1H), 10.27 (s, 1H), 8.68 (d, J = 2.1 Hz, 1H), 8.55 (d, J = 8.5 Hz, 1H), 8.29 (dd, J = 8.8, 2.0 Hz, 1H), 8.18-8.08 (m, 2H), 7.74 (dd, J = 8.8, 2.5 Hz, 1H), 7.65 (d, J = 8.5 Hz, 1H), 7.58-7.48 (m, 3H), 7.00 (d, J = 8.4 Hz, 1H), 4.61-4.01 (m, 6H), 3.23 (brs, 4H), 1.27 (s, 6H). | Found [M + H]$^+$ 557.1963 $C_{31}H_{30}N_4O_4Cl$ requires 557.1956. |

Compound 237, N-(2-bromo-5-nitrophenyl)-2-methylquinoline-6-carboxamide

To a suspension of 2-methylquinoline-6-carboxylic acid (1.5 g, 8.01 mmol) in dry DCM (20 mL), DMF (1.114 μl, 0.014 mmol) and oxalyl chloride (0.588 mL, 6.95 mmol) were added dropwise and the resulting green solution was allowed to stir at 20° C. for 3 hours after which it was concentrated under vacuum to afford a dry pale green solid. The solid was dissolved in pyridine (20.0 mL) and 2-bromo-5-nitroaniline (1.257 g, 5.79 mmol) was added in one portion. The resulting dark yellow suspension was allowed to stir for 2 hours after which it was poured onto water and the yellow precipitate was filtered and washed several times with water, Et$_2$O and finally with a minimum amount of DCM to afford the crude product as a yellow solid which does not require further purification (2.47 g, 110%). $^1$H-NMR (500 MHz, DMSO): δ 10.56 (s, 1H), 8.65 (d, J=1.78 Hz, 1H), 8.52 (app t, J=1.78 Hz, 1H), 8.44 (d, J=8.32 Hz, 1H), 8.26 (dd, J=8.92, 1.78 Hz, 1H), 8.09-8.05 (m, 3H), 7.55 (d, J=8.32 Hz, 1H), 2.71 (s, 3H). HRMS (ESI$^+$): Found [M+H]$^+$ 386.0129 C$_{17}$H$_{13}$BrN$_3$O$_3$ requires 386.0135.

Compound 238, N-(5-amino-2-bromophenyl)-2-methylquinoline-6-carboxamide

To a solution of N-(2-bromo-5-nitrophenyl)-2-methylquinoline-6-carboxamide (2.00 g, 5.18 mmol) in water (7.00 mL) and EtOH (21 mL), ammonium chloride (1.939 g, 36.3 mmol) and iron powder (2.025 g, 36.3 mmol) were added and the resulting suspension was allowed to stir at 90° C. for 1 hour. The reaction mixture was allowed to cool to room temperature, diluted with MeOH and DCM and filtered through a pad of Celite. The resulting filtrate was concentrated under vacuum to afford a light brown solid as crude product, which was taken directly onto the next step without any further purification (1.80 g, 98%). $^1$H-NMR (500 MHz, DMSO): δ 9.94 (s, 1H), 8.59 (d, J=1.76 Hz, 1H), 8.40 (d, J=8.78 Hz, 1H), 8.22 (dd, J=8.78, 1.76 Hz, 1H), 8.02 (d, J=8.78 Hz, 1H), 7.52 (d, J=8.78 Hz, 1H), 7.28 (d, J=8.78 Hz, 1H), 6.86 (d, J=1.76 Hz, 1H), 6.45 (dd, J=8.78, 1.76 Hz, 1H), 5.40 (bs, 2H), 2.70 (s, 3H). HRMS (ESI$^+$): Found [M+H]$^+$ 358.0369 C$_{17}$H$_{15}$BrN$_3$O requires 358.0374.

Compound 239, N-(2-bromo-5-(2,3-dihydrobenzo[b][1,4]dioxine-6-carboxamido)phenyl)-2-methylquinoline-6-carboxamide To a suspension of 2,3-dihydrobenzo[b][1,4]dioxine-6-carboxylic acid (1.001 g, 5.56 mmol) in dry DCM (20 mL), DMF (0.972 μl, 0.013 mmol) and oxalyl chloride (0.513 mL, 6.06 mmol) were added dropwise and the resulting green solution was allowed to stir at 20° C. for 3 hours after which it was concentrated under vacuum to afford a dry pale green solid. The solid was dissolved in pyridine (20.00 mL) and N-(5-amino-2-bromophenyl)-2-methylquinoline-6-carboxamide (1.80 g, 5.05 mmol) was added in one portion. The resulting dark yellow suspension was allowed to stir for 72 hours after which it was poured onto water. The yellow precipitate was filtered and washed several times with water, Et$_2$O and finally with a minimum amount of DCM to afford the crude product as a pale yellow solid which does not require further purification (2.11 g, 81%). $^1$H-NMR (500 MHz, DMSO): δ 10.29 (s, 1H), 10.27 (s, 1H), 8.63 (s, 1H), 8.42 (d, J=9.11 Hz, 1H), 8.25 (d, J=7.29 Hz, 1H), 8.10 (s, 1H), 8.05 (d, J=8.20 Hz, 1H), 7.69 (bs, 2H), 7.58-7.49 (m, 3H), 6.99 (d, J=9.11 Hz, 1H), 4.37-4.27 (m, 4H), 2.71 (s, 3H). HRMS (ESI$^+$): Found [M+H]$^+$ 520.0723 C$_{26}$H$_{21}$BrN$_3$O$_4$ requires 520.0693.

Compound 240, N-(2-bromo-5-(2,3-dihydrobenzo[b][1,4]dioxine-6-carboxamido)phenyl)-2-formylquinoline-6-carboxamide A solution of N-(2-bromo-5-(2,3-dihydrobenzo[b][1,4]dioxine-6-carboxamido)phenyl)-2-methylquinoline-6-carboxamide (1.00 g, 1.929 mmol) and selenium dioxide (0.235 g, 2.122 mmol) in dry DMF (4.00 mL) and dioxane (12.00 mL) was heated at 152° C. for 1 h. The reaction mixture was allowed to cool to room temperature and it was diluted with DCM and filtered through a pad of Celite. The filtrate was concentrated under vacuum to afford the crude product as a yellow solid which was taken directly onto the next step without any further purification (1.00 g, 97%). $^1$H-NMR (500 MHz, DMSO): δ 10.47 (s, 1H), 10.28 (s, 1H), 10.17 (d, J=0.53 Hz, 1H), 8.81-8.77 (m, 2H), 8.42-8.36 (m, 2H), 8.13-8.11 (m, 1H), 8.09 (d, J=8.38 Hz, 1H), 7.70 (d, J=1.08 Hz, 2H), 7.55 (d, J=2.15 Hz, 1H), 7.52 (dd, J=8.60, 2.15 Hz, 1H), 7.00 (d, J=8.60 Hz, 1H), 4.36-4.23 (m, 4H). HRMS (ESI$^+$): Found [M+H]$^+$ 532.0550 C$_{26}$H$_{19}$BrN$_3$O$_5$ requires 532.0503.

Compound 241, N-(5-(2,3-dihydrobenzo[b][1,4]dioxine-6-carboxamido)-2-methylphenyl)-2-formylquinoline-6-carboxamide A solution of N-(5-(2,3-dihydrobenzo[b][1,4]dioxine-6-carboxamido)-2-methylphenyl)-2-methylquinoline-6-carboxamide (0.165 g, 0.364 mmol) and selenium dioxide (0.444 g, 0.400 mmol) in dry dioxane (0.6 mL) and dry DMF (0.6 mL) was heated at 152° C. for 1 h after which the reaction mixture was allowed to cool to room temperature, diluted with DCM and filtered through a pad of Celite. The filtrate was concentrated under vacuum to afford the crude product as a brown solid which was taken directly onto the next step without any further purification (0.17 g, 100%). $^1$H-NMR (500 MHz, DMSO): δ 10.29 (s, 1H), 10.17 (s, 1H), 10.09 (s, 1H), 8.81-8.77 (m, 1H), 8.41 (dd, J=8.29, 1.66 Hz, 1H), 8.36 (d, J=8.29 Hz, 1H), 8.17-8.12 (m, 1H), 8.08 (d, J=9.12 Hz, 1H), 7.90 (d, J=2.49 Hz, 1H), 7.58 (dd, J=8.29, 2.49 Hz, 1H), 7.54 (d, J=2.49 Hz, 1H), 7.52 (dd, J=8.29, 2.49 Hz, 1H), 7.25 (d, J=8.29 Hz, 1H), 6.98 (d, J=8.29 Hz, 1H), 4.35-4.28 (m, 4H), 2.31 (s, 3H).

Example 202, N-(5-(2,3-dihydrobenzo[b][1,4]dioxine-6-carboxamido)-2-methylphenyl)-2-((4-isopropylpiperazin-1-yl)methyl)quinoline-6-carboxamide To a solution of N-(5-(2,3-dihydrobenzo[b][1,4]dioxine-6-carboxamido)-2-methylphenyl)-2-formylquinoline-6-carboxamide (0.170 g, 0.364 mmol) in dry DCM (5 mL), 1-isopropylpiperazine (0.156 mL, 1.091 mmol) was added dropwise and the resulting mixture was allowed to stir at 20° C. for 2.5 hours, after which sodium triacetoxyborohydride (0.231 g, 1.091 mmol) was added in one portion and the resulting mixture was allowed to stir at 20° C. for 12 h. The reaction was diluted with DCM (5 mL), quenched with NaHCO$_3$ saturated aqueous solution (10 mL) and extracted with a DCM/MeOH 9/1 mixture (3×5 mL). The crude product (brown oil) was purified via flash column chromatography on silica gel in gradient from 0 to 10% MeOH in DCM followed by water wash and Et$_2$O trituration to afford the desired product as a pale yellow solid (0.030 g, 14%). $^1$H-NMR (500 MHz, DMSO): δ 10.15 (s, 1H), 10.07 (s, 1H), 8.63 (d, J=1.42 Hz, 1H), 8.49 (d, J=8.51 Hz, 1H), 8.26 (dd, J=9.22, 1.42 Hz, 1H), 8.08 (d, J=8.51 Hz, 1H), 7.88 (d, J=2.13 Hz, 1H), 7.72 (d, J=8.51 Hz, 1H), 7.59 (dd, J=8.51, 2.13 Hz, 1H), 7.54 (d, J=1.42 Hz, 1H), 7.51 (d, J=8.51, 1.42 Hz, 1H), 7.25 (d, J=8.51 Hz, 1H), 6.98 (d, J=8.51 Hz, 1H), 4.34-4.27 (m, 4H), 3.78 (s, 2H), 2.61 (heptet, J=5.87 Hz, 1H), 2.47 (bs, 8H), 2.24 (s, 3H), 0.96 (d, J=5.87 Hz, 6H). HRMS (ESI$^+$): Found [M+H]$^+$ 580.2938 $C_{34}H_{38}N_5O_4$ requires 580.2918.

The following compounds were synthesised according to the procedure for Example 202, by substituting the appropriate amine for 1-isopropylpiperazine.

Example 203, 2-(azetidin-1-ylmethyl)-N-(5-(2,3-dihydrobenzo[b][1,4]dioxine-6-carboxamido)-2-methylphenyl)quinoline-6-carboxamide Example 204, N-(5-(2,3-dihydrobenzo[b][1,4]dioxine-6-carboxamido)-2-methylphenyl)-2-((4-ethylpiperazin-1-yl)methyl)quinoline-6-carboxamide Example 205, N-(5-(2,3-dihydrobenzo[b][1,4]dioxine-6-carboxamido)-2-methylphenyl)-2-((2-methylpyrrolidin-1-yl)methyl)quinoline-6-carboxamide Example 206, (R)—N-(5-(2,3-dihydrobenzo[b][1,4]dioxine-6-carboxamido)-2-methylphenyl)-2-((3-fluoropyrrolidin-1-yl)methyl)quinoline-6-carboxamide Example 207, (S)—N-(5-(2,3-dihydrobenzo[b][1,4]dioxine-6-carboxamido)-2-methylphenyl)-2-((3-fluoropyrrolidin-1-yl)methyl)quinoline-6-carboxamide Example 208, N-(5-(2,3-dihydrobenzo[b][1,4]dioxine-6-carboxamido)-2-methylphenyl)-2-((3-methoxypyrrolidin-1-yl)methyl)quinoline-6-carboxamide Example 209, N-(5-(2,3-dihydrobenzo[b][1,4]dioxine-6-carboxamido)-2-methylphenyl)-2-(piperidin-1-ylmethyl)quinoline-6-carboxamide

TABLE H

| Compound | 1H NMR | Mass Spec |
| --- | --- | --- |
| Example 203 | $^1$H-NMR (500 MHz, MeOD): δ 8.60 (d, J = 2.03 Hz, 1H), 8.48 (d, J = 8.14 Hz, 1H), 8.30 (dd, J = 8.81, 2.03 Hz, 1H), 8.15 (dd, J = 8.81, 1H), 7.81 (d, J = 2.03 Hz, 1H), 7.65 (d, J = 8.14 Hz, 1H), 7.54 (d, J = 8.14, 2.03 Hz, 1H), 7.49 (d, J = 2.03 Hz, 1H), 7.47 (dd, J = 8.14, 2.03 Hz, 1H), 7.32 (d, J = 8.14 Hz, 1H), 6.95 (d, J = 8.14 Hz, 1H), 4.35-4.28 (m, 4H), 4.06 (s, 2H), 3.54 (t, J = 7.36 Hz, 4H), 2.34 (s, 3H), 2.24 (q, J = 7.36 Hz, 2H). | Found [M + H]$^+$ 509.2183 $C_{30}H_{29}N_4O_4$ requires 509.2183 |
| Example 204 | $^1$H-NMR (500 MHz, MeOD): δ 8.59 (d, J = 1.69 Hz, 1H), 8.48 (d, J = 8.43 Hz, 1H), 8.29 (dd, J = 8.43, 1.69 Hz, 1H), 8.19 (d, J = 9.27 Hz, 1H), 7.82 (d, J = 1.69 Hz, 1H), 7.80 (d, J = 8.43 Hz, 1H), 7.53 (dd, J = 7.59, 1.69 Hz, 1H), 7.47 (d, J = 2.53 Hz, 1H), 7.46 (dd, J = 8.43, 2.53 Hz, 1H), 7.29 (d, J = 8.43 Hz, 1H), 6.93 (d, J = 8.43 Hz, 1H), 4.33-4.26 (m, 4H), 3.89 (s, 2H), 2.58 (bs, 8H), 2.46 (q, J = 7.28 Hz, 2H), 2.32 (s, 3H), 1.11 (t, J = 7.28 Hz, 3H). | Found [M + H]$^+$ 566.2845 $C_{33}H_{36}N_5O_4$ requires 566.2762 |
| Example 205 | $^1$H-NMR (500 MHz, DMSO): δ$_H$ 10.16 (s, 1H), 10.09 (s, 1H), 8.64 (s, 1H), 8.48 (d, J = 8.81 Hz, 1H), 8.27 (dd, J = 8.81, 1.47 Hz, 1H), 8.09 (d, J = 8.81 Hz, 1H), 7.89 (d, J = 1.47 Hz, 1H), 7.72 (d, J = 8.81 Hz, 1H), 7.59 (dd, J = 8.81, 2.20 Hz, 1H), 7.54 (d, J = 2.20 Hz, 1H), 7.52 (dd, J = 2.20, 8.81 Hz, 1H), 7.25 (d, J = 8.81 Hz, 1H), 6.99 (d, J = 8.81 Hz, 1H), 4.39-4.24 (m, 5H), 3.64 (bs, 1H), 2.93 (bs, 1H), 2.25 (s, 3H), 2.03-1.94 (m, 1H), 1.76-1.63 (m, 2H), 1.49-1.36 (m, 1H), 1.30-1.21 (m, 1H), 1.15 (d, J = 5.38 Hz, 3H). | Found [M + H]$^+$ 537.2539 $C_{32}H_{33}N_4O_4$ requires 537.2496 |
| Example 206 | $^1$H-NMR (500 MHz, DMSO): δ 10.16 (s, 1H), 10.08 (s, 1H), 8.64 (bs, 1H), 8.50 (d, J = 8.23 Hz, 1H), 8.26 (d, J = 8.23 Hz, 1H), 8.09 (d, J = 8.23 Hz, 1H), 8.08 (d, J = 8.81 Hz, 1H), 7.88 (bs, 1H), 7.72 (d, J = 8.23 Hz, 1H), 7.59 (dd, J = 8.23, 1.50 Hz, 1H), 7.54 (d, J = 1.50 Hz, 1H), 7.51 (dd, J = 8.23, 1.50 Hz, 1H), 7.25 (d, J = 8.23 Hz, 1H), 6.99 (d, J = 8.23 Hz, 1H), 5.33-5.14 (m, 1H), 4.36-4.28 (m, 4H), 3.95 (s, 2H), 2.94-2.84 (m, 2H), 2.79-2.68 (m, 1H), 2.48-2.41 (m, 1H), 2.25 (s, 3H), 2.01-1.86 (m, 1H). | Found [M + H]$^+$ 541.2234 $C_{31}H_{30}FN_4O_4$ requires 541.2246 |
| Example 207 | $^1$H-NMR (500 MHz, DMSO): δ 10.16 (s, 1H), 10.08 (s, 1H), 8.64 (bs, 1H), 8.50 (d, J = 8.23 Hz, 1H), 8.26 (d, J = 8.23 Hz, 1H), 8.09 (d, J = 8.23 Hz, 1H), 8.08 (d, J = 8.81 Hz, 1H), 7.88 (bs, 1H), 7.72 (d, J = 8.23 Hz, 1H), 7.59 (dd, J = 8.23, 1.50 Hz, 1H), 7.54 (d, J = 1.50 Hz, 1H), 7.51 (dd, J = 8.23, 1.50, Hz, 1H), 7.25 (d, J = 8.23 Hz, 1H), 6.99 (d, J = 8.23 Hz, 1H), 5.33-5.14 (m, 1H), 4.36-4.28 (m, 4H), 3.95 (s, 2H), 2.94-2.84 (m, 2H), 2.79-2.68 (m, 1H), 2.48-2.41 (m, 1H), 2.25 (s, 3H), 2.01-1.86 (m, 1H). | Found [M + H]$^+$ 541.2236 $C_{31}H_{30}FN_4O_4$ requires 541.2246 |
| Example 208 | $^1$H-NMR (500 MHz, DMSO): δ 10.15 (s, 1H), 10.08 (s, 1H), 8.63 (bs, 1H), 8.48 (d, J = 8.84 Hz, 1H), 8.26 (dd, J = 8.84, 1.47 Hz, 1H), 8.08 (d, J = 8.84 Hz, 1H), 7.88 (bs, 1H), 7.70 (d, J = 8.84 Hz, 1H), 7.59 (dd, J = 7.37, 1.47 Hz, 1H), 7.54 (d J = 1.47 Hz, 1H), 7.52 (dd J = 7.37, 1.47 Hz, 1H), 7.25 (d, J = 8.84 Hz, 1H), 6.99 (d, J = 8.84 Hz, 1H), 4.36-4.26 (m, 4H), 3.95-3.88 (m, 3H), 3.16 (s, 3H), 2.79-2.70 (m, 1H), 2.71-2.63 (m, 1H), 2.59-2.54 (m, 2H), 2.25 (s, 3H), 2.07-1.99 (m, 1H), 1.75-1.66 (m, 1H). | Found [M + H]$^+$ 553.2418 $C_{32}H_{33}N_4O_5$ requires 553.2445 |

TABLE H-continued

| Compound | 1H NMR | Mass Spec |
|---|---|---|
| Example 209 | $^1$H-NMR (500 MHz, DMSO): δ 10.15 (s, 1H), 10.08 (s, 1H), 8.63 (bs, 1H), 8.48 (d, J = 8.11 Hz, 1H), 8.26 (d, J = 8.11 Hz, 1H), 8.08 (d, J = 8.11 Hz, 1H), 7.88 (bs, 1H), 7.73 (d, J = 8.11 Hz, 1H), 7.59 (dd, J = 8.11, 2.32 Hz, 1H), 7.54 (d J = 1.16 Hz, 1H), 7.51 (dd, J = 8.11, 2.32 Hz, 1H), 7.25 (d, J = 8.11 Hz, 1H), 6.98 (d, J = 8.11 Hz, 1H), 4.36-4.28 (m, 4H), 3.76 (bs, 2H), 2.48-2.38 (m, 4H), 2.24 (s, 3H), 1.59-1.49 (m, 4H), 1.47-1.37 (m, 2H). | Found [M + H]$^+$ 537.2488 $C_{32}H_{33}N_4O_4$ requires 537.2496 |

Compound 249, N-(4-iodo-3-nitrophenyl)-2,3-dihydrobenzo[b][1,4]dioxine-6-carboxamide Oxalyl chloride (0.37 mL, 4.23 mmol) was added dropwise to a stirred solution of 1,4-benzodioxane-6-carboxylic acid (0.635 g, 3.52 mmol) and DMF (6.82 μL, 0.088 mmol) in dry DCM (10 mL). The reaction mixture was stirred for 30 minutes, then concentrated in vacuo, dissolved in DCM (10 mL) and concentrated in vacuo. The concentrate was dissolved in DCM (10 mL) and added drop wise to a stirred solution of pyridine (0.57 mL, 7.04 mmol) and 4-iodo-3-nitroaniline (0.93 g, 3.52 mmol) in DCM (10 mL). After stirring for 16 hours, the reaction mixture was concentrated in vacuo. The concentrate was suspended in MeOH (30 mL) and diluted with water (60 mL). The solid was filtered, washed with water and dried on the high vac to afford the desired product as a pale yellow solid (1.310 g, 87%). 1H-NMR (500 MHz, DMSO): δ 10.50 (s, 1H), 8.49 (d, J=2.4 Hz, 1H), 8.07 (d, J=8.6 Hz, 1H), 7.80 (dd, J=8.7, 2.5 Hz, 1H), 7.62-7.43 (m, 2H), 7.01 (d, J=8.4 Hz, 1H), 4.49-4.18 (m, 4H). HRMS (ESI$^+$): Found [M+H]$^+$ 426.9789 $C_{15}H_{12}N_2O_5$ requires 426.9785.

Compound 242, N-(3-amino-4-iodophenyl)-2,3-dihydrobenzo[b][1,4]dioxine-6-carboxamide To a solution of N-(4-iodo-3-nitrophenyl)-2,3-dihydrobenzo[b][1,4]dioxine-6-carboxamide (400 mg, 0.939 mmol) in ethanol (3 mL) and water (0.3 mL), ammonium chloride (351 mg, 6.57 mmol) and iron powder (367 mg, 6.57 mmol) were added and the resulting suspension was allowed to stir at 90° C. for 16 hours. The reaction mixture was allowed to cool to room temperature, filtered and the filtrate was partitioned between DCM (5 mL) and a saturated aqueous solution of sodium hydrogen carbonate (5 mL). The layers were separated and the aqueous layer was extracted with DCM (3×5 mL). The combined organic layers were dried over magnesium sulphate, filtered and concentrated in vacuo to afford a brown solid which was taken directly onto the next step without any further purification (0.934 g, 100%). 1H-NMR (500 MHz, DMSO): δ 9.90 (s, 1H), 7.56-7.42 (m, 3H), 7.36 (d, J=2.4 Hz, 1H), 6.97 (d, J=8.4 Hz, 1H), 6.74 (dd, J=8.6, 2.4 Hz, 1H), 5.22 (s, 2H), 4.30 (tt, J=6.3, 3.1 Hz, 4H). HRMS (ESI$^+$): Found [M+H]$^+$ 397.0042 $C_{15}H_{14}IN_2O_3$ requires 397.0044.

Compound 243, N-(5-(2,3-dihydrobenzo[b][1,4]dioxine-6-carboxamido)-2-iodophenyl)-2-methylquinoline-6-carboxamide Oxalyl chloride (0.08 mL, 0.909 mmol) was added dropwise to a solution of 2-methylquinoline-6-carboxylic acid (170 mg, 0.909 mmol) and DMF (1.466 μL, 0.019 mmol) in dry DCM (2.3 mL). The reaction mixture was stirred for 30 minutes, then concentrated in vacuo, dissolved in DCM (5 mL) and concentrated in vacuo. The concentrate was dissolved in DCM (5 mL) and added drop wise to a stirred solution of pyridine (0.122 mL) and N-(3-amino-4-iodophenyl)-2,3-dihydrobenzo[b][1,4]dioxine-6-carboxamide (300 mg, 0.757 mmol) in DCM (2.3 mL). After stirring for 16 hours, the reaction mixture was concentrated in vacuo. The concentrate was suspended in MeOH (10 mL) and diluted with water (60 mL). The solid was filtered, washed with water and dried on the high vac to afford the desired product as a pale yellow solid (351 mg, 82%). $^1$H-NMR (500 MHz, DMSO): δ 10.29 (s, 1H), 10.24 (s, 1H), 8.63 (d, J=2.0 Hz, 1H), 8.45-8.39 (m, 1H), 8.26 (dd, J=8.8, 2.1 Hz, 1H), 8.05 (d, J=8.8 Hz, 1H), 8.01 (d, J=2.5 Hz, 1H), 7.88 (d, J=8.7 Hz, 1H), 7.63-7.49 (m, 4H), 4.39-4.26 (m, 5H), 2.71 (s, 3H). HRMS (ESI$^+$): Found [M+H]$^+$ 566.0533 $C_{26}H_{21}IN_3O_4$ requires 566.0571.

Example 210, N-(5-(2,3-dihydrobenzo[b][1,4]dioxine-6-carboxamido)-2-vinylphenyl)-2-methylquinoline-6-carboxamide Tetrakis(triphenylphosphine)palladium(O) (12.3 mg, 10.6 Pmol) was added to a stirred solution of vinylboronic acid pinacol ester (27.0 μL, 0.159 μmol), N-(5-(2,3-dihydrobenzo[b][1,4]dioxine-6-carboxamido)-2-iodophenyl)-2-methylquinoline-6-carboxamide (60 mg, 0.106 mmol) and an aqueous solution of potassium hydroxide (3 M, 106 μL, 0.318 mmol) in THF (1.1 mL). After stirring for 16 hours the reaction mixture was concentrated in vacuo. Purification using a Biotage 10 g snap column with 0-5% MeOH in DCM to afford the desired product as a pale yellow solid (12 mg, 24%). $^1$H-NMR (500 MHz, DMSO): δ 10.33 (s, 1H), 10.19 (s, 1H), 8.63 (d, J=2.0 Hz, 1H), 8.41 (d, J=8.4 Hz, 1H), 8.25 (dd, J=8.8, 2.1 Hz, 1H), 8.03 (d, J=8.7 Hz, 1H), 7.90 (d, J=1.9 Hz, 1H), 7.76-7.67 (m, 2H), 7.58-7.47 (m, 3H), 6.99 (d, J=8.4 Hz, 1H), 6.87 (dd, J=17.5, 11.1 Hz, 1H), 5.78 (dd, J=17.5, 1.4 Hz, 1H), 5.24 (dd, J=11.0, 1.3 Hz, 1H), 4.31 (td, J=5.3, 3.7 Hz, 4H), 2.71 (s, 3H). HRMS (ESI$^+$): Found [M+H]$^+$ 466.1767 $C_{28}H_{24}N_3O_4$ requires 466.1774.

Example 211, N-(2-chloro-5-(2,3-dihydrobenzo[b][1,4]dioxine-6-carboxamido)phenyl)-2-(2-(pyrrolidin-1-yl)ethoxy)quinoline-6-carboxamide 2-(2-(pyrrolidin-1-yl)ethoxy)quinoline-6-carboxylic acid hydrochloride (75 mg, 0.23 mmol) was suspended in thionyl chloride (2.0 mL) and heated to 60° C. under argon for 4 h. The solvent was then removed in vacuo. The residue was re-dissolved in anhydrous DCM (2.0 mL) and the solvent removed in vacuo (×2). The acid chloride was re-suspended in anhydrous DCM (2.0 mL) and anhydrous dioxane (1.0 mL) then N-(3-amino-4-chlorophenyl)-2,3-dihydrobenzo[b][1,4]dioxine-6-carboxamide (78 mg, 0.26 mmol) was added, followed by triethylamine (0.16 mL, 118.0 mg, 1.16 mmol). The reaction mixture was allowed to stir at RT for 16 h, after which time the solvents were removed in vacuo. The crude material was purified by SCX chromatography, eluting with MeOH followed by 10% 2M NH$_3$ in MeOH/MeOH. Further purification by column chromatography using a gradient of 0 to 10% MeOH/DCM, followed by purification using preparative TLC (eluting with 2×5% MeOH/DCM) gave the title compound as a white solid (0.9 mg, 0.7%). $^1$H NMR (500 MHz, Methanol-d$_4$) δ 8.54 (d, J=2.0 Hz, 1H), 8.37 (d, J=8.9 Hz, 1H), 8.27-8.24 (m, 2H), 7.96 (d, J=8.8 Hz, 1H), 7.64 (dd, J=8.8, 2.5 Hz, 1H), 7.52-7.47 (m, 3H), 7.17 (d, J=8.9 Hz, 1H), 6.96 (d, J=8.3 Hz, 1H), 4.35-4.29 (m, 4H), 3.73-3.67 (m, 2H), 3.49-3.41 (m, 2H), 2.15-2.10 (s, 4H), 1.36-1.30 (m, 4H). HRMS (ESI$^+$): calcd for C$_{31}$H$_{30}$$^{35}$ClN$_4$O$_5$(M+H)$^+$, 573.1905; found 573.1880.

Example 212, (R)—N-(5-(2,3-dihydrobenzo[b][1,4]dioxine-6-carboxamido)-2-fluorophenyl)-2-((4-ethyl-2-methylpiperazin-1-yl)methyl)quinoline-6-carboxamide A solution of N-(5-(2,3-dihydrobenzo[b][1,4]dioxine-6-carboxamido)-2-fluorophenyl)-2-formylquinoline-6-carboxamide (0.200 g, 0.424 mmol) and (R)-tert-butyl 3-methylpiperazine-1-carboxylate in dry DCM (2.00 mL) was allowed to stir at 20° C. for 12 h, after which sodium triacetoxyborohydride (0.270 g, 1.273 mmol) was added in one portion and the resulting mixture was allowed to stir at 20° C. for 2 h. The reaction was quenched with NaHCO$_3$ saturated aqueous solution (5 mL) and extracted with a mixture DCM/MeOH 9/1 (3×5 mL). The organic layers were dried over Na$_2$SO$_4$ and concentrated under reduced pressure to afford the crude product (R)-tert-butyl 4-((6-((5-(2,3-dihydrobenzo[b][1,4]dioxine-6-carboxamido)-2-fluorophenyl)carbamoyl)quinolin-2-yl)methyl)-3-methylpiperazine-1-carboxylate, which was dissolved in dry DCM (2.5 mL) and treated with TFA (0.162 mL, 2.120 mmol). The resulting mixture was allowed to stir for 18 h, after which it was concentrated under vacuum to afford the crude product (R)—N-(5-(2,3-dihydrobenzo[b][1,4]dioxine-6-carboxamido)-2-fluorophenyl)-2-((2-methylpiperazin-1-yl)methyl)quinoline-6-carboxamide, which was taken directly onto the next step without any further purification. To a solution of (R)—N-(5-(2,3-dihydrobenzo[b][1,4]dioxine-6-carboxamido)-2-fluorophenyl)-2-((2-methylpiperazin-1-yl)methyl)quinoline-6-carboxamide (0.185 g, 0.333 mmol) in dry methanol (3 mL) at 0° C., sodium cyanoborohydride (23.02 mg, 0.366 mmol) was added in one portion, followed by the dropwise addition of acetaldehyde (0.013 mL, 0.233 mmol) and the resulting solution was allowed to warm to 20° C. and stir under argon for 18 h. The solvent was removed under reduced pressure and the crude was redissolved in DCM (5 mL) and washed with NaOH aqueous solution (1 M, 5 mL). Purification via flash column chromatography on silica gel in gradient: DCM/MeOH from 0 to 20% followed by water wash and trituration in Et$_2$O afforded the title compound as a white solid (27 mg, 14%). $^1$H-NMR (500 MHz, DMSO): δ 10.38 (s, 1H), 10.18 (s, 1H), 8.64 (d, J 2.20 Hz, 1H), 8.48 (d, J=8.79 Hz, 1H), 8.24 (dd, J=8.79, 2.20 Hz, 1H), 8.14 (dd, J=6.55, 2.20 Hz, 1H), 8.07 (d, J=8.79 Hz, 1H), 7.74 (d, J=8.79 Hz, 1H), 7.68-7.63 (m, 1H), 7.54 (d, J=2.20 Hz, 1H), 7.52 (d, J=8.79, 2.20 Hz, 1H), 7.29 (app t, J=10.28 Hz, 1H), 6.99 (d, J=8.79 Hz, 1H), 4.35-4.28 (m, 4H), 4.23 (d, J=14.21 Hz, 1H), 3.53 (d, J=14.21 Hz, 1H), 2.74-2.57 (m, 3H), 2.34-2.21 (m, 4H), 2.12-1.99 (m, 1H), 1.95-1.82 (m, 1H), 1.09 (d, J=6.50 Hz, 3H), 0.98 (t, J=7.00 Hz, 3H). HRMS (ESI$^+$): Found [M+H]$^+$ 584.2665 C$_{33}$H$_{35}$FN$_5$O$_4$ requires 584.2668.

Example 213, (S)—N-(5-(2,3-dihydrobenzo[b][1,4]dioxine-6-carboxamido)-2-fluorophenyl)-2-((4-ethyl-2-methylpiperazin-1-yl)methyl)quinoline-6-carboxamide A solution of N-(5-(2,3-dihydrobenzo[b][1,4]dioxine-6-carboxamido)-2-fluorophenyl)-2-formylquinoline-6-carboxamide (0.200 g, 0.424 mmol) and (S)-tert-butyl 3-methylpiperazine-1-carboxylate in dry DCM (2.00 mL) was allowed to stir at 20° C. for 12 h, after which sodium triacetoxyborohydride (0.270 g, 1.273 mmol) was added in one portion and the resulting mixture was allowed to stir at 20° C. for 2 h. The reaction was quenched with NaHCO$_3$ saturated aqueous solution (5 mL) and extracted with a mixture DCM/MeOH 9/1 (3×5 mL). The organic layers were dried over Na$_2$SO$_4$ and concentrated under reduced pressure to afford the crude product (S)-tert-butyl 4-((6-((5-(2,3-dihydrobenzo[b][1,4]dioxine-6-carboxamido)-2-fluorophenyl)carbamoyl)quinolin-2-yl)methyl)-3-methylpiperazine-1-carboxylate, which was dissolved in dry DCM (2.5 mL) and treated with TFA (0.162 mL, 2.120 mmol). The resulting mixture was allowed to stir for 18 h, after which it was concentrated under vacuum to afford the crude product (S)—N-(5-(2,3-dihydrobenzo[b][1,4]dioxine-6-carboxamido)-2-fluorophenyl)-2-((2-methylpiperazin-1-yl)methyl)quinoline-6-carboxamide, which was taken directly onto the next step without any further purification. To a solution of (S)—N-(5-(2,3-dihydrobenzo[b][1,4]dioxine-6-carboxamido)-2-fluorophenyl)-2-((2-methylpiperazin-1-yl)methyl)quinoline-6-carboxamide (0.185 g, 0.333 mmol) in dry methanol (3 mL) at 0° C., sodium cyanoborohydride (23.02 mg, 0.366 mmol) was added in one portion, followed by the dropwise addition of acetaldehyde (0.013 mL, 0.233 mmol) and the resulting solution was allowed to warm to 20° C. and stir under argon for 18 h. The solvent was removed under reduced pressure and the crude was redissolved in DCM (5 mL) and washed with NaOH aqueous solution (1 M, 5 mL). Purification via flash column chromatography on silica gel in gradient: DCM/MeOH from 0 to 20% followed by water wash and trituration in Et$_2$O afforded the title compound as a white solid (60 mg, 29%). $^1$H-NMR (500 MHz, DMSO): δ 10.38 (s, 1H), 10.18 (s, 1H), 8.64 (d, J=2.16 Hz, 1H), 8.48 (d, J=8.66 Hz, 1H), 8.24 (dd, J=8.66, 2.16 Hz, 1H), 8.14 (dd, J=6.55, 2.16 Hz, 1H), 8.07 (d, J=8.66 Hz, 1H), 7.74 (d, J=8.66 Hz, 1H), 7.68-7.63 (m, 1H), 7.54 (d, J=2.16 Hz, 1H), 7.52 (d, J=8.66, 2.16 Hz, 1H), 7.29 (app t, J=10.28 Hz, 1H), 6.99 (d, J=8.66 Hz, 1H), 4.34-4.22 (m, 5H), 3.61 (bs, 1H), 3.12-2.56 (m, 6H), 2.49-1.87 (m, 3H), 1.13 (bs, 6H). HRMS (ESI$^+$): Found [M+H]$^+$ 584.2665 C$_{33}$H$_{35}$FN$_5$O$_4$ requires 584.2668.

Example 214, N-(5-(2,3-dihydrobenzo[b][1,4]dioxine-6-carboxamido)-2-fluorophenyl)-2-(1-(4-ethylpiperazin-1-yl)ethyl)quinoline-6-carboxamide To a solution of N-(5-(2,3-dihydrobenzo[b][1,4]dioxine-6-carboxamido)-2-fluorophenyl)-2-formylquinoline-6-carboxamide (0.300 g, 0.636 mmol) in dry dioxane (8 mL) and THF (4.00 mL) under argon at 20° C., MeMgBr (0.409 mL, 0.573 mmol) was added dropwise to obtain a yellow suspension which was allowed to stir for 1.5 h. The reaction was quenched with NaHCO$_3$ saturated aqueous solution (10 mL) and extracted with a mixture DCM/MeOH 9/1 (3×5 mL). The crude was taken onto the next step without purification.

To a solution of N-(5-(2,3-dihydrobenzo[b][1,4]dioxine-6-carboxamido)-2-fluorophenyl)-2-(1-hydroxyethyl)quinoline-6-carboxamide (0.200 g, 0.410 mmol) and DMAP (5.01 mg, 0.041 mmol) in dry DCM (4 mL) at 20° C., Et$_3$N (0.243 mL, 4.10 mmol) was added dropwise followed by the addition of methanesulfonic anhydride (429 mg, 2.462 mmol) in one portion. The reaction mixture was allowed to stir at 20° C. for 2 hours after which it was concentrate under reduced pressure to afford the crude product which was taken onto the next step without purification. To a solution of 1-(6-((5-(2,3-dihydrobenzo[b][1,4]dioxine-6-carboxamido)-2-fluorophenyl)carbamoyl)quinolin-2-yl)ethyl methanesulfonate (232 mg, 0.410 mmol) in dry acetonitrile (4 mL) at 20° C., 1-ethylpiperazine (0.052 mL, 0.410 mmol) was added dropwise and the resulting mixture was allowed to stir for 20 hours. The reaction mixture was concentrated under reduced pressure and washed with Et$_2$O to afford a crude product as a dark yellow solid. Flash column chromatography on silica gel (from 0 to 15% MeOH in DCM) followed by preparative TLC (DCM/MeOH 9/1), wash in water and trituration in Et$_2$O afforded the pure product as a pale yellow solid (22 mg, 9%). $^1$H-NMR (500 MHz, DMSO): δ 10.46 (s, 1H), 10.26 (s, 1H), 8.68 (s, 1H), 8.48 (d, J=8.56 Hz, 1H), 8.27 (dd, J=9.27, 2.14 Hz, 1H), 8.14 (dd, J=7.37, 2.14 Hz, 1H), 8.08 (d, J=8.56 Hz, 1H), 7.72 (d, J=8.56 Hz, 1H), 7.71-7.65 (m, 1H), 7.57 (d, J=2.14 Hz, 1H), 7.54 (dd, J=8.56, 2.14 Hz, 1H), 7.29 (app t, J=9.60 Hz, 1H), 6.98 (d, J=8.56 Hz, 1H), 4.37-4.25 (m, 4H), 3.83-3.72 (m, 1H), 2.77-2.21 (m, 10H), 1.40 (d, J=8.67 Hz, 3H), 1.00 (bs, 3H). HRMS (ESI$^+$): Found [M+H]$^+$ 584.2655 C$_{33}$H$_{35}$FN$_5$O$_4$ requires 584.2668.

Example 215, N-(2-bromo-5-(2,3-dihydrobenzo[b][1,4]dioxine-6-carboxamido)phenyl)-2-((4-ethylpiperazin-1-yl)methyl)quinoline-6-carboxamide A solution of N-(2-bromo-5-(2,3-dihydrobenzo[b][1,4]dioxine-6-carboxamido)phenyl)-2-formylquinoline-6-carboxamide (0.5 g, 0.939 mmol) and 1-ethylpiperazine in dry DCM (8 mL) was allowed to stir at 20° C. for 12 h, after which sodium triacetoxyborohydride (0.597 g, 2.82 mmol) was added in one portion and the resulting mixture was allowed to stir at 20° C. for 1 h. The reaction was quenched with NaHCO$_3$ saturated aqueous solution (10 mL) and extracted with a mixture DCM/MeOH 9/1 (3×10 mL). Purification via flash column chromatography on silica gel in gradient DCM/MeOH from 0 to 20%, followed by wash in water, trituration in Et$_2$O and quick flush through SCX-2 cartridge, afforded the desired product as a bright yellow solid (110 mg, 18%). $^1$H-NMR (500 MHz, DMSO): δ 10.31 (s, 1H), 10.27 (s, 1H), 8.66 (d, J=2.18 Hz, 1H), 8.50 (d, J=8.70 Hz, 1H), 8.27 (dd, J=8.70, 2.18 Hz, 1H), 8.13-8.08 (m, 2H), 7.73 (d, J=8.70 Hz, 1H), 7.70-7.68 (m, 2H), 7.55 (d, J=2.18 Hz, 2H), 7.52 (dd, J=8.70, 2.18 Hz, 1H), 7.00 (d, J=8.70 Hz, 1H), 4.35-4.28 (m, 4H), 3.81 (bs, 2H), 2.51 (bs, 10H), 1.02 (bt, J=6.68 Hz, 3H). HRMS (ESI$^+$): Found [M+H]$^+$ 632.1662 C$_{32}$H$_{33}$BrN$_5$O$_4$ requires 632.1696.

Example 216, 2-(azetidin-1-ylmethyl)-N-(2-bromo-5-(2,3-dihydrobenzo[b][1,4]dioxine-6-carboxamido)phenyl)quinoline-6-carboxamide A solution of N-(2-bromo-5-(2,3-dihydrobenzo[b][1,4]dioxine-6-carboxamido)phenyl)-2-formylquinoline-6-carboxamide (0.5 g, 0.939 mmol) and azetidine in dry DCM (8 mL) was allowed to stir at 20° C. for 12 h, after which sodium triacetoxyborohydride (0.597 g, 2.82 mmol) was added in one portion and the resulting mixture was allowed to stir at 20° C. for 1 h. The reaction was quenched with NaHCO$_3$ saturated aqueous solution (10 mL) and extracted with a mixture DCM/MeOH 9/1 (3×10 mL). Purification via flash column chromatography on silica gel in gradient DCM/MeOH from 0 to 20%, followed by wash in water, trituration in Et$_2$O and quick flush through SCX-2 cartridge, afforded the desired product as a bright yellow solid. (54 mg, 10%). $^1$H-NMR (500 MHz, DMSO): δ 10.33 (s, 1H), 10.27 (s, 1H), 8.67 (d, J=1.52 Hz, 1H), 8.53 (d, J=7.99 Hz, 1H), 8.29 (dd, J=8.79, 1.52 Hz, 1H), 8.13-8.09 (m, 2H), 7.69 (d, J=1.52 Hz, 1H), 7.65 (d, J=8.79 Hz, 2H), 7.55 (d, J=2.40 Hz, 1H), 7.52 (dd, J=7.99, 1.52 Hz, 1H), 7.00 (d, J=7.99 Hz, 1H), 4.35-4.28 (m, 4H) 4.19 (bs, 2H), 3.59 (bs, 4H), 2.18 (bs, 2H). HRMS (ESI$^+$): Found [M+H]$^+$ 575.1088 C$_{29}$H$_{26}$BrN$_4$O$_4$ requires 575.1116.

Example 217, (S)—N-(5-(2,3-dihydrobenzo[b][1,4]dioxine-6-carboxamido)-2-fluorophenyl)-2-((4-isopropyl-2-methylpiperazin-1-yl)methyl)quinoline-6-carboxamide A solution of N-(5-(2,3-dihydrobenzo[b][1,4]dioxine-6-carboxamido)-2-fluorophenyl)-2-formylquinoline-6-carboxamide (200 mg, 0.424 mmol) and (S)-tert-butyl 3-methylpiperazine-1-carboxylate (255 mg, 1.273 mmol) in dry DCM (2.000 mL) was allowed to stir at 20° C. for 12 h, after which sodium triacetoxyborohydride (270 mg, 1.273 mmol) was added in one portion and the resulting mixture was allowed to stir at 20° C. for 2 h. The reaction was quenched with NaHCO$_3$ saturated aqueous solution (5 mL) and extracted with a mixture DCM/MeOH 9/1 (3×5 mL). The organic layers were dried over Na$_2$SO$_4$ and concentrated under reduced pressure to afford the crude product (S)-tert-butyl 4-((6-((5-(2,3-dihydrobenzo[b][1,4]dioxine-6-carboxamido)-2-fluorophenyl)carbamoyl)quinolin-2-yl)methyl)-3-methylpiperazine-1-carboxylate which was dissolved in dry DCM (4 mL) and treated with TFA (0.162 mL, 2.120 mmol). The resulting mixture was allowed to stir for 18 h, after which it was concentrated under vacuum to afford the crude product as a beige solid, which was purified via flash column chromatography on silica gel in gradient DCM/MeOH from 0 to 10% to afford a beige solid as pure product (157 mg, 67%). $^1$H-NMR (500 MHz, MeOD): δ8.61 (d, J 1.47 Hz, 1H), 8.54 (d, J=8.83 Hz, 1H), 8.32 (dd, J=8.83, 1.47 Hz, 1H), 8.22 (dd, J=6.62, 2.21 Hz, 1H), 8.17 (d, J=8.83 Hz, 1H), 7.84 (d, J=8.83 Hz, 1H), 7.59-7.54 (m, 1H), 7.50 (d, J=2.21 Hz, 1H), 7.48 (d, J=8.09, 1.47 Hz, 1H), 7.29 (app t, J=9.56 Hz, 1H), 6.96 (d, J=8.09 Hz, 1H), 4.45 (d, J=13.95 Hz, 1H), 4.34-4.28 (m, 4H), 3.82 (d, J=13.95 Hz, 1H), 3.36 (bs, 2H), 3.23-3.16 (m, 1H), 3.07-2.94 (m, 3H), 2.76-2.67 (m, 1H), 1.30 (d, J=5.17 Hz, 3H). HRMS (ESI$^+$): Found [M+H]$^+$ 556.2341 C$_{31}$H$_{31}$FN$_5$O$_4$ requires 556.2355. To a solution of (S)—N-(5-(2,3-dihydrobenzo[b][1,4]dioxine-6-carboxamido)-2-fluorophenyl)-2-((2-methylpiperazin-1-yl)methyl)quinoline-6-carboxamide (150 mg, 0.270 mmol) in dry DCM (2 mL), propan-2-one (0.059 mL, 0.810 mmol) and acetic acid (0.015 mL, 0.270 mmol) were added dropwise and the resulting mixture was allowed to stir at 20° C. for 6 hours, after which sodium triacetoxyborohydride (172 mg, 0.810 mmol) was added in one portion and the resulting mixture was allowed to stir at 20° C. for 18 hours. The reaction was quenched with NaHCO$_3$ saturated aqueous solution and extracted with a mixture DCM/MeOH 9/1. Purification via flash column chromatography on silica gel in gradient DCM/MeOH from 0 to 15%, followed by quick flush through SCX-2 cartridge with MeOH and NH$_3$, afforded the desired product as a very pale yellow solid (40 mg, 25%). $^1$H-NMR (500 MHz, DMSO): δ 10.41 (s, 1H), 10.20 (s, 1H), 8.66 (d, J=1.76 Hz, 1H), 8.50 (d, J=8.24 Hz, 1H), 8.26 (dd, J=8.82, 1.76 Hz, 1H), 8.15 (dd, J=7.06, 1.76 Hz, 1H), 8.09 (d, J=8.82 Hz, 1H), 7.74 (d, J=8.82 Hz, 1H), 7.68-7.63 (m, 1H), 7.55 (d, J=1.76 Hz, 1H), 7.52 (d, J=8.82, 1.76 Hz, 1H), 7.29 (app t, J=9.41 Hz, 1H), 6.99 (d, J=8.24 Hz, 1H), 4.36-4.21 (m, 5H), 3.61 (bs, 1H), 3.26-2.53 (m, 8H), 1.16 (bs, 9H). HRMS (ESI$^+$): Found [M+H]$^+$ 598.2805 $C_{34}H_{37}FN_5O_4$ requires 598.2824.

Example 218, (R)—N-(5-(2,3-dihydrobenzo[b][1,4]dioxine-6-carboxamido)-2-fluorophenyl)-2-((4-isopropyl-2-methylpiperazin-1-yl)methyl)quinoline-6-carboxamide A solution of N-(5-(2,3-dihydrobenzo[b][1,4]dioxine-6-carboxamido)-2-fluorophenyl)-2-formylquinoline-6-carboxamide (200 mg, 0.424 mmol) and (R)-tert-butyl 3-methylpiperazine-1-carboxylate (255 mg, 1.273 mmol) in dry DCM (2.000 mL) was allowed to stir at 20° C. for 12 h, after which sodium triacetoxyborohydride (270 mg, 1.273 mmol) was added in one portion and the resulting mixture was allowed to stir at 20° C. for 2 h. The reaction was quenched with NaHCO$_3$ saturated aqueous solution (5 mL) and extracted with a mixture DCM/MeOH 9/1 (3×5 mL). The organic layers were dried over Na$_2$SO$_4$ and concentrated under reduced pressure to afford the crude product (R)-tert-butyl 4-((6-((5-(2,3-dihydrobenzo[b][1,4]dioxine-6-carboxamido)-2-fluorophenyl)carbamoyl)quinolin-2-yl)methyl)-3-methylpiperazine-1-carboxylate which was dissolved in dry DCM (4 mL) and treated with TFA (0.162 mL, 2.120 mmol). The resulting mixture was allowed to stir for 18 h, after which it was concentrated under vacuum to afford the crude product as a beige solid, which was purified via flash column chromatography on silica gel in gradient DCM/MeOH from 0 to 10% to afford a beige solid as pure product (220 mg, 93%). $^1$H-NMR (500 MHz, MeOD): b8.58 (d, J 1.49 Hz, 1H), 8.51 (d, J=8.21 Hz, 1H), 8.28 (dd, J=8.96, 1.49 Hz, 1H), 8.21 (dd, J=6.72, 2.24 Hz, 1H), 8.14 (d, J=8.96 Hz, 1H), 7.82 (d, J=8.21 Hz, 1H), 7.57-7.52 (m, 1H), 7.47 (d, J=2.24 Hz, 1H), 7.46 (d, J=8.21, 2.24 Hz, 1H), 7.20 (app t, J=9.70 Hz, 1H), 6.92 (d, J=8.21 Hz, 1H), 4.47 (d, J=13.59 Hz, 1H), 4.33-4.26 (m, 4H), 3.86 (d, J=13.59 Hz, 1H), 3.26-3.18 (m, 1H), 3.12-2.98 (m, 3H), 2.83-2.74 (m, 1H), 1.29 (d, J=5.82 Hz, 3H). HRMS (ESI$^+$): Found [M+H]$^+$ 556.2343 $C_{31}H_{31}FN_5O_4$ requires 556.2355. To a solution of (R)—N-(5-(2,3-dihydrobenzo[b][1,4]dioxine-6-carboxamido)-2-fluorophenyl)-2-((2-methylpiperazin-1-yl)methyl)quinoline-6-carboxamide (150 mg, 0.270 mmol) in dry DCM (2 mL), propan-2-one (0.059 mL, 0.810 mmol) and acetic acid (0.015 mL, 0.270 mmol) were added dropwise and the resulting mixture was allowed to stir at 20° C. for 6 hours, after which sodium triacetoxyborohydride (172 mg, 0.810 mmol) was added in one portion and the resulting mixture was allowed to stir at 20° C. for 18 hours. The reaction was quenched with NaHCO$_3$ saturated aqueous solution and extracted with a mixture DCM/MeOH 9/1. Purification via flash column chromatography on silica gel in gradient DCM/MeOH from 0 to 10% afforded the desired product as a white solid (165 mg, 67%). $^1$H-NMR (500 MHz, DMSO): δ 10.39 (s, 1H), 10.19 (s, 1H), 8.65 (d, J=2.04 Hz, 1H), 8.49 (d, J=8.17 Hz, 1H), 8.25 (dd, J=8.17, 2.04 Hz, 1H), 8.15 (dd, J=6.80, 2.04 Hz, 1H), 8.08 (d, J=8.17 Hz, 1H), 7.74 (d, J=8.17 Hz, 1H), 7.67-7.63 (m, 1H), 7.54 (d, J=2.04 Hz, 1H), 7.52 (d, J=8.17, 2.04 Hz, 1H), 7.29 (app t, J=8.85 Hz, 1H), 6.99 (d, J=8.17 Hz, 1H), 4.34-4.28 (m, 4H), 4.24 (bd, J=12.95 Hz, 1H), 3.57 (bs, 1H), 2.95-1.97 (m, 8H), 1.12 (bs, 3H), 1.01 (bs, 6H). HRMS (ESI$^+$): Found [M+H]$^+$ 598.2794 $C_{34}H_{37}FN_5O_4$ requires 598.2824.

Biological Activity

The exemplified compounds above were tested in the assays described above in the biological assay section (the Arrayscan, Cellisa and Titre Blue assays). The following data was obtained:

| Example No. | Arrayscan (μM) | Cellisa (μM)[1] | Titre Blue (μM) |
|---|---|---|---|
| 1 | nd | 0.005 | 0.014 |
| 2 | nd | 0.007 | 0.025 |
| 3 | nd | 0.007 | 0.029 |
| 4 | nd | 0.010 | 0.018 |
| 5 | nd | 0.053 | 0.047 |
| 6 | nd | 0.017 | 0.077 |
| 7 | nd | 0.055 | 0.037 |
| 8 | nd | 0.205 | 0.108 |
| 9 | nd | 0.022 | 0.090 |
| 10 | nd | 0.029 | 0.015 |
| 11 | nd | 0.038 | 0.095 |
| 12 | nd | 0.051 | nd |
| 13 | nd | 0.262 | 0.217 |
| 14 | nd | 0.081 | 0.094 |
| 15 | nd | 0.076 | 0.075 |
| 16 | nd | 0.094 | 0.031 |
| 17 | nd | 0.097 | 0.073 |
| 18 | nd | 0.062 | 0.034 |
| 19 | nd | 0.289 | 0.320 |
| 20 | nd | 1.477 | nd |
| 21 | nd | 0.141 | 0.084 |
| 22 | nd | 0.160 | nd |
| 23 | nd | 0.161 | nd |
| 24 | nd | 0.174 | 0.169 |
| 25 | nd | 1.609 | 1.126 |
| 26 | nd | 0.262 | 0.071 |
| 27 | nd | 0.371 | 0.106 |
| 28 | nd | 0.416 | 0.415 |
| 29 | nd | 0.499 | 0.626 |
| 30 | nd | 0.507 | nd |
| 31 | nd | 0.545 | nd |
| 32 | nd | 0.665 | nd |
| 33 | nd | 0.797 | 0.230 |
| 34 | nd | 0.850 | 0.413 |
| 35 | nd | 0.867 | 0.432 |
| 36 | nd | 1.147 | 0.567 |
| 37 | nd | 1.963 | nd |
| 38 | 0.046 | 0.041 | nd |
| 39 | 0.082 | 0.008 | 0.023 |
| 40 | nd | 1.163 | nd |
| 41 | nd | 0.104 | 0.154 |
| 42 | nd | 0.546 | 0.665 |
| 43 | nd | 0.022 | 0.034 |
| 44 | nd | 0.011 | 0.024 |
| 45 | nd | 0.036 | 0.085 |
| 46 | nd | 0.004 | 0.012 |
| 47 | nd | 0.004 | 0.012 |
| 48 | nd | 0.141 | 0.172 |
| 49 | nd | 0.002 | 0.008 |
| 50 | nd | 0.003 | 0.010 |
| 51 | nd | 0.004 | 0.010 |
| 52 | nd | 0.012 | 0.006 |
| 53 | nd | 0.007 | 0.007 |
| 54 | nd | 0.010 | 0.007 |
| 55 | nd | 0.013 | 0.020 |
| 56 | nd | 0.013 | 0.003 |
| 57 | nd | 0.037 | 0.031 |
| 58 | nd | 0.015 | 0.033 |
| 59 | nd | 0.015 | 0.410 |
| 60 | nd | 0.016 | 0.013 |
| 61 | nd | 0.016 | 0.018 |
| 62 | nd | 0.017 | 0.016 |
| 63 | nd | 0.022 | 0.007 |
| 64 | nd | 0.025 | 0.032 |
| 65 | nd | 0.029 | 0.007 |
| 66 | nd | 0.030 | 0.040 |
| 67 | nd | 0.035 | 0.033 |

-continued

| Example No. | Arrayscan (μM) | Cellisa (μM)[1] | Titre Blue (μM) |
|---|---|---|---|
| 68 | nd | 0.041 | 0.012 |
| 69 | nd | 0.057 | 0.305 |
| 70 | nd | 0.059 | 0.092 |
| 71 | nd | 0.082 | 0.118 |
| 72 | nd | 0.105 | 0.060 |
| 73 | nd | 0.090 | 0.021 |
| 74 | nd | 0.232 | nd |
| 75 | nd | 0.017 | 0.056 |
| 76 | nd | 0.021 | 0.010 |
| 77 | nd | 0.026 | nd |
| 78 | nd | 0.045 | 0.091 |
| 79 | nd | 0.070 | 0.054 |
| 80 | nd | 0.070 | 0.032 |
| 81 | nd | 0.100 | 0.044 |
| 82 | nd | 0.156 | nd |
| 83 | nd | 0.161 | nd |
| 84 | nd | 0.184 | 0.095 |
| 85 | nd | 1.144 | nd |
| 86 | nd | 0.195 | nd |
| 87 | nd | 0.608 | 0.260 |
| 88 | nd | 0.770 | nd |
| 89 | nd | 0.013 | 0.015 |
| 90 | 3.919 | nd | 1.365 |
| 91 | 0.286 | 0.070 | 0.115 |
| 92 | 4.503 | 4.408 | 3.282 |
| 93 | 1.598 | 2.460 | 0.798 |
| 94 | 0.079 | 0.073 | |
| 95 | 0.129 | 0.089 | 0.156 |
| 96 | 2.625 | 4.445 | 1.349 |
| 97 | 0.170 | 0.059 | 0.032 |
| 98 | 3.090 | 2.663 | nd |
| 99 | 0.214 | 0.042 | 0.062 |
| 100 | 0.128 | 0.043 | 0.054 |
| 101 | 0.425 | 0.122 | 0.059 |
| 102 | 2.440 | 0.835 | nd |
| 103 | 0.123 | 0.060 | 0.074 |
| 104 | 1.693 | 0.482 | nd |
| 105 | 0.896 | nd | nd |
| 106 | 3.881 | nd | nd |
| 107 | 0.373 | 0.295 | 0.227 |
| 108 | 0.545 | 0.483 | nd |
| 109 | 0.482 | nd | nd |
| 110 | 0.130 | 0.410 | 0.168 |
| 111 | 0.173 | 1.840 | nd |
| 112 | 1.877 | nd | nd |
| 113 | 1.036 | 0.160 | 0.117 |
| 114 | 0.167 | 0.035 | nd |
| 115 | 0.317 | nd | nd |
| 116 | 1.328 | nd | nd |
| 117 | 0.077 | 0.635 | nd |
| 118 | 1.984 | 0.618 | nd |
| 119 | 0.814 | nd | nd |
| 120 | 2.892 | 2.731 | nd |
| 121 | 0.412 | nd | 0.338 |
| 122 | 0.953 | nd | nd |
| 123 | 0.321 | nd | nd |
| 124 | 0.066 | nd | nd |
| 125 | 0.493 | nd | nd |
| 126 | 3.214 | nd | nd |
| 127 | 0.647 | nd | nd |
| 128 | 0.292 | nd | nd |
| 129 | 0.519 | 0.344 | 0.162 |
| 130 | 1.072 | 0.156 | nd |
| 131 | 0.237 | 0.171 | 0.074 |
| 132 | nd | 0.226 | nd |
| 133 | nd | 0.127 | 0.111 |
| 134 | nd | 0.051 | 0.049 |
| 135 | nd | 0.027 | 0.029 |
| 136 | nd | 0.014 | 0.004 |
| 137 | nd | 0.015 | 0.026 |
| 138 | nd | 0.031 | 0.010 |
| 139 | nd | 0.020 | 0.023 |
| 140 | nd | 0.031 | 0.034 |
| 141 | nd | 0.032 | 0.044 |
| 142 | nd | 0.051 | nd |
| 143 | nd | 0.055 | 0.026 |
| 144 | nd | 0.060 | 0.080 |
| 145 | nd | 0.064 | 0.017 |
| 146 | nd | 0.077 | 0.020 |
| 147 | nd | 0.083 | 0.054 |
| 148 | nd | 0.088 | 0.104 |
| 149 | nd | 0.063 | 0.020 |
| 150 | nd | 0.098 | 0.086 |
| 151 | nd | 0.100 | 0.026 |
| 152 | nd | 0.105 | 0.153 |
| 153 | nd | 0.140 | nd |
| 154 | nd | 0.145 | nd |
| 155 | nd | 0.227 | nd |
| 156 | nd | 0.161 | 0.079 |
| 157 | nd | 0.221 | nd |
| 158 | nd | 0.239 | 0.202 |
| 159 | nd | 0.345 | nd |
| 160 | nd | 0.383 | nd |
| 161 | nd | 0.911 | 0.557 |
| 162 | nd | 0.984 | nd |
| 163 | nd | 1.131 | 1.851 |
| 164 | nd | 1.545 | 0.859 |
| 165 | nd | 0.005 | 0.001 |
| 166 | nd | 0.298 | 0.068 |
| 167 | nd | 0.176 | 0.086 |
| 168 | nd | 0.014 | 0.019 |
| 169 | | 0.056 | |
| 170 | | 0.379 | |
| 171 | | 0.45 | |
| 172 | | 0.675 | |
| 173 | | 0.1 | |
| 174 | | 0.078 | |
| 175 | | 0.647 | |
| 176 | | 0.313 | |
| 177 | | 0.07 | |
| 178 | | 0.044 | |
| 179 | | 0.019 | |
| 180 | | 0.208 | |
| 181 | | 0.149 | |
| 182 | | 0.232 | |
| 183 | | 0.131 | |
| 184 | | 0.06 | |
| 185 | | 0.137 | |
| 186 | | 0.013 | |
| 187 | | 0.01 | |
| 188 | | 0.057 | |
| 189 | | 0.027 | |
| 190 | | 0.267 | |
| 191 | | 0.134 | |
| 192 | | 0.128 | |
| 193 | | 0.066 | |
| 194 | | 0.213 | |
| 195 | | 0.066 | |
| 196 | | 0.048 | |
| 197 | | 0.043 | |
| 198 | | 0.173 | |
| 199 | | 0.085 | |
| 200 | | 0.084 | |
| 201 | | 0.083 | |
| 202 | | 0.061 | |
| 203 | | 0.023 | |
| 204 | | 0.056 | |
| 205 | | 0.065 | |
| 206 | | 0.076 | |
| 207 | | 0.08 | |
| 208 | | 0.053 | |
| 209 | | 0.208 | |
| 210 | | 0.419 | |
| 211 | | 0.073 | |
| 212 | | 0.085 | |
| 213 | | 0.057 | |

| Example No. | Arrayscan (μM) | Cellisa (μM)[1] | Titre Blue (μM) |
|---|---|---|---|
| 214 | | 0.957 | |
| 215 | | 0.039 | |
| 216 | | 0.055 | |
| 217 | | 0.137 | |
| 218 | | 0.08 | |

[1]Examples 1-168 were tested using U2OS cells and Examples 169-218 were tested using SK-OV-3 cells.

REFERENCES

1. Altenbach, R. J.; Black, L. A.; Chang, S.-j.; Cowart, M. D.; Faghih, R.; Gfesser, G. A.; Ku, Y.-y.; Liu, H.; Lukin, K. A.; Nersesian, D. L.; Pu, Y.-m.; Sharma, P. N.; Bennani, Y. L. Preparation of pyrrolidine derivatives as histamine-3 receptor ligands. US20040092521A1, 2004.
2. Sagi, K.; Fujita, K.; Sugiki, M.; Takahashi, M.; Takehana, S.; Tashiro, K.; Kayahara, T.; Yamanashi, M.; Fukuda, Y.; Oono, S.; Okajima, A.; Iwata, S.; Shoji, M.; Sakurai, K., Optimization of a coagulation factor VIIa inhibitor found in factor Xa inhibitor library. *Bioorganic & Medicinal Chemistry* 2005, 13 (5), 1487-1496.
3. Giardina, G.; Clarke, G. D.; Dondio, G.; Petrone, G.; Sbacchi, M.; Vecchietti, V., Selective .kappa.-Opioid Agonists: Synthesis and Structure-Activity Relationships of Piperidines Incorporating an Oxo-Containing Acyl Group. *Journal of Medicinal Chemistry* 1994, 37(21), 3482-3491.
4. Wishka, D. G.; Walker, D. P.; Yates, K. M.; Reitz, S. C.; Jia, S.; Myers, J. K.; Olson, K. L.; Jacobsen, E. J.; Wolfe, M. L.; Groppi, V. E.; Hanchar, A. J.; Thornburgh, B. A.; Cortes-Burgos, L. A.; Wong, E. H. F.; Staton, B. A.; Raub, T. J.; Higdon, N. R.; Wall, T. M.; Hurst, R. S.; Walters, R. R.; Hoffmann, W. E.; Hajos, M.; Franklin, S.; Carey, G.; Gold, L. H.; Cook, K. K.; Sands, S. B.; Zhao, S. X.; Soglia, J. R.; Kalgutkar, A. S.; Arneric, S. P.; Rogers, B. N., Discovery of N-[(3R)-1-Azabicyclo[2.2.2]oct-3-yl]furo[2,3-c]pyridine-5-carboxamide, an Agonist of the α7 Nicotinic Acetylcholine Receptor, for the Potential Treatment of Cognitive Deficits in Schizophrenia: Synthesis and Structure-Activity Relationship. *Journal of Medicinal Chemistry* 2006, 49 (14), 4425-4436.
5. Nagase, T.; Mizutani, T.; Ishikawa, S.; Sekino, E.; Sasaki, T.; Fujimura, T.; Ito, S.; Mitobe, Y.; Miyamoto, Y.; Yoshimoto, R.; Tanaka, T.; Ishihara, A.; Takenaga, N.; Tokita, S.; Fukami, T.; Sato, N., Synthesis, Structure-Activity Relationships, and Biological Profiles of a Quinazolinone Class of Histamine H3 Receptor Inverse Agonists. *Journal of Medicinal Chemistry* 2008, 51 (15), 4780-4789.
6. Boys, M. L.; Bradley, M.; Delisle, R. K.; Hennings, D. D.; Kennedy, A. L.; Marmsater, F. P.; Medina, M.; Munson, M. C.; Rast, B.; Rizzi, J. P.; Rodriguez, M. E.; Topalov, G. T.; Zhao, Q. Preparation of substituted N-(1H-indazol-4-yl)imidazo[1,2-a]pyridine-3-carboxamides as cFMS inhibitors. WO2011079076A1, 2011.
7. Kahraman, M.; Govek, S. P.; Nagasawa, J. Y.; Smith, N. D. Preparation of chromen-6-ol derivatives as modulators of estrogen receptor. WO2011156518A2, 2011.
8. Radford, P.; Attygalle, A. B.; Meinwald, J.; Smedley, S. R.; Eisner, T., Pyrrolidinoöxazolidine Alkaloids from Two Species of Ladybird Beetles1. *Journal of Natural Products* 1997, 60 (8), 755-759.
9. Azizi, N.; Saidi, M. R., Highly Chemoselective Addition of Amines to Epoxides in Water. *Organic Letters* 2005, 7 (17), 3649-3651.
10. Bai, H.; Bailey, S.; Bhumralkar, D. R.; Bi, F.; Guo, F.; He, M.; Humphries, P. S.; Ling, A. L.; Lou, J.; Nukui, S.; Zhou, R. Preparation of fused phenyl amido heterocycles for the prevention and treatment of glucokinase-mediated diseases. WO2007122482A1, 2007.

The invention claimed is:

1. A method of treating ovarian cancer in a patient in need thereof, comprising administering to the patient a therapeutically effective amount of a compound represented by:

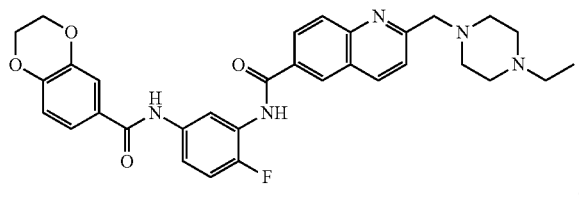

or a pharmaceutically acceptable salt thereof.

* * * * *